United States Patent
Courtemanche et al.

(10) Patent No.: US 7,396,958 B2
(45) Date of Patent: Jul. 8, 2008

(54) SULPHONAMIDE DERIVATIVES, THEIR PREPARATION AND THEIR THERAPEUTIC APPLICATION

(75) Inventors: Gilles Courtemanche, Antony (FR); Pierre Despeyroux, Antony (FR); Evelyne Fontaine, Antony (FR); Pierrick Rochard, Antony (FR); Claudine Serradeil-Le Gal, Antony (FR)

(73) Assignee: Sanofi Aventis, Paris (FR)

( * ) Notice: Subject to any disclaimer, the term of this patent is extended or adjusted under 35 U.S.C. 154(b) by 0 days.

(21) Appl. No.: 11/670,586

(22) Filed: Feb. 2, 2007

(65) Prior Publication Data

US 2007/0185136 A1    Aug. 9, 2007

Related U.S. Application Data

(63) Continuation of application No. PCT/FR2005/002017, filed on Aug. 2, 2005.

(30) Foreign Application Priority Data

Aug. 3, 2004  (FR) .................................. 04 08546

(51) Int. Cl.
C07C 303/00  (2006.01)
A01N 41/06   (2006.01)

(52) U.S. Cl. ......................................... 564/92; 514/604

(58) Field of Classification Search ....................... None
See application file for complete search history.

(56) References Cited

FOREIGN PATENT DOCUMENTS

| EP | 0358571 | 9/1989 |
|---|---|---|
| WO | WO 99/12916 | 3/1999 |
| WO | WO 00/47580 | 8/2000 |
| WO | WO 03/032991 | 4/2003 |

OTHER PUBLICATIONS

McAtee et al., Bioorg Med Chem Lett, 14, 2004, 4225-4229.*
Patoiseau et al., caplus an 1990:478394.*
Wagnon et al., caplus an 1995:777639.*
Sakurai, T., et. al., Orexins and Orexin Receptors: A Family of Hypothalamic Neuropeptides and G Protein-Coupled Receptors that Regulate Feeding Behavior, Cell, vol. 92, pp. 573-585 (1998).

* cited by examiner

*Primary Examiner*—Kamal Saeed
*Assistant Examiner*—Sun Jae Y Loewe
(74) *Attorney, Agent, or Firm*—Balaram Gupta

(57) ABSTRACT

Disclosed are compounds having the general formula (I)

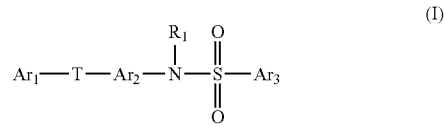

as defined herein, the preparation thereof, and the use thereof for the prophylaxis or treatment of any disease involving a dysfunction associated with the orexin 2 receptor such as obesity, appetite or taste disorders including cachexia, anorexia and bulimia, diabetes, metabolic syndromes, vomiting and nausea, depression and anxiety, addictions, mood and behaviour disorders, schizophrenia, sleep disorders, restless legs syndrome, memory learning disorders, sexual and psychosexual dysfunctions, pain, visceral or neuropathic pain, hyperalgesia, allodynia, digestive disorders, irritable bowel syndrome, neuronal degenerescence, ischaemic or haemorrhagic attacks, Cushing's disease, Guillain-Barré syndrome, myotonic dystrophy, urinary incontinence, hyperthyroidism, pituitary function disorders, hypertension or hypotension.

9 Claims, No Drawings

SULPHONAMIDE DERIVATIVES, THEIR PREPARATION AND THEIR THERAPEUTIC APPLICATION

FIELD OF THE INVENTION

The present invention relates to sulfonamide derivatives, to the process for preparing them and to their therapeutic use.

BACKGROUND OF THE INVENTION

Orexins A and B (or hypocretins 1 and 2) are hypothalamus neuropeptides of 33 and 28 amino acids, respectively, recently identified as endogenous ligands of two seven-domain transmembrane receptors, known as orexin 1 and orexin 2 receptors (Sakurai T., Cell, Vol. 92, 573-585, 1998; De Lecea L., Proc. Natl. Acad. Sci., Vol. 95, 322-327, 1998).

The orexin 2 receptor has the property of recognizing the two forms of orexin A and B equivalently. In contrast, the orexin 1 receptor, which shows 64% homology with the orexin 2 receptor, is more selective and binds orexin A ten times better than orexin B (Sakurai T., Cell, Vol. 92, 573-585, 1998).

Via these receptors, the orexins control various central and peripheral functions, especially taking of food and drink, certain cardiovascular endocrine functions and the awake/sleep cycle (Sakurai T., Regulatory Peptides, Vol. 85, 25-30, 1999).

SUMMARY OF THE INVENTION

It has now been found that certain sulfonamide derivatives show strong affinity for the orexin 2 receptors and are powerful antagonists of these receptors.

Thus, one subject of the present invention is compounds corresponding to the general formula (I)

$$Ar_1-T-Ar_2-\underset{R_1}{N}-\underset{O}{\overset{O}{\underset{\|}{S}}}-Ar_3 \quad (I)$$

in which $Ar_1$ represents
an aryl group such as a phenyl group optionally substituted with one or more groups chosen, independently of each other, from the following groups: a halogen atom, a $(C_1-C_4)$ alkyl group, a $(C_1-C_4)$ alkoxy group, a fluoro$(C_1-C_4)$alkyl group, a cyano group, a group —CO—$NR_aR_b$, a group —$NR_aR_b$, with $R_a$ and $R_b$ being, independently of each other, a hydrogen atom or a $(C_1-C_4)$ alkyl group, a heterocyclyl group chosen from pyridyl, pyrimidinyl, thiazolyl and thienyl, the said heterocyclyl groups being optionally substituted with a halogen atom, a $(C_1-C_4)$ alkyl group or a $(C_1-C_4)$ alkoxy group, a $(C_3-C_6)$ cycloalkyl group;

T represents
a group —$(CH_2)_n$— with n=0, 1 or 2,
a group $$\diagdown_{CH-R_2}\diagup$$

with $R_2$ being a hydroxyl group or a $(C_1-C_4)$ alkyl group, a group $$\diagdown_{N-R_3}\diagup$$

with $R_3$ being a $(C_1-C_4)$ alkyl group, a group $$\diagdown_{C(OH)-R_4}\diagup$$

with $R_4$ being a $(C_1-C_4)$ alkyl group;

$Ar_2$ represents
an aryl group such as phenyl optionally substituted with one or more groups chosen, independently of each other, from the following groups: a halogen atom, a $(C_1-C_4)$ alkyl group, a $(C_1-C_4)$ alkoxy group, a fluoro$(C_1-C_4)$ alkyl group, a fluoro$(C_1-C_4)$alkoxy group, or with a group —$NR_cR_d$ with $R_c$ and $R_d$ being, independently of each other, a hydrogen atom or a $(C_1-C_4)$ alkyl group, a heterocyclyl group such as pyridyl optionally substituted with a $(C_1-C_4)$ alkyl group or a $(C_1-C_4)$ alkoxy group;

$Ar_3$ represents
an aryl group chosen from phenyl and naphthyl, the said aryl groups being optionally substituted with one or more groups chosen, independently of each other, from the following groups: a halogen atom, a $(C_1-C_4)$ alkyl group, a $(C_1-C_4)$ alkoxy group, a fluoro$(C_1-C_4)$alkyl group, a fluoro$(C_1-C_4)$alkoxy group, a nitro group, a hydroxyl group, or with a group —$NR_5R_6$ with $R_5$ and $R_6$ being, independently of each other, a hydrogen atom or a $(C_1-C_4)$ alkyl group, a heterocyclyl group such as pyridyl optionally substituted with a $(C_1-C_4)$ alkyl group or a $(C_1-C_4)$ alkoxy group, or with a group —$NR_xR_y$ with $R_x$ and $R_y$ being, independently of each other, a hydrogen atom, a $(C_1-C_4)$ alkyl group or a $(C_1-C_4)$ alkoxy group, a group chosen from

[structures: benzodioxine and benzodioxole]

$R_1$ represents
a —$C(O)$—$CF_3$ group,
a group of formula

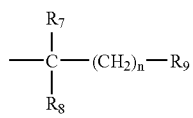

in which
n=0, 1, 2 or 3
$R_7$ represents
- a hydrogen atom, a $(C_1$-$C_4)$ alkyl group, a fluorine atom or a $(C_1$-$C_4)$ alkoxy group,
- a group —$(CH_2)_m$-aryl, with m=1 or 2 and the aryl group being a phenyl group optionally substituted with a halogen atom, a $(C_1$-$C_4)$ alkyl group or a $(C_1$-$C_4)$ alkoxy group, $R_8$ represents
- a hydrogen atom, a fluorine atom or a $(C_1$-$C_4)$ alkyl group, $R_9$ represents
- a hydrogen atom, a $(C_1$-$C_4)$ alkyl group, a $(C_3$-$C_6)$ cycloalkyl group, a hydroxyl group, a $(C_1$-$C_4)$ alkoxy group, a fluoro$(C_1$-$C_4)$alkyl group, a —C≡CH group, a —C≡N group, a phenoxy group or a $(C_1$-$C_4)$ alkenyl group,
- a group —$NR_{10}R_{11}$ with $R_{10}$ and $R_{11}$ being, independently of each other, a hydrogen atom, a $(C_1$-$C_4)$ alkyl group, a $(C_1$-$C_4)$ alkylcarbonyl group, a $(C_1$-$C_4)$ alkylsulfonyl group, a benzyl group or a —$(CH_2)_2$—$N(CH_3)_2$ group, or alternatively $R_{10}$ and $R_{11}$ form, together with the nitrogen atom that bears them, a pyrrolidine, a pyrrolidinone, a morpholine or a piperidine,
- a group —CO—$NR_{12}R_{13}$ with $R_{12}$ and $R_{13}$ being, independently of each other,
  - a hydrogen atom,
  - a $(C_1$-$C_4)$ alkyl group optionally substituted with a —C≡N group, an aryl group such as phenyl or a heterocyclyl group such as pyridyl, the said aryl and heterocyclyl groups being optionally substituted with a $(C_1$-$C_4)$ alkyl group or a hydroxyl group,
  - or alternatively $R_{12}$ and $R_{13}$ form, together with the nitrogen atom that bears them, a group

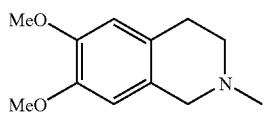

- a group —$COOR_{14}$ with $R_{14}$ being a $(C_1$-$C_4)$ alkyl group,
- a group —NH—CO—$NR_{15}R_{16}$ with $R_{15}$ and $R_{16}$ being, independently of each other, a hydrogen atom, a $(C_1$-$C_4)$ alkyl group, a phenyl group or a benzyl group, the said phenyl and benzyl groups being optionally substituted with one or more substituents chosen from a halogen atom, a $(C_1$-$C_4)$ alkyl group and a $(C_1$-$C_4)$ alkoxy group,
- a group —$SO_2$—$NR_{17}R_{18}$ with $R_{17}$ and $R_{18}$ being, independently of each other, a hydrogen atom or a $(C_1$-$C_4)$ alkyl group,
- a group —$SO_2$—$R_{19}$ with $R_{19}$ being a $(C_1$-$C_4)$ alkyl group or an aryl group such as phenyl,
- a heterocyclyl group chosen from 1,3-dioxolanyl, imidazolyl, tetrazolyl, triazolyl optionally substituted with a $(C_1$-$C_4)$ alkyl group, thiazolyl, pyrimidyl, oxadiazolyl or pyridyl, the imidazolyl being optionally substituted on the nitrogen atom with a $(C_1$-$C_4)$ alkyl group or a benzyl, the tetrazolyl being optionally substituted with a $(C_1$-$C_4)$ alkyl group or a benzyl, and the oxadiazolyl being optionally substituted with a $(C_1$-$C_4)$ alkyl,
- a group —NH—CO—$OR_{15}$, $R_{15}$ corresponding to the above definition, in the form of base, of acid-addition salt, of hydrate or of solvate, in the form of enantiomers, diastereoisomers, rotamers or atropoisomers, or mixtures thereof.

DETAILED DESCRIPTION

Among the compounds that are the subject of the invention, mention may be made of a first group of compounds of general formula (I) in which
$Ar_1$ represents
- an aryl group such as a phenyl group optionally substituted with one or more groups chosen, independently of each other, from the following groups: a halogen atom, a $(C_1$-$C_4)$ alkyl group, a $(C_1$-$C_4)$ alkoxy group, a fluoro$(C_1$-$C_4)$alkyl group,
- a heterocyclyl group chosen from pyridyl, thiazolyl and thienyl, the thienyl being optionally substituted with a $(C_1$-$C_4)$ alkyl group,
- a $(C_3$-$C_6)$ cycloalkyl group;

T represents
a group —$(CH_2)_n$— with n=1
a group

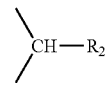

with $R_2$ being a hydroxyl group or a $(C_1$-$C_4)$ alkyl group,
a group

with $R_3$ being a $(C_1$-$C_4)$ alkyl group,
a group

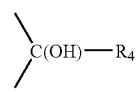

with $R_4$ being a $(C_1$-$C_4)$ alkyl group;
$Ar_2$ represents
an aryl group such as phenyl optionally substituted with one or more groups chosen, independently of each other, from the following groups: a halogen atom, a $(C_1$-$C_4)$ alkyl group, a $(C_1$-$C_4)$ alkoxy group, a fluoro$(C_1$-$C_4)$ alkoxy group, a group —NR$_c$R$_d$ with R$_c$ and R$_d$ being, independently of each other, a hydrogen atom or a (C$_1$-C$_4$) alkyl group;

Ar$_3$ represents an aryl group chosen from phenyl and naphthyl, the phenyl group being optionally substituted with one or more groups chosen, independently of each other, from the following groups: a halogen atom, a (C$_1$-C$_4$) alkyl group, a (C$_1$-C$_4$) alkoxy group, a fluoro (C$_1$-C$_4$)alkyl group, a fluoro(C$_1$-C$_4$)alkoxy group, a nitro group, or a group —NR$_5$R$_6$ with R$_5$ and R$_6$ being, independently of each other, a hydrogen atom or a (C$_1$-C$_4$) alkyl group, a group chosen from

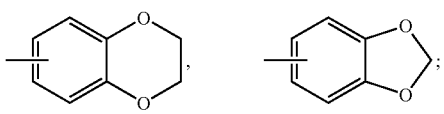

R$_1$ represents a —C(O)—CF$_3$ group, a group of formula

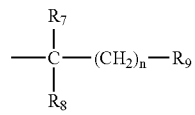

in which n=0, 1 or 2,

R$_7$ represents a hydrogen atom or a (C$_1$-C$_4$) alkyl group

R$_8$ represents a hydrogen atom,

R$_9$ represents a hydrogen atom, a (C$_1$-C$_4$) alkyl group, a hydroxyl group, a (C$_1$-C$_4$) alkoxy group, a fluoro(C$_1$-C$_4$) alkyl group, a —C≡CH group or a —C≡N group, a group —NR$_{10}$R$_{11}$ with R$_{10}$ and R$_{11}$ being, independently of each other, a hydrogen atom, a (C$_1$-C$_4$) alkyl group, a (C$_1$-C$_4$) alkylcarbonyl group or a benzyl, or alternatively R$_{10}$ and R$_{11}$ form, together with the nitrogen atom that bears them, a pyrrolidine, a piperidine or a pyrrolidinone, a group —CO—NR$_{12}$R$_{13}$ with R$_{12}$ and R$_{13}$ being, independently of each other, a hydrogen atom or a (C$_1$-C$_4$) alkyl group, or alternatively R$_{12}$ and R$_{13}$ form, together with the nitrogen atom that bears them, a group

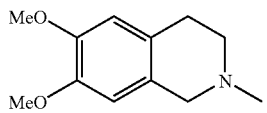

or a group —COOR$_{14}$ with R$_{14}$ being a (C$_1$-C$_4$) alkyl group, a group —NH—CO—NR$_{15}$R$_{16}$ with R$_{15}$ and R$_{16}$ being, independently of each other, a hydrogen atom, a (C$_1$-C$_4$) alkyl group, a phenyl or a benzyl, a heterocyclyl group chosen from imidazolyl optionally substituted on the nitrogen atom with a (C$_1$-C$_4$) alkyl group, tetrazolyl optionally substituted with a (C$_1$-C$_4$) alkyl group, and triazolyl, in the form of base, of acid-addition salt, of hydrate or of solvate, in the form of enantiomers, diastereoisomers, rotamers or atropoisomers, or mixtures thereof.

Among the compounds that are the subject of the invention, mention may be made of a second group of compounds of general formula (I) in which Ar$_1$ represents an aryl group such as phenyl optionally substituted with one or more groups chosen, independently of each other, from the following groups: a halogen atom, a (C$_1$-C$_4$) alkyl group, a (C$_1$-C$_4$) alkoxy group, a fluoro (C$_1$-C$_4$) alkyl group, a heterocyclyl group chosen from pyridyl, thiazolyl and thienyl, the thienyl being optionally substituted with a (C$_1$-C$_4$) alkyl group;

T represents a group —(CH$_2$)$_n$— with n=1 a group

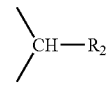

with R$_2$ being a hydroxyl group;

Ar$_2$ represents an aryl group such as phenyl optionally substituted with one or more groups chosen, independently of each other, from the following groups: a halogen atom, a (C$_1$-C$_4$) alkyl group, a (C$_1$-C$_4$) alkoxy group; a group —NR$_c$R$_d$ with R$_c$ and R$_d$ being, independently of each other, a hydrogen atom or a (C$_1$-C$_4$) alkyl group;

Ar$_3$ represents an aryl group such as phenyl, the phenyl group being optionally substituted with one or more groups chosen, independently of each other, from the following groups: a halogen atom, a (C$_1$-C$_4$) alkyl group, a (C$_1$-C$_4$) alkoxy group, or alternatively a group —NR$_5$R$_6$ with R$_5$ and R$_6$ being, independently of each other, a hydrogen atom or a (C$_1$-C$_4$) alkyl group;

R$_1$ represents a group of formula

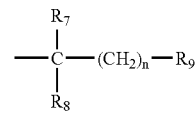

in which
n=0, 1 or 2,
$R_7$ represents
   a hydrogen atom or a ($C_1$-$C_4$) alkyl group,
$R_8$ represents
   a hydrogen atom,
$R_9$ represents
   a hydrogen atom, a —C≡CH group or a —C≡N group,
   a group —CO—$NR_{12}R_{13}$ with $R_{12}$ and $R_{13}$ being, independently of each other, a hydrogen atom or a ($C_1$-$C_4$) alkyl group,
   a heterocyclyl chosen from imidazolyl optionally substituted on the nitrogen atom with a ($C_1$-$C_4$) alkyl group, tetrazolyl optionally substituted with a ($C_1$-$C_4$) alkyl group, and triazolyl, in the form of base, of acid-addition salt, of hydrate or of solvate, in the form of enantiomers, diastereoisomers, rotamers or atropoisomers, or mixtures thereof.

Among the compounds that are the subject of the invention, mention may be made of a third group of compounds of general formula (I) in which
$Ar_1$ represents
   an aryl group such as phenyl optionally substituted with one or more groups chosen, independently of each other, from the following groups: a halogen atom, a ($C_1$-$C_4$) alkyl group, a ($C_1$-$C_4$) alkoxy group,
a heterocyclyl group such as thienyl, optionally substituted with a ($C_1$-$C_4$) alkyl group,
T represents
a group —$(CH_2)_n$— with n=1
$Ar_2$ represents
   a phenyl group optionally substituted with one or more groups chosen, independently of each other, from the following groups: a halogen atom, a ($C_1$-$C_4$) alkyl group, a ($C_1$-$C_4$) alkoxy group, a group —$NR_cR_d$ with $R_c$ and $R_d$ being, independently of each other, a hydrogen atom or a ($C_1$-$C_4$) alkyl group;
$Ar_3$ represents
   a phenyl group optionally substituted with one or more groups chosen, independently of each other, from the following groups: a halogen atom, a ($C_1$-$C_4$) alkyl group, a ($C_1$-$C_4$) alkoxy group, or alternatively a group —$NR_5R_6$ with $R_5$ and $R_6$ being, independently of each other, a hydrogen atom or a ($C_1$-$C_4$) alkyl group;
$R_1$ represents
a group of formula

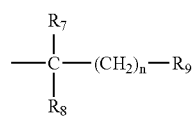

in which
n=0, 1 or 2,
$R_7$ represents
   a hydrogen atom or a ($C_1$-$C_4$) alkyl group;
$R_8$ represents
   a hydrogen atom;
$R_9$ represents
   a group —CO—$NR_{12}R_{13}$ with $R_{12}$ and $R_{13}$ being, independently of each other, a hydrogen atom or a ($C_1$-$C_4$) alkyl group,
   a heterocycle chosen from imidazolyl substituted on the nitrogen atom with a ($C_1$-$C_4$) alkyl group, tetrazolyl substituted with a ($C_1$-$C_4$) alkyl group, and triazolyl, in the form of base, of acid-addition salt, of hydrate or of solvate, in the form of enantiomers, diastereoisomers, rotamers or atropoisomers, or mixtures thereof.

When $Ar_2$ is an optionally substituted phenyl group, the bonds T-$Ar_2$, on the one hand, and $Ar_2$—N, on the other hand, are in an ortho position. In other words, the nitrogen atom and the substituent T are on two adjacent carbon atoms.

Examples of compounds according to the invention that may be mentioned include the following compounds:

Compound 1:

Ethyl N-{4-chloro-2-[(2-chlorophenyl)(hydroxy)methyl]phenyl}-N-[(3,4-dimethoxyphenyl)sulfonyl]glycinate

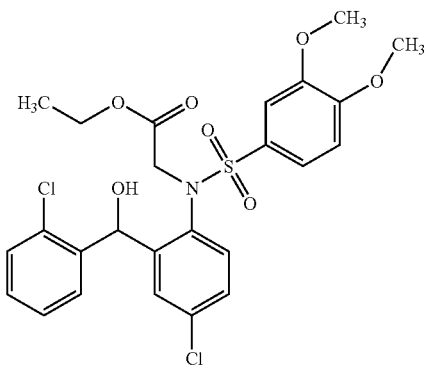

Compound 2:

Ethyl N-(2-benzyl-4-chlorophenyl)-N-[(3,4-dimethoxyphenyl)sulfonyl]glycinate

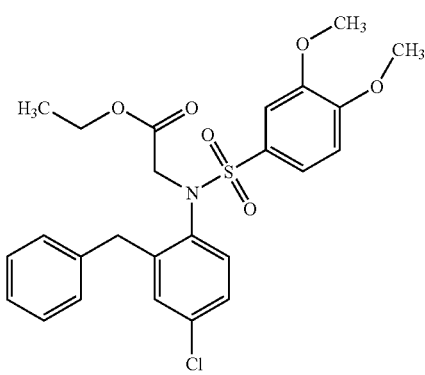

Compound 3:

Ethyl N-[4-chloro-2-(2-chlorobenzyl)phenyl]-N-[(3-methoxyphenyl)sulfonyl]glycinate

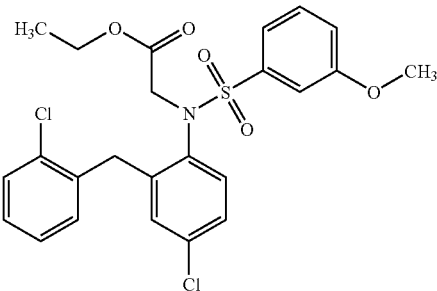

Compound 4:

Ethyl N-[4-chloro-2-(2-chlorobenzyl)phenyl]-N-[(2-methoxyphenyl)sulfonyl]glycinate

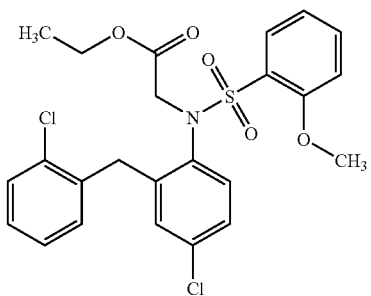

Compound 5:

Ethyl N-[4-chloro-2-(2-chlorobenzyl)phenyl]-N-[(2,5-dimethoxyphenyl)sulfonyl]glycinate

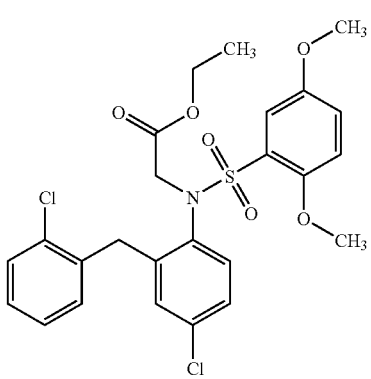

Compound 6:

Ethyl N-[4-chloro-2-(2-chlorobenzyl)phenyl]-N-[(2,4-dimethoxyphenyl)sulfonyl]glycinate

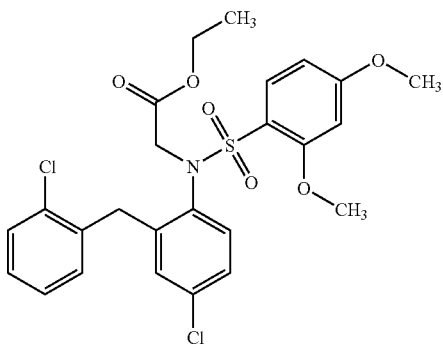

Compound 7:

Ethyl N-{4-chloro-2-[hydroxy(phenyl)methyl]phenyl}-N-[(3,4-dimethoxyphenyl)sulfonyl]glycinate

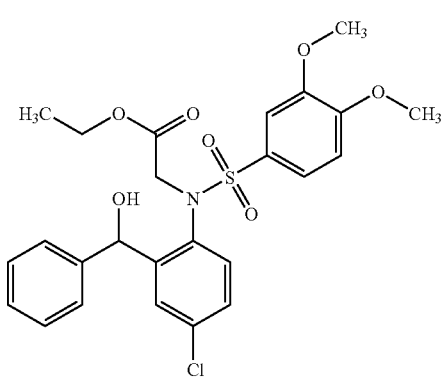

Compound 8:

Ethyl N-[(3,4-dimethoxyphenyl)sulfonyl]-N-{2-[hydroxy(phenyl)methyl]phenyl}glycinate

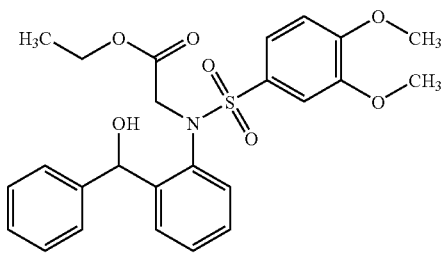

Compound 9:

Ethyl N-{4-chloro-2-[(2-chlorophenyl)(hydroxy)methyl]phenyl}-N-[(2,4-dimethoxyphenyl)sulfonyl]glycinate

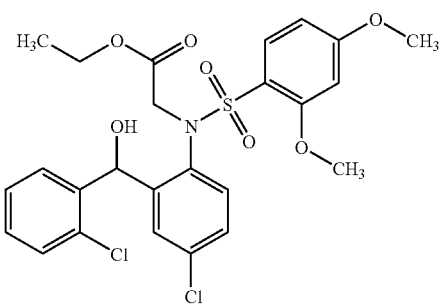

Compound 10:

Ethyl N-{4-chloro-2-[(2-chlorophenyl)(hydroxy)methyl]phenyl}-N-(phenylsulfonyl)glycinate

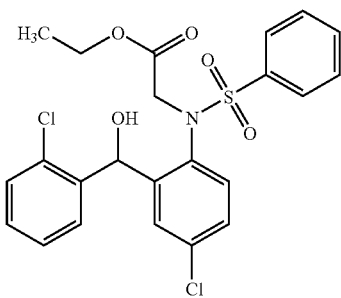

Compound 11:

N-{4-chloro-2-[(2-chlorophenyl)(hydroxy)methyl]phenyl}-N-[(2-ethyl-2H-tetrazol-5-yl)methyl]-3,4-dimethoxybenzenesulfonamide

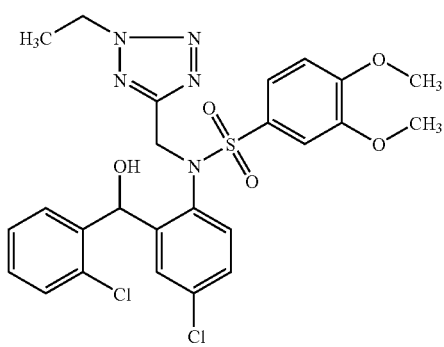

Compound 12:

N-{4-chloro-2-[(2-chlorophenyl)(hydroxy)methyl]phenyl}-N-[(1-ethyl-1H-tetrazol-5-yl)methyl]-3,4-dimethoxybenzenesulfonamide

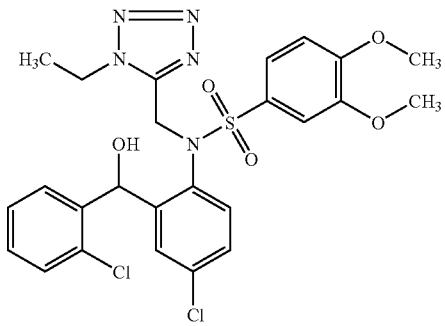

Compound 13:

Ethyl N-{4-chloro-2-[(2-chlorophenyl)(hydroxy)methyl]phenyl}-N-[(4-methoxyphenyl)sulfonyl]glycinate

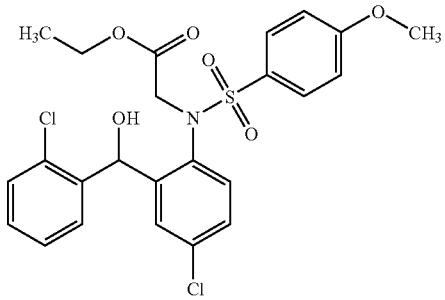

Compound 14:

N-{4-chloro-2-[(2-chlorophenyl)(hydroxy)methyl]phenyl}-3,4-dimethoxy-N-[(2-methyl-2H-tetrazol-5-yl)methyl]benzenesulfonamide

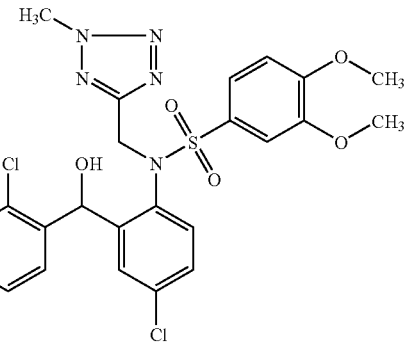

Compound 15:

N-{4-chloro-2-[(2-chlorophenyl)(hydroxy)methyl]phenyl}-3,4-dimethoxy-N-[(1-methyl-1H-tetrazol-yl)methyl]benzenesulfonamide

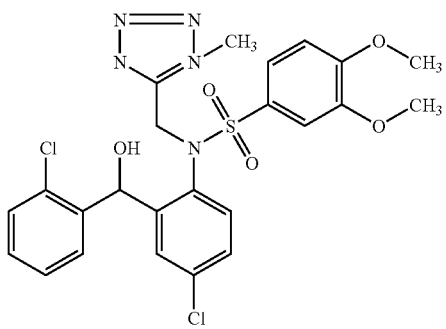

Compound 16:

Ethyl N-{4-chloro-2-[(3-chlorophenyl)(hydroxy)methyl]phenyl}-N-[(3,4-dimethoxyphenyl)sulfonyl]glycinate

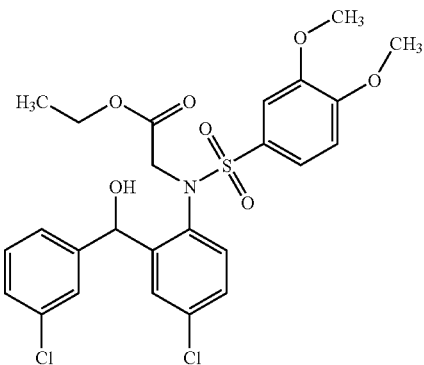

Compound 17:

Ethyl N-{4-chloro-2-[hydroxy(2-methoxyphenyl)methyl]phenyl}-N-[(3,4-dimethoxyphenyl)sulfonyl]glycinate

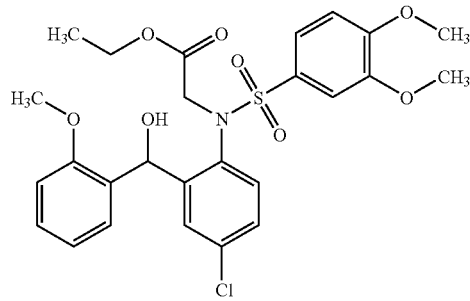

Compound 18:

Ethyl N-{4-chloro-2-[(2-chlorophenyl)(hydroxy)methyl]phenyl}-N-[(3,4-dichlorophenyl)sulfonyl]glycinate

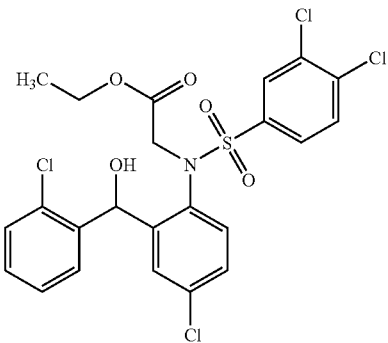

Compound 19:

$N^2$-{4-chloro-2-[(2-chlorophenyl)(hydroxy)methyl]phenyl}-N~2~-[(3,4-dimethoxyphenyl)sulfonyl]glycinamide

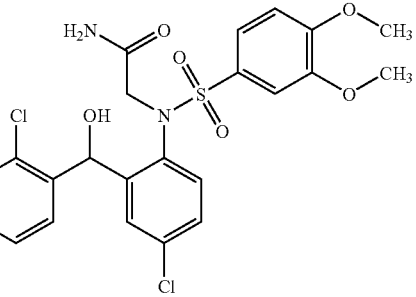

Compound 20:

N-{4-chloro-2-[(2-chlorophenyl)(hydroxy)methyl]phenyl}-N-ethyl-3,4-dimethoxybenzenesulfonamide

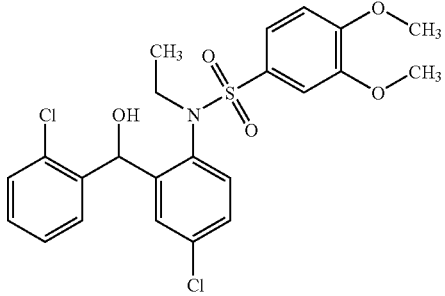

Compound 21:

Methyl N-{4-chloro-2-[(2-chlorophenyl)(hydroxy)methyl]phenyl}-N-[(3,4-dimethoxyphenyl)sulfonyl]glycinate

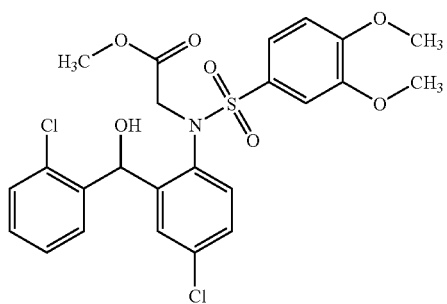

Compound 22:

N-{4-chloro-2-[(2-chlorophenyl)(hydroxy)methyl]phenyl}-3,4-dimethoxy-N-[(1-methyl-1H-imidazol-2-yl)methyl]benzenesulfonamide

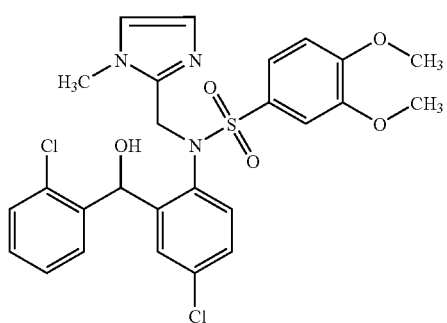

Compound 23:

N-(4-chloro-2-[(2-chlorophenyl)(hydroxy)methyl]phenyl)-3,4-dimethoxy-N-(2-methoxyethyl)benzenesulfonamide

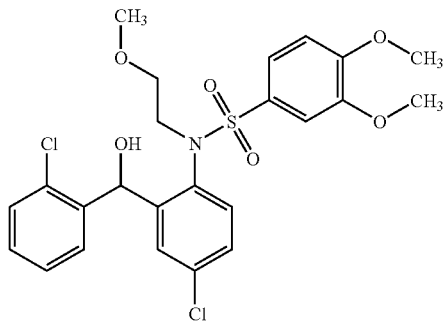

Compound 24:

N-{4-chloro-2-[(2-chlorophenyl)(hydroxy)methyl]phenyl}-N-(2-hydroxyethyl)-3,4-dimethoxybenzenesulfonamide

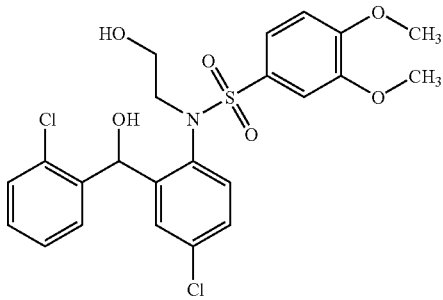

Compound 25:

N-{4-chloro-2-[(2-chlorophenyl)(hydroxy)methyl]phenyl}-3,4-dimethoxy-N-methylbenzenesulfonamide Compound 26:

Ethyl N-{4-chloro-2-[hydroxy(2-methylphenyl)methyl]phenyl}-N-[(3,4-dimethoxyphenyl)sulfonyl]glycinate

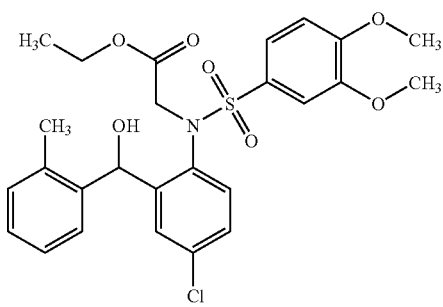

Compound 27:

N²-[4-chloro-2-(2-chlorobenzyl)phenyl]-N²-[(3-methoxyphenyl)sulfonyl]glycinamide

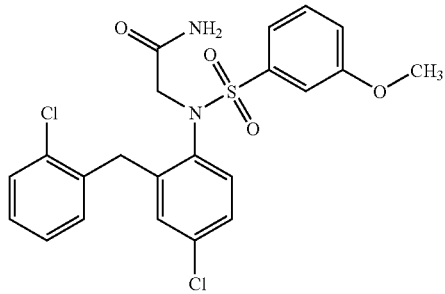

Compound 28:

N²-{4-chloro-2-[(2-chlorophenyl)(hydroxy)methyl]phenyl}-N²-[(3,4-dimethylphenyl)sulfonyl]glycinamide

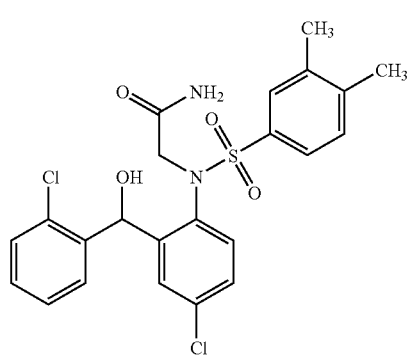

Compound 29:

N²-{4-chloro-2-[(2-chlorophenyl)(hydroxy)methyl]phenyl}-N²-(2-naphthylsulfonyl)glycinamide

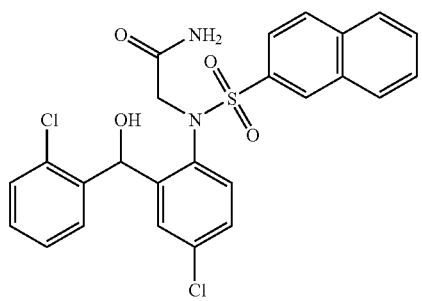

Compound 30:

N²-{4-chloro-2-[(2-chlorophenyl)(hydroxy)methyl]phenyl}-N-[(3-methoxyphenyl)sulfonyl]glycinamide

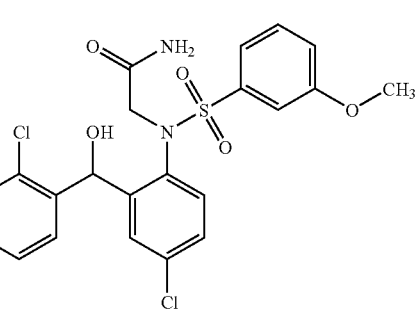

Compound 31:

N²-{4-chloro-2-[(2-chlorophenyl)(hydroxy)methyl]phenyl}-N²-[(3-chlorophenyl)sulfonyl]glycinamide

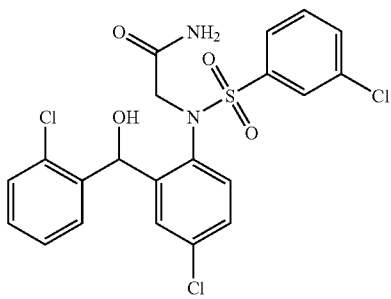

Compound 32:

N²-{4-chloro-2-[(2-chlorophenyl)(hydroxy)methyl]phenyl}-N²-[(4-methoxyphenyl)sulfonyl]glycinamide

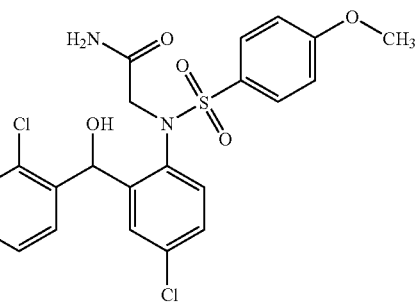

Compound 33:

N²-{4-chloro-2-[(2-chlorophenyl)(hydroxy)methyl]phenyl}-N²-[(2,4-dimethoxyphenyl)sulfonyl]glycinamide

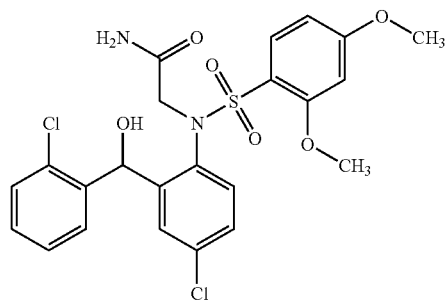

Compound 34:

N²-{4-chloro-2-[(2-chlorophenyl)(hydroxy)methyl]phenyl}-N²-[(3,4-dichlorophenyl)sulfonyl]glycinamide

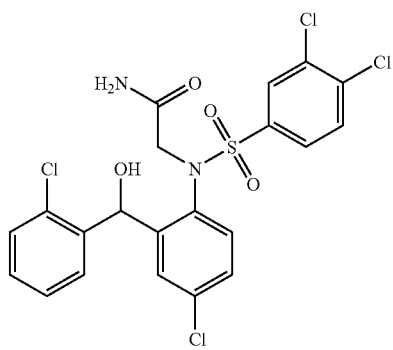

Compound 35:

N²-{4-chloro-2-[(2-chlorophenyl)(hydroxy)methyl]phenyl}-N N²-[(4-chlorophenyl)sulfonyl]glycinamide

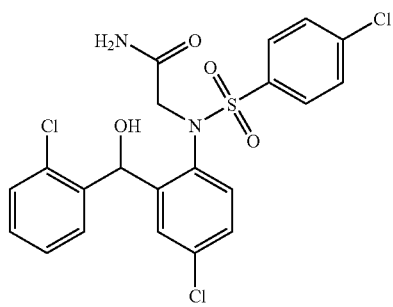

Compound 36:

N²{4-chloro-2-[(2-chlorophenyl)(hydroxy)methyl]phenyl}-N²-[(2,5-dimethoxyphenyl)sulfonyl]glycinamide

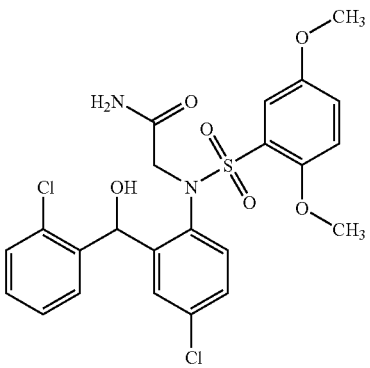

Compound 37:

N²-{4-chloro-2-[(2-chlorophenyl)(hydroxy)methyl]phenyl}-N²-[(2-chlorophenyl)sulfonyl]glycinamide

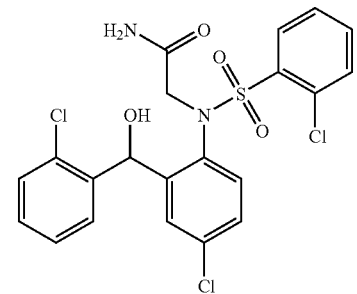

Compound 38:

N²-{4-chloro-2-[(2-chlorophenyl)(hydroxy)methyl]phenyl}-N²-[(4-chloro-2,5-dimethylphenyl)sulfonyl]glycinamide

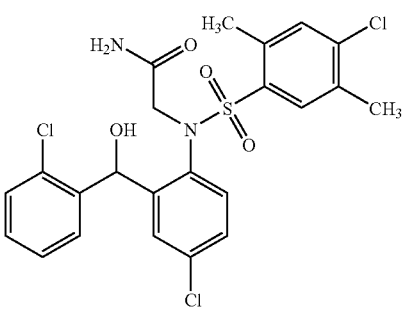

Compound 39:

N²-[4-chloro-2-(2-chlorobenzyl)phenyl]-N²-[(4-methoxyphenyl)sulfonyl]glycinamide

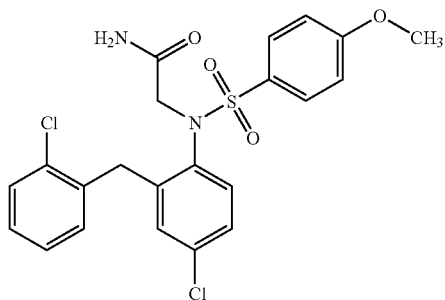

Compound 40:

N²-[4-chloro-2-(2-chlorobenzyl)phenyl]-N²-[(2,5-dimethoxyphenyl)sulfonyl]glycinamide

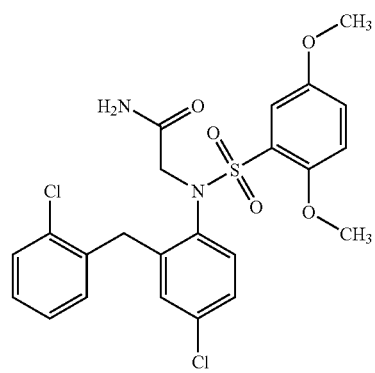

Compound 41:

N²-{4-chloro-2-[(2-chlorophenyl)(hydroxy)methyl]phenyl}-N²-[(2,3-dimethoxyphenyl)sulfonyl]glycinamide

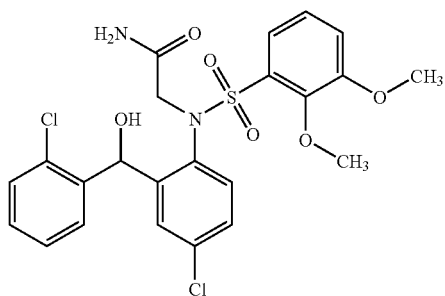

Compound 42:

N²-[4-chloro-2-(2-chlorobenzyl)phenyl]-N²-{[3-(trifluoromethyl)phenyl]sulfonyl}-glycinamide

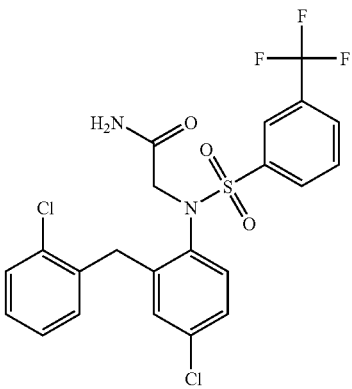

Compound 43:

N²-[4-chloro-2-(2-chlorobenzyl)phenyl]-N²-{[3-(trifluoromethoxy)phenyl]sulfonyl}-glycinamide

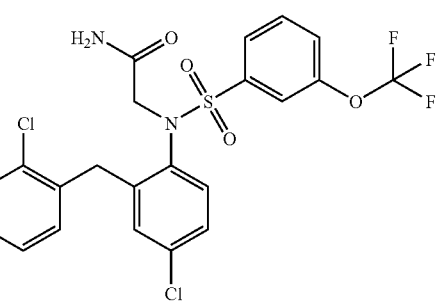

Compound 44:

N²-{4-chloro-2-[(3-chlorophenyl)(hydroxy)methyl]phenyl}-N²-[(3,4-dimethoxyphenyl)sulfonyl]glycinamide

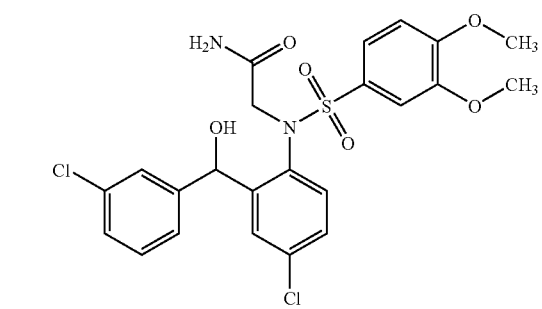

Compound 45:

N²-[4-chloro-2-(2-chlorobenzyl)phenyl]-N²-[(2-methoxyphenyl)sulfonyl]glycinamide

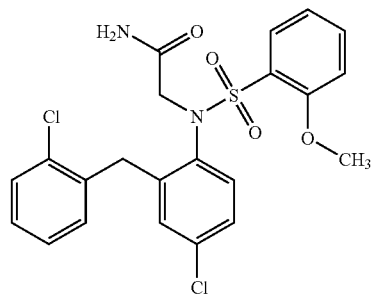

Compound 46:

N²-[4-chloro-2-(2-chlorobenzyl)phenyl]-N²-[(3,4-dimethoxyphenyl)sulfonyl]-N¹-methylglycinamide

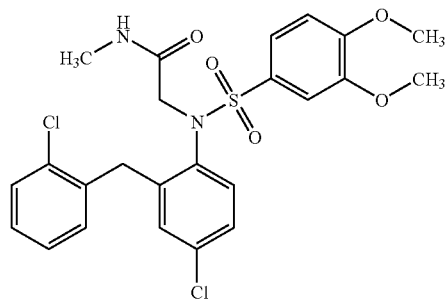

Compound 47:

N²-[4-chloro-2-(2-chlorobenzyl)phenyl]-N²-[(4-chlorophenyl)sulfonyl]glycinamide

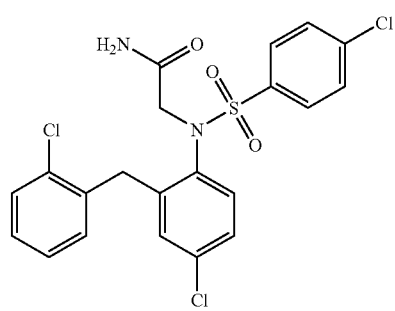

Compound 48:

N²-[4-chloro-2-(2-chlorobenzyl)phenyl]-N²-[(3,4-dichlorophenyl)sulfonyl]glycinamide

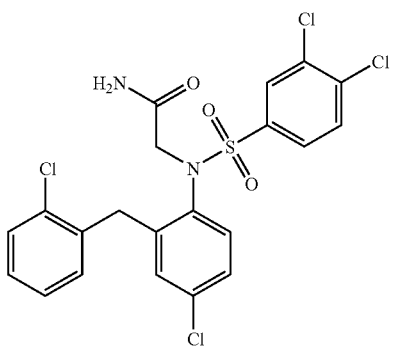

Compound 49:

N²-[4-chloro-2-(2-chlorobenzyl)phenyl]-N²-[(4-chloro-2,5-dimethylphenyl)sulfonyl]glycinamide

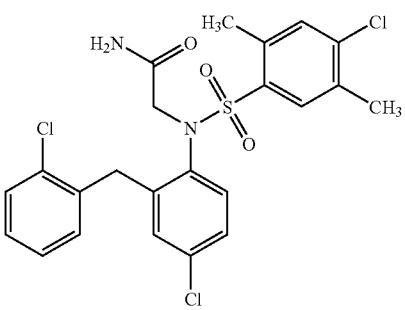

Compound 50:

N²-[4-chloro-2-(2-chlorobenzyl)phenyl]-N²-[(2-chlorophenyl)sulfonyl]glycinamide

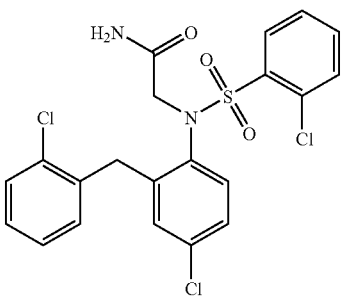

Compound 51:

N$^2$-{4-chloro-2-[hydroxy(3-methoxyphenyl)methyl]phenyl}-N$^2$-[(3,4-dimethoxyphenyl)sulfonyl]glycinamide

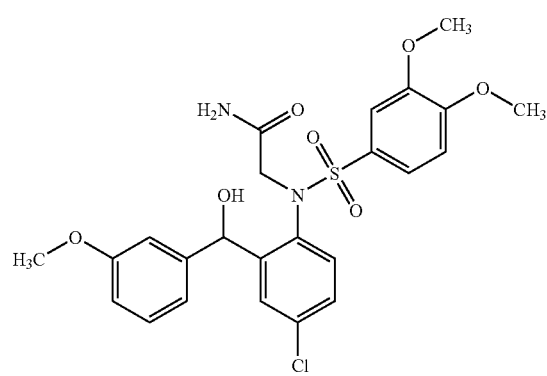

Compound 52:

N$^2$-{4-chloro-2-[(2-chlorophenyl)(hydroxy)methyl]phenyl}-N$^2$-(phenylsulfonyl)glycinamide

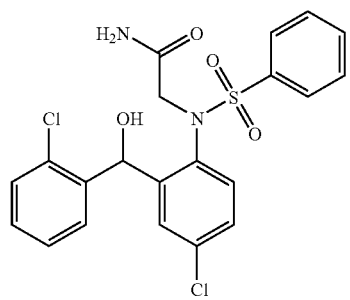

Compound 53:

N$^2$-[4-chloro-2-(2-chlorobenzyl)phenyl]-N$^2$-(phenylsulfonyl)glycinamide

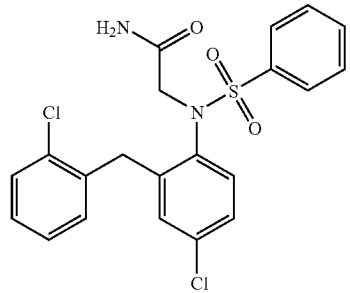

Compound 54:

N-[4-chloro-2-(2-chlorobenzyl)phenyl]-3,4-dimethoxy-N-methylbenzenesulfonamide

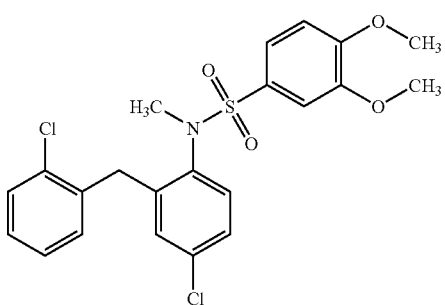

Compound 55:

N$^2$-[4-chloro-2-(2-fluorobenzyl)phenyl]-N$^2$-[(3,4-dimethoxyphenyl)sulfonyl]glycinamide

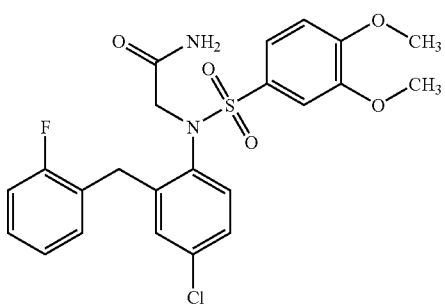

Compound 56:

N$^2$-[4-chloro-2-(2-methoxybenzyl)phenyl]-N$^2$-[(3,4-dimethoxyphenyl)sulfonyl]glycinamide

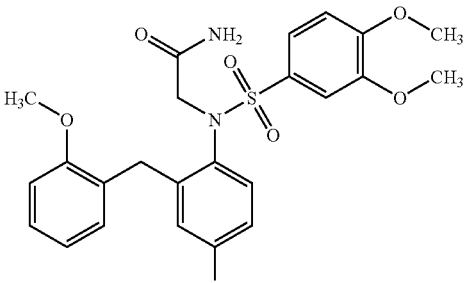

Compound 57:

N²-{4-chloro-2-[(2-fluorophenyl)(hydroxy)methyl]phenyl}-N²-[(3,4-dimethoxyphenyl)sulfonyl]glycinamide

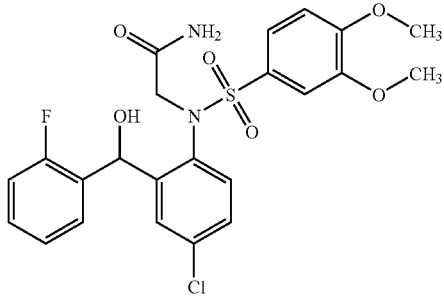

Compound 58:

N~2~-[4-chloro-2-(3-methoxybenzyl)phenyl]-N~2~-[(3,4-dimethoxyphenyl)sulfonyl]glycinamide

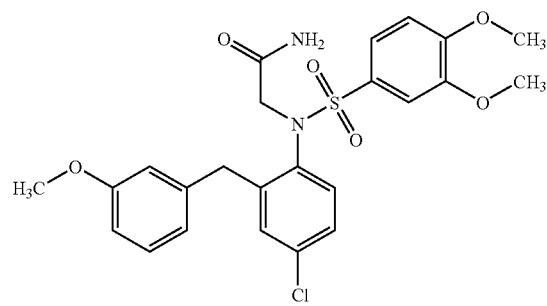

Compound 59:

N²-{4-chloro-2-[hydroxy(4-methoxyphenyl)methyl]phenyl}-N²-[(3,4-dimethoxyphenyl)sulfonyl]glycinamide

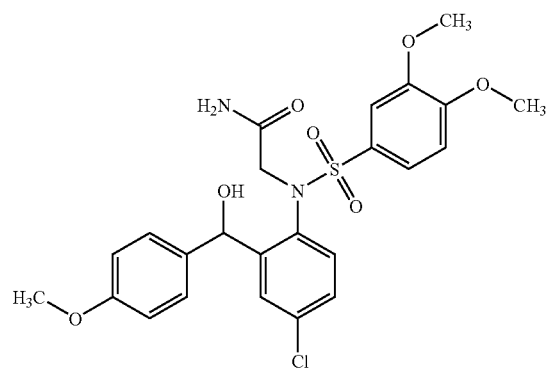

Compound 60:

N²-[4-chloro-2-(4-methoxybenzyl)phenyl]-N²-[(3,4-dimethoxyphenyl)sulfonyl]glycinamide

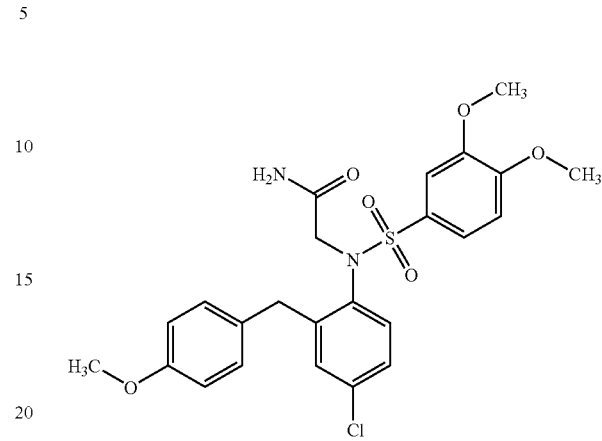

Compound 61:

N²-{2-[(2-chlorophenyl)(hydroxy)methyl]-4-fluorophenyl}-N-²-[(3,4-dimethoxyphenyl)sulfonyl]glycinamide

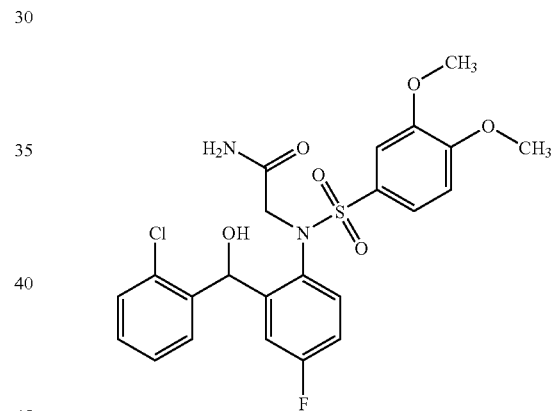

Compound 62:

N²-[4-chloro-2-(2-chlorobenzyl)phenyl]-N²-[(3-methylphenyl)sulfonyl]glycinamide

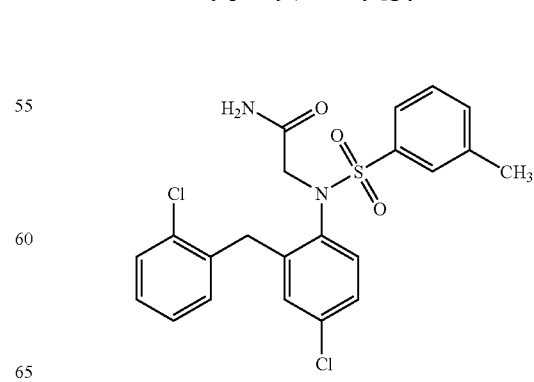

Compound 63:

N²-[4-chloro-2-(2-chlorobenzyl)phenyl]-N²-(2,3-dihydro-1,4-benzodioxin-6-ylsulfonyl)glycinamide

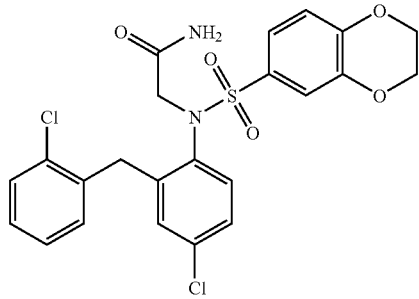

Compound 64:

N²-{4-chloro-2-[(2-chlorophenyl)(hydroxy)methyl]phenyl}-N²-(2,3-dihydro-1,4-benzodioxin-6-ylsulfonyl)glycinamide

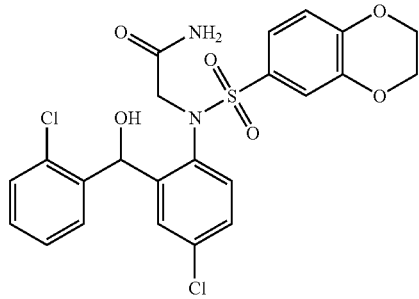

Compound 65:

N²-(2-benzyl-4-chlorophenyl)-N²-[(3,4-dimethoxyphenyl)sulfonyl]glycinamide

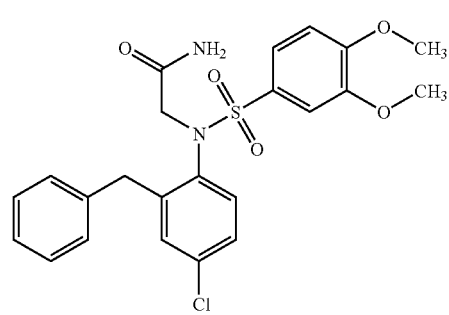

Compound 66:

N²-{4-chloro-2-[hydroxy(phenyl)methyl]phenyl}-N²-[(3,4-dimethoxyphenyl)sulfonyl]glycinamide

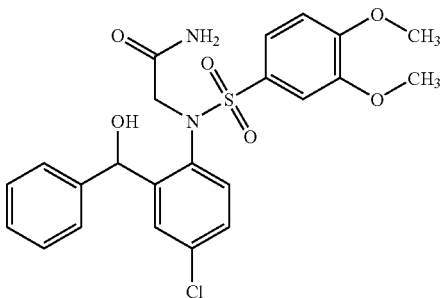

Compound 67:

N²-[2-(2-chlorobenzyl)phenyl]-N²-[(3,4-dimethoxyphenyl)sulfonyl]glycinamide

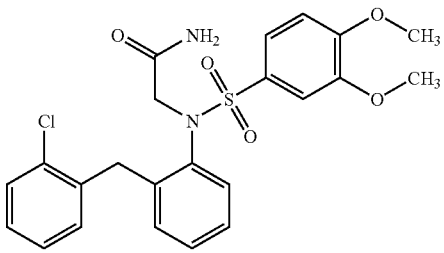

Compound 68:

N²-{4-chloro-2-[hydroxy(2-methoxyphenyl)methyl]phenyl}-N²-[(3,4-dimethoxyphenyl)sulfonyl]glycinamide

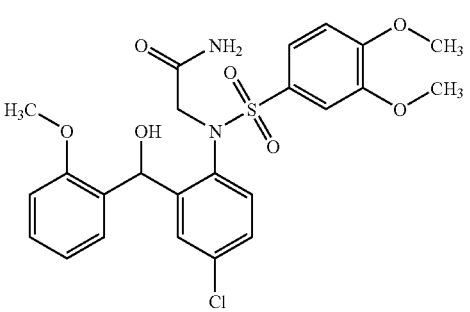

Compound 69:

N²-{2-[(2-chlorophenyl)(hydroxy)methyl]-4-methoxyphenyl}-N²-[(3,4-dimethoxyphenyl)sulfonyl]glycinamide

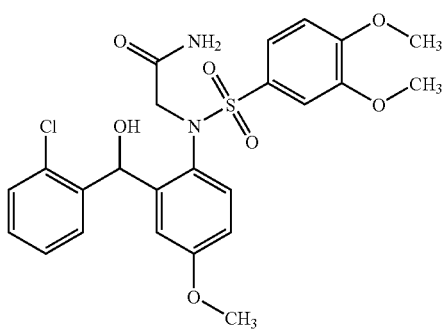

Compound 70:

N²-[4-chloro-2-(2-chlorobenzyl)phenyl]-N²-[(3,4-dimethoxyphenyl)sulfonyl]-N¹, N¹-dimethylglycinamide

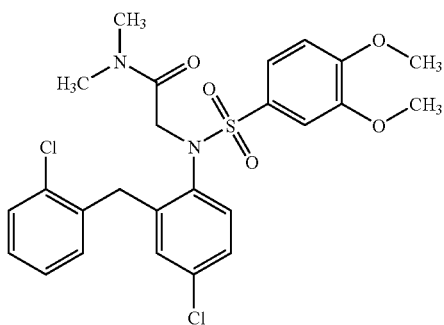

Compound 71:

N²-(1,3-benzodioxol-5-ylsulfonyl)-N²-[4-chloro-2-(2-chlorobenzyl)phenyl]glycinamide

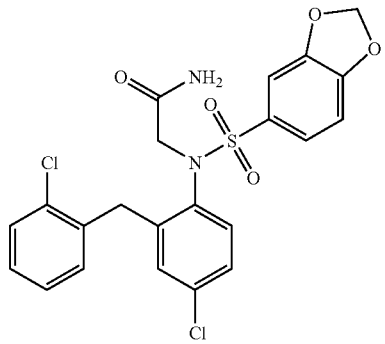

Compound 72:

N²-{4-chloro-2-[(2-chlorophenyl)(hydroxy)methyl]phenyl}-N²-[(3,4-dimethoxyphenyl)sulfonyl]-N¹-methylglycinamide

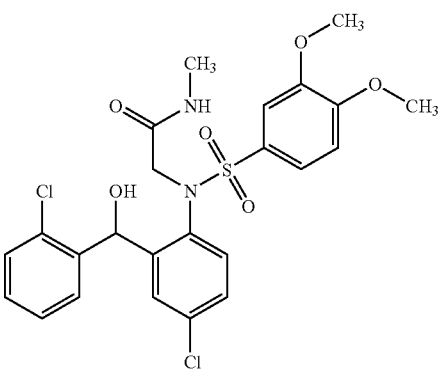

Compound 73:

N²-[4-chloro-2-(2-methylbenzyl)phenyl]-N²-[(3,4-dimethoxyphenyl)sulfonyl]glycinamide

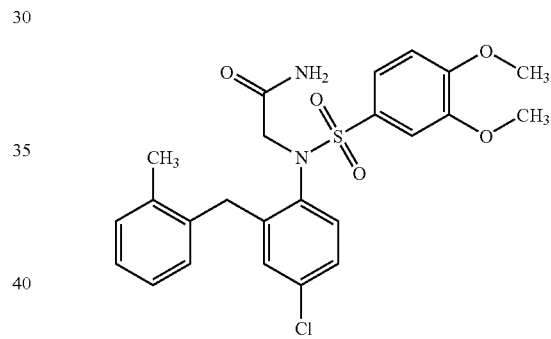

Compound 74:

N²-{4-chloro-2-[(2,5-dichlorophenyl)(hydroxy)methyl]phenyl}-N²-[(3,4-dimethoxyphenyl)sulfonyl]glycinamide

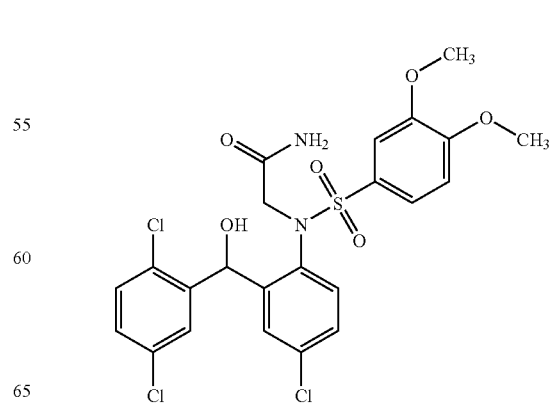

Compound 75:

N²-[4-chloro-2-(2-chlorobenzyl)phenyl]-N²-[(3,4-dimethoxyphenyl)sulfonyl]-N¹-ethylglycinamide

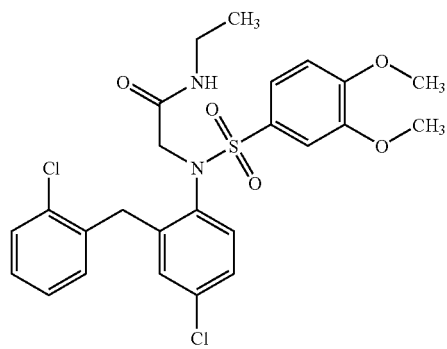

Compound 76:

N²-(1,3-benzodioxol-5-ylsulfonyl)-N²-{4-chloro-2-[(2-chlorophenyl)(hydroxy)methyl]phenyl}-glycinamide

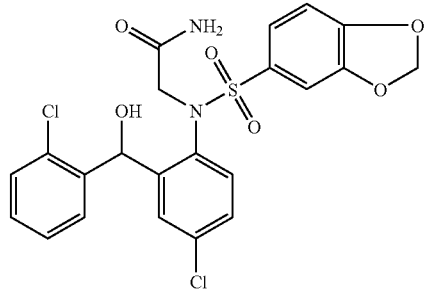

Compound 77:

N²-[2-[(2-chlorophenyl)(hydroxy)methyl]-4-(trifluoromethoxy)phenyl]-N²-[(3,4-dimethoxyphenyl)sulfonyl]glycinamide

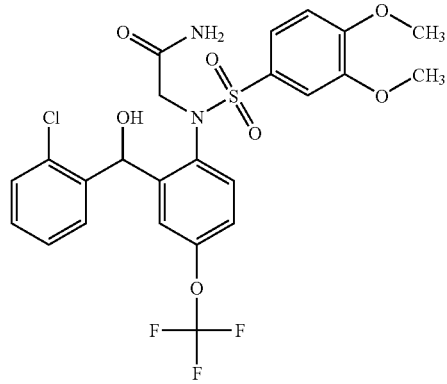

Compound 78:

N²-[4-chloro-2-(2,6-dichlorobenzyl)phenyl]-N²-[(3,4-dimethoxyphenyl)sulfonyl]glycinamide

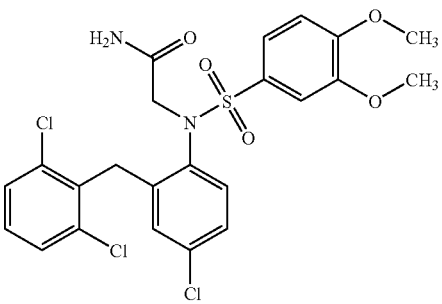

Compound 79:

N²-{4-chloro-2-[(2-chlorophenyl)(hydroxy)methyl]phenyl}-N²-[(2-methylphenyl)sulfonyl]glycinamide

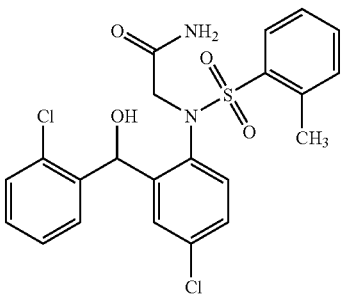

Compound 80:

N²-[4-chloro-2-(2,5-dichlorobenzyl)phenyl]-N²-[(3,4-dimethoxyphenyl)sulfonyl]glycinamide

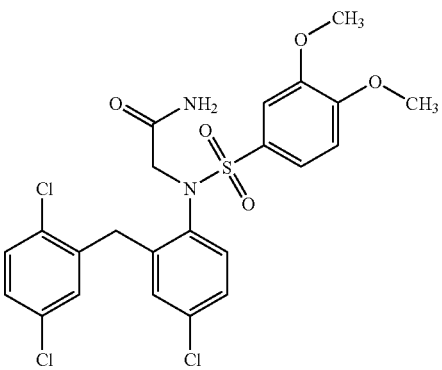

Compound 81:

$N^2$-[4-chloro-2-(2-chlorobenzyl)phenyl]-$N^2$-[(2-methylphenyl)sulfonyl]glycinamide

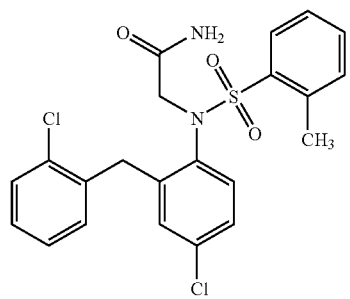

Compound 82:

$N^2$-[4-chloro-2-(2-chlorobenzyl)phenyl]-$N^2$-[(3,4-dimethylphenyl)sulfonyl]glycinamide

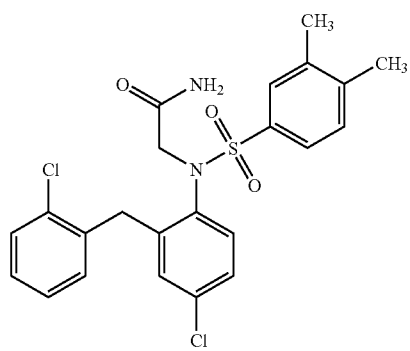

Compound 83:

N-{4-chloro-2-[(2-chlorophenyl)(hydroxy)methyl]phenyl}-3,4-dimethoxy-N-[(3-methyl-1,2,4-oxadiazol-5-yl)methyl]benzenesulfonamide

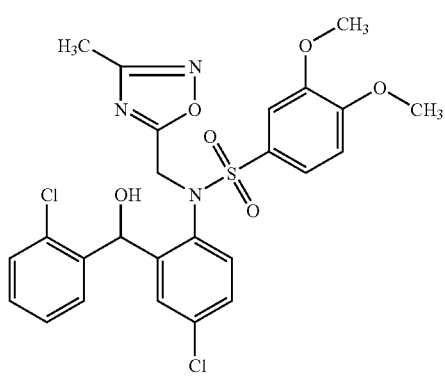

Compound 84:

N-[4-chloro-2-(2-chlorobenzyl)phenyl]-3,4-dimethoxy-N-[(3-methyl-1,2,4-oxadiazol-5-yl)methyl]benzenesulfonamide

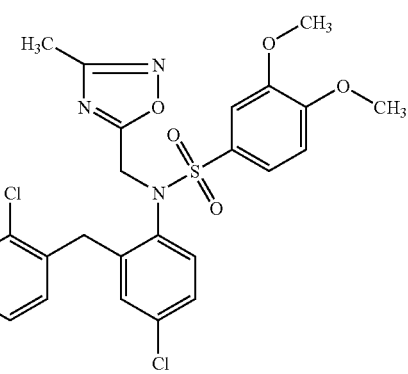

Compound 85:

$N^2$-{4-chloro-2-[(2-chlorophenyl)(hydroxy)methyl]phenyl}-$N^2$-[(2,6-dichlorophenyl)sulfonyl]glycinamide

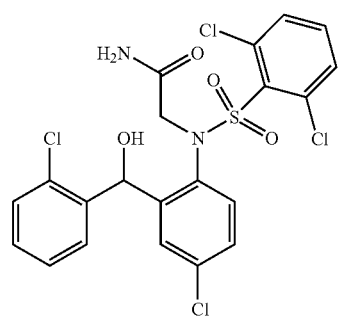

Compound 86:

$N^2$-{4-chloro-2-[(2-chlorophenyl)(hydroxy)methyl]phenyl}-$N^2$-[(3,5-dimethylphenyl)sulfonyl]glycinamide

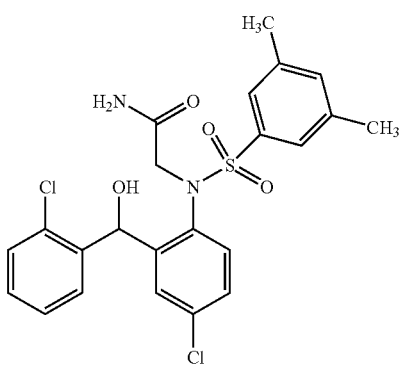

Compound 87:

N²-[4-chloro-2-(2-chlorobenzyl)phenyl]-N²-[(2,6-dichlorophenyl)sulfonyl]glycinamide

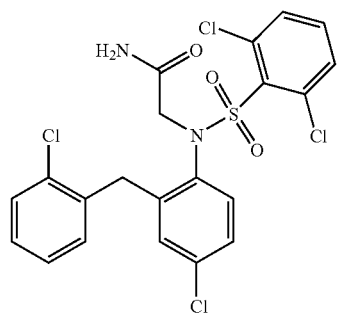

Compound 88:

N-[4-chloro-2-(2-chlorobenzyl)phenyl]-3,4-dimethoxy-N-[(1-methyl-1H-tetrazol-5-yl)methyl]benzenesulfonamide

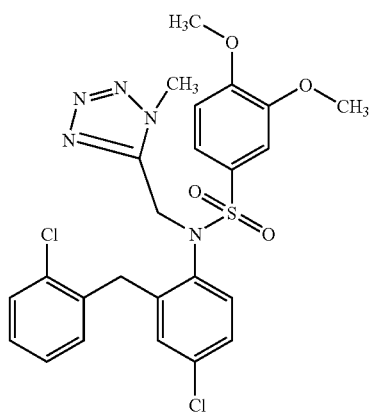

Compound 89:

N²-[4-chloro-2-(2-chlorobenzyl)phenyl]-N²-[(3,5-dimethylphenyl)sulfonyl]glycinamide

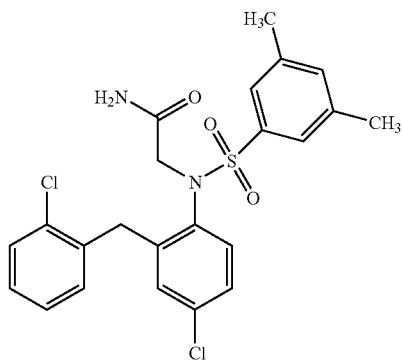

Compound 90:

N-[4-chloro-2-(2-chlorobenzyl)phenyl]-N-[(1-ethyl-1H-tetrazol-5-yl)methyl]-3,4-dimethoxybenzenesulfonamide

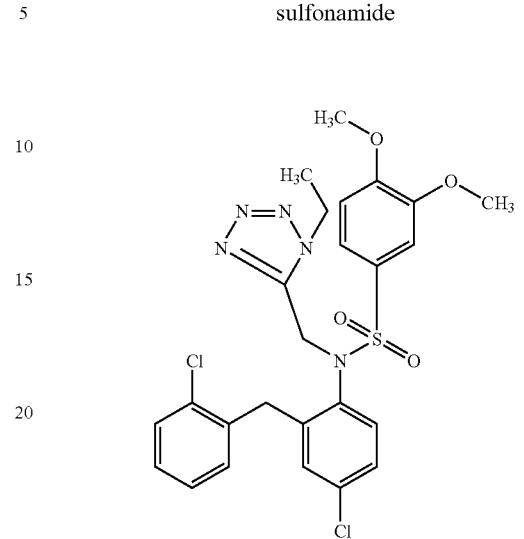

Compound 91:

N²-[4-chloro-2-(2,6-difluorobenzyl)phenyl]-N²-[(3,4-dimethoxyphenyl)sulfonyl]glycinamide

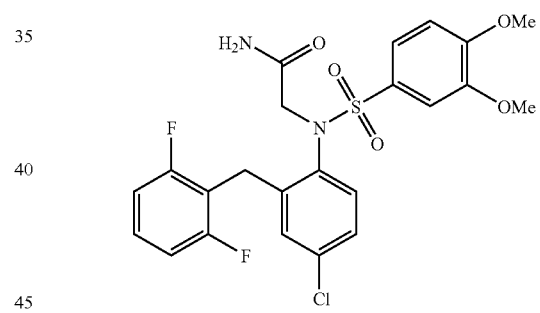

Compound 92:

N²-{4-chloro-2-[methyl(phenyl)amino]phenyl}-N²-[(3,4-dimethoxyphenyl)sulfonyl]glycinamide

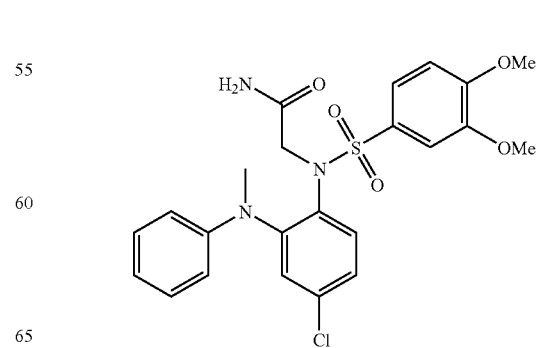

Compound 93:

N²-[2-(2-chlorobenzyl)-4-ethylphenyl]-N²-[(3,4-dimethoxyphenyl)sulfonyl]glycinamide

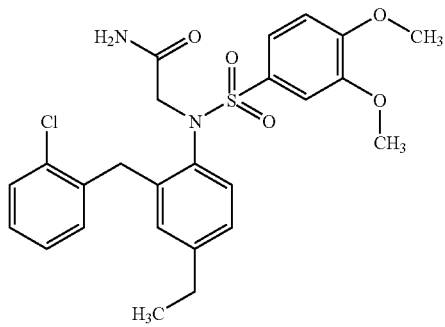

Compound 94:

N²-{4-chloro-2-[(2-chlorophenyl)(hydroxy)methyl]phenyl}-N²-[(2,5-dimethoxy-4-methylphenyl)sulfonyl]glycinamide

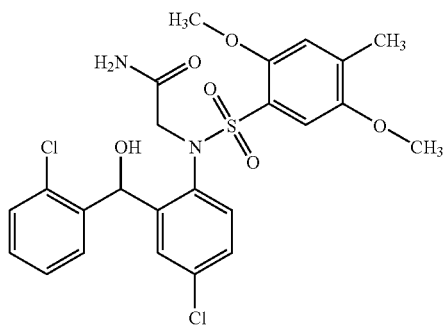

Compound 95:

N²-(2-benzyl-4-chlorophenyl)-N²-[(3,4-dimethoxyphenyl)sulfonyl]-N¹, N¹-dimethylglycinamide

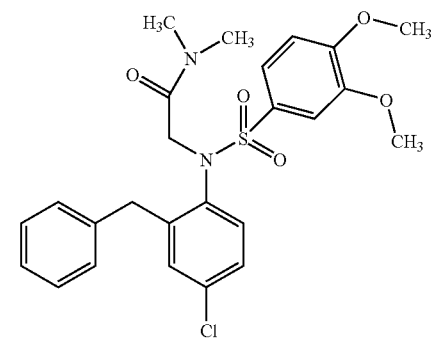

Compound 96:

N²-(2-benzyl-4-chlorophenyl)-N²-[(3,4-dimethoxyphenyl)sulfonyl]-N¹-methylglycinamide

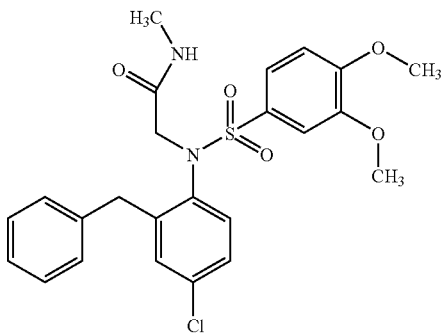

Compound 97:

N²-[4-chloro-2-(2-fluorobenzyl)phenyl]-N²-[(3,4-dimethoxyphenyl)sulfonyl]-N¹,N¹-dimethylglycinamide

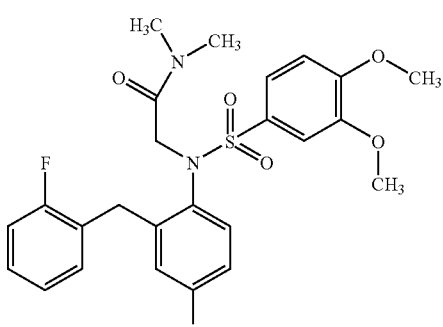

Compound 98:

N²-[4-chloro-2-(2-fluorobenzyl)phenyl]-N²-[(3,4-dimethoxyphenyl)sulfonyl]-N¹-methylglycinamide

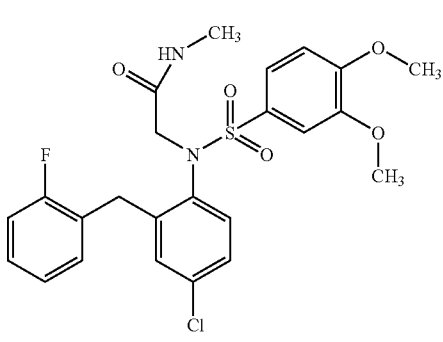

Compound 99:

N²-[4-chloro-2-(2-chlorobenzyl)phenyl]-N²-[(2,5-dimethoxy-4-methylphenyl)sulfonyl]glycinamide

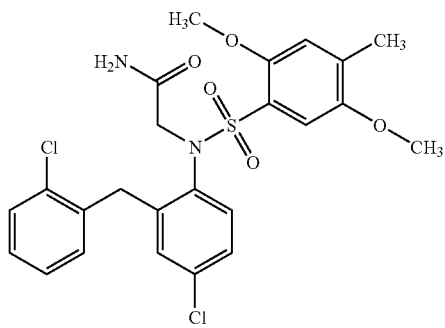

Compound 100:

N²-[4-chloro-2-(2-chlorobenzyl)phenyl]-N²-[(2,4-dichloro-5-methylphenyl)sulfonyl]glycinamide

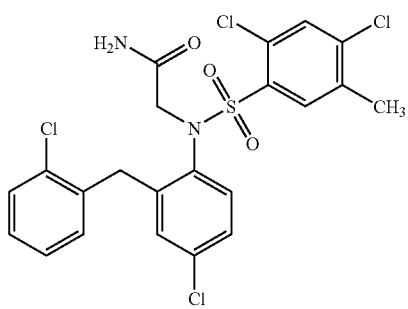

Compound 101:

N²-{4-chloro-2-[(2,6-difluorophenyl)(hydroxy)methyl]phenyl}-N²-[(3,4-dimethoxyphenyl)sulfonyl]glycinamide

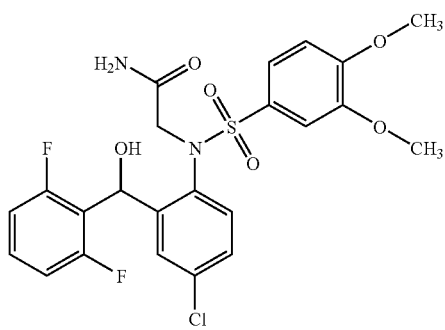

Compound 102:

N²-{4-chloro-2-[(2-chlorophenyl)(hydroxy)methyl]phenyl}N²-[(2,4,5-trimethoxyphenyl)sulfonyl]glycinamide

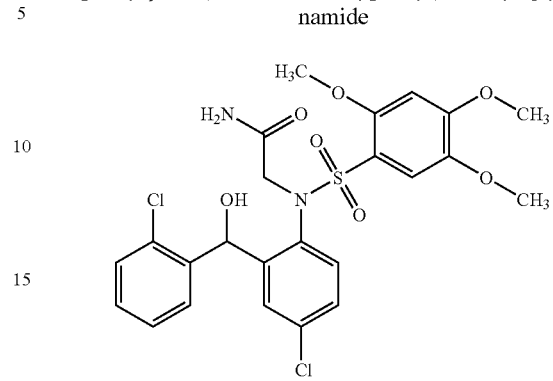

Compound 103:

N²-[2-(2-chlorobenzyl)-4-ethylphenyl]-N²-[(3,4-dimethoxyphenyl)sulfonyl]-N¹, N¹-dimethylglycinamide

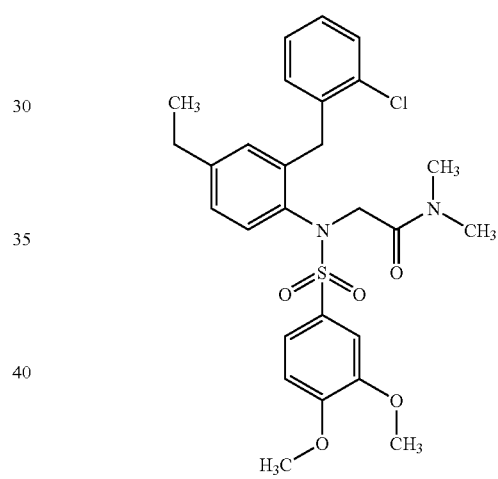

Compound 104:

N²-[4-chloro-2-(2-chlorobenzyl)phenyl]-N²-[(2,4,5-trimethoxyphenyl)sulfonyl]glycinamide

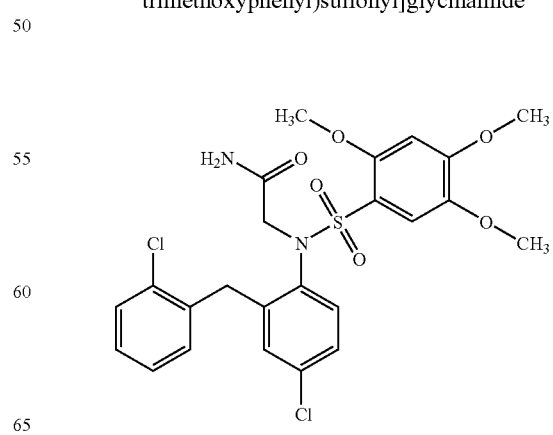

Compound 105:

N²-[4-chloro-2-(2-chlorobenzyl)phenyl]-N²-[(4-chloro-2,5-dimethylphenyl)sulfonyl]-N¹-methylglycinamide

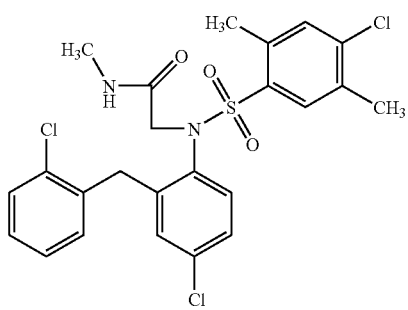

Compound 106:

N²-{4-chloro-2-[(2-chlorophenyl)(hydroxy)methyl]phenyl}-N²-[(2,4,5-trimethylphenyl)sulfonyl]glycinamide

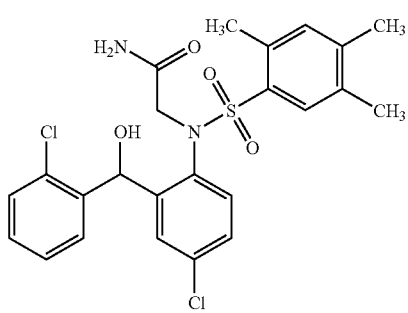

Compound 107:

N-[4-chloro-2-(2-chlorobenzyl)phenyl]-3,4-dimethoxy-N-[(1-methyl-1H-imidazol-2-yl)methyl]benzenesulfonamide

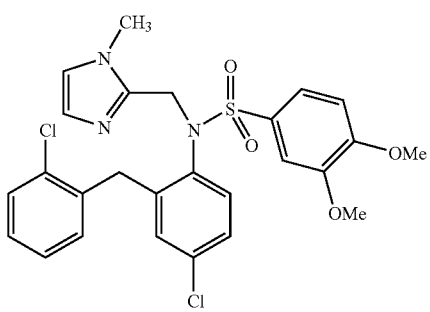

Compound 108:

N-[4-chloro-2-(2-chlorobenzyl)phenyl]-N-[(1-isopropyl-1H-tetrazol-5-yl)methyl]-3,4-dimethoxybenzenesulfonamide

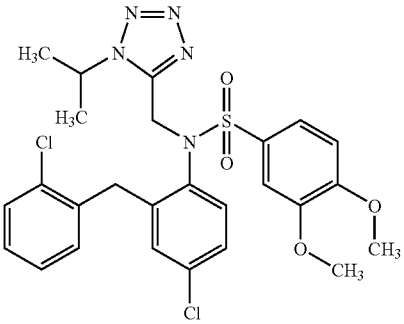

Compound 109:

N²-[4-chloro-2-(2-chlorobenzyl)phenyl]-N¹-methyl-N²-[(2,4,5-trimethoxyphenyl)sulfonyl]glycinamide

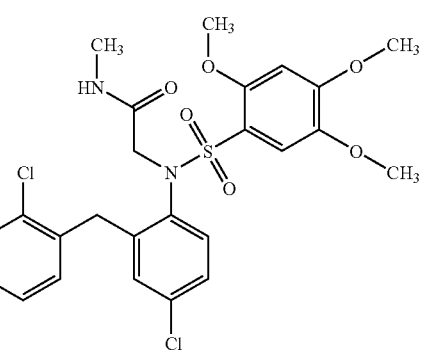

Compound 110:

N²-{4-chloro-2-[(2-chlorophenyl)(hydroxy)methyl]phenyl}-N¹-methyl-N²-[(2,4,5-trimethylphenyl)sulfonyl]glycinamide

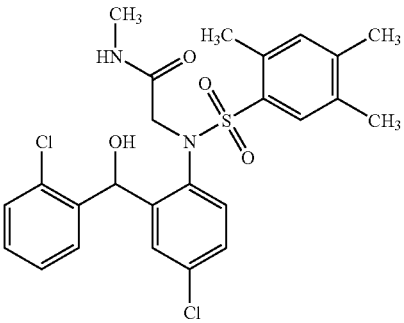

Compound 111:

N-[(1-benzyl-1H-tetrazol-5-yl)methyl]-N-[4-chloro-2-(2-chlorobenzyl)phenyl]-3,4-dimethoxybenzene-sulfonamide

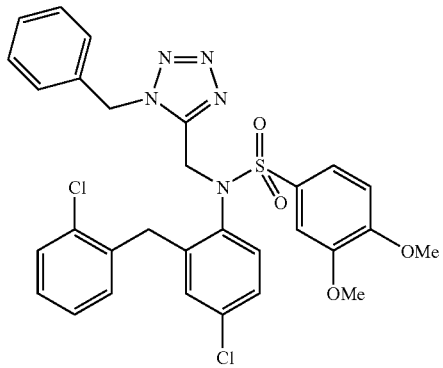

Compound 112:

N-[4-chloro-2-(2-chlorobenzyl)phenyl]-3,5-dimethyl-N-[(1-methyl-1H-imidazol-2-yl)methyl]benzenesulfonamide

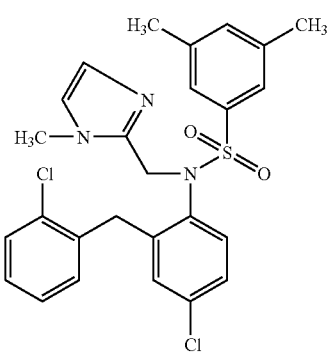

Compound 113:

$N^2$-{4-chloro-2-[(2-chlorophenyl)(hydroxy)methyl]phenyl}-$N^1$-methyl-$N^2$-[(2,4,5-trimethoxyphenyl)sulfonyl]glycinamide

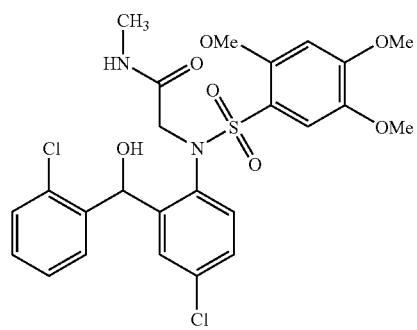

Compound 114:

$N^2$-[4-chloro-2-(2-chlorobenzyl)phenyl]-$N^2$-[(2,4,5-trimethylphenyl)sulfonyl]glycinamide

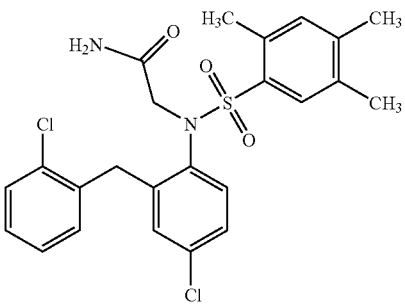

Compound 115:

$N^2$-[4-chloro-2-(2-chlorobenzyl)phenyl]-$N^1$-methyl-$N^2$-[(2,4,5-trimethylphenyl)sulfonyl]glycinamide

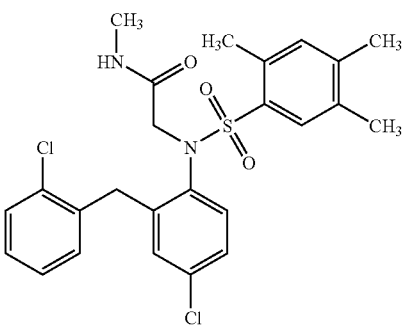

Compound 116:

$N^2$-[4-chloro-2-(3-chlorobenzyl)phenyl]-$N^2$-[(3,4-dimethoxyphenyl)sulfonyl]glycinamide

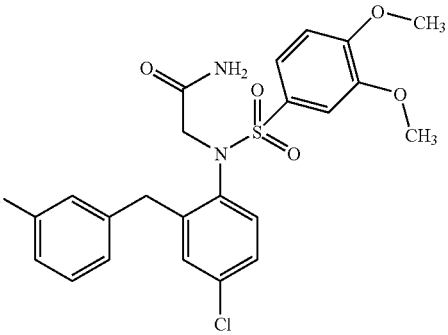

Compound 117:

N$^2$-{4-chloro-2-[(2,6-dichlorophenyl)(hydroxy)methyl]phenyl}-N$^2$-[(3,4-dimethoxyphenyl)sulfonyl]glycinamide

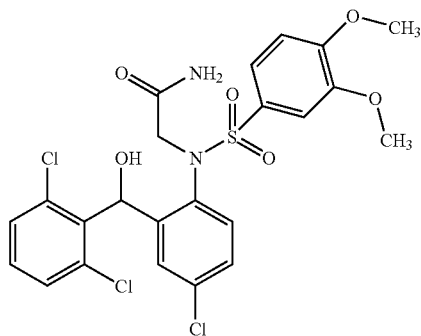

Compound 118:

N$^2$-[4-chloro-2-(2-chlorobenzyl)phenyl]-N$^2$-[(4-chloro-2,5-dimethylphenyl)sulfonyl]-N$^1$,N$^1$-dimethylglycinamide

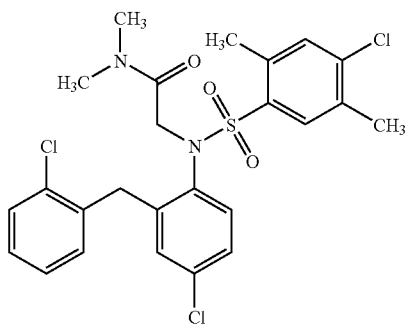

Compound 119:

N$^2$-[4-chloro-2-(2-chlorobenzyl)phenyl]-N$^2$-[(3,5-dimethoxyphenyl)sulfonyl]glycinamide

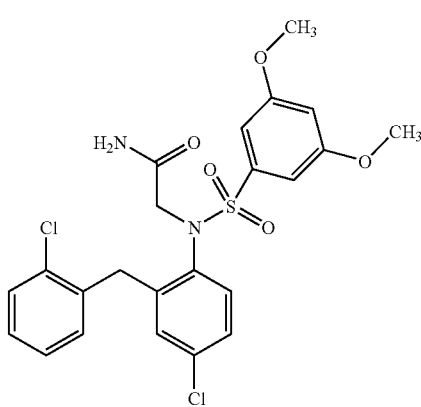

Compound 120:

N$^2$-{4-chloro-2-[hydroxy(1,3-thiazol-2-yl)methyl]phenyl}-N$^2$-[(3,4-dimethoxyphenyl)sulfonyl]glycinamide

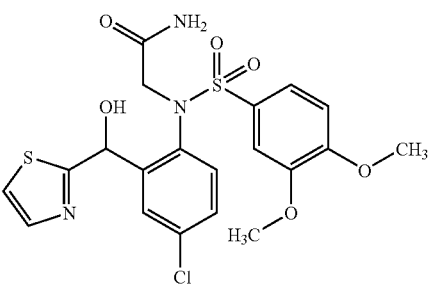

Compound 121:

N$^2$-{4-chloro-2-[hydroxy(1,3-thiazol-2-yl)methyl]phenyl}-N$^2$-[(3,4-dimethoxyphenyl)sulfonyl]-N$^1$-methylglycinamide

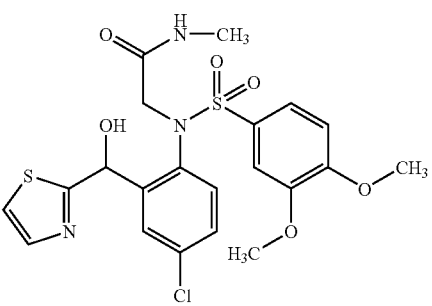

Compound 122:

N-[4-chloro-2-(2-chlorobenzyl)phenyl]-N-[(2-ethyl-2H-tetrazol-5-yl)methyl]-3,5-dimethylbenzenesulfonamide

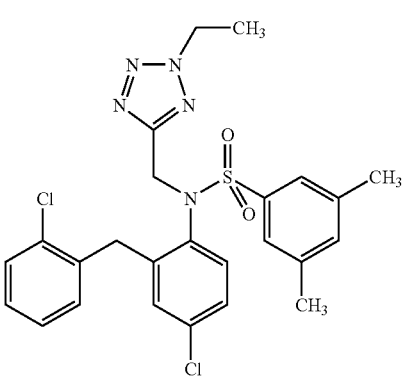

Compound 123:

N-[4-chloro-2-(2-chlorobenzyl)phenyl]-N-[(1-ethyl-1H-tetrazol-5-yl)methyl]-3,5-dimethylbenzenesulfonamide

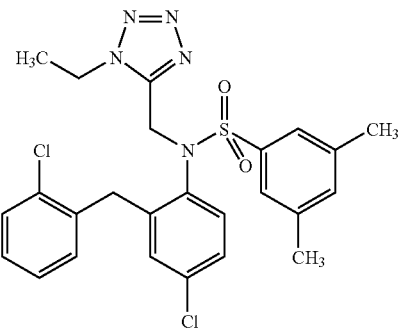

Compound 124:

$N^2$-{4-chloro-2-[methyl(phenyl)amino]phenyl}-$N^2$-[(3,4-dimethoxyphenyl)sulfonyl]-$N^1$-methylglycinamide

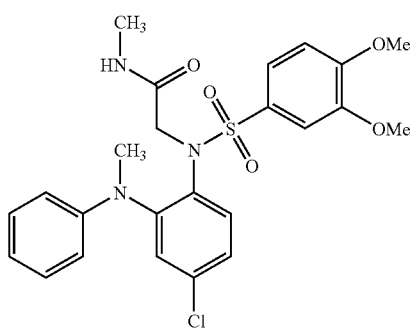

Compound 125:

$N^2$-(4-chloro-2-{hydroxy[2-(trifluoromethyl)phenyl]methyl}phenyl)-$N^2$[(3,4-dimethoxyphenyl)sulfonyl]glycinamide

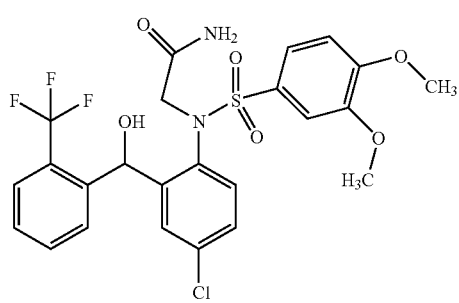

Compound 126:

$N^2$-{4-chloro-2-[(2,3-difluorophenyl)(hydroxy)methyl]phenyl}-$N^2$-[(3,4-dimethoxyphenyl)sulfonyl]glycinamide

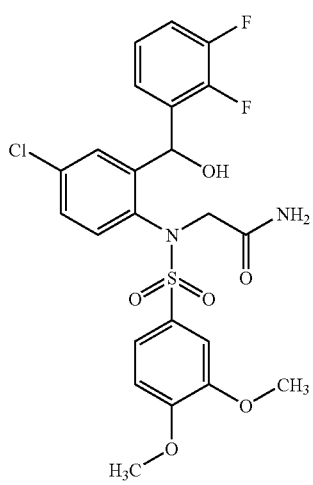

Compound 127:

$N^2$-{4-chloro-2-[(2,3-difluorophenyl)(hydroxy)methyl]phenyl}-$N^2$-[(3,4-dimethoxyphenyl)sulfonyl]-$N^1$-ethylglycinamide

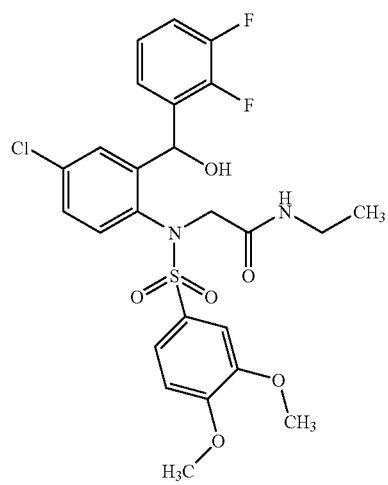

Compound 128:

N²-{4-chloro-2-[(2,3-difluorophenyl)(hydroxy)methyl]phenyl}-N²-[(3,4-dimethoxyphenyl)sulfonyl]-N¹,N¹-dimethylglycinamide

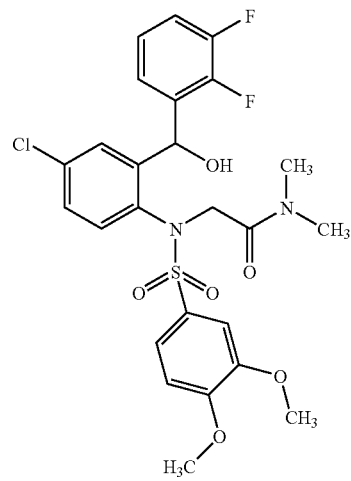

Compound 129:

N²-{4-chloro-2-[(2-chlorophenyl)(hydroxy)methyl]phenyl}-N²-[(2,4-dichloro-5-methylphenyl)sulfonyl]-N¹,N¹-dimethylglycinamide

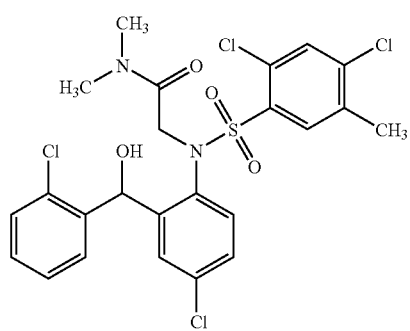

Compound 130:

N²-[4-chloro-2-(2,6-dichlorobenzyl)phenyl]-N²-[(3,4-dimethoxyphenyl)sulfonyl]-N¹-methylglycinamide

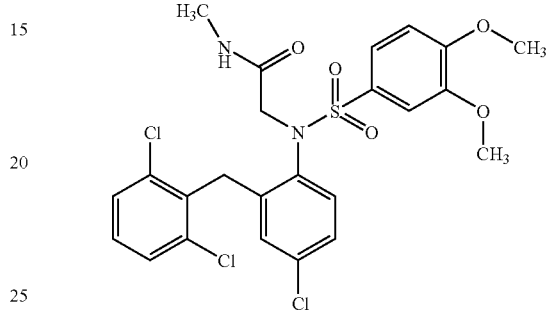

Compound 131:

N²-{4-chloro-2-[hydroxy(2-methylphenyl)methyl]phenyl}-N²-[(3,4-dimethoxyphenyl)sulfonyl]glycinamide

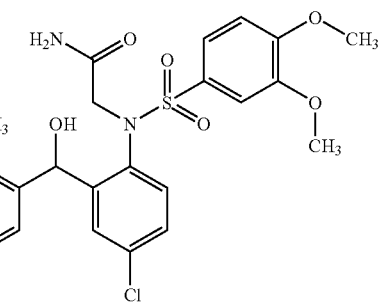

Compound 132:

N²-{4-chloro-2-[(2-chlorophenyl)(hydroxy)methyl]phenyl}-N²-[(3,5-dimethylphenyl)sulfonyl]-N¹-methylglycinamide

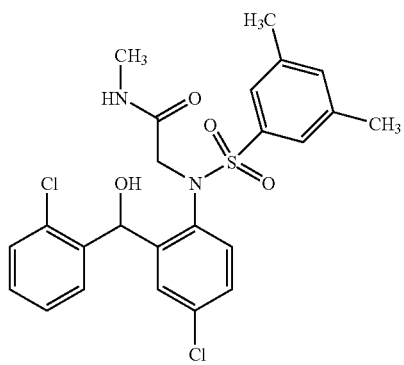

Compound 133:

N²-{4-chloro-2-[(2-chlorophenyl)(hydroxy)methyl]phenyl}-N²-[(3,5-dimethylphenyl)sulfonyl]-N¹,N¹-dimethylglycinamide

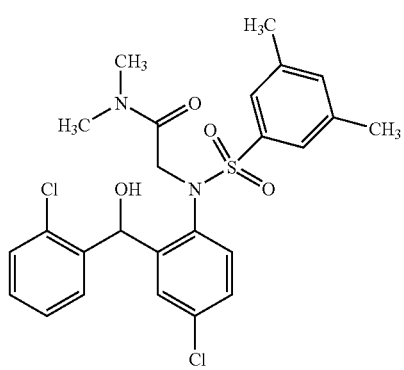

Compound 134:

N²-[4-chloro-2-(2-chlorobenzyl)phenyl]-N²-[(3-nitrophenyl)sulfonyl]glycinamide

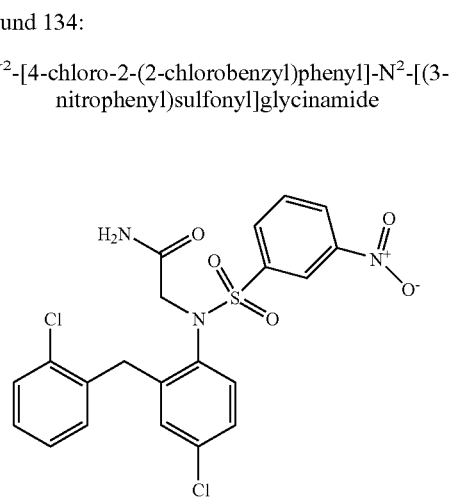

Compound 135:

N²-[(3-aminophenyl)sulfonyl]-N²-[4-chloro-2-(2-chlorobenzyl)phenyl]glycinamide

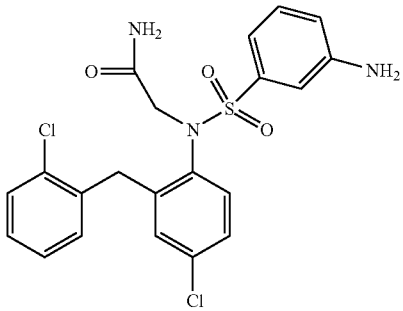

Compound 136:

N²-{2-[(2-chlorophenyl)(hydroxy)methyl]-4-methylphenyl}-N²-[(3,4-dimethoxyphenyl)sulfonyl]glycinamide

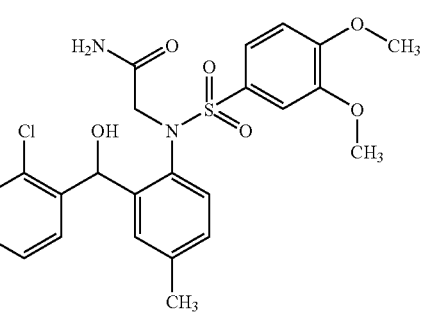

Compound 137:

N²-{4-chloro-2-[hydroxy(phenyl)methyl]phenyl}-N²-[(3,4-dimethoxyphenyl)sulfonyl]-N¹-methylglycinamide

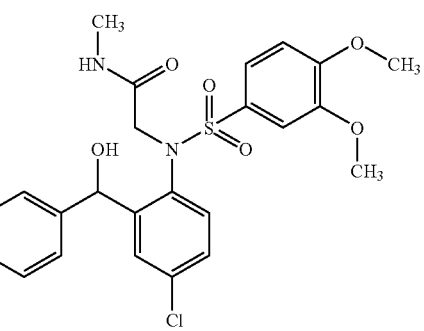

Compound 138:

N²-[2-(2-chlorobenzyl)-4-methoxyphenyl]-N²-[(3,4-dimethoxyphenyl)sulfonyl]glycinamide

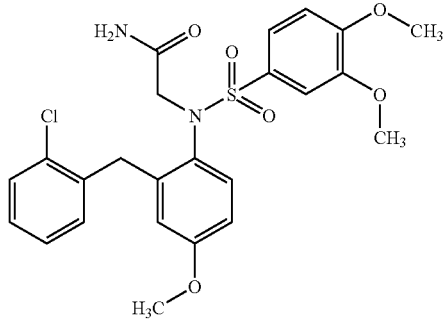

Compound 139:

N²-[4-chloro-2-(2,6-difluorobenzyl)phenyl]-N²-[(3,4-dimethoxyphenyl)sulfonyl]-N¹-methylglycinamide

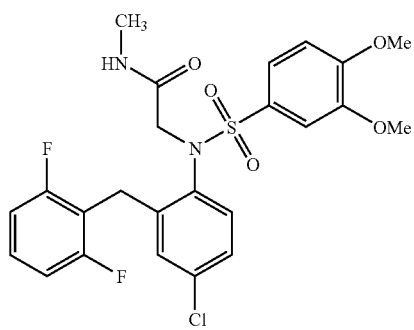

Compound 140:

N-[4-chloro-2-(2,6-difluorobenzyl)phenyl]-3,4-dimethoxy-N-propylbenzenesulfonamide

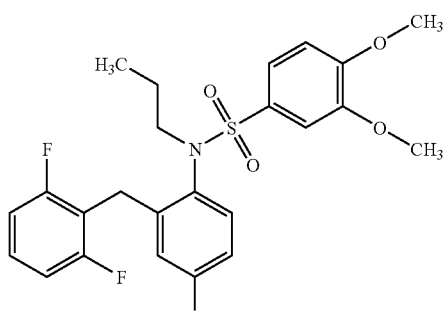

Compound 141:

N²-[4-chloro-2-(2,3-difluorobenzyl)phenyl]-N²-[(3,4-dimethoxyphenyl)sulfonyl]-N¹-methylglycinamide

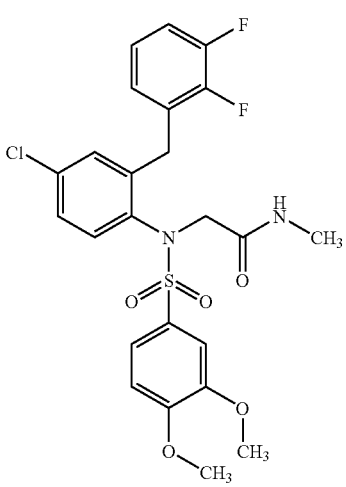

Compound 142:

N²-[4-chloro-2-(2,3-difluorobenzyl)phenyl]-N²-[(3,4-dimethoxyphenyl)sulfonyl]glycinamide

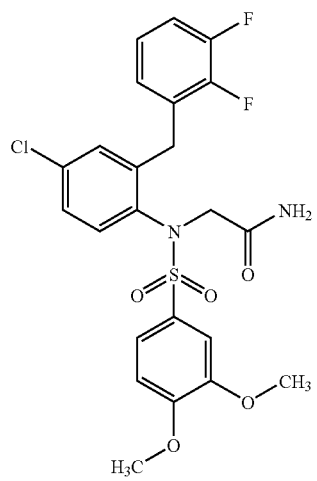

Compound 143:

N²-[4-chloro-2-(2,3-difluorobenzyl)phenyl]-N²-[(3,4-dimethoxyphenyl)sulfonyl]-N¹,N¹-dimethylglycinamide

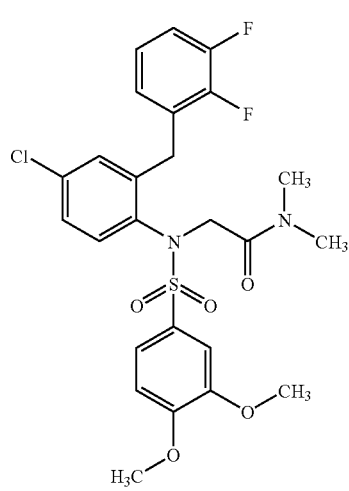

Compound 144:

N-[4-chloro-2-(2,6-difluorobenzyl)phenyl]-3,4-dimethoxy-N-methylbenzenesulfonamide

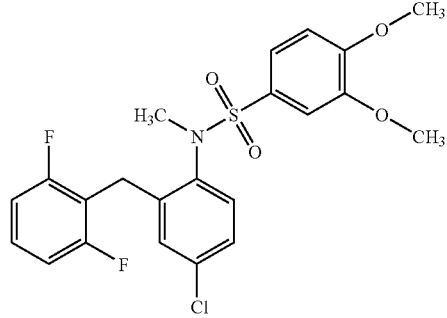

Compound 145:

N-[4-chloro-2-(2,6-difluorobenzyl)phenyl]-N-[2-(dimethylamino)ethyl]-3,4-dimethoxybenzenesulfonamide

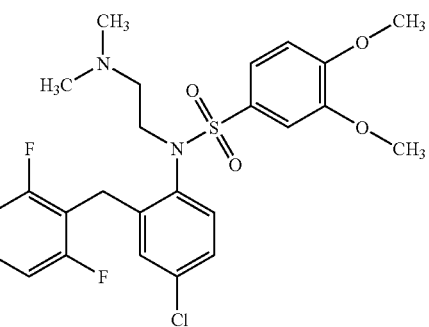

Compound 146:

N²-{4-chloro-2-[hydroxy(2-thienyl)methyl]phenyl}-N²-[(3,4-dimethoxyphenyl)sulfonyl]-N¹-methylglycinamide

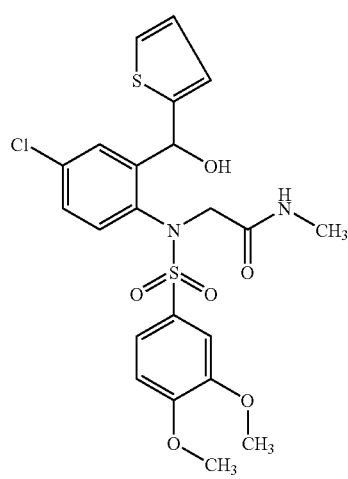

Compound 147:

N²-{4-chloro-2-[(2,6-difluorophenyl)(hydroxy)methyl]phenyl}-N²-[(3,5-dimethylphenyl)sulfonyl]glycinamide

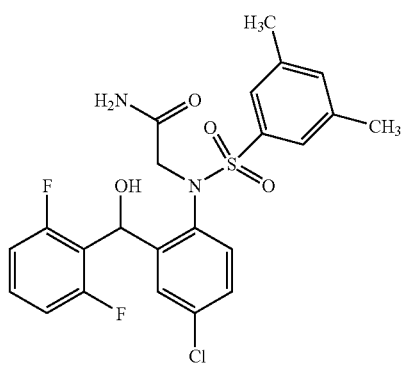

Compound 148:

N²-[(3-aminophenyl)sulfonyl]-N²-{4-chloro-2-[(2-chlorophenyl)(hydroxy)methyl]phenyl}-glycinamide

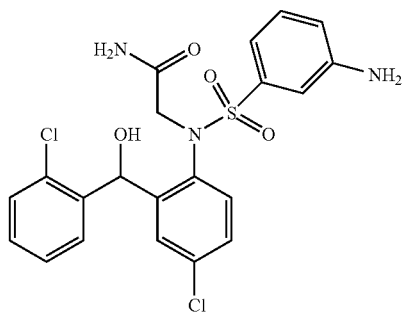

Compound 149:

N²-{4-chloro-2-[(2-fluoro-6-methoxyphenyl)(hydroxy)methyl]phenyl-}-N²-[(3,4-dimethoxyphenyl)sulfonyl]glycinamide

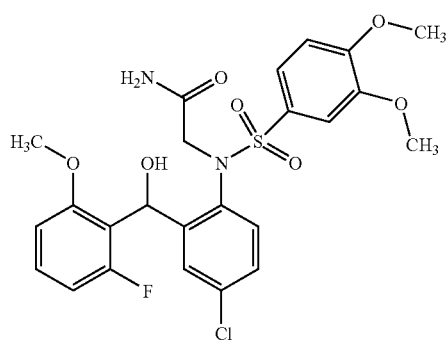

Compound 150:

N²-[4-chloro-2-(2,6-difluorobenzyl)phenyl]-N²-[(3,4-dimethoxyphenyl)sulfonyl]-N¹,N¹-dimethylglycinamide

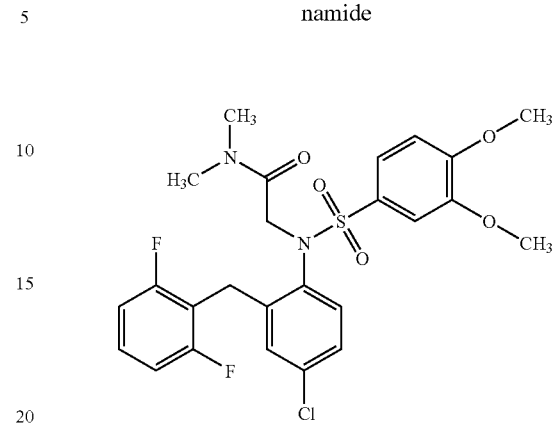

Compound 151:

N-[4-chloro-2-(2,6-difluorobenzyl)phenyl]-3,4-dimethoxy-N-[(2-methyl-2H-tetrazol-5-yl)methyl]benzenesulfonamide

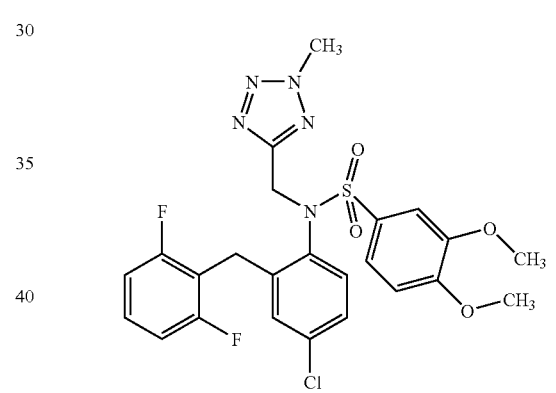

Compound 152:

N-[4-chloro-2-(2,6-difluorobenzyl)phenyl]-3,4-dimethoxy-N-[(1-methyl-1H-tetrazol-5-yl)methyl]benzenesulfonamide

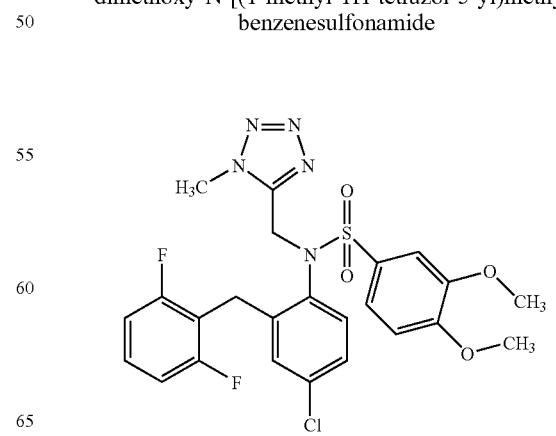

Compound 153:

N-[4-chloro-2-(2,6-difluorobenzyl)phenyl]-N-[(2-ethyl-2H-tetrazol-5-yl)methyl]-3,4-dimethoxybenzenesulfonamide

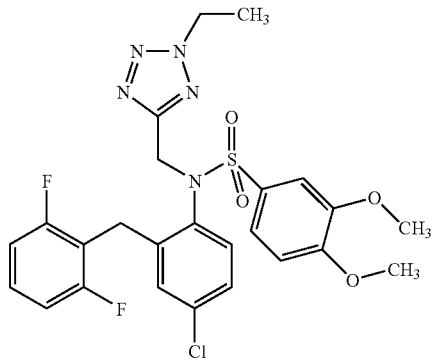

Compound 154:

N-[4-chloro-2-(2,6-difluorobenzyl)phenyl]-N-[(1-ethyl-1H-tetrazol-5-yl)methyl]-3,4-dimethoxybenzenesulfonamide

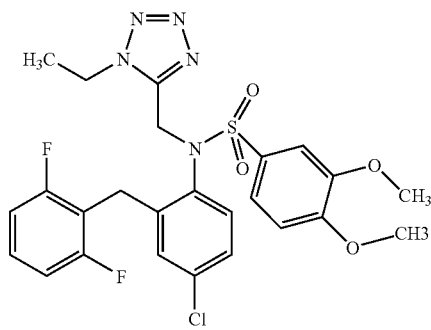

Compound 155:

$N^2$-{4-chloro-2-[hydroxy(2-thienyl)methyl]phenyl}-$N^2$-[(3,4-dimethoxyphenyl)sulfonyl]glycinamide

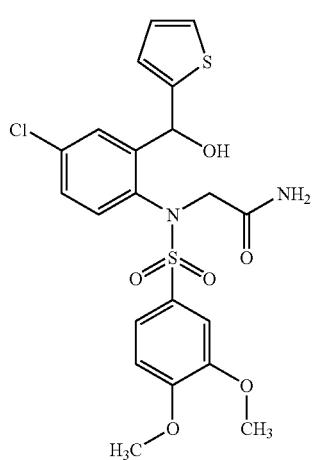

Compounds 156:

N-[4-chloro-2-(2,6-difluorobenzyl)phenyl]-N-[2-(6,7-dimethoxy-3,4-dihydroisoquinolin-2(1H)-yl)-2-oxoethyl]-3,4-dimethoxybenzenesulfonamide

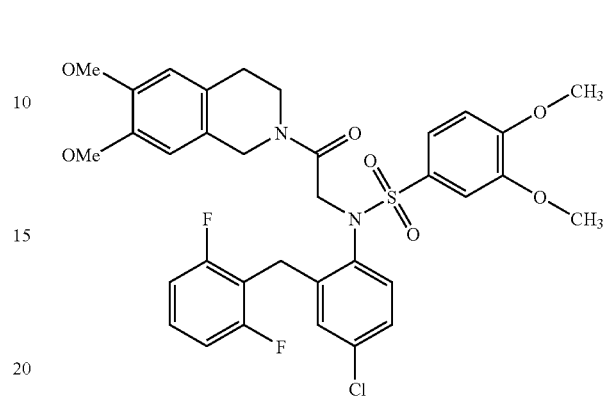

Compound 157:

N-[4-chloro-2-(2,6-difluorobenzyl)phenyl]-3,5-dimethyl-N-[(2-methyl-2H-tetrazol-5-yl)methyl]benzenesulfonamide

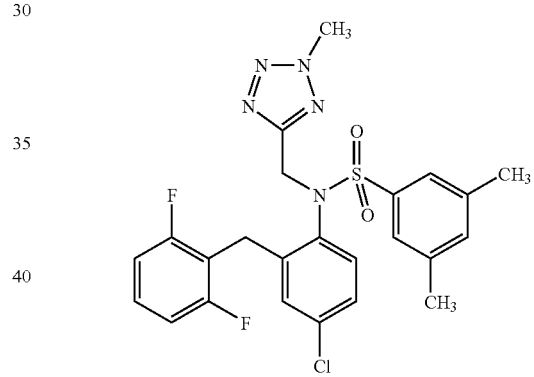

Compound 158:

N-[4-chloro-2-(2,6-difluorobenzyl)phenyl]-3,5-dimethyl-N-[(1-methyl-1H-tetrazol-5-yl)methyl]benzenesulfonamide

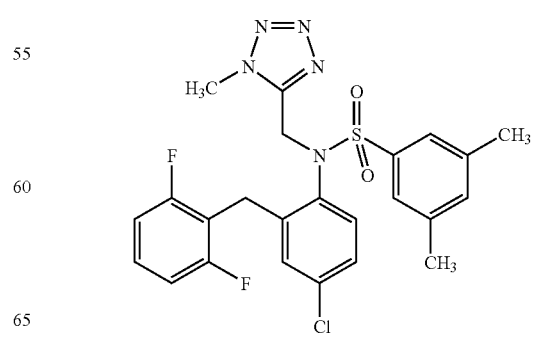

Compound 159:

N-[4-chloro-2-(2,6-difluorobenzyl)phenyl]-N-[(2-ethyl-2H-tetrazol-5-yl)methyl]-3,5-dimethylbenzenesulfonamide

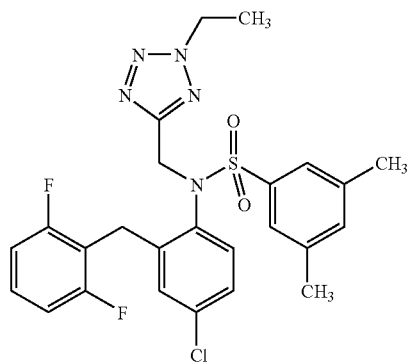

Compound 160:

N-[4-chloro-2-(2,6-difluorobenzyl)phenyl]-N-[(1-ethyl-1H-tetrazol-5-yl)methyl]-3,5-dimethylbenzenesulfonamide

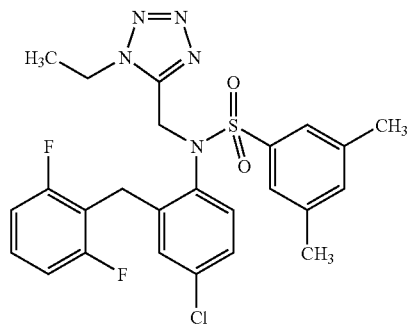

Compound 161:

$N^2$-[4,5-dichloro-2-(2-chlorobenzyl)phenyl]-$N^2$-[(3,4-dimethoxyphenyl)sulfonyl]glycinamide

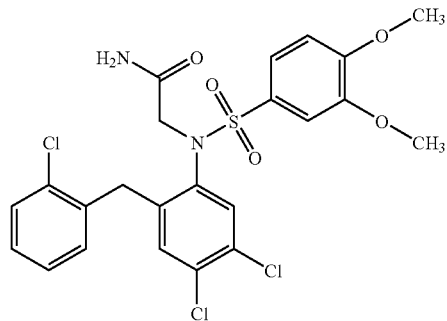

Compound 162:

$N^2$-{4-chloro-2-[hydroxy(2,4,6-trifluorophenyl)methyl]phenyl}-$N^2$-[(3,4-dimethoxyphenyl)sulfonyl]glycinamide

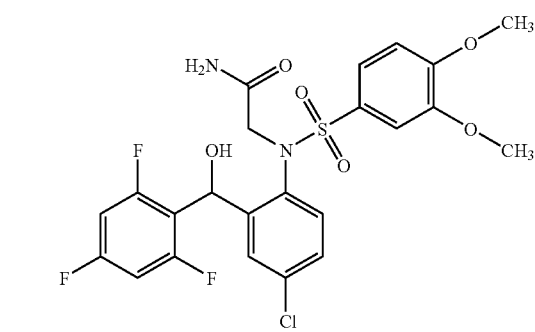

Compound 163:

$N^2$-{4-chloro-2-[(2,4-difluorophenyl)(hydroxy)methyl]phenyl}-$N^2$-[(3,4-dimethoxyphenyl)sulfonyl]glycinamide

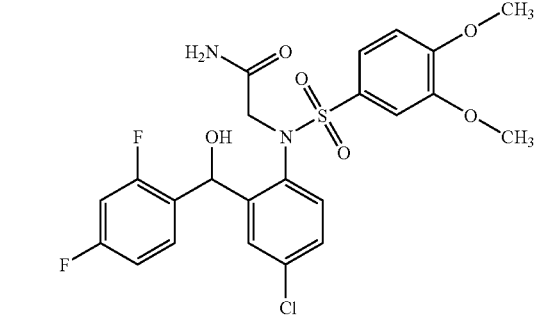

Compound 164:

$N^2$-{4,5-dichloro-2-[(2-chlorophenyl)(hydroxy)methyl]phenyl}-$N^2$-[(3,4-dimethoxyphenyl)sulfonyl]glycinamide

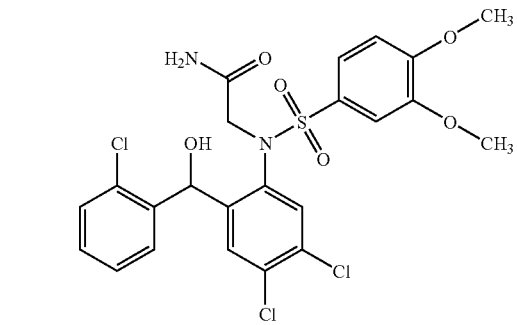

Compound 165:

N²-[2-(2-chlorobenzyl)-4-methylphenyl]-N²-[(3,4-dimethoxyphenyl)sulfonyl]glycinamide

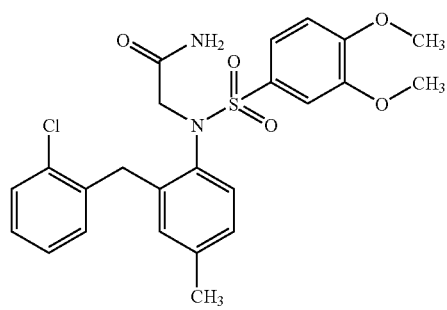

Compound 166:

N²-[4-chloro-2-(2,6-dichlorobenzyl)phenyl]-N²-[(3,4-dimethoxyphenyl)sulfonyl]-N¹,N¹-dimethylglycinamide

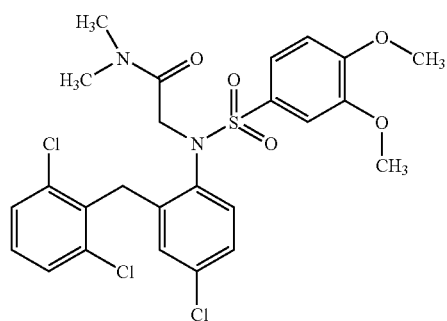

Compound 167:

N²-{4-chloro-2-[(4-chloro-2-fluorophenyl)(hydroxy)methyl]phenyl}-N²-[(3,4-dimethoxyphenyl)sulfonyl]glycinamide

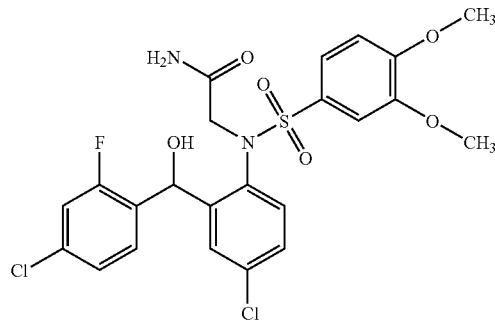

Compound 168:

N²-[4-chloro-2-(4-chloro-2-fluorobenzyl)phenyl]-N²-[(3,4-dimethoxyphenyl)sulfonyl]glycinamide

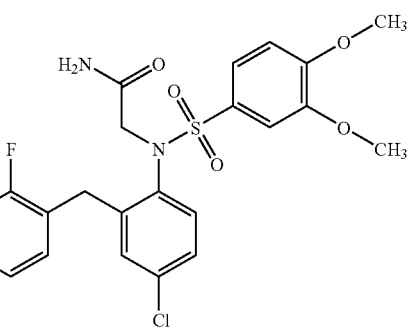

Compound 169:

N²-[4-chloro-2-(2,6-difluorobenzyl)phenyl]-N²-[(3,5-dimethylphenyl)sulfonyl]glycinamide

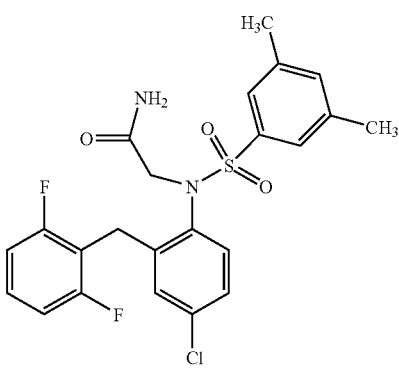

Compound 170:

N²-[4-chloro-2-(2-fluoro-6-methoxybenzyl)phenyl]-N²-[(3,4-dimethoxyphenyl)sulfonyl]glycinamide

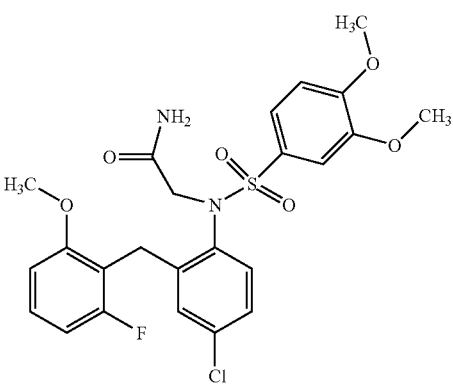

Compound 171:

N²-[4-chloro-2-(2,6-difluorobenzyl)phenyl]-N²-[(3,5-dimethylphenyl)sulfonyl]-N¹-methylglycinamide

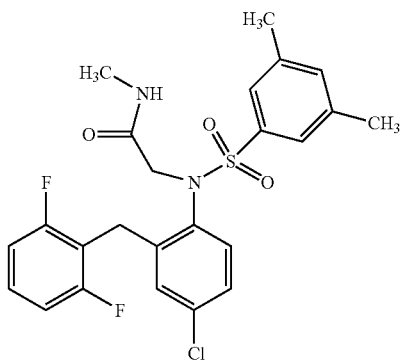

Compound 172:

N²-{4-chloro-2-[1-(2-chlorophenyl)-1-hydroxyethyl]phenyl}-N²-[(3,4-dimethoxyphenyl)sulfonyl]glycinamide

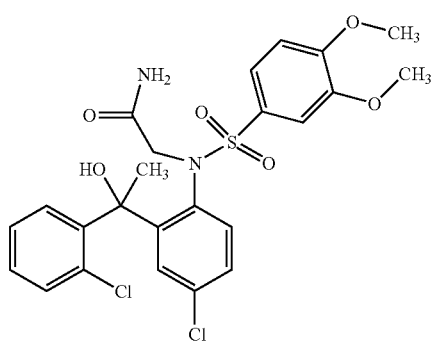

Compound 173:

N²-[4-chloro-2-(2-chlorobenzyl)phenyl]-N²-[(2,4-dichloro-5-methylphenyl)sulfonyl]-N¹-methylglycinamide

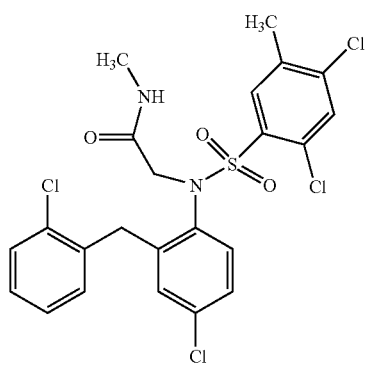

Compound 174:

N²-[4-chloro-2-(2-chlorobenzyl)phenyl]-N²-[(2,4-dichloro-5-methylphenyl)sulfonyl]-N~1~,N~1~-dimethylglycinamide

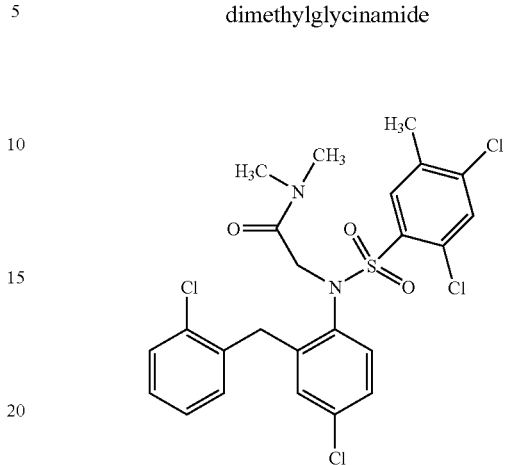

Compound 175:

N²-{5-chloro-2-[(2-chlorophenyl)(hydroxy)methyl]phenyl}-N~2~-[(3,4-dimethoxyphenyl)sulfonyl]glycinamide

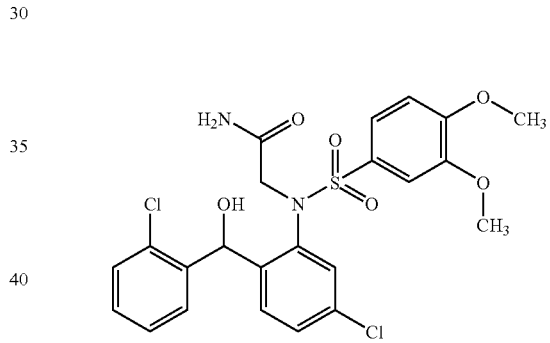

Compound 176:

N²-{4-chloro-2-[(5-chloro-2-fluorophenyl)(hydroxy)methyl]phenyl}-N²-[(3,4-dimethoxyphenyl)sulfonyl]glycinamide

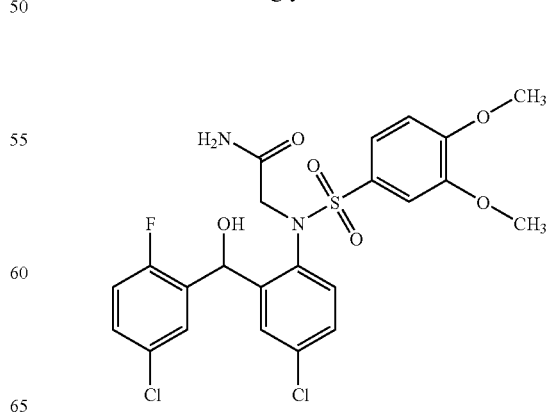

Compound 177:

N²-[4-chloro-2-(2,5-difluorobenzyl)phenyl]-N²-[(3,4-dimethoxyphenyl)sulfonyl]glycinamide

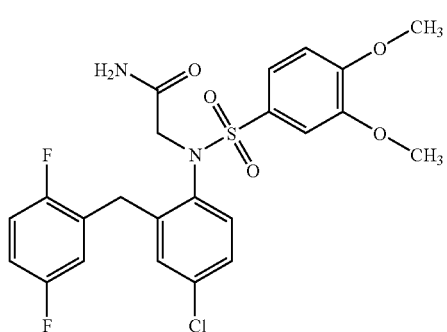

Compound 178:

N²-{4-chloro-2-[(3,5-difluorophenyl)(hydroxy)methyl]phenyl}N²-[(3,4-dimethoxyphenyl)sulfonyl]glycinamide

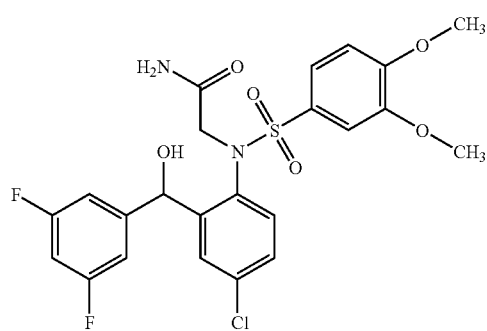

Compound 179:

N²-[5-chloro-2-(2-chlorobenzyl)phenyl]-N²-[(3,4-dimethoxyphenyl)sulfonyl]glycinamide

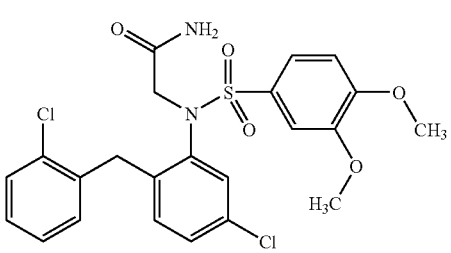

Compound 180:

N²-[4-chloro-2-(2-thienylmethyl)phenyl]-N²-[(3,4-dimethoxyphenyl)sulfonyl]glycinamide

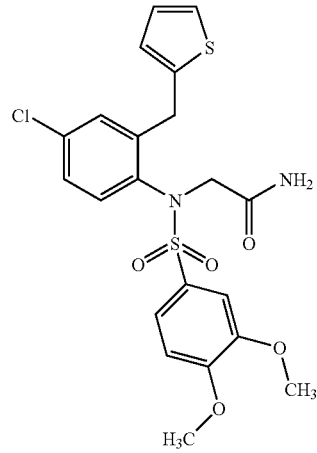

Compound 181:

N-[4-chloro-2-(2,6-difluorobenzyl)phenyl]-3,4-dimethoxy-N-[(1-methyl-1H-imidazol-2-yl)methyl]benzenesulfonamide

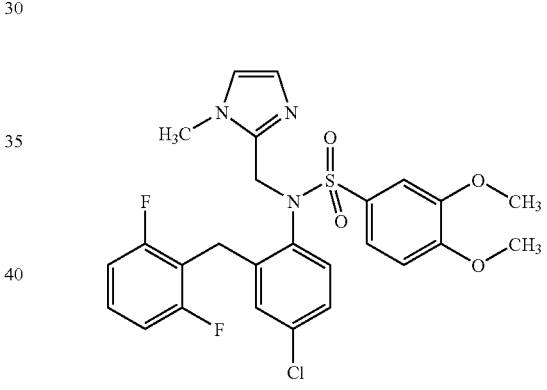

Compound 182:

N²-[4-chloro-2-(5-chloro-2-fluorobenzyl)phenyl]-N²-[(3,4-dimethoxyphenyl)sulfonyl]glycinamide

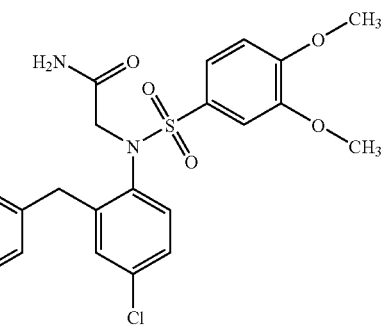

Compound 183:

N²-[4-chloro-2-(3,5-difluorobenzyl)phenyl]-N²-[(3,4-dimethoxyphenyl)sulfonyl]glycinamide

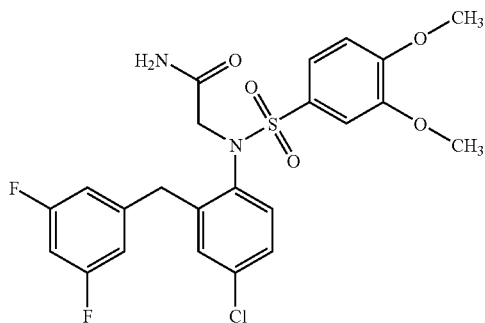

Compound 184:

N²-{4-chloro-2-[hydroxy(pyridin-4-yl)methyl]phenyl}-N²-[(3,4-dimethoxyphenyl)sulfonyl]glycinamide

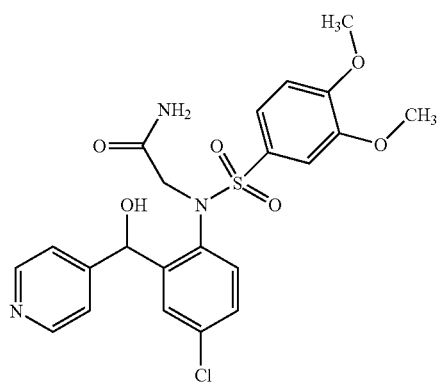

Compound 185:

N-[4-chloro-2-(2,6-difluorobenzyl)phenyl]-3,4-dimethoxy-N-prop-2-yn-1-ylbenzenesulfonamide

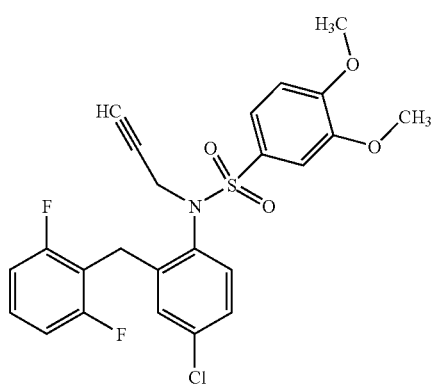

Compound 186:

N²-{4-chloro-2-[1-(2-chlorophenyl)ethyl]phenyl}-N²-[(3,4-dimethoxyphenyl)sulfonyl]glycinamide

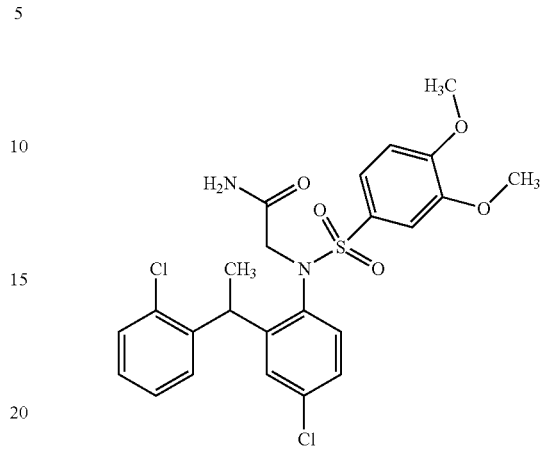

Compound 187:

N²-{4-chloro-2-[1-(2-chlorophenyl)ethyl]phenyl}-N²-[(3,4-dimethoxyphenyl)sulfonyl]-N¹-methylglycinamide

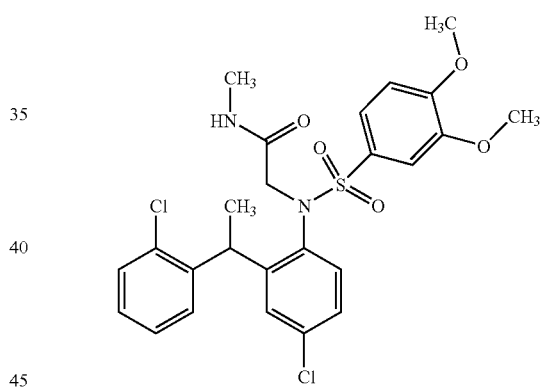

Compound 188:

N²-[4-chloro-2-(2,6-difluorobenzyl)phenyl]-N²-{[3-(dimethylamino)phenyl]sulfonyl}-glycinamide

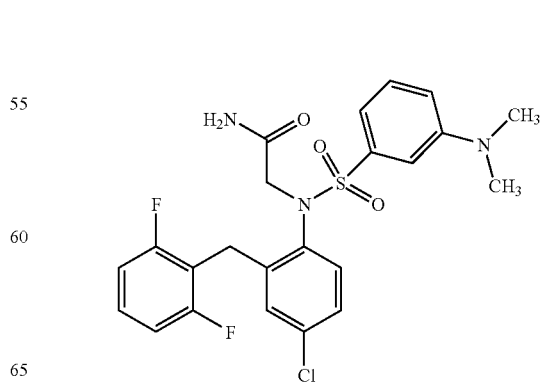

Compound 189:

N²-[4-chloro-2-(2,6-difluorobenzyl)phenyl]-N²-{[3-(methylamino)phenyl]sulfonyl}-glycinamide

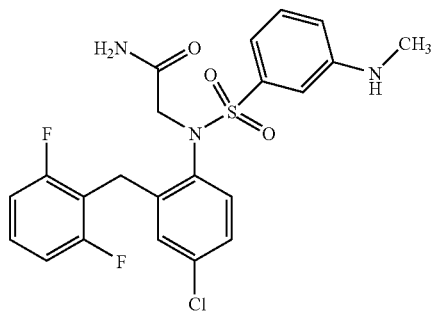

Compound 190:

N-[4-chloro-2-(2,6-difluorobenzyl)phenyl]-3,4-dimethoxy-N-(2,2,2-trifluoroethyl)benzenesulfonamide

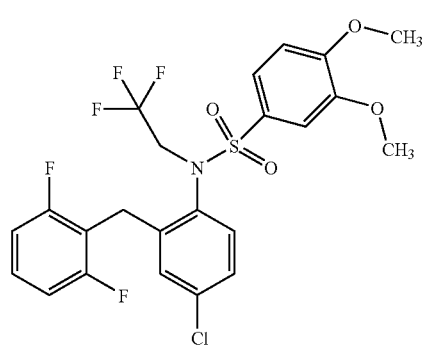

Compound 191:

N²-{4-chloro-2-[(2-chloro-6-methoxyphenyl)(hydroxy)methyl]phenyl}-N²-[(3,4-dimethoxyphenyl)sulfonyl]glycinamide

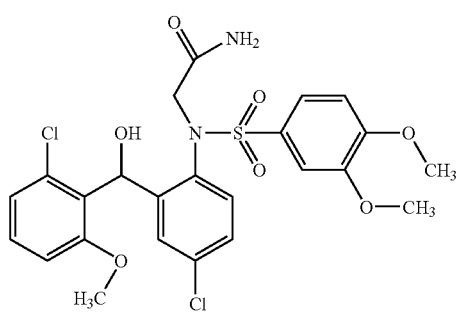

Compound 192:

N²-[4-chloro-2-(2-chloro-6-methoxybenzyl)phenyl]-N²-[(3,4-dimethoxyphenyl)sulfonyl]glycinamide

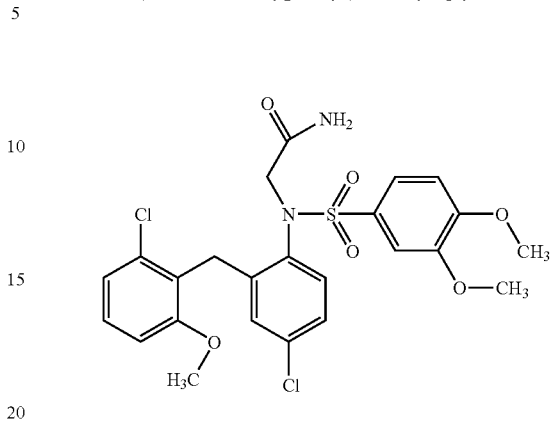

Compound 193:

N²-[2-(2,6-difluorobenzyl)-4-methoxyphenyl]-N²-[(3,4-dimethoxyphenyl)sulfonyl]glycinamide

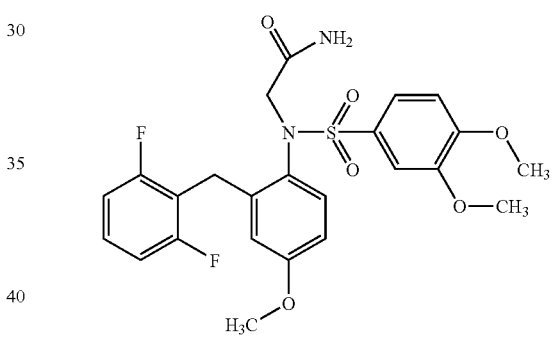

Compound 194:

N²-{4-chloro-2-[(2-fluoro-5-methylphenyl)(hydroxy)methyl]phenyl}-N²-[(3,4-dimethoxyphenyl)sulfonyl]glycinamide

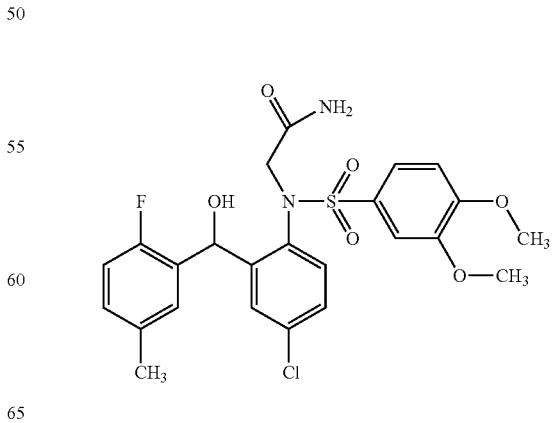

Compound 195:

N²-[3-chloro-2-(2,6-difluorobenzyl)phenyl]-N²-[(3,4-dimethoxyphenyl)sulfonyl]glycinamide

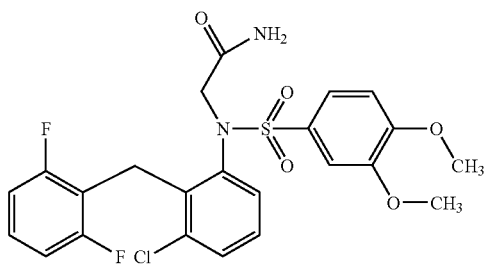

Compound 196:

N²-[4-chloro-2-(2-fluoro-5-methylbenzyl)phenyl]-N²-[(3,4-dimethoxyphenyl)sulfonyl]glycinamide

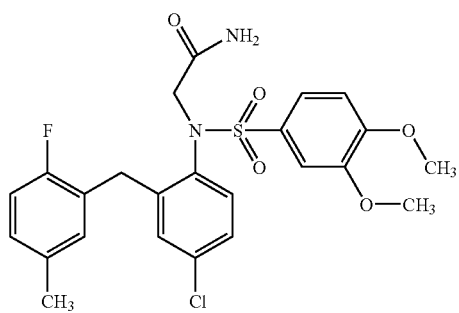

Compound 197:

N-[4-chloro-2-(2,6-difluorobenzyl)phenyl]-N-[3-(dimethylamino)propyl]-3,4-dimethoxybenzenesulfonamide

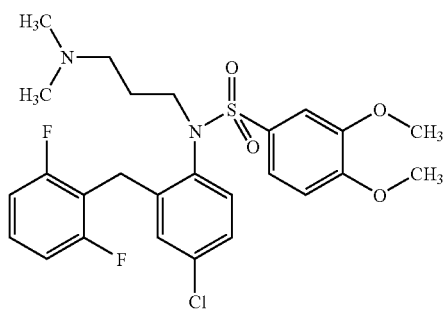

Compound 198:

N²-{2-[(2,6-difluorophenyl)(hydroxy)methyl]-4-methylphenyl}-N²-[(3,4-dimethoxyphenyl)sulfonyl]glycinamide

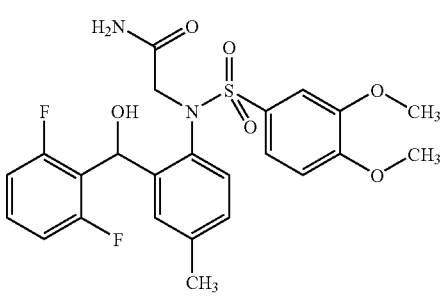

Compound 199:

N-[4-chloro-2-(2,6-difluorobenzyl)phenyl]-3,4-dimethoxy-N-(2-pyrrolidin-1-ylethyl)benzenesulfonamide

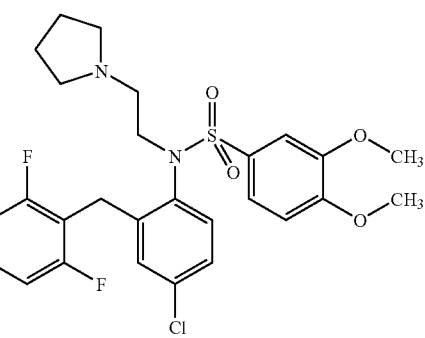

Compound 200:

N²-[2-(2,6-difluorobenzyl)-4-methylphenyl]-N²-[(3,4-dimethoxyphenyl)sulfonyl]glycinamide

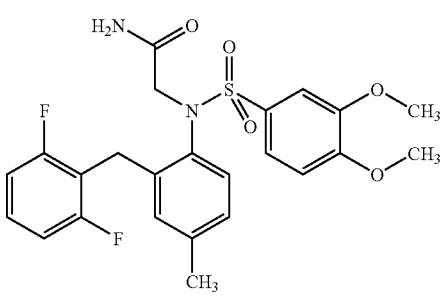

Compound 201:

N-[4-chloro-2-(2,6-difluorobenzyl)phenyl]-N-[2-(dimethylamino)-1-methylethyl]-3,4-dimethoxybenzenesulfonamide

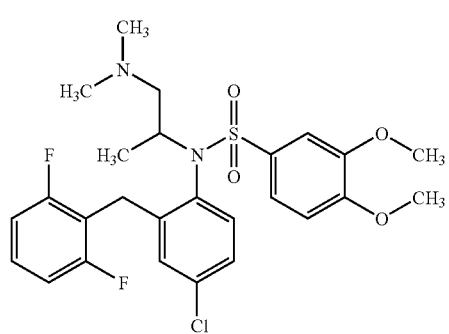

Compound 202:

N²-[2-(2,6-difluorobenzyl)-5-(dimethylamino)phenyl]-N²-[(3,4-dimethoxyphenyl)sulfonyl]glycinamide

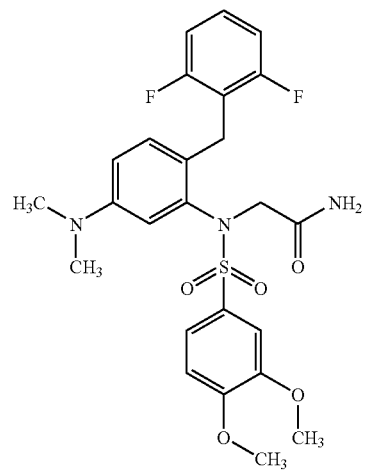

Compound 203:

N-{2-[benzyl(methyl)amino]ethyl}-N-[4-chloro-2-(2,6-difluorobenzyl)phenyl]-3,4-dimethoxybenzenesulfonamide

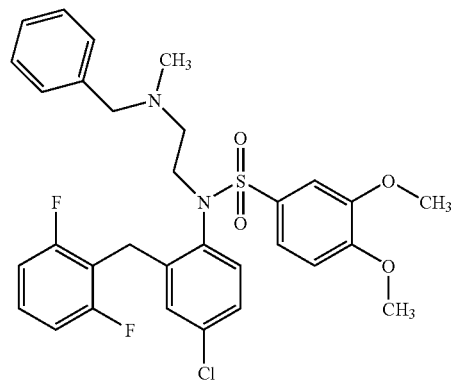

Compound 204:

4-{[4-chloro-2-(2,6-difluorobenzyl)phenyl][(3,4-dimethoxyphenyl)sulfonyl]amino}-butanamide

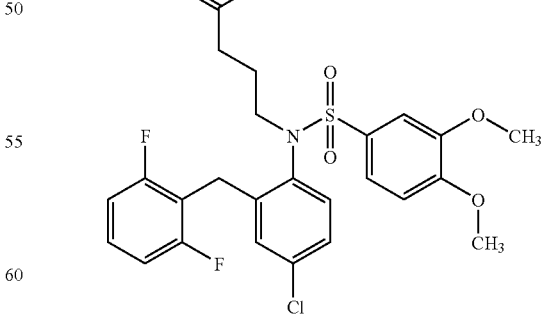

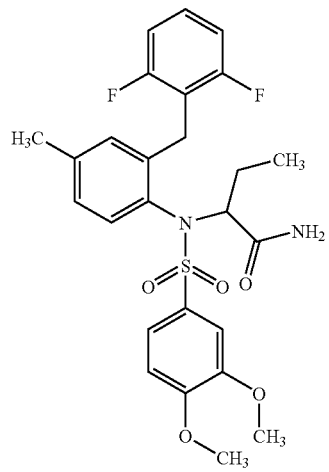

Compound 205:

2-{[2-(2,6-difluorobenzyl)-4-methylphenyl][(3,4-dimethoxyphenyl)sulfonyl]amino}-butanamide Compound 206:

$N^2$-{2-[(2,6-difluorophenyl)(hydroxy)methyl]-4-fluorophenyl}-$N^2$-[(3,4-dimethoxyphenyl)sulfonyl]glycinamide

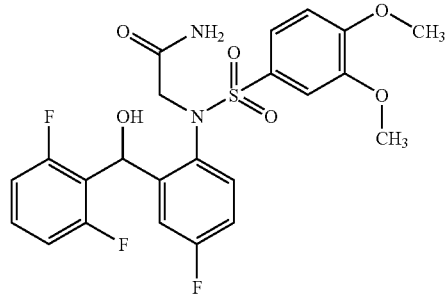

Compound 207:

$N^2$-{4-chloro-2-[2-(trifluoromethyl)benzyl]phenyl)-$N^2$-[(3,4-dimethoxyphenyl)sulfonyl]glycinamide

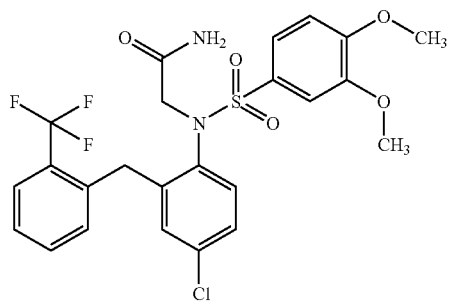

Compound 208:

$N^2$-[2-(2,6-difluorobenzyl)-4,6-dimethoxyphenyl]-$N^2$-[(3,4-dimethoxyphenyl)sulfonyl]glycinamide

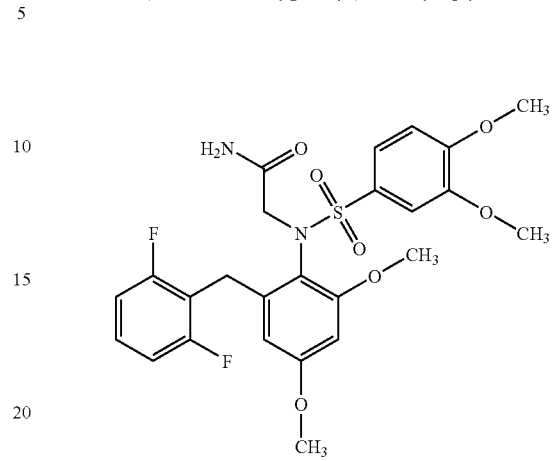

Compound 209:

$N^2$-{2-[(2,6-difluorophenyl)(hydroxy)methyl]-4-methoxyphenyl}-$N^2$-[(3,4-dimethoxyphenyl)sulfonyl]glycinamide

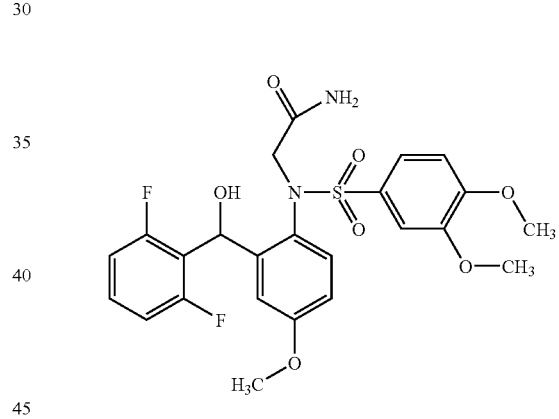

Compound 210:

$N^2$-[2-(2,6-difluorobenzyl)-3,6-dimethoxyphenyl]-$N^2$-[(3,4-dimethoxyphenyl)sulfonyl]glycinamide

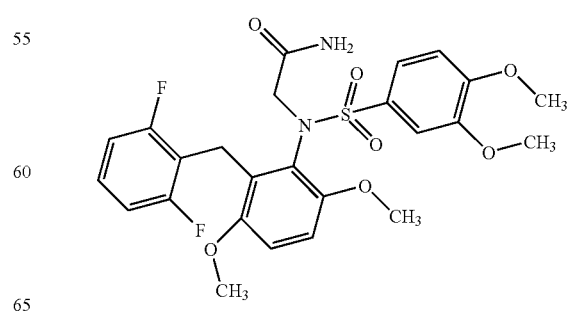

Compound 211:

N-[4-chloro-2-(2,6-difluorobenzyl)phenyl]-N-(cyanomethyl)-3,4-dimethoxybenzenesulfonamide

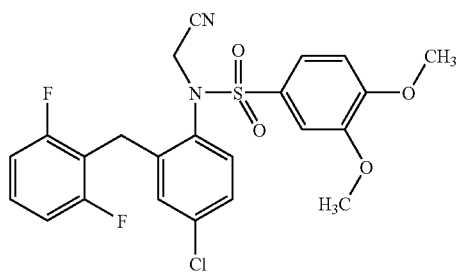

Compound 212:

N²-{4-chloro-2-[(5-methyl-2-thienyl)methyl]phenyl}-N²-[(3,4-dimethoxyphenyl)sulfonyl]glycinamide

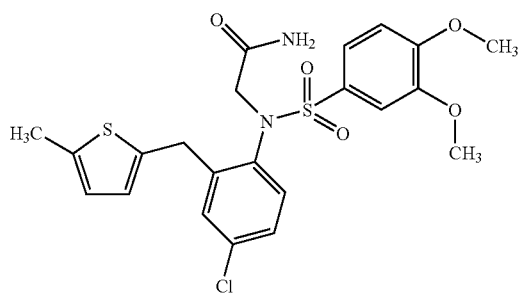

Compound 213:

N²-{4-chloro-2-[(2-chloro-6-methylphenyl)(hydroxy)methyl]phenyl}-N²-[(3,4-dimethoxyphenyl)sulfonyl]glycinamide

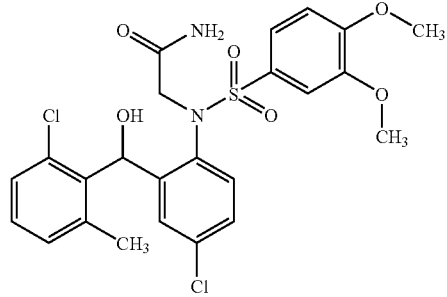

Compound 214:

N²-{2,4-dichloro-6-[(2,6-difluorophenyl)(hydroxy)methyl]phenyl}-N²-[(3,4-dimethoxyphenyl)sulfonyl]glycinamide

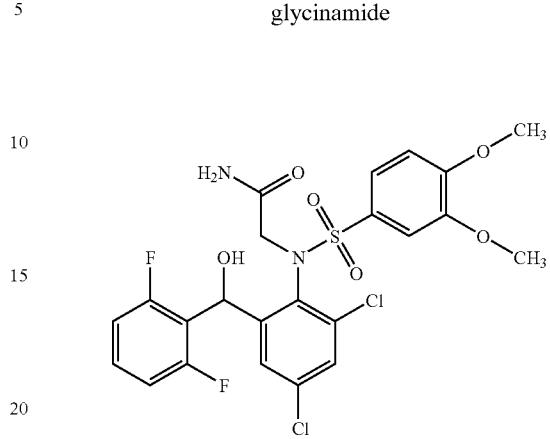

Compound 215:

N-(2-aminoethyl)-N-[2-(2,6-difluorobenzyl)-4-methylphenyl]-3,4-dimethoxybenzenesulfonamide

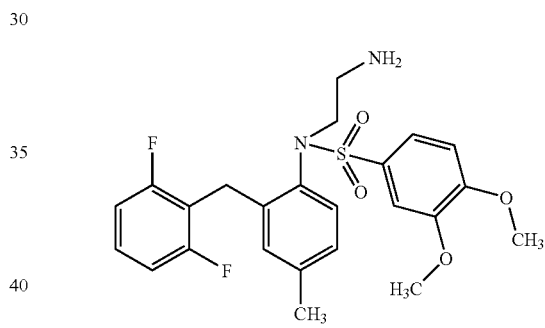

Compound 216:

N²-{2,4-dichloro-6-[(2,6-difluorophenyl)(hydroxy)methyl]phenyl}-N²-[(3,4-dimethoxyphenyl)sulfonyl]glycinamide

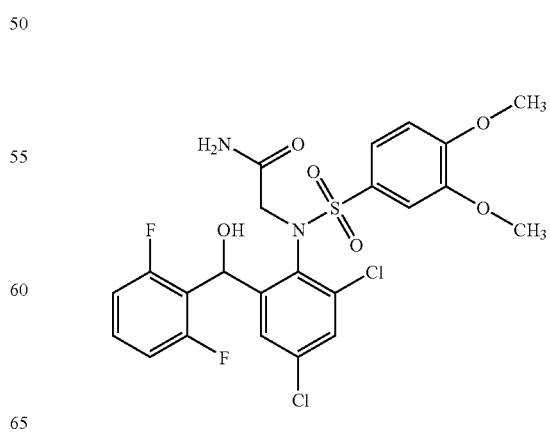

Compound 217:

N-{2-[(anilinocarbonyl)amino]ethyl}-N-[2-(2,6-difluorobenzyl)-4-methylphenyl]-3,4-dimethoxybenzenesulfonamide

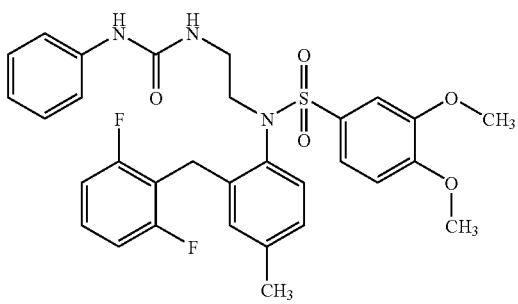

Compound 218:

N-(2-{[(benzylamino)carbonyl]amino}ethyl)-N-[2-(2,6-difluorobenzyl)-4-methylphenyl]-3,4-dimethoxybenzenesulfonamide

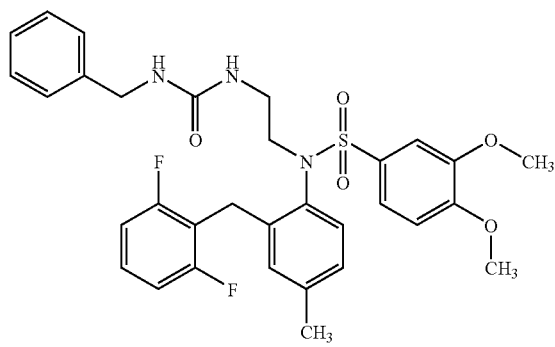

Compound 219:

N-(2-{[2-(2,6-difluorobenzyl)-4-methylphenyl][(3,4-dimethoxyphenyl)sulfonyl]amino}ethyl)acetamide

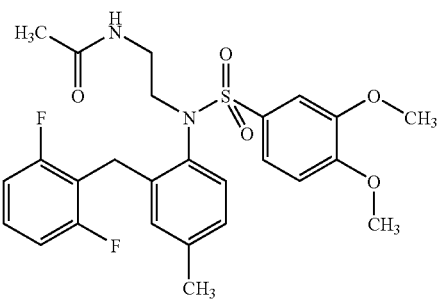

Compound 220:

$N^2$-[2-(2,6-difluorobenzyl)-4-fluorophenyl]-$N^2$-[(3,4-dimethoxyphenyl)sulfonyl]glycinamide

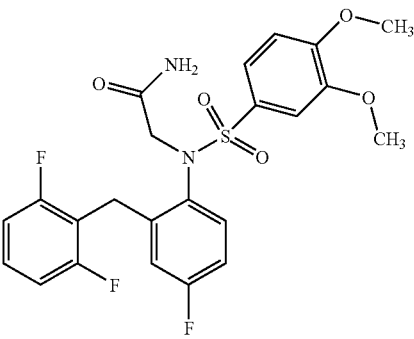

Compound 221:

$N^2$-{4,5-dichloro-2-[(2,6-difluorophenyl)(hydroxy)methyl]phenyl}-$N^2$-[(3,4-dimethoxyphenyl)sulfonyl]glycinamide

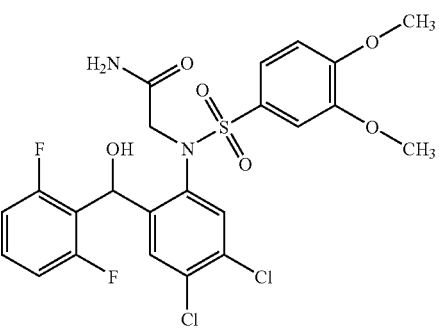

Compound 222:

$N^2$-{4-chloro-2-[(2-chloro-6-fluorophenyl)(hydroxy)methyl]phenyl}-$N^2$-[(3,4-dimethoxyphenyl)sulfonyl]glycinamide

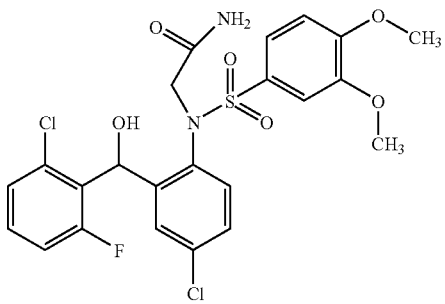

Compound 223:

N-[4-chloro-2-(2,6-difluorobenzyl)phenyl]-N-[(3,4-dimethoxyphenyl)sulfonyl]-2,2,2-trifluoroacetamide

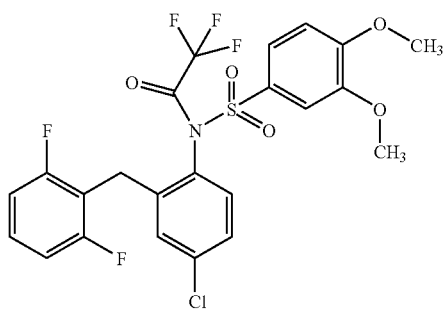

Compound 224:

$N^2$-[4-chloro-2-(2-chloro-6-fluorobenzyl)phenyl]-$N^2$-[(3,4-dimethoxyphenyl)sulfonyl]glycinamide

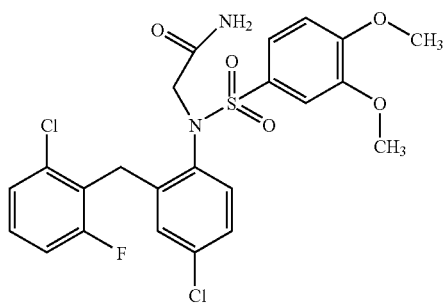

Compound 225:

$N^2$-{2-[(2,6-difluorophenyl)(hydroxy)methyl]-6-methoxyphenyl}-$N^2$-[(3,4-dimethoxyphenyl)sulfonyl]glycinamide

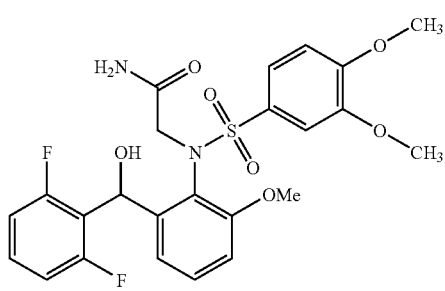

Compound 226:

$N^2$-{2-[(2,6-difluorophenyl)(hydroxy)methyl]-6-methoxyphenyl}-$N^2$-[(3,4-dimethoxyphenyl)sulfonyl]glycinamide

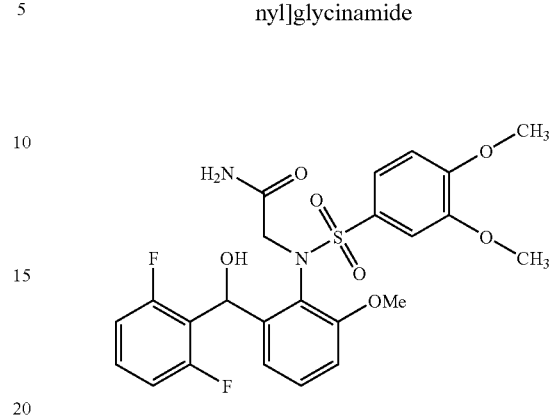

Compound 227:

$N^2$-{2-[(2,6-difluorophenyl)(hydroxy)methyl]-5-methoxy-4-methylphenyl}$N^2$-[(3,4-dimethoxyphenyl)sulfonyl]glycinamide

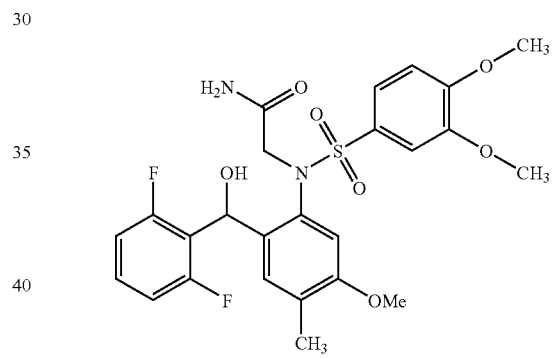

Compound 228:

$N^2$-[4,5-dichloro-2-(2,6-difluorobenzyl)phenyl]-$N^2$-[(3,4-dimethoxyphenyl)sulfonyl]glycinamide

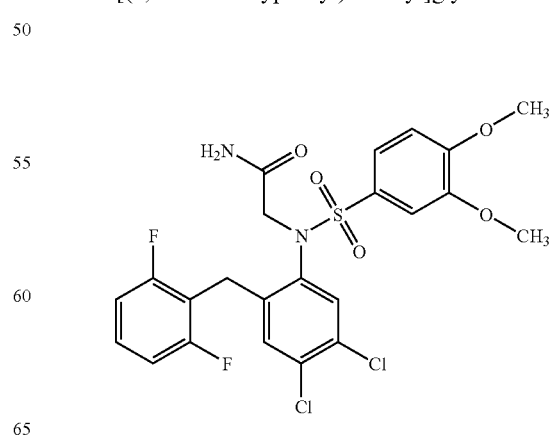

Compound 229:

N-[4-chloro-2-(2,6-difluorobenzyl)phenyl]-N-{3-[(diethylamino)sulfonyl]propyl}-3,4-dimethoxybenzenesulfonamide

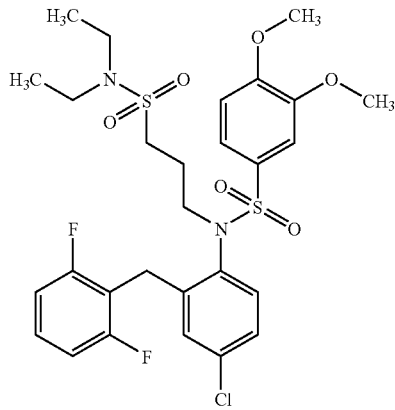

Compound 230:

N-[4-chloro-2-(2,6-difluorobenzyl)phenyl]-N-{3-[(dimethylamino)sulfonyl]propyl}-3,4-dimethoxybenzenesulfonamide

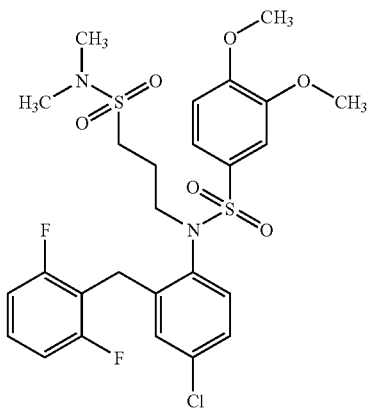

Compound 231:

N-{(2-[(aminocarbonyl)amino]ethyl}-N-[4-chloro-2-(2,6-difluorobenzyl)phenyl]-3,4-dimethoxybenzenesulfonamide

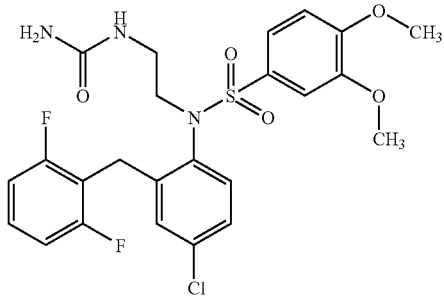

Compound 232:

N-[4-chloro-2-(2,6-difluorobenzyl)phenyl]-3,4-dimethoxy-N-(3-pyridin-3-ylpropyl)benzenesulfonamide

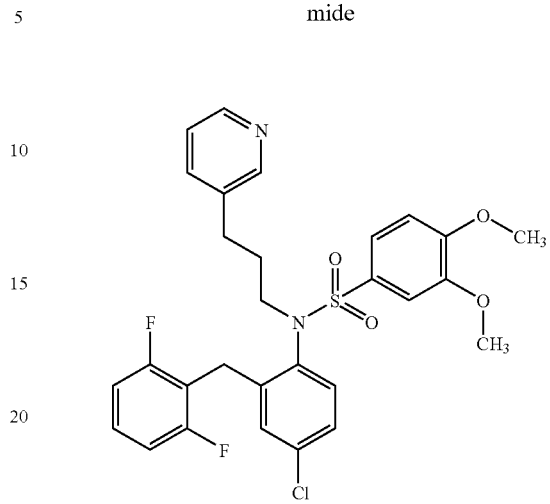

Compound 233:

$N^2$-[4-chloro-2-(2-chlorobenzyl)phenyl]-$N^2$-[(3,4-dimethoxyphenyl)sulfonyl]glycinamide

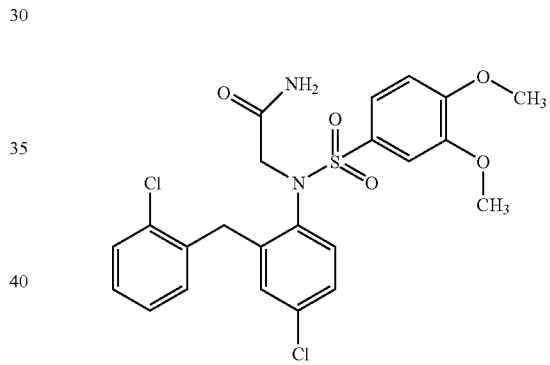

Compound 234:

N-[4-chloro-2-(2,6-difluorobenzyl)phenyl]-3,4-dimethoxy-N-[2-(2-oxopyrrolidin-1-yl)ethyl]benzenesulfonamide

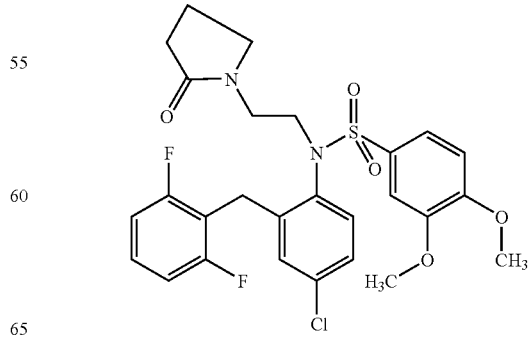

Compound 235:

4-{([4-chloro-2-(2,6-difluorobenzyl)phenyl][(4-chloro-2,5-dimethylphenyl)sulfonyl]amino}-butanamide

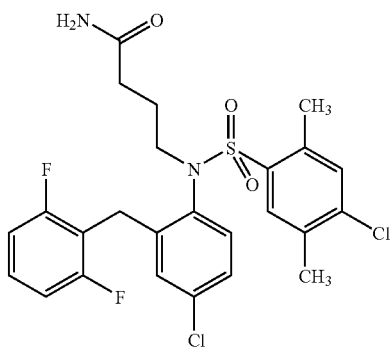

Compound 236:

N-[4-chloro-2-(2,6-difluorobenzyl)phenyl]-3,4-dimethoxy-N-(2-methoxyethyl)benzenesulfonamide

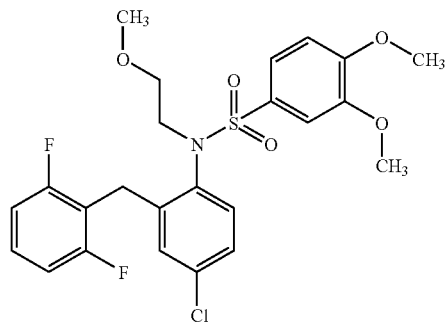

Compound 237:

N-[4-chloro-2-(2,6-difluorobenzyl)phenyl]-N-(2-hydroxyethyl)-3,4-dimethoxybenzenesulfonamide

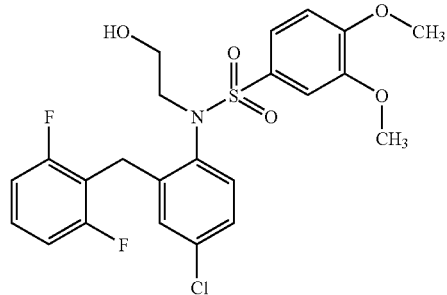

Compound 238:

N-[4-chloro-2-(2,6-difluorobenzyl)phenyl]-N-[2-({[(3-chlorophenyl)amino]carbonyl}amino)-ethyl]-3,4-dimethoxybenzenesulfonamide

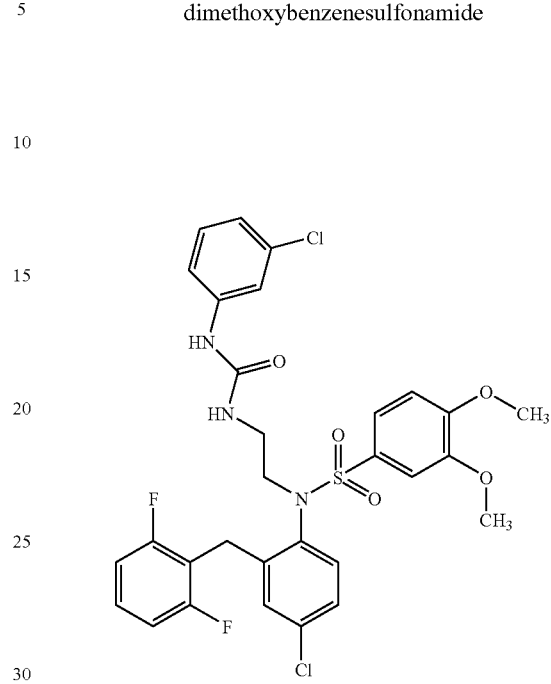

Compound 239:

N-[4-chloro-2-(2,6-difluorobenzyl)phenyl]-N-(2}[(dimethylamino)carbonyl]amino}ethyl)-3,4-dimethoxybenzenesulfonamide

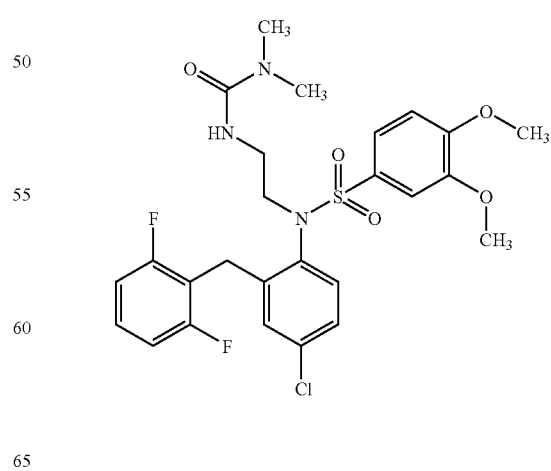

Compound 240:

N-[4-chloro-2-(2,6-difluorobenzyl)phenyl]-N-[2-({[(2-chlorophenyl)amino]carbonyl}amino)ethyl]-3,4-dimethoxybenzenesulfonamide

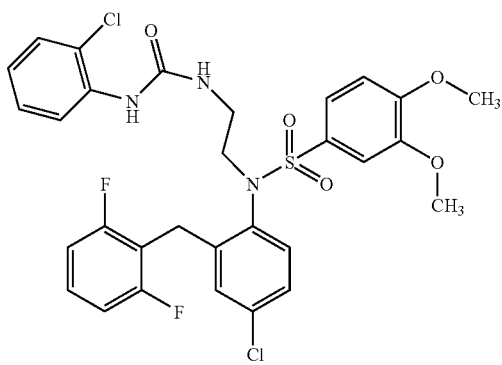

Compound 241:

N~2~-[5-bromo-2-(2,6-difluorobenzyl)phenyl]-N~2~-[(3,4-dimethoxyphenyl)sulfonyl]glycinamide

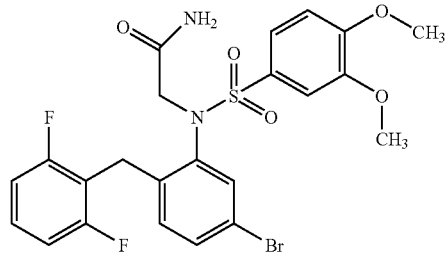

Compound 242:

N~2~-[4-bromo-2-(2,6-difluorobenzyl)phenyl]-N~2~-[(3,4-dimethoxyphenyl)sulfonyl]glycinamide

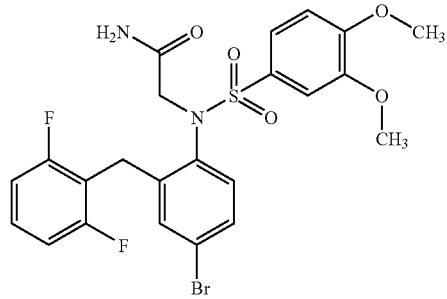

Compound 243:

N-[4-chloro-2-(2,6-difluorobenzyl)phenyl]-3,4-dimethoxy-N-[1-(2-methyl-2H-tetrazol-5-yl)ethyl]benzenesulfonamide

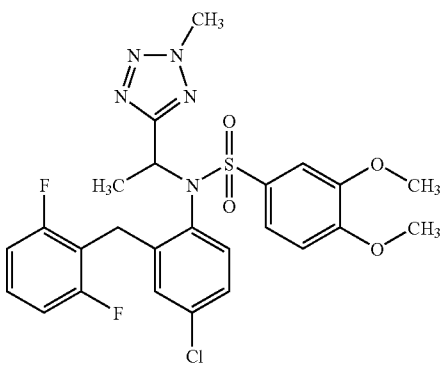

Compound 244:

N-[4-chloro-2-(2,6-difluorobenzyl)phenyl]-3,4-dimethoxy-N-[1-(1-methyl-1H-tetrazol-5-yl)ethyl]benzenesulfonamide

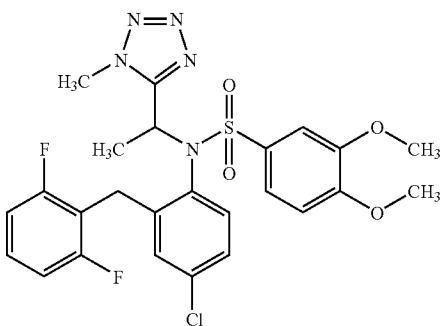

Compound 245:

N-[4-chloro-2-(2,6-difluorobenzyl)phenyl]-3,4-dimethoxy-N-(3-pyridin-3-ylpropyl)benzenesulfonamide

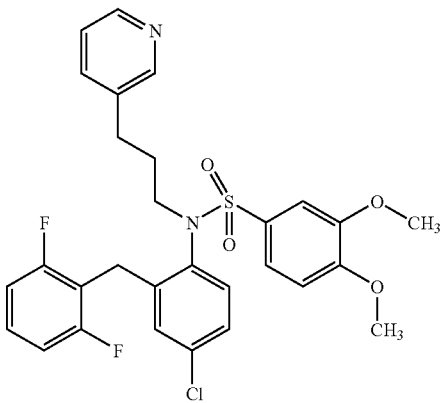

Compound 246:

N-[4-chloro-2-(2,6-difluorobenzyl)phenyl]-N-(1-cyanoethyl)-3,4-dimethoxybenzenesulfonamide

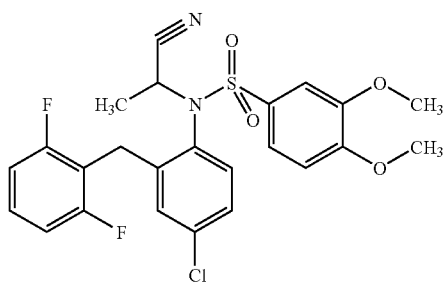

Compound 247:

N~2~-[2-(2,6-difluorobenzyl)-6-methoxyphenyl]-N~2~-[(3,4-dimethoxyphenyl)sulfonyl]glycinamide

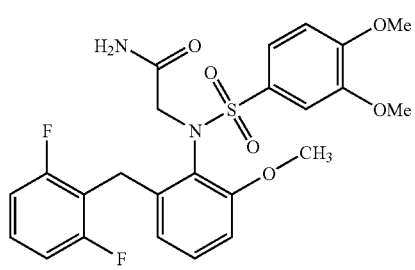

Compound 248:

N-[4-chloro-2-(2,6-difluorobenzyl)phenyl]-N-(cyclopropylmethyl)-3,4-dimethoxybenzenesulfonamide

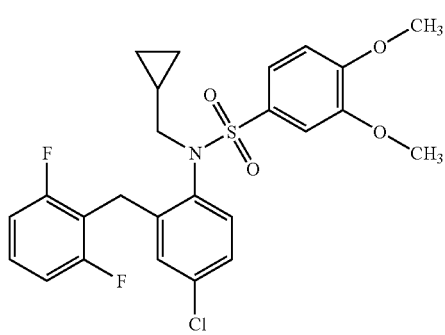

Compound 249:

N~2~-[4-chloro-2-(2,6-difluorobenzyl)phenyl]-N~2~-[(4-chloro-2,5-dimethylphenyl)sulfonyl]glycinamide

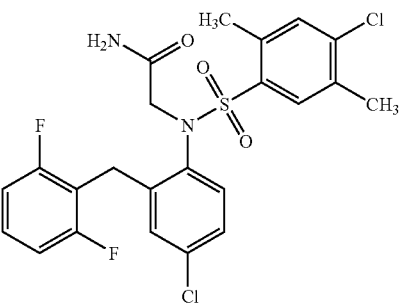

Compound 250:

N-[4-chloro-2-(2,6-difluorobenzyl)phenyl]-3,4-dimethoxy-N-(2-pyridin-2-ylethyl)benzenesulfonamide

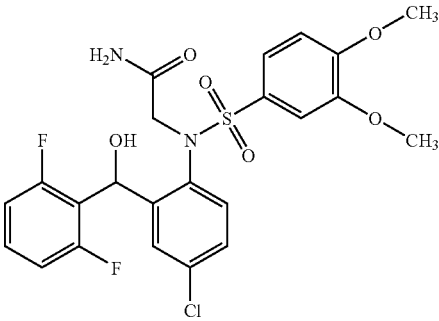

Compound 251:

N~2~-{4-chloro-2-[(2,6-difluorophenyl)(hydroxy)methyl]phenyl}-N~2~-[(3,4-dimethoxyphenyl)sulfonyl]glycinamide Compound 252:

N-[4-chloro-2-(2,6-difluorobenzyl)phenyl]-N-[2-({[(3,4-dimethoxyphenyl)amino]carbonyl}amino)ethyl]-3,4-dimethoxybenzenesulfonamide

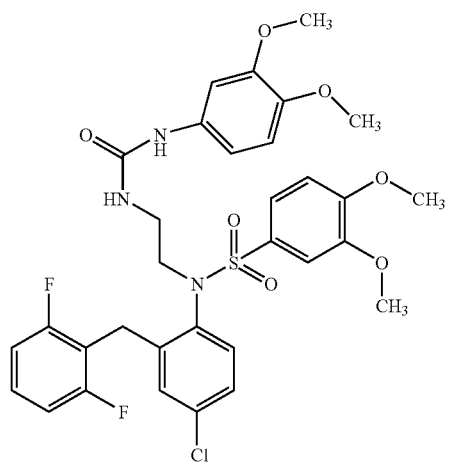

Compound 253:

N-[4-chloro-2-(2,6-difluorobenzyl)phenyl]-3,4-dimethoxy-N-(2-{[(methylamino)carbonyl]amino}ethyl)-benzenesulfonamide

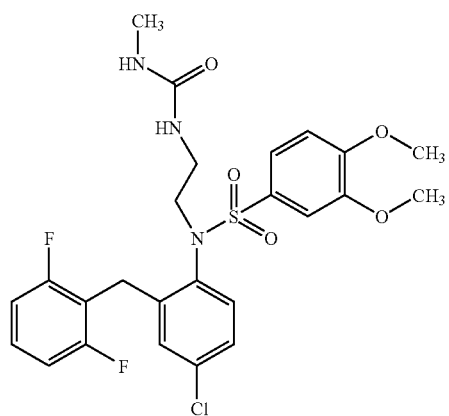

Compound 254:

N-[4-chloro-2-(2,6-difluorobenzyl)phenyl]-3,4-dimethoxy-N-(2-pyridin-3-ylethyl)benzenesulfonamide

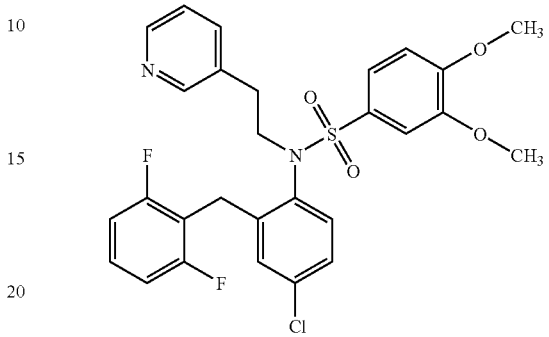

Compound 255:

N-[4-chloro-2-(2,6-difluorobenzyl)phenyl]-3,4-dimethoxy-N-(2-pyridin-4-ylethyl)benzenesulfonamide

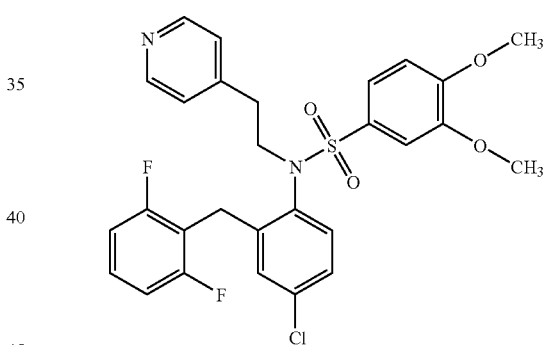

Compound 256:

N-(2-aminoethyl)-N-[4-chloro-2-(2,6-difluorobenzyl)phenyl]-3,4-dimethoxybenzenesulfonamide

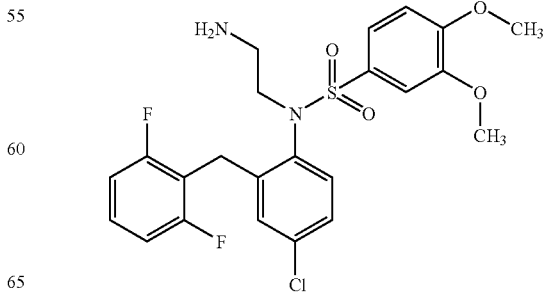

Compound 257:

N-(2-aminoethyl)-N-[2-(2,5-difluorobenzyl)-4-methylphenyl]-3,4-dimethoxybenzenesulfonamide

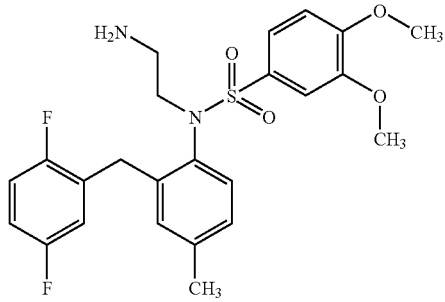

Compound 258:

N-[2-(2,6-difluorobenzyl)-4-methylphenyl]-3,4-dimethoxy-N-[2-(methylamino)ethyl]benzenesulfonamide

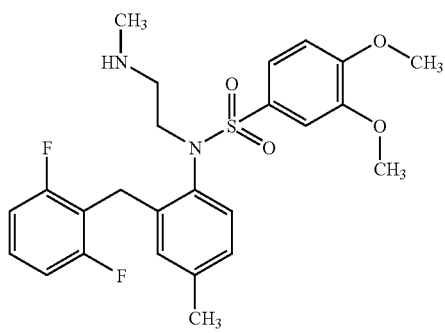

Compound 259:

N~2~-[4-chloro-2-(2,6-difluorobenzyl)phenyl]-N~2~-[(4-methoxy-3-methylphenyl)sulfonyl]glycinamide

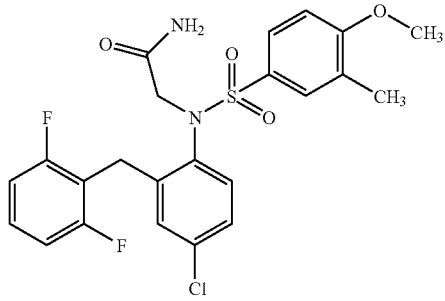

Compound 260:

N-[4-chloro-2-(2,6-difluorobenzyl)phenyl]-3,4-dimethoxy-N-(2-phenoxyethyl)benzenesulfonamide

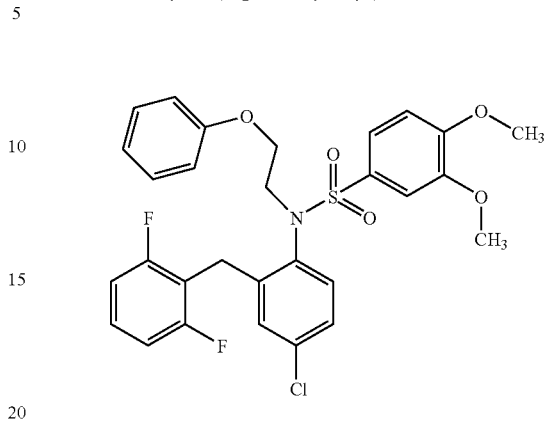

Compound 261:

N~2~-[4-chloro-2-(2,6-difluorobenzyl)phenyl]-N~2~-[(3,4-dimethoxyphenyl)sulfonyl]alaninamide

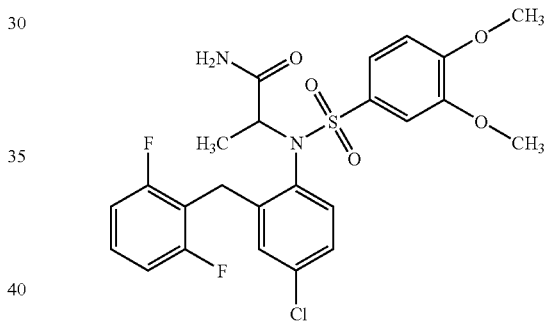

Compound 262:

N-(2-aminoethyl)-N-[4-chloro-2-(2,5-difluorobenzyl)phenyl]-3,4-dimethoxybenzenesulfonamide

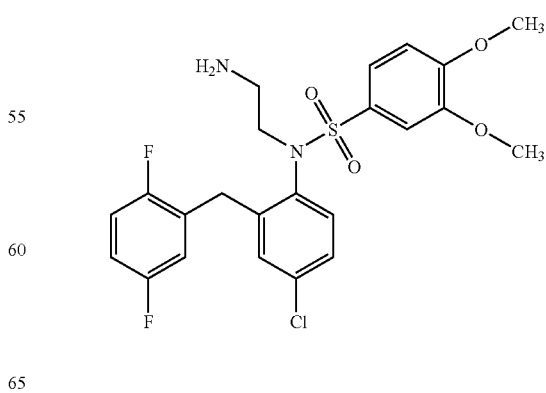

Compound 263:

N~2~-[(4-tert-butylphenyl)sulfonyl]-N~2~-[4-chloro-2-(2,6-difluorobenzyl)phenyl]glycinamide

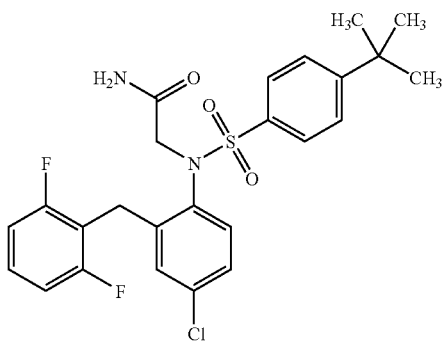

Compound 264:

N-[4-chloro-2-(2,6-difluorobenzyl)phenyl]-N-(2-hydroxy-1-methylethyl)-3,4-dimethoxybenzene-sulfonamide

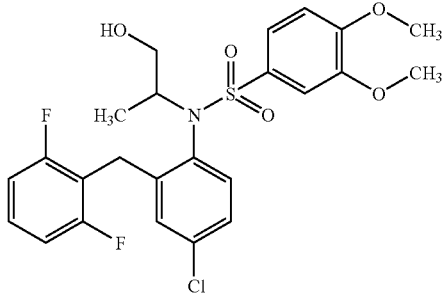

Compound 265:

N~2~-[2-(2-chlorobenzyl)-4-(dimethylamino)phenyl]-N~2~-[(3,4-dimethoxyphenyl)sulfonyl]glycinamide

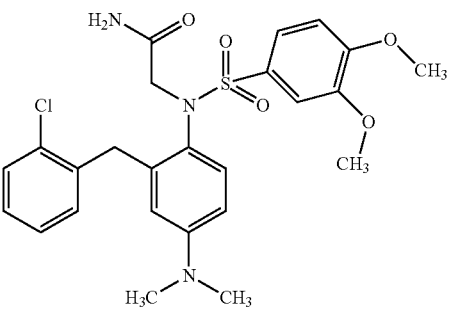

Compound 266:

4-{[4-chloro-2-(2,5-difluorobenzyl)phenyl][(3,4-dimethoxyphenyl)sulfonyl]amino}-butanamide

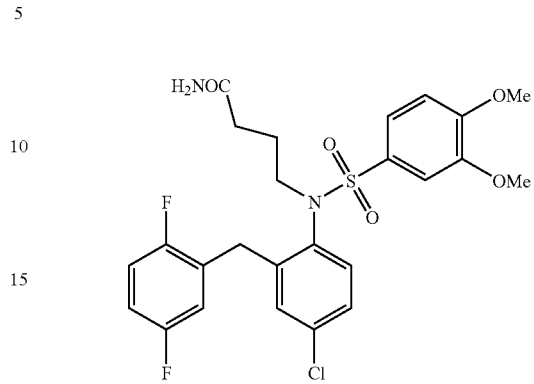

Compound 267:

N~2~-[4-chloro-2-(2,5-difluorobenzyl)phenyl]-N~2~-[(4-chloro-2,5-dimethylphenyl)sulfonyl]glycinamide

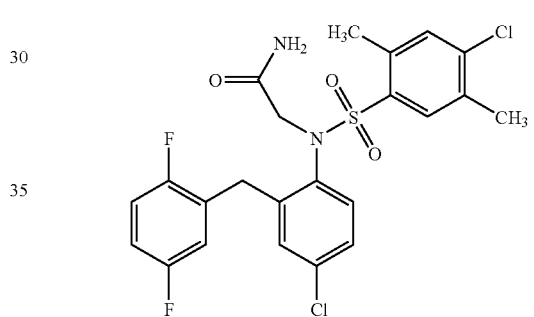

Compound 268:

N-[4-chloro-2-(2,6-difluorobenzyl)phenyl]-N-[2-(1,3-dioxolan-2-yl)ethyl]-3,4-dimethoxybenzene-sulfonamide

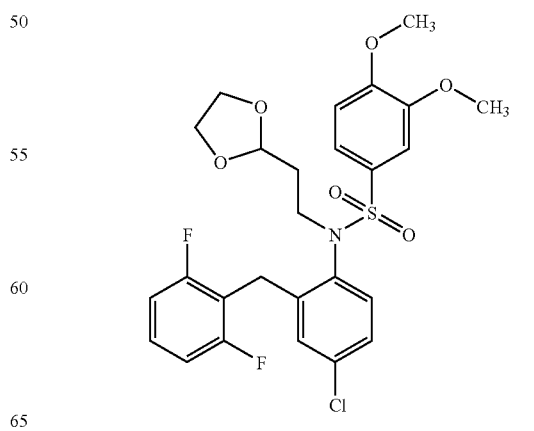

Compound 269:

phenyl (2-{[4-chloro-2-(2,6-difluorobenzyl)phenyl][(3,4-dimethoxyphenyl)sulfonyl]amino}ethyl)-carbamate

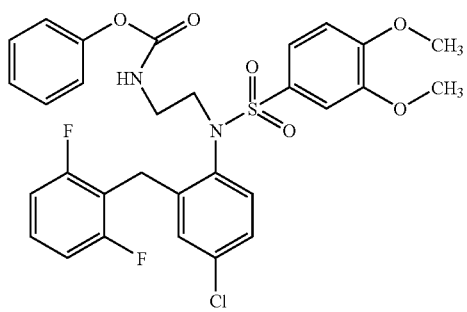

Compound 270:

N-[4-chloro-2-(2,6-difluorobenzyl)phenyl]-N-(3-hydroxypropyl)-3,4-dimethoxybenzenesulfonamide

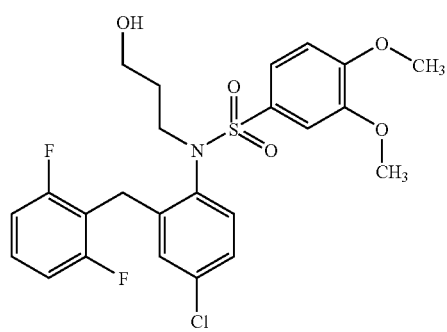

Compound 271:

N-[4-chloro-2-(2,6-difluorobenzyl)phenyl]-N-[2-(1H-imidazol-1-yl)ethyl]-3,4-dimethoxybenzene-sulfonamide

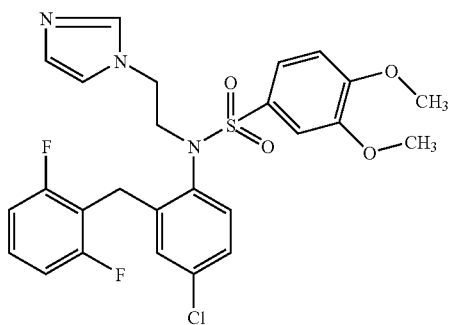

Compound 272:

4-{[2-(2,6-difluorobenzyl)-6-methoxyphenyl][(3,4-dimethoxyphenyl)sulfonyl]amino}-butanamide

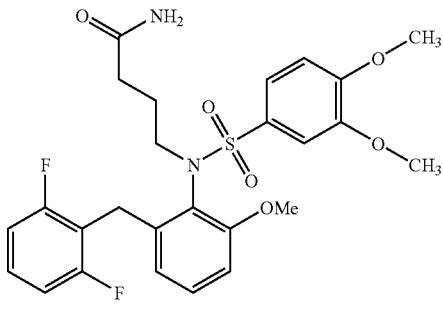

Compound 273:

N~3~-[4-chloro-2-(2,6-difluorobenzyl)phenyl]-N~3~-[(3,4-dimethoxyphenyl)sulfonyl]-beta-alaninamide

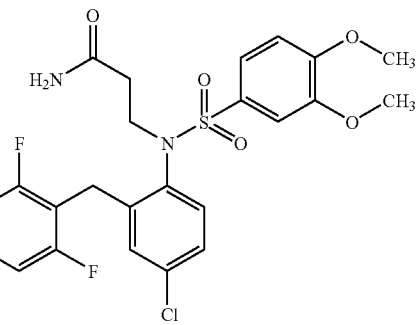

Compound 274:

N-[4-chloro-2-(2,6-difluorobenzyl)phenyl]-3,4-dimethoxy-N-[(2R)-pyrrolidin-2-ylmethyl]benzene-sulfonamide

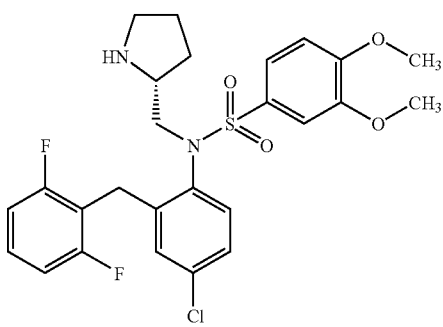

Compound 275:

N-[4-chloro-2-(2,6-difluorobenzyl)phenyl]-3,4-dimethoxy-N-[(2S)-pyrrolidin-2-ylmethyl]benzenesulfonamide

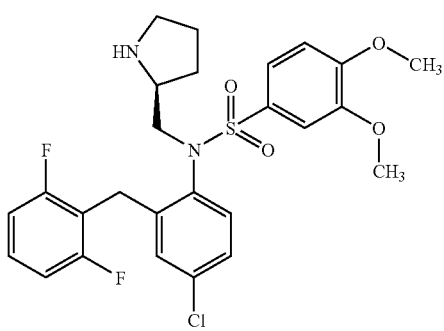

Compound 276:

2-{[4-chloro-2-(2,6-difluorobenzyl)phenyl][(3,4-dimethoxyphenyl)sulfonyl]amino}-2-ethoxyacetamide

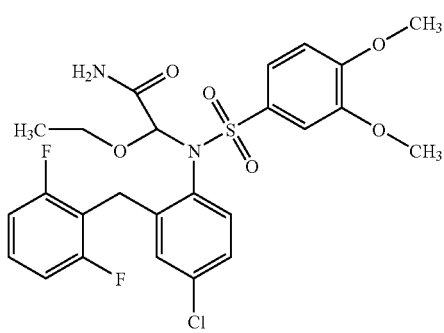

Compound 277:

N-[4-chloro-2-(2,6-difluorobenzyl)phenyl]-3,4-dimethoxy-N-[2-(1H-1,2,4-triazol-1-yl)ethyl]benzenesulfonamide

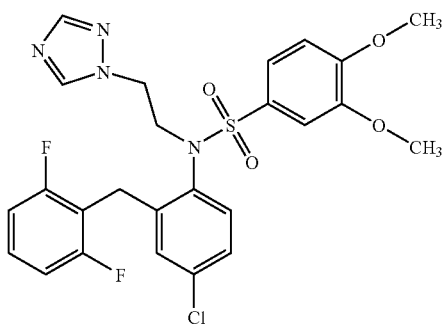

Compound 278:

N-[4-chloro-2-(2,6-difluorobenzyl)phenyl]-N-(2-{[2-(dimethylamino)ethyl]amino}ethyl)-3,4-dimethoxybenzenesulfonamide

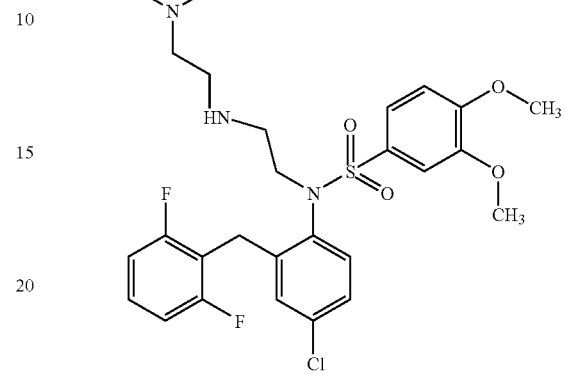

Compound 279:

N~2~-[(4-aminophenyl)sulfonyl]-N~2~-[4-chloro-2-(2,6-difluorobenzyl)phenyl]glycinamide

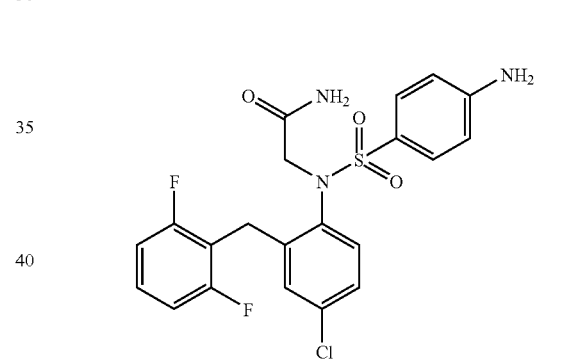

Compound 280:

N~2~-[2-(2,5-difluorobenzyl)-4-methylphenyl]-N~2~-[(3,4-dimethoxyphenyl)sulfonyl]glycinamide

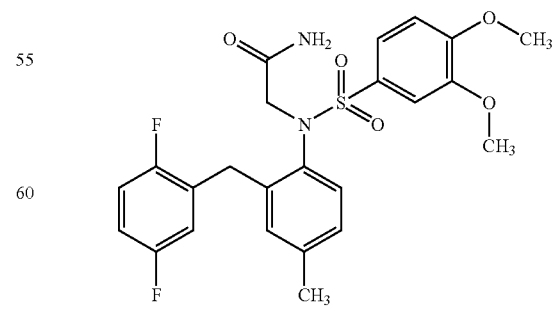

Compound 281:

N-(2-aminoethyl)-N-[2-(2,6-difluorobenzyl)-6-methoxyphenyl]-3,4-dimethoxybenzenesulfonamide

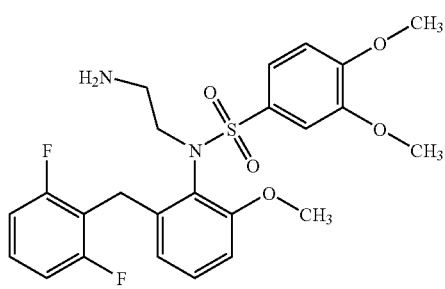

Compound 282:

N-[2-(2,6-difluorobenzyl)-6-methoxyphenyl]-3,4-dimethoxy-N-[2-(methylamino)ethyl]benzenesulfonamide

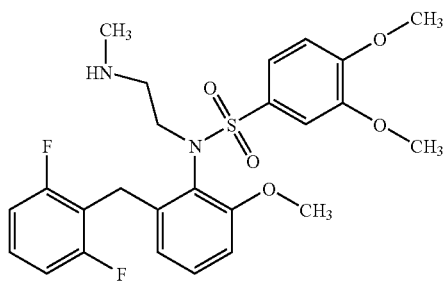

Compound 283:

N~2~-[4-chloro-2-(2,6-difluorobenzyl)phenyl]-N~2~-[(6-methoxypyridin-3-yl)sulfonyl]glycinamide

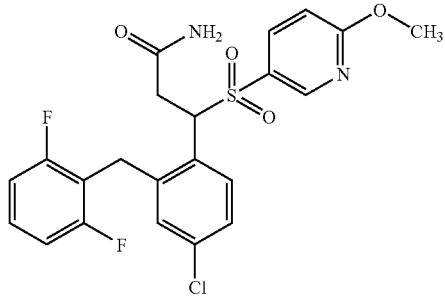

Compound 284:

N-[4-chloro-2-(2,6-difluorobenzyl)phenyl]-3,4-dimethoxy-N-[2-(methylamino)ethyl]benzenesulfonamide

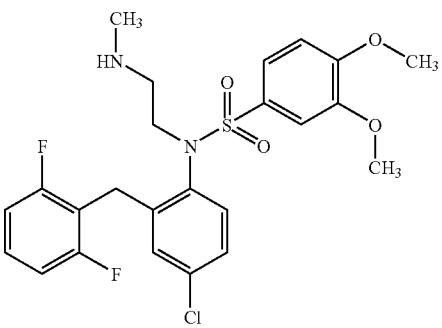

Compound 285:

N~2~-[2-(2,5-difluorobenzyl)-6-methoxyphenyl]-N~2~-[(3,4-dimethoxyphenyl)sulfonyl]glycinamide

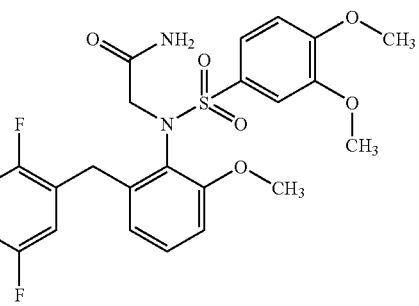

Compound 286:

N~2~-[5-chloro-2-(2,6-difluorobenzyl)phenyl]-N~2~-[(3,4-dimethoxyphenyl)sulfonyl]glycinamide

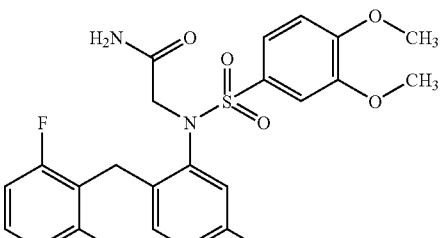

Compound 287:

N-(3-aminopropyl)-N-[4-chloro-2-(2,6-difluorobenzyl)phenyl]-3,4-dimethoxybenzenesulfonamide

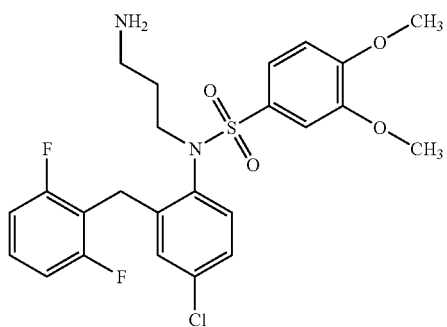

Compound 288:

N~2~-[2-(2,6-difluorobenzyl)-6-methylphenyl]-N~2~-[(3,4-dimethoxyphenyl)sulfonyl]glycinamide

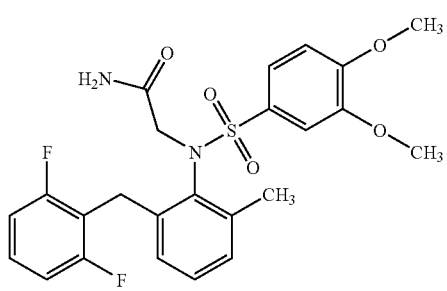

Compound 289:

N-[4-chloro-2-(2,6-difluorobenzyl)phenyl]-3,4-dimethoxy-N-vinylbenzenesulfonamide

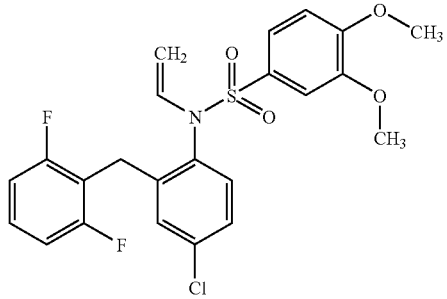

Compound 290:

N-[4-chloro-2-(2,6-difluorobenzyl)phenyl]-3,4-dimethoxy-N-(1,3-thiazol-2-ylmethyl)benzenesulfonamide

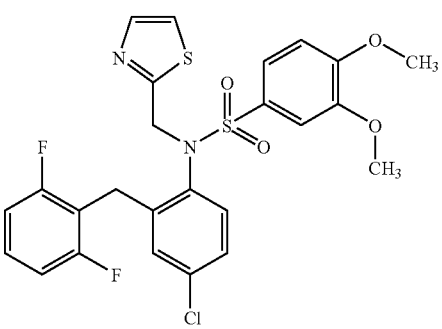

Compound 291:

N-[4-chloro-2-(2,6-difluorobenzyl)phenyl]-3,4-dimethoxy-N-(pyrimidin-2-ylmethyl)benzenesulfonamide

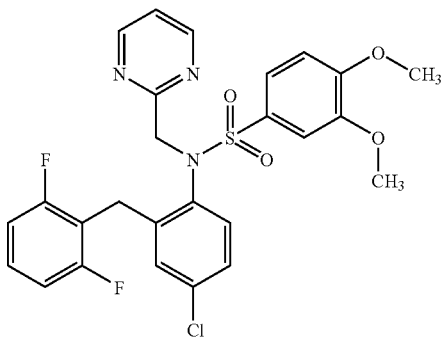

Compound 292:

N-[4-chloro-2-(2,6-difluorobenzyl)phenyl]-3,4-dimethoxy-N-(2-morpholin-4-ylethyl)benzenesulfonamide

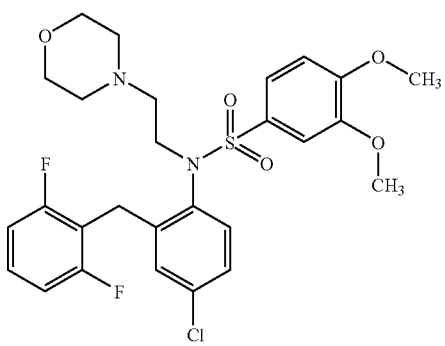

Compound 293:

N~2~-[2-chloro-6-(2,6-difluorobenzyl)phenyl]-
N~2~-[(3,4-dimethoxyphenyl)sulfonyl]glycinamide

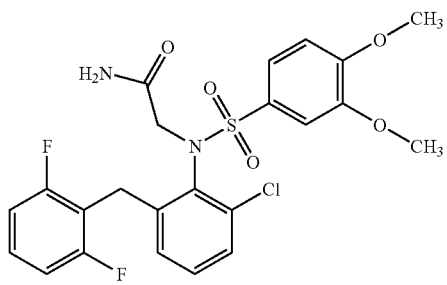

Compound 294:

N-(2-aminoethyl)-N-[2-(2,5-difluorobenzyl)-6-methoxyphenyl]-3,4-dimethoxybenzenesulfonamide

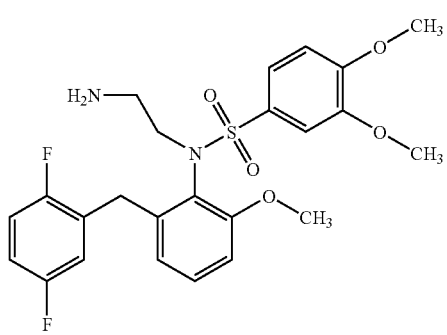

Compound 295:

N-[4-chloro-2-(2,6-difluorobenzyl)phenyl]-3,4-dimethoxy-N-(pyridin-2-ylmethyl)benzenesulfonamide

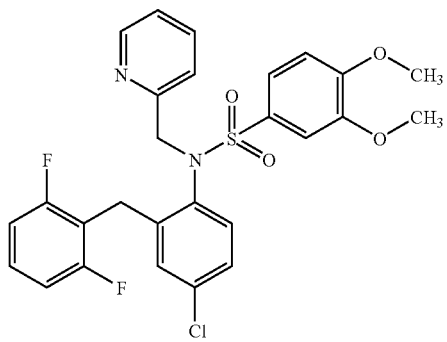

Compound 296:

N~2~-[2-(2,6-difluorobenzyl)-5-methoxyphenyl]-
N~2~-[(3,4-dimethoxyphenyl)sulfonyl]glycinamide

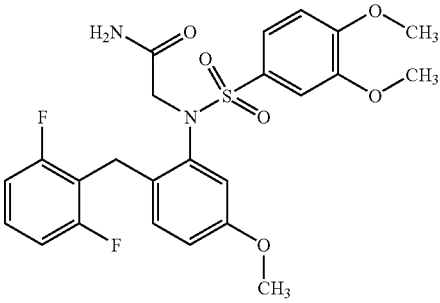

Compound 297:

N-[2-(2,6-difluorobenzyl)-6-methoxyphenyl]-3,4-dimethoxy-N-methylbenzenesulfonamide

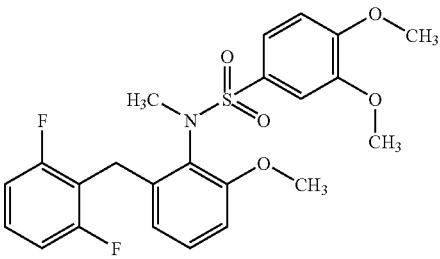

Compound 298:

3-{[4-chloro-2-(2,6-difluorobenzyl)phenyl][(3,4-dimethoxyphenyl)sulfonyl]amino}-butanamide

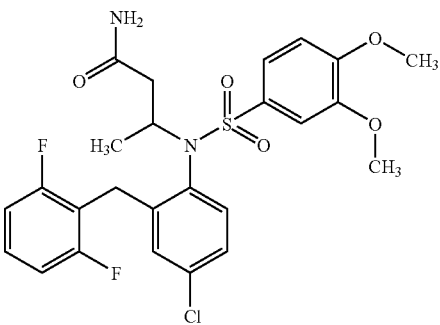

Compound 299:

4-{[2-(2,5-difluorobenzyl)-6-methoxyphenyl][(3,4-dimethoxyphenyl)sulfonyl]amino}-butanamide

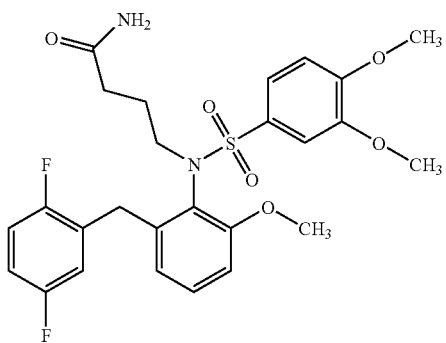

Compound 300:

N-(2-aminoethyl)-N-[4-chloro-2-(2,6-difluorobenzyl)-6-methoxyphenyl]-3,4-dimethoxybenzenesulfonamide

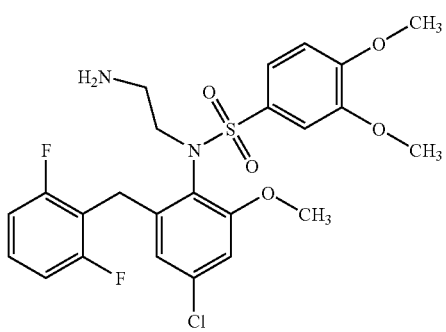

Compound 301:

N-[2-(2,6-difluorobenzyl)-6-methoxyphenyl]-N-[2-(1H-imidazol-1-yl)ethyl]-3,4-dimethoxybenzenesulfonamide

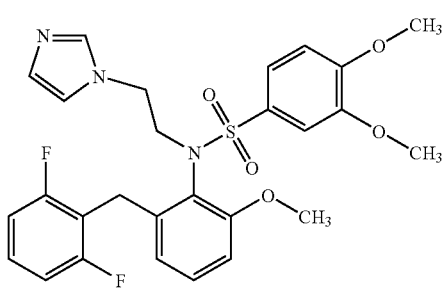

Compound 302:

N~2~-[4-chloro-2-(2,6-difluorobenzyl)-6-methoxyphenyl]-N~2~-[(3,4-dimethoxyphenyl)sulfonyl]glycinamide

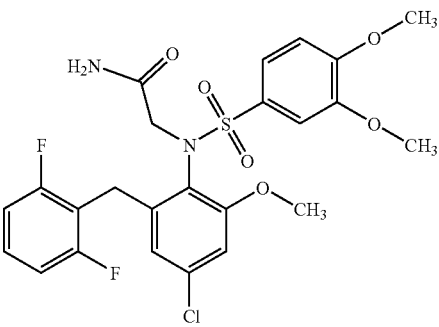

Compound 303:

N~2~-[2-(2,6-difluorobenzyl)-6-methoxy-4-methylphenyl]-N~2~-[(3,4-dimethoxyphenyl)sulfonyl]glycinamide

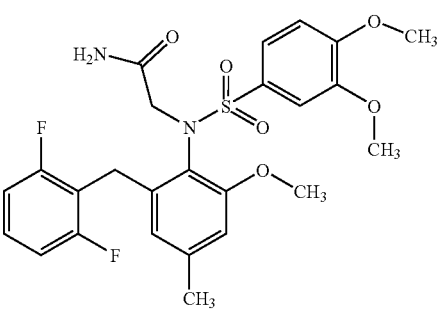

Compound 304:

(+)N~2~-[4-chloro-2-(2,6-difluorobenzyl)phenyl]-N~2~-[(3,4-dimethoxyphenyl)sulfonyl]alaninamide

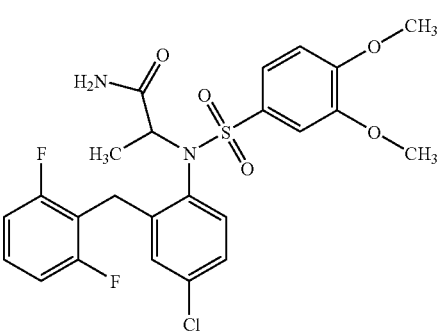

Compound 305:

(−)N~2~-[4-chloro-2-(2,6-difluorobenzyl)phenyl]-N~2~-[(3,4-dimethoxyphenyl)sulfonyl]alaninamide

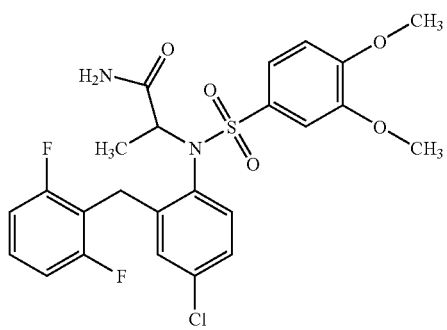

Compound 306:

N-[2-(2,6-difluorobenzyl)-6-methoxyphenyl]-3,4-dimethoxy-N-[2-(1H-1,2,4-triazol-1-yl)ethyl]benzenesulfonamide

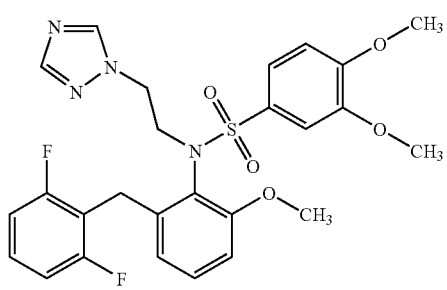

Compound 307:

N~2~-[4-chloro-2-(2,6-difluorobenzyl)phenyl]-N~2~-[(3,5-dimethoxyphenyl)sulfonyl]glycinamide

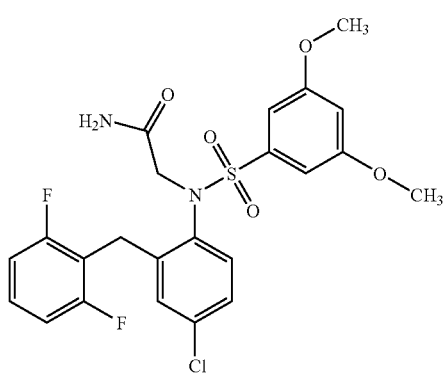

Compound 308:

N~2~-[4-chloro-2-(2,6-difluorobenzyl)phenyl]-N~2~-[(3-methoxy-4-methylphenyl)sulfonyl]glycinamide

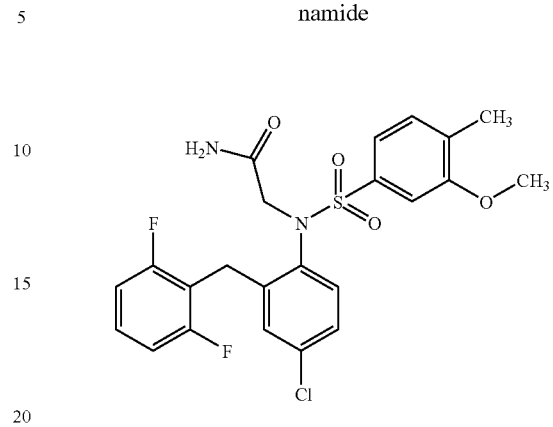

Compound 309:

N~2~-[2-(2,6-difluorobenzyl)-6-methoxyphenyl]-N~2~-[(3,4-dimethoxyphenyl)sulfonyl]-N-ethylglycinamide

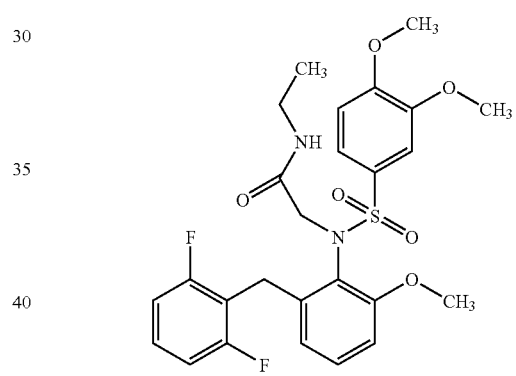

Compound 310:

N-[2-(2,6-difluorobenzyl)-6-methoxyphenyl]-N-[(2-ethyl-2H-tetrazol-5-yl)methyl]-3,4-dimethoxybenzenesulfonamide

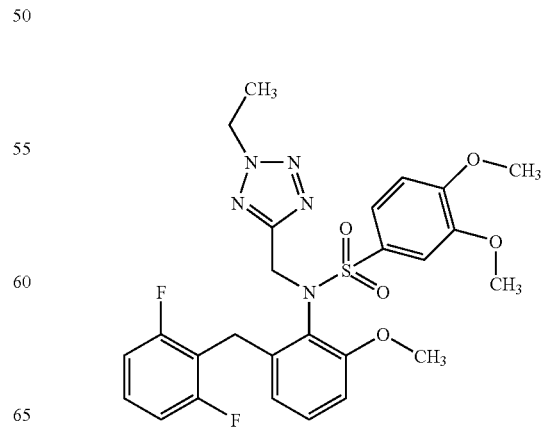

Compound 311:

N-[2-(2,6-difluorobenzyl)-6-methoxyphenyl]-N-[(1-ethyl-1H-tetrazol-5-yl)methyl]-3,4-dimethoxybenzenesulfonamide

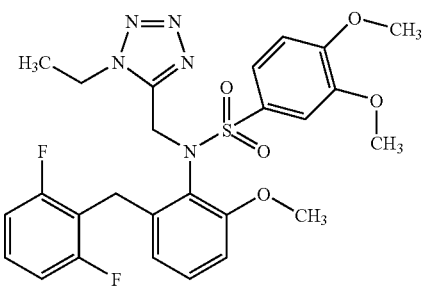

Compound 312:

N~2~-[(3,4-dimethoxyphenyl)sulfonyl]-N~2~-(3-methoxybiphenyl-2-yl)glycinamide

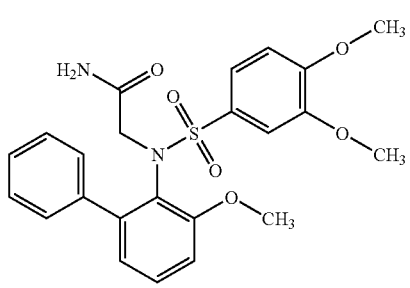

Compound 313:

N-[4-chloro-2-(2,6-difluorobenzyl)phenyl]-3,4-dimethoxy-N-{2-[(methylsulfonyl)amino]ethyl}-benzenesulfonamide

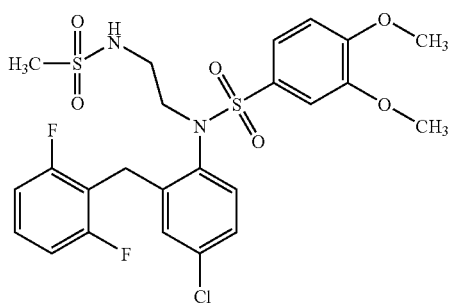

Compound 314:

N~2~-[4-chloro-2-(2,6-difluorobenzyl)phenyl]-N~2~-[(2-fluoro-4,5-dimethoxyphenyl)sulfonyl]glycinamide

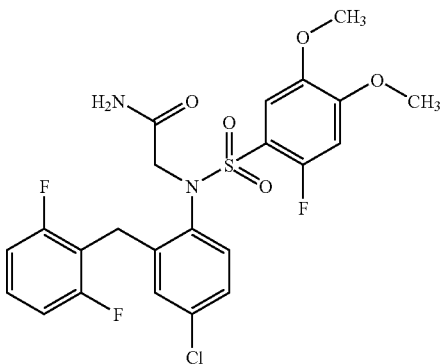

Compound 315:

methyl N-[2-(2,6-difluorobenzyl)-6-methoxyphenyl]-N-[(3,4-dimethoxyphenyl)sulfonyl]-L-alaninate

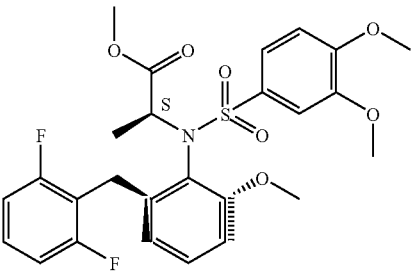

Compound 316:

methyl N-[2-(2,6-difluorobenzyl)-6-methoxyphenyl]-N-[(3,4-dimethoxyphenyl)sulfonyl]-L-alaninate

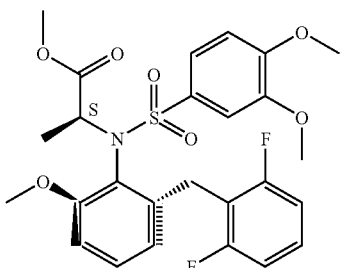

Compound 317:

methyl N-[2-(2,6-difluorobenzyl)-6-methoxyphenyl]-N-[(3,4-dimethoxyphenyl)sulfonyl]-D-alaninate

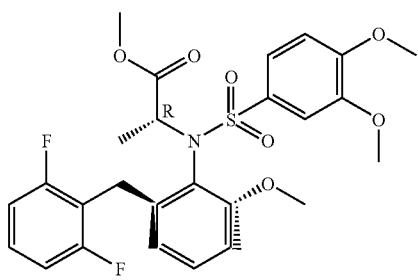

Compound 318:

methyl N-[2-(2,6-difluorobenzyl)-6-methoxyphenyl]-N-[(3,4-dimethoxyphenyl)sulfonyl]-D-alaninate

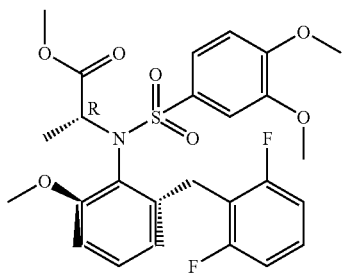

Compound 319:

N~2~-[(4-tert-butylphenyl)sulfonyl]-N~2~-[2-(2,6-difluorobenzyl)-6-methoxyphenyl]glycinamide

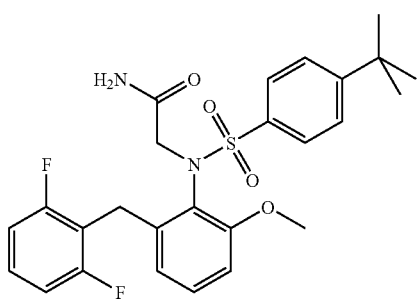

Compound 320:

N~2~-[2-(2,6-difluorobenzyl)-6-methoxyphenyl]-N~2~-[(3,4-difluorophenyl)sulfonyl]glycinamide

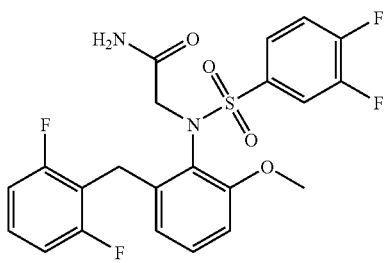

Compound 321:

N²-[2-(2,6-difluorobenzyl)-6-methoxyphenyl]-N²-[(3,4-dimethoxy phenyl)sulfonyl]-R-alaninamide Compound 322:

N²-[2-(2,6-difluorobenzyl)-6-methoxyphenyl]-N²-[(3,4-dimethoxyphenyl)sulfonyl]-S-alaninamide

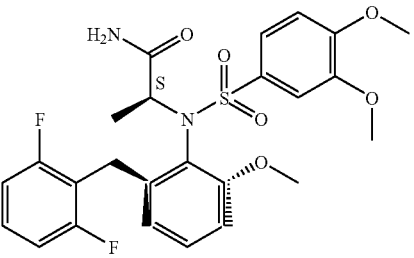

Compound 323:

N²-[2-methoxy-6-(2-phenylethyl)phenyl]-N²-[(3,4-dimethoxy phenyl)sulfonyl]glycinamide

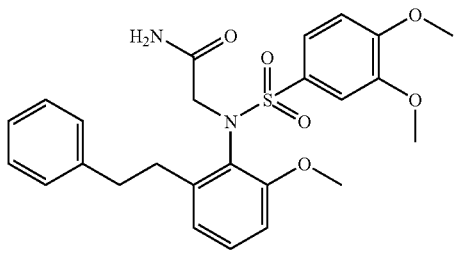

In the context of the invention, the following meanings apply:
- a ($C_1$-$C_4$) alkyl group: a saturated, linear or branched aliphatic group containing from 1 to 4 carbon atoms, such as methyl, ethyl, propyl, isopropyl, butyl, isobutyl, sec-butyl or tert-butyl;
- an optionally substituted ($C_1$-$C_4$) alkyl group: an alkyl group as defined above in which one or more hydrogen atoms have been substituted with a substituent;
- a ($C_3$-$C_6$) cycloalkyl group: a saturated cyclic alkyl group containing from 3 to 6 carbon atoms, for example cyclopropyl, cyclobutyl, cyclopentyl or cyclohexyl. The cycloalkyl group may optionally be substituted with a ($C_1$-$C_4$) alkyl group, for example methylcyclopropyl, dimethylcyclopropyl, methylcyclobutyl, methylcyclopentyl, methylcyclohexyl or dimethylcyclohexyl;
- a ($C_1$-$C_4$) alkoxy group: a ($C_1$-$C_4$) alkyl-O-radical in which the ($C_1$-$C_4$) alkyl group is as defined above, for example methoxy, ethoxy, propoxy, isopropoxy, butoxy, isobutoxy, sec-butoxy or tert-butoxy;
- a ($C_1$-$C_4$) alkylcarbonyl group: a ($C_1$-$C_4$) alkyl-C(O)- group in which the ($C_1$-$C_4$) alkyl group is as defined above;
- a fluoro ($C_1$-$C_4$)alkyl group: a ($C_1$-$C_4$) alkyl group as defined above, one or more hydrogen atoms of which have been substituted with one or more fluorine atoms. Examples that may be mentioned include the —$CF_3$ and —$CH_2$—$CF_3$ groups;
- a ($C_1$-$C_4$) alkenyl group: a linear or branched monounsaturated or polyunsaturated aliphatic group containing from 1 to 4 carbon atoms, for example having one or two ethylenic unsaturations;
- a fluoro ($C_1$-$C_4$)alkoxy group: a ($C_1$-$C_4$) alkoxy group as defined above, one or more hydrogen atoms of which have been substituted with one or more fluorine atoms. Examples that may be mentioned include the —O—$CF_3$ and —O—$CH_2$—$CF_3$ groups;
- a halogen atom; a fluorine atom, a chlorine atom, a bromine atom or an iodine atom;
- an aryl group: a monocyclic or bicyclic aromatic group containing between 6 and 10 carbon atoms, for example phenyl or naphthyl. The aryl group may optionally be substituted with 1, 2, 3 or 4 substituents. Examples of substituents that may be mentioned include a halogen atom, a ($C_1$-$C_4$) alkyl group, a ($C_1$-$C_4$) alkoxy group, a fluoro ($C_1$-$C_4$)alkyl group, a fluoro ($C_1$-$C_4$)alkoxy group, a hydroxyl group, a —CN group, a nitro group and a group —CO—$NR_aR_b$ with $R_a$ and $R_b$ being, independently of each other, a hydrogen atom or a ($C_1$-$C_4$) alkyl group;
- a heterocyclyl group: a saturated, unsaturated or aromatic monocyclic or bicyclic group containing between 5 and 10 atoms and comprising from 1 to 4 hetero atoms chosen from nitrogen, oxygen and sulfur. Examples that may be mentioned include 1,3-dioxolanyl, imidazolyl, tetrazolyl, oxadiazolyl, pyridyl, thiazolyl, thienyl, pyrimidinyl and triazolyl. The heterocyclyl group may optionally be substituted with 1, 2, 3, 4 or 5 substituents. Examples of substituents that may be mentioned include a halogen atom, a ($C_1$-$C_4$) alkyl group, a ($C_1$-$C_4$) alkoxy group, a hydroxyl group and a —CN group.

As already indicated, the compounds of general formula (I) may comprise one or more asymmetric carbons. They may therefore exist in the form of enantiomers or diastereoisomers. These enantiomers and diastereoisomers, and also mixtures thereof, including racemic mixtures, form part of the invention.

By virtue of their structure, the compounds of general formula (I) may also exist in the form of rotamers. In the context of the invention, the term "rotamers" means compounds that have identical structural formulae but different set spatial conformations. These differences in the set spatial conformations of these compounds can give them different physicochemical properties and even, in certain cases, different biological activities.

The compounds of general formula (I) may also exist in the form of atropoisomers. Atropoisomers are compounds of identical structural formulae, but which have a particular spatial configuration, resulting from a restricted rotation about a single bond, due to large steric hindrance on either side of this single bond. Atropoisomerism is independent of the presence of stereogenic components, such as an asymmetric carbon.

The compounds of formula (I) may exist in the form of bases or of acid-addition salts. Such addition salts form part of the invention.

These salts are advantageously prepared with pharmaceutically acceptable acids, but the salts of other acids that are useful, for example, for purifying or separating the compounds of general formula (I) also form part of the invention.

The compounds of general formula (I) may also be in the form of hydrates or solvates, i.e. in the form of associations or combinations with one or more water molecules or with a solvent. Such hydrates and solvates also form part of the invention.

In the text hereinbelow, the term "leaving group" means a group that may be readily cleaved from a molecule, with loss of an electron pair, by breaking a heterolytic bond. This group may thus be readily replaced with another group, for example during a substitution reaction. Such leaving groups are, for example, halogens, or an activated hydroxyl group such as a mesylate, tosylate, triflate, acetyl, etc. Examples of leaving groups and references for preparing them are given in "Advanced Organic Chemistry", J. March, 3$^{rd}$ Edition, Wiley Interscience, pp. 310-316.

A subject of the present invention is also the process for preparing the compounds of general formula (I).

Thus, the compounds of general formula (I) may be prepared via the processes illustrated in scheme 1. According to this scheme, the compounds of formula (I) may be obtained:
- either via alkylation of the compounds of general formula (II) with compounds of general formula (IV), in the presence of a base, according to an adaptation of the process described by Levin et al., Bioorg. Med. Chem., 2001, EN 11; 22; 2975-2978;

or via a Mitsunobu reaction between the alcohols of formula (X) and the compounds of general formula (II).

In the compounds of general formulae (II), (IV) and (X), $Ar_1$, $Ar_2$, $Ar_3$, T and $R_1$ are as defined in formula (I) and Z is a leaving group such as a halogen atom chosen from bromine, chlorine and iodine; or alternatively a mesylate, a tosylate or a triflate.

The base may be an organic base, for instance potassium tert-butoxide, or a mineral base, for instance potassium carbonate, or alternatively a phase-transfer agent, for instance tetrabutylammonium bromide.

In the Mitsunobu reaction, diisopropyl azodicarboxylate (DIAD) may be replaced with analogues thereof, for instance diethyl azodicarboxylate and ditert-butyl azodicarboxylate, and the triphenylphosphine may be grafted onto a resin (R. G. Gentles et al., J. Comb. Chem. 2002, 4, 442-456).

The compounds of structure (I) for which T=

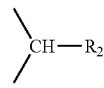

with $R_2$ being a hydroxyl group may be obtained, in certain cases, from the corresponding compounds for which

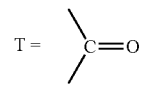

via the action of hydride, for example sodium borohydride.

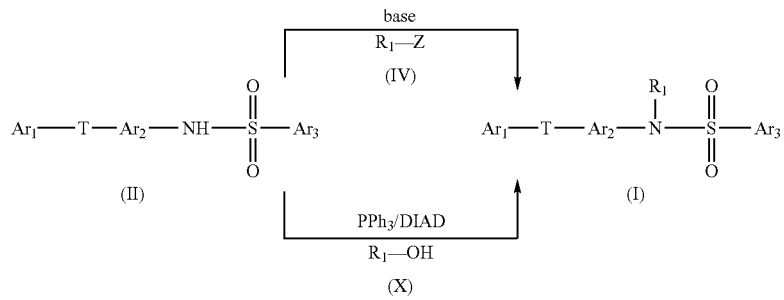

The compounds of structure (I) for which $R^1$ is a sequence of the type —$CR_7R_8$—$(CH_2)_n$—$R_9$, with $R_9$=$CONR_{12}R_{13}$, may be obtained from the corresponding esters of formula —$CR_7R_8$—$(CH_2)_n COOR_{14}$, according to the following reaction sequence: saponification of the carboxylate function —$COOR_{14}$; activation of the carboxylic acid function generated, for example with chloroformates to form mixed anhydrides; amidation reaction with amines of the type $NHR_{12}R_{13}$ with n, $R_7$, $R_8$, $R_{12}$, $R_{13}$ and $R_{14}$ as defined above.

The compounds of structure (I) for which $R_1$ is a sequence of the type —$CR_7R_8$—$(CH_2)_n$—$R_9$ with $R_9$=—NH—CO—$NR_{15}R_{16}$ may be obtained from compounds (I) for which $R_9$=$NH_2$ via the action of isocyanates of the type $R_{15}$NCO or $R_{16}$NCO with n, $R_7$, $R_8$, $R_{15}$ and $R_{16}$ as defined above.

The compounds of structure (I) for which $R_1$ is a sequence of the type —$CR_7R_8$—$(CH_2)_n$—$R_9$, $R_9$=—$NR_{10}R_{11}$ in which $R_{10}$ and $R_{11}$, independently of each other, represent a hydrogen atom and a ($C_1$-$C_4$) alkylcarbonyl group, may be obtained from compounds (I) for which $R_9$=$NH_2$ via the action of carboxylic acids of formula ($C_1$-$C_4$)alkyl-COOH or the acid chlorides thereof of formula ($C_1$-$C_4$)alkyl-COCl with n, $R_7$, $R_8$, $R_{10}$ and $R_{11}$, as defined above.

The compounds (I) for which $R_9$ is a heterocyclyl group such as substituted tetrazolyl are obtained via standard chemical reactions known to those skilled in the art, from compounds (I) for which $R_9$ is a cyano group.

The compounds of structure (I) for which T=—$(CH_2)_n$ with n=1 may be obtained, in certain cases, from compounds of structure (I) for which T=—CHOH, via the action of hydride, for example triethylsilane, in the presence of boron trifluoride etherate.

The compounds of structure (II) are obtained beforehand according to scheme 2, via sulfonylation of the compound of formula (III) with sulfonyl chlorides of formula (V) in the presence of a base chosen from tertiary amines such as pyridine, according to the process described by Stauffer et al., Bioorg. Med. Chem., 2000, EN 8, 6, 1293-1316. Tertiary amines that may also be used include triethylamine and diisopropylethylamine.

In certain cases, it may even be envisaged to use a mixture of tertiary amines.

The compounds of formula (V) are commercial or may be obtained by adaptation of the processes described, for example, by A. J. Prinsen et al., Recl. Trav. Chim. Netherlands 1965, EN 84, 24.

In the compounds of formulae (III) and (V), $Ar_1$, $Ar_2$, $Ar_3$ and T are as defined in formula (I).

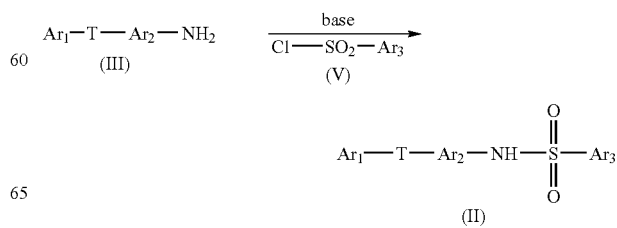

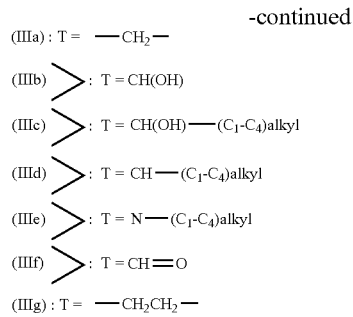

(IIIa) : T = —CH₂—

(IIIb) >: T = CH(OH)

(IIIc) >: T = CH(OH)—(C₁-C₄)alkyl (IIId) >: T = CH—(C₁-C₄)alkyl (IIIe) >: T = N—(C₁-C₄)alkyl (IIIf) >: T = CH=O (IIIg) : T = —CH₂CH₂—

The compounds of formulae (IIIa), (IIIb) and (IIIf) are prepared according to schemes 3 to 5. The 2-nitroaldehyde derivatives of formula (VI) react with organometallic compounds of formula (VII) in which M represents an MgBr, MgI, ZnI or Li group to give the compounds of structure (VIII). The organometallic compounds of formula (VII) are commercial or are formed according to the standard processes described in the literature. The nitro alcohols of formula (VIII) are reduced via hydrogenation, for example under the action of tin metal and concentrated hydrochloric acid in ethanol, to give the compounds of structure (IIIb). The derivatives of formula (IIIb) are reduced via the action of hydrides, for example with a mixture of triethylsilane and trifluoroacetic acid in dichloromethane to give the derivatives of formula (IIIa).

The nitroaldehydes of formula (VI) are commercial or may be prepared, for example, according to an adaptation of the process described by J. Kenneth Horner et al., J. Med. Chem., 1968, 11; 5; 946.

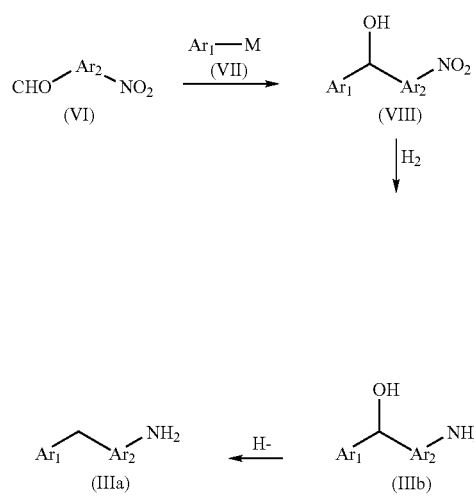

Scheme 3

Other possibilities for synthesizing the compounds of general formula (IIIb) and (IIIf) are presented in scheme 4.

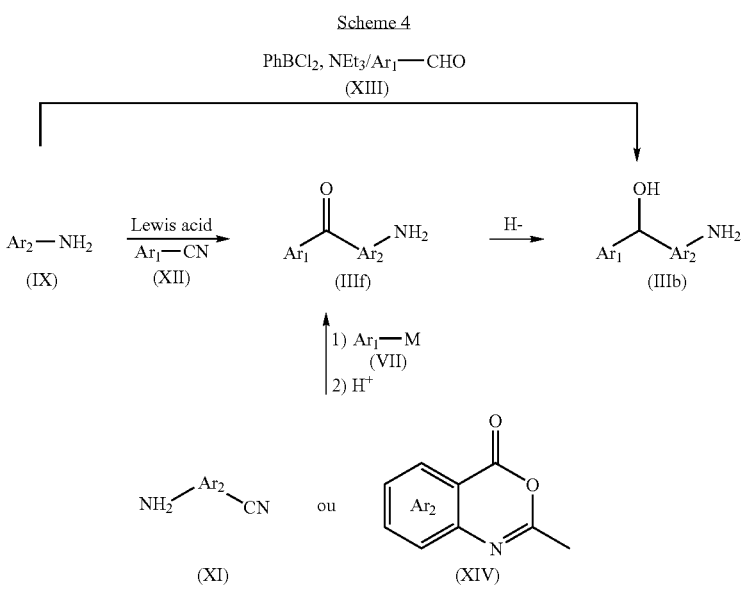

Scheme 4

The anilines of formula (IX) are condensed with nitriles of formula (XII), in the presence of a Lewis acid, for instance boron trichloride with aluminium trichloride or with gallium trichloride, to give the compounds of formula (IIIf), according to the process described by T. Sugasawa et al., J.A.C.S. 1978; 100; 4842. The compounds of formula (IIIf) may be obtained via condensation of aminonitriles (XI) with the organometallic derivatives (VII), according to the process described by R. Fryer et al., J. Heterocycl. Chem., 1991, EN 28; 7, 1661. The compounds of formula (IIIf) may also be obtained from the intermediate (XIV) according to an adaptation of the process described by D. Lednicer, J. Heterocyclic. Chem., 1971; 903.

The carbonyl function of the compounds (IIIf) is reduced via the action of a hydride, for example sodium borohydride in ethanol, to give the compounds of structure (IIIb).

Another method for preparing the compounds of formula (IIIb) consists in condensing the anilines of formula (IX) with benzaldehyde derivatives of formula (XIII) in the presence of phenyldichloroborane and triethylamine, according to the process described by T. Toyoda et al., Tet. Lett., 1980, 21, 173.

It should be noted that the compounds of formula (IIIf), under the action of triethylsilane and trifluoroacetic acid, for example, may give the compounds of formula (IIIa).

Another possibility for synthesizing the compounds of general formula (IIIa), in which $Ar_1$ represents a heteroaryl, is presented in scheme 5.

Scheme 5

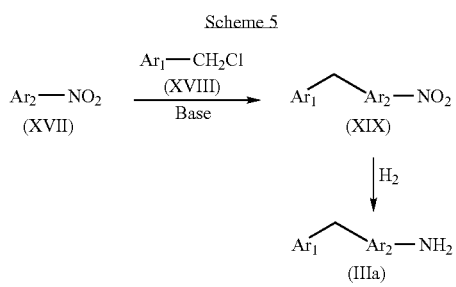

The nitrophenyls of formula (XVII) are condensed onto chloromethyl heteroaryls of formula (XVIII) in the presence of a base, for example potassium tert-butoxide, to give the derivatives (XIX) according to the process described by Florio S. et al., Eur. J. Org. Chem., 2004, 2118, which are reduced, for example, via the action of tin metal in the presence of 12M hydrochloric acid, to give the derivatives of formula (IIIa).

The compounds of formulae (IIIc) and (IIId) are prepared according to scheme 6.

The compounds of formula (IIIf), under the action of a $(C_1-C_4)$ alkylmagnesium reagent, give the derivatives of formula (IIIc). These compounds are dehydroxylated under the action of aluminium trichloride and lithium aluminium hydride to give the compounds (IIId).

Scheme 6

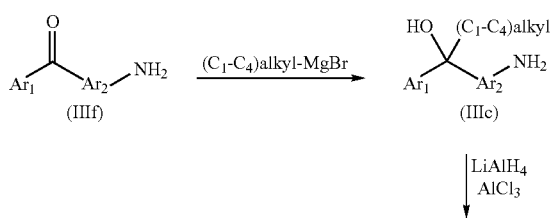

-continued

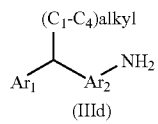

The compounds of formula (IIIe) are prepared according to scheme 7. The derivatives (XV), under the action of a base, for example caesium carbonate and a $C_1-C_4$ alkyl halide, give the derivatives (XVI). The nitro group of these derivatives may be reduced, for example, in the presence of tin metal and hydrochloric acid in ethanol to give the compounds of formula (IIIe).

Scheme 7

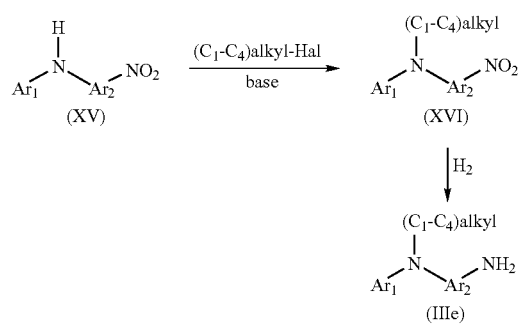

The compounds of formula (IIIg) are prepared according to scheme 8. The nitroaldehydes (VI), via condensation with the derivatives (XX) according to a Wittig reaction, give the compounds (XXI). These derivatives are reduced, for example by catalytic hydrogenation with palladium, to give the compounds of formula (IIIg).

Scheme 8

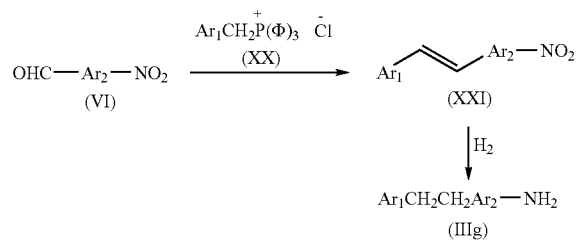

In all the schemes and for all the compounds of formulae (II) to (XXI), the meanings of $Ar_1$, T, $Ar_2$, $Ar_3$ and $R_1$ are as defined for the compounds of general formula (I).

In schemes 1 to 8, the starting compounds and the reagents, when their mode of preparation is not described, are commercially available or described in the literature, or alternatively may be prepared via methods described therein or known to those skilled in the art.

When a compound comprises a reactive function, for example a hydroxyl group, it may necessitate prior protection before reaction. A person skilled in the art can determine the need for prior protection.

The compounds of formulae (II) to (XXI) are useful as synthetic intermediates for the preparation of the compounds of general formula (I) and form an integral part of the present invention.

The examples that follow describe the preparation of the compounds in accordance with the invention. These examples are not limiting and serve merely to illustrate the invention.

The numbers of the compounds given as examples refer to those given in the above table. The elemental microanalyses, the mass spectra and the NMR spectra confirm the structures of the compounds obtained.

The analysis conditions by liquid chromatography coupled to mass spectrometry LC/MS are the following:
for the liquid chromatography part: C18 symmetry column (2.1×50 mm) 3-5 μm. Eluent A=$H_2O$+0.005% TFA, pH=3.14; eluent B=$CH_3CN$+0.005% TFA, with a gradient of from 100% A to 90% B over 10 minutes, then 5 minutes at 90% B
for the mass spectrometry part: positive electrospray ionization mode.

When the $^1H$ NMR spectrum reveals rotamers, only the interpretation corresponding to the major rotamer is described.

In the following tables:
m.p. (° C.) represents the melting point of the compound in degrees Celsius
$MH^+$ represents the mass peak of the ionized product
the retention time is expressed in minutes
n.d. means "not determined".

EXAMPLE 1

Ethyl N-{4-chloro-2-[(2-chlorophenyl)(hydroxy) methyl]phenyl}-N-[(3,4-dimethoxyphenyl)sulfonyl] glycinate (compound 1)

EXAMPLE 1.1

N-[4-chloro-2-(2-chlorobenzoyl)phenyl]-3,4-dimethoxybenzene sulfonamide

To 5.3 g of (2-amino-5-chlorophenyl)(2-chlorophenyl)methanone dissolved in 50 ml of pyridine are added 5.29 g of 3,4-dimethoxybenzenesulfonyl chloride, and the mixture is left for 3 hours at room temperature. The reaction medium is concentrated, the residue is taken up in diisopropyl ether and the precipitate formed is filtered off to give, after drying, 5.2 g of the expected product.

$^1H$ NMR δ in ppm (DMSO d6): 3.75 (s, 3H); 3.83 (s, 3H); 7.06-7.69 (unresolved complex, 11H).

EXAMPLE 1.2

N-{4-chloro-2-[(2-chlorophenyl)(hydroxy)methyl] phenyl}-3,4-dimethoxybenzenesulfonamide 16 g of N-[4-chloro-2-(2-chlorobenzoyl)phenyl]-3,4-dimethoxybenzenesulfonamide dissolved in 900 ml of ethanol are added portionwise 3.93 g of sodium borohydride, and the mixture is left for 18 hours at room temperature. The reaction medium is concentrated and the residue is taken up in ethyl acetate and washed with water. The organic phase is dried over anhydrous sodium sulfate and concentrated. The residue is solidified with diisopropyl ether; after filtering off and drying the precipitate, 14.66 g of the expected product are obtained.

$^1H$ NMR δ in ppm (DMSO d6): 3.77 (s, 3H); 3.84 (s, 3H); 6.27 (s, 1H); 6.96-7.44 (unresolved complex, 10H).

EXAMPLE 1.3

Ethyl N-{4-chloro-2-[(2-chlorophenyl)(hydroxy) methyl]phenyl}-N-[(3,4-dimethoxyphenyl)sulfonyl] glycinate To 6 g of N-{4-chloro-2-[(2-chlorophenyl)(hydroxy)methyl]phenyl}-3,4-dimethoxybenzenesulfonamide dissolved in 50 ml of DMF at 0° C. is added portionwise 0.674 g of sodium hydride. After 1 hour at 0° C., 1.4 ml of ethyl 2-bromoacetate are introduced and the mixture is left for 18 hours at room temperature. The reaction medium is taken up in ethyl acetate and washed with water. The organic phase is dried over anhydrous sodium sulfate and concentrated. The residue is chromatographed on a column of silica gel, eluting with dichloromethane to give 1.3 g of the expected product.

$^1H$ NMR δ in ppm (DMSO d6): 1.03 (t, 3H); 2.90 (d, 1H); 3.77 (s, 3H); 3.87 (t, 3H); 4.11 (d, 1H); 4.73 (q, 2H); 5.94 (d, 1H); 6.47 (s, 1H); 7.10-7.77 (unresolved complex, 10H). m.p.=86° C.

Table I illustrates the chemical structures and physical properties of a number of compounds of the invention obtained according to this example.

TABLE I

| Compound No. | Ar₁ | Ar₂ | R₁ | Ar₃ | m.p. (° C.) | $MH^+$/ retention time |
|---|---|---|---|---|---|---|
| 8 | H | H | $CH_2CO_2Et$ | 3,4-diOMe | 58.8 | 486/8.15 |
| 7 | H | 4-Cl | $CH_2CO_2Et$ | 3,4-diOMe | 152 | 521/8.78 |
| 9 | 2-Cl | 4-Cl | $CH_2CO_2Et$ | 2,4-diOMe | 155 | 555/9.34 |
| 10 | 2-Cl | 4-Cl | $CH_2CO_2Et$ | H | 109.8 | 495/9.40 |
| 13 | 2-Cl | 4-Cl | $CH_2CO_2Et$ | 4-OMe | 98.2 | 524/9.47 |
| 18 | 2-Cl | 4-Cl | $CH_2CO_2Et$ | 3,4-diCl | 140 | 562/10.46 |
| 19 | 2-Cl | 4-Cl | $CH_2CONH_2$ | 3,4-diOMe | 154.7 | 526/7.52 |
| 28 | 2-Cl | 4-Cl | $CH_2CONH_2$ | 3,4-diMe | 205 | n.d. |
| 31 | 2-Cl | 4-Cl | $CH_2CONH_2$ | 3-Cl | 187 | 499/8.32 |
| 32 | 2-Cl | 4-Cl | $CH_2CONH_2$ | 4-OMe | 207 | 495/7.86 |

EXAMPLE 2

N-{4-chloro-2-[(2-chlorophenyl)(hydroxy)methyl] phenyl}-N-ethyl-3,4-dimethoxybenzenesulfonamide (compound 20)

To 1 g of N-{4-chloro-2-[(2-chlorophenyl)(hydroxy)methyl]phenyl}-3,4-dimethoxybenzenesulfonamide, obtained in Example 1.2, dissolved in 43 ml of acetonitrile are successively added 1.2 ml of triethylamine and 0.68 ml of iodoethane, and the mixture is refluxed for 8 hours. The reaction medium is taken up in ethyl acetate and washed with water. The organic phase is dried over anhydrous sodium sulfate and concentrated. The residue is chromatographed on a column of silica gel, eluting with a 4/6 (v/v) cyclohexane/ethyl acetate solvent mixture to obtain, after crystallization from cyclohexane, 0.418 g of the expected product.

$^1$H NMR δ in ppm (DMSO d6): 0.12 (t, 3H); 2.94 (m, 1H); 3.21 (m, 1H); 3.75 (s, 3H); 3.88 (s, 3H); 6.02 (d, 1H); 6.51 (d, 1H); 6.80 (d, 1H); 6.96-7.49 (unresolved complex, 8H); 7.91 (d, 1H). m.p.=153.9° C.

Table II illustrates the chemical structures and the physical properties of a number of compounds of the invention obtained according to this example.

TABLE II

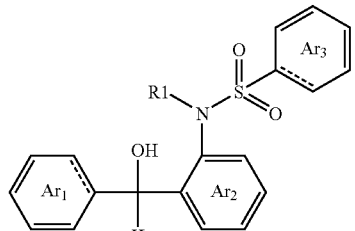

| Compound No. | Nature and position of the substituents | | | | m.p. (° C.) | MH+/ retention time |
|---|---|---|---|---|---|---|
| | Ar$_1$ | Ar$_2$ | R$_1$ | Ar$_3$ | | |
| 21 | 2-Cl | 4-Cl | CH$_2$COCH$_3$ | 3,4-diOMe | 158.5 | 540/8.72 |
| 23 | 2-Cl | 4-Cl | (CH$_2$)$_2$OMe | 3,4-diOMe | 112.2 | 526/8.77 |
| 29 | 2-Cl | 4-Cl | CH$_2$CONH$_2$ | naphthyl | 218 | 515/8.52 |
| 30 | 2-Cl | 4-Cl | CH$_2$CONH$_2$ | 3-OMe | 114.8 | 495/7.87 |

EXAMPLE 3

N$^2$-{4-chloro-2-[(2-chlorophenyl)(hydroxy)methyl]phenyl}-N$^2$-[(2,4-dimethoxyphenyl)sulfonyl]-glycinamide (compound 33)

To 1.5 g of N-{4-chloro-2-[(chlorophenyl)(hydroxy)methyl]phenyl}-3,4-dimethoxybenzenesulfonamide, obtained in Example 1.2, dissolved in 15 ml of DMF are added at room temperature 1.25 g of caesium carbonate and 0.68 g of 2-bromoacetamide, and the mixture is maintained at 100° C. for 2 hours. The reaction medium is taken up in ethyl acetate and washed with water. The organic phase is dried over anhydrous sodium sulfate and concentrated. The residue is chromatographed on a column of silica gel, eluting with a dichloromethane/methanol solvent gradient to give 0.601 g of the expected product.

$^1$H NMR δ in ppm (DMSO d6): 3.85 (s, 6H); 4.40 (d, 1H); 4.66 (d, 1H); 6.45-7.62 (unresolved complex, 14H). m.p.=158° C.

Table III illustrates the chemical structures and the physical properties of a number of compounds of the invention obtained according to this example.

TABLE III

| Compound No. | Nature and position of the substituents | | | | m.p. (° C.) | MH+/ retention time |
|---|---|---|---|---|---|---|
| | Ar$_1$ | Ar$_2$ | R$_1$ | Ar$_3$ | | |
| 36 | 2-Cl | 4-Cl | CH$_2$CONH$_2$ | 2,5-diOMe | 109 | 525/7.57 |
| 38 | 2-Cl | 4-Cl | CH$_2$CONH$_2$ | 2,5-diMe, 4-Cl | 126.3 | 527/9.16 |

EXAMPLE 4

N$^2$-{4-chloro-2-[(2-chlorophenyl)(hydroxy)methyl]phenyl}-N$^2$-[(3,4-dichlorophenyl)sulfonyl]glycinamide (compound 34)

EXAMPLE 4.1

(2-amino-5-chlorophenyl)(2-chlorophenyl)methanol

To 20 g of (2-amino-5-chlorophenyl)(2-chlorophenyl)methanone dissolved in 80 ml of ethanol are introduced portionwise 8.6 g of sodium borohydride, and the mixture is left for 18 hours at room temperature. The reaction medium is taken up in ethyl acetate and washed with water. The organic phase is dried over anhydrous sodium sulfate and concentrated to give 21.63 g of the expected product.

$^1$H NMR δ in ppm (DMSO d6): 5.16 (s, 2H); 5.70 (d, 1H); 5.98 (d, 1H); 6.63 (d, 1H); 6.85-7.29 (unresolved complex, 6H).

EXAMPLE 4.2

N-{4-chloro-2-[(2-chlorophenyl)(hydroxy)methyl]phenyl}-3,4-dichlorobenzenesulfonamide To 0.9 g of (2-amino-5-chlorophenyl)(2-chlorophenyl)methanol dissolved in 4 ml of pyridine is added 0.822 g of 3,4-dichlorobenzenesulfonyl chloride, and the mixture is left for 30 minutes at room temperature. The reaction medium is taken up in ethyl acetate and washed with water, and then with 1M hydrochloric acid solution. The organic phase is dried over anhydrous sodium sulfate and concentrated. The residue is chromatographed on a column of silica gel, eluting with dichloromethane, to give 0.601 g of the expected product.

$^1$H NMR δ in ppm (DMSO d6): 6,07 (s, 1H); 6.25 (s, 1H); 7.06-7.69 (unresolved complex, 11H).

EXAMPLE 4.3

N²-{4-chloro-2-[(2-chlorophenyl) (hydroxy)methyl]phenyl}-N²-[(3,4-dichlorophenyl)sulfonyl]glycinamide To 1.315 g of N-{4-chloro-2-[(2-chlorophenyl)(hydroxy)methyl]phenyl}-3,4-dimethoxybenzenesulfonamide, obtained in Example 1.2, dissolved in 10 ml of tetrahydrofuran are added, at room temperature, 0.37 g of potassium tert-butoxide and 0.46 g of 2-bromoacetamide, and the mixture is refluxed for 3 hours. After 18 hours at room temperature, the reaction medium is taken up in ethyl acetate and washed with water. The organic phase is dried over anhydrous sodium sulfate and concentrated. The residue is chromatographed on a column of silica gel, eluting with a dichloromethane/methanol solvent gradient to give 1.06 g of the expected product.

¹H NMR δ in ppm (DMSO d6): 4.41 (q, 2H); 6.42 (d, 1H); 6.67 (s, 2H); 7.02 (m, 1H); 7.18-7.92 (unresolved complex, 10H) m.p.=135° C.

Table IV illustrates the chemical structures and the physical properties of a number of compounds of the invention obtained according to this process.

Compound 83 is obtained by alkylation with the derivative 5-bromomethyl-3-methyl[1,2,4]oxadiazole, which is synthesized as follows:

Synthesis of (1,3-dioxo-1,3-dihydro-2H-isoindol-2-yl)acetyl chloride

To 10.25 g of (1,3-dioxo-1,3-dihydro-2H-isoindol-2-yl) acetic acid dissolved in 50 ml of dichloromethane are added, at room temperature, 4.6 ml of oxalyl chloride and 2 drops of DMF, and the mixture is left for 18 hours at room temperature. The resulting mixture is evaporated to dryness to give 11 g of the expected product.

Synthesis of 2-(3-methyl[1,2,4]oxadiazol-5-yl)isoindol-1,3-dione

To 4.4 g of (1,3-dioxo-1,3-dihydro-2H-isoindol-2-yl) acetyl chloride in 20 ml of pyridine are added 1.48 g of acetamidoxime, and the mixture is refluxed for 1 hour. The reaction medium is concentrated and taken up in ethyl acetate and water. The organic phase is dried over anhydrous sodium sulfate and concentrated. The residue is chromatographed on

TABLE IV

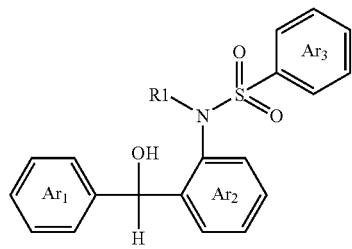

| Compound No. | \multicolumn{4}{c}{Nature and position of the substituents} | m.p. (° C.) | MH⁺/retention time |
|---|---|---|---|---|---|---|
| | Ar₁ | Ar₂ | R₁ | Ar₃ | | |
| 35 | 2-Cl | 4-Cl | CH₂CONH₂ | 4-Cl | 130 | 499/8.41 |
| 37 | 2-Cl | 4-Cl | CH₂CONH₂ | 2-Cl | 137 | 4997.75 |
| 41 | 2-Cl | 4-Cl | CH₂CONH₂ | 2,3-diOMe | 222 | 526/8.76 |
| 64 | 2-Cl | 4-Cl | CH₂CONH₂ | 3,4-ethylenedioxy | 102.1 | 523/7.64 |
| 79 | 2-Cl | 4-Cl | CH₂CONH₂ | 2-Me | 134 | 479/8.24 |
| 106 | 2-Cl | 4-Cl | CH₂CONH₂ | 2,4,5-triMe | 150.2 | 507/8.95 |
| 110 | 2-Cl | 4-Cl | CH₂CONHMe | 2,4,5-triMe | 171.7 | 521/9.25 |
| 113 | 2-Cl | 4-Cl | CH₂CONHMe | 2,4,5-triOMe | 119.6 | 569/7.67 |
| 129 | 2-Cl | 4-Cl | CH₂CON(Me)₂ | 2,4-diCl-5-Me | 204.8 | 557/10.35 |
| 132 | 2-Cl | 4-Cl | CH₂CONHMe | 3,5-diMe | 109 | 489*/9.48 |
| 133 | 2-Cl | 4-Cl | CH₂CON(Me)₂ | 3,5-diMe | 142 | 520/9.85 |
| 52 | 2-Cl | 4-Cl | CH₂CONH₂ | H | 170.6 | 465/7.75 |
| 85 | 2-Cl | 4-Cl | CH₂CONH₂ | 2,6-diCl | 149 | 533/8.01 |
| 72 | 2-Cl | 4-Cl | CH₂CONHMe | 3,4-diOMe | 88 | 539/7.89 |
| 86 | 2-Cl | 4-Cl | CH₂CONH₂ | 3,5-diMe | 137 | 493/8.60 |
| 94 | 2-Cl | 4-Cl | CH₂CONH₂ | 2,5-diOMe, 4-Me | 180.8 | 539/8.25 |
| 102 | 2-Cl | 4-Cl | CH₂CONH₂ | 2,4,5-triOMe | 123.5 | 555/7.36 |
| 83 | 2-Cl | 4-Cl | (3-methyl-1,2,4-oxadiazol-5-yl) methyl | 3,4-diOMe | 90 | 564/9.15 |
| 22 | 2-Cl | 4-Cl | (1-methyl-1H-imidazol-2-yl) methyl | 3,4-diOMe | 199 | 562/5.30 |
| 148 | 2-Cl | 4-Cl | CH₂CONH₂ | 3-NH2 | 189.6 | 462*/7.86 |

*the ion observed is the M-H₂O + H⁺ a column of silica gel, eluting with a 7/3 (v/v) toluene/ethyl acetate mixture to give 1.2 g of expected product.

$^1$H NMR δ in ppm (DMSO d6): 2.26 (s, 2H); 2.34 (s, 3H); 3.92 (s, 2H).

Synthesis of 1-(3-methyl[1,2,4]oxadiazol-5-yl)methanamine

To 5 g of 2-(3-methyl[1,2,4]oxadiazol-5-yl)isoindol-1,3-dione dissolved in 100 ml of ethanol are added 2 ml of hydrazine hydrate, and the mixture is refluxed for 2 hours. The insoluble material is filtered off and the filtrate is concentrated. The residue is taken up in diethyl ether, the insoluble material is filtered off and the filtrate is concentrated to give 2 g of the expected product.

$^1$H NMR δ in ppm (DMSO d6): 2.39 (s, 3H); 4.88 (s, 2H).

Synthesis of 5-bromomethyl-3-methyl[1,2,4]oxadiazole

To 2.26 g of 1-(3-methyl[1,2,4]oxadiazol-5-yl)methanamine dissolved in 10 ml of water and 20 ml of 6M hydrobromic acid are added dropwise, at 70° C., 2.76 g of sodium nitrite dissolved in 10 ml of water. After 1 hour at 80° C., the medium is cooled to room temperature, taken up in ethyl acetate and washed with water. The organic phase is dried over anhydrous sodium sulfate and concentrated to give 2.6 g of the expected product.

$^1$H NMR δ in ppm (DMSO d6): 2.39 (s, 3H); 4.88 (s, 2H).

Compound 22 is obtained by alkylation with the derivative 2-chloromethyl-1-methylimidazole, which is synthesized as follows:

Synthesis of 1-methyl-2-imidazolemethanol

To 10 g of 1-methyl-2-imidazolecarboxaldehyde dissolved in 200 ml of methanol are added 5.2 g of sodium borohydride, and the mixture is left for 48 hours at room temperature. The solvents are evaporated off and the residue is taken up in ethyl acetate and washed with water. The organic phase is dried over anhydrous sodium sulfate and concentrated to give 6.5 g of the expected product.

$^1$H NMR δ in ppm (DMSO d6): 3.67 (s, 3H); 4.49 (d, 2H); 5.36 (t, 1H); 6.78 (d, 1H); 7.08 (d, 1H). m.p.=108.2° C.

Synthesis of 2-chloromethyl-1-methylimidazole

To 1.12 g of 1-methyl-2-imidazolemethanol are added dropwise 1.8 ml of thionyl chloride at 0° C. After 18 hours at 20° C., the mixture is heated at 70° C. for 2 hours. The reaction medium is concentrated to give the expected product quantitatively.

$^1$H NMR δ in ppm (DMSO d6): 3.90 (s, 3H); 5.22 (s, 2H); 5.36 (t, 1H); 7.77 (d, 1H); 7.80 (d, 1H).

Compound 148 is obtained from the corresponding nitro derivative via a reduction reaction with nascent hydrogen.

EXAMPLE 5

N-{4-chloro-2-[(2-chlorophenyl)(hydroxy)methyl]phenyl}-3,4-dimethoxy-N-methylbenzenesulfonamide (compound 25)

EXAMPLE 5.1

N-[4-chloro-2-(2-chlorobenzoyl)phenyl]-3,4-dimethoxy-N-methylbenzenesulfonamide

To 1 g of N-[4-chloro-2-(2-chlorobenzoyl)phenyl]-3,4-dimethoxybenzenesulfonamide, obtained in Example 1.1, dissolved in 20 ml of dimethylformamide is added, at 0° C., 0.094 g of sodium hydride; after one hour at this temperature, 0.16 ml of iodomethane is introduced and the mixture is left at room temperature for 18 hours. The precipitate is filtered off, taken up in ethyl acetate, dried over anhydrous sodium sulfate and concentrated. The residue is washed with diethyl ether and filtered to give, after drying, 0.735 g of the expected product.

$^1$H NMR δ in ppm (DMSO d6): 2.75 (s, 3H); 3.69 (s, 3H); 3.86 (s, 3H); 6.76-7.15 (unresolved complex, 4H); 7.51-7.75 (unresolved complex, 6H). m.p.=136.6° C.

EXAMPLE 5.2

N-{4-chloro-2-[(2-chlorophenyl)(hydroxy)methyl]phenyl}-3,4-dimethoxy-N-methylbenzenesulfonamide To 0.152 g of the compound obtained in Example 5.1 dissolved in 5 ml of ethanol is added 0.036 g of sodium borohydride and the mixture is left for 18 hours at room temperature. The reaction medium is taken up in ethyl acetate and washed with water. The organic phase is dried over anhydrous sodium sulfate and concentrated. The residue is taken up in a minimum amount of ethyl acetate and the precipitate formed is filtered off and dried to give 0.067 g of the expected product.

$^1$H NMR δ in ppm (DMSO d6): 2.33 (s, 3H); 3.75 (s, 3H); 3.88 (s, 3H); 6.06 (d, 1H); 6.45 (d, 1H); 6.68 (m, 1H); 6.96-7.81 (unresolved complex, 9H). m.p.=173.2° C.

Table V illustrates the chemical structures and the physical properties of a number of compounds of the invention obtained according to this process.

TABLE V

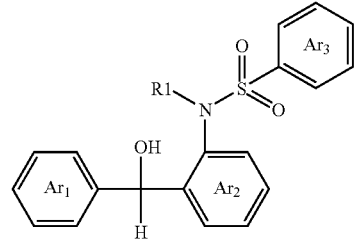

| Compound No. | Nature and position of the substituents | | | | m.p. (° C.) | MH+/retention time |
|---|---|---|---|---|---|---|
| | Ar$_1$ | Ar$_2$ | R$_1$ | Ar$_3$ | | |
| 66 | H | 4-Cl | CH$_2$CONH$_2$ | 3,4-diOMe | 201.6 | 491/7.39 |
| 137 | H | 4-Cl | CH$_2$CONHMe | 3,4-diOMe | 111.5 | 487*/8.58 |
| 57 | 2-F | 4-Cl | CH$_2$CONH$_2$ | 3,4-diOMe | 192.1 | 509/7.10 |

*the ion observed is the M-H$_2$O + H$^+$

EXAMPLE 6

Synthesis of N$^2$-{4-chloro-2-[hydroxy(3-methoxyphenyl)methyl]phenyl}-N$^2$-[(3,4-dimethoxyphenyl)sulfonyl]glycinamide (compound 51)

EXAMPLE 6.1

(2-amino-5-chlorophenyl)(3-methoxyphenyl)methanone

To 5 g of 2-amino-5-chlorobenzonitrile dissolved in 100 ml of diethyl ether are added dropwise, at −5° C., 100 ml of a molar solution in tetrahydrofuran of 3-bromobenzenemagnesium, and the mixture is left for 18 hours at room temperature. The reaction medium is hydrolysed with ice containing 6M hydrochloric acid. The resulting mixture is extracted with ethyl acetate. The organic phase is dried over anhydrous sodium sulfate and concentrated. The residue is chromatographed on a column of silica gel, eluting with a gradient of from 100 cyclohexane to 60/40 cyclohexane/dichloromethane (v/v) to give 7.26 g of the expected product.

$^1$H NMR δ in ppm (DMSO d6): 3.83 (s, 3H); 6.92 (d, 1H); 7.10-7.50 (unresolved complex, 8H).

EXAMPLE 6.2

(2-amino-5-chlorophenyl)(3-methoxyphenyl)methanol

To 3.66 g of (2-amino-5-chlorophenyl)(3-methoxyphenyl) methanone dissolved in 15 ml of ethanol are added, at 20° C., 1.59 g of sodium borohydride. After 24 hours at 20° C., the reaction medium is concentrated, taken up in ethyl acetate and washed twice with water. The organic phase is dried over anhydrous sodium sulfate and concentrated. The residue is solidified with dichloromethane to give 2.37 g of the expected product.

$^1$H NMR δ in ppm (DMSO d6): 3.74 (s, 3H); 5.14 (s, 2H); 5.70 (d, 1H); 5.94 (d, 1H); 6.61 (d, 1H); 6.81-7.27 (unresolved complex, 6H).

EXAMPLE 6.3

N-{4-chloro-2-[(3-methoxyphenyl)(hydroxy)methyl] phenyl}-3,4-dimethoxybenzenesulfonamide To 1 g of (2-amino-5-chlorophenyl)(3-methoxyphenyl) methanol dissolved in 6 ml of pyridine are added, at room temperature, 1.08 g of 3,4-dimethoxybenzenesulfonyl chloride. After 18 hours, the reaction medium is taken up in ethyl acetate and washed with water. The organic phase is dried over anhydrous sodium sulfate and concentrated. The residue is chromatographed on a column of silica gel, eluting with dichloromethane to give 1.65 g of the expected product.

$^1$H NMR δ in ppm (DMSO d6): 3.74 (s, 3H); 3.75 (s, 3H) 3.85 (s, 3H); 6.07 (s, 1H); 6.25 (s, 1H); 6.76-7.33 (unresolved complex, 10H); 9.43 (s, 1H).

EXAMPLE 6.4

N$^2$-{4-chloro-2-[hydroxy(3-methoxyphenyl)methyl] phenyl}-N$^2$-[(3,4-dimethoxyphenyl)sulfonyl]glycinamide To 0.7 g of N-{4-chloro-2-[(3-methoxyphenyl)(hydroxy) methyl]phenyl}-3,4-dimethoxybenzenesulfonamide dissolved in 5 ml of THF are added, at room temperature, 0.2 g of potassium tert-butoxide and 0.25 g of 2-bromoacetamide. After 48 hours at 20° C., the reaction medium is concentrated, taken up in ethyl acetate and washed with water. The organic phase is dried over anhydrous sodium sulfate and concentrated. The residue is chromatographed on a column of silica gel, eluting with dichloromethane to give 0.4 g of the expected product.

$^1$H NMR δ in ppm (DMSO d6): 3.76 (s, 3H); 3.78 (s, 3H); 3.90 (s, 3H); 4.12-4.53 (unresolved complex, 2H); 6.16 (d, 1H); 6.47 (d, 1H); 6.81-7.42 (unresolved complex, 11H); 7.76 (s, 1H). m.p.=100° C.

Table VI illustrates the chemical structures and the physical properties of a number of compounds of the invention obtained according to this process.

TABLE VI

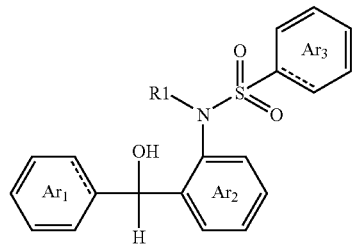

| Compound No. | Nature and position of the substituents | | | | m.p. (° C.) | MH$^+$/retention time |
|---|---|---|---|---|---|---|
| | Ar$_1$ | Ar$_2$ | R$_1$ | Ar$_3$ | | |
| 16 | 3-Cl | 4-Cl | CH$_2$CO$_2$Et | 3,4-diOMe | 149 | 554/9.48 |
| 17 | 2-OMe | 4-Cl | CH$_2$CO$_2$Et | 3,4-diOMe | 119.6 | 550/8.98 |
| 26 | 2-Me | 4-Cl | CH$_2$CO$_2$Et | 3,4-diOMe | 85.4 | 534/9.04 |
| 44 | 3-Cl | 4-Cl | CH$_2$CONH$_2$ | 3,4-diOMe | 120.1 | 525/8.95 |
| 59 | 4-OMe | 4-Cl | CH$_2$CONH$_2$ | 3,4-diOMe | 181 | 521/7.30 |
| 68 | 2-OMe | 4-Cl | CH$_2$CONH$_2$ | 3,4-diOMe | 104.6 | 521/7.26 |
| 131 | 2-Me | 4-Cl | CH$_2$CONH$_2$ | 3,4-diOMe | 144.6 | 487/8.42 |
| 76 | 3-Cl | 4-Cl | CH$_2$CONH$_2$ | 3,4-methylene-dioxy | 229 | 509/7.73 |

EXAMPLE 7

N$^2$-{4-chloro-2-{hydroxy[2-(trifluoromethyl)phenyl] methyl}phenyl)-N$^2$-[(3,4-dimethoxyphenyl)sulfonyl] glycinamide (compound 125)

EXAMPLE 7.1

6-chloro-2-methylbenzo[d][1,3]oxazin-4-one

To 15 g of 2-amino-5-chlorobenzoic acid are added 80 ml of acetic anhydride, and the mixture is refluxed for 2 hours. The reaction medium is concentrated and the residue is recrystallized from ethanol. After filtering off and rinsing the precipitate, 10.25 g of the expected product are obtained.

$^1$H NMR δ in ppm (DMSO d6): 2.40 (s, 3H); 7.58 (d, 1H) 7.97 (m, 2H).

EXAMPLE 7.2

(2-amino-5-chlorophenyl)-(2-trifluoromethylphenyl) methanone

To 1.1 g of magnesium in 22 ml of diethyl ether are added dropwise 6.05 ml of 2-trifluoromethylbromobenzene. To the magnesium reagent formed are added over 15 minutes 8 g of 6-chloro-2-methylbenzo[d][1,3]oxazin-4-one dissolved in 60 ml of dichloromethane, and the mixture is left for 18 hours at room temperature. The reaction medium is hydrolysed with saturated ammonium chloride solution and extracted with diethyl ether. After concentrating the organic phase, 7 ml of ethanol and 7 ml of 3M sodium hydroxide solution are added to the residue and the mixture is refluxed for 1 hour 30 minutes. At room temperature, the medium is extracted with diethyl ether and the ether phase is dried over anhydrous sodium sulfate and concentrated. The residue is chromatographed to give 3.3 g of the expected product.

$^1$H NMR δ in ppm (DMSO d6): 6.98 (d, 1H); 7.08-7.58 (unresolved complex, 8H).

EXAMPLE 7.3

N-[4-chloro-2-(2-trifluoromethylbenzoyl)phenyl]-3,4-dimethoxybenzenesulfonamide

Starting with 3.295 g of (2-amino-5-chlorophenyl)(2-trifluoromethylphenyl)methanone according to the process described in Example 1.1, 1.22 g of the expected product are obtained.

EXAMPLE 7.4

N-{4-chloro-2-[(2-trifluoromethylphenyl)(hydroxy)methyl]phenyl}-3,4-dimethoxybenzenesulfonamide Starting with 3 g of N-[4-chloro-2-(2-trifluoromethylbenzoyl)phenyl]-3,4-dimethoxybenzenesulfonamide according to the process described in Example 1.2, 1.566 g of the expected product are obtained.

$^1$H NMR δ in ppm (DMSO d6): 3.76 (s, 3H); 3.84 (s, 3H); 6.27 (s, 1H); 6.96-7.44 (unresolved complex, 12H).

EXAMPLE 7.5

$N^2$-{4-chloro-2-{hydroxy[2-(trifluoromethyl)phenyl]methyl}phenyl}-$N^2$-[(3,4-dimethoxyphenyl)sulfonyl]glycinamide Starting with 0.7 g of N-{4-chloro-2-[(2-trifluoromethylphenyl)(hydroxy)methyl]phenyl}-3,4-dimethoxybenzenesulfonamide according to the process described in Example 1.3, 0.265 g of expected product is obtained.

$^1$H NMR δ in ppm (DMSO d6): 3.77 (s, 3H); 3.94 (s, 3H); 4.14-4.41 (unresolved complex, 2H); 6.50 (s, 1H); 6.80 (d, 1H); 6.80-7.88 (unresolved complex, 12H). m.p.=128.8° C.

EXAMPLE 8

$N^2$-{2-[(2-chlorophenyl)(hydroxy)methyl]-4-fluorophenyl}-$N^2$-[(3,4-dimethoxyphenyl)sulfonyl]glycinamide (compound 61)

EXAMPLE 8.1

(2-nitro-5-fluorophenyl)(2-chlorophenyl)methanone

To 2.6 g of chromium trichloride suspended in 50 ml of THF are successively added 30 ml of a 0.5M solution in THF of 2-chlorophenyliodozinc, 2.54 g of 2-nitro-5-fluorobenzaldehyde and 5.7 ml of trimethylsilyl chloride. The mixture is heated at 65° C. for 1 hour and then left at room temperature for 18 hours. 1M hydrochloric acid solution is added to the reaction medium, the precipitate formed is filtered off and the filtrate is concentrated. The residue is taken up in ethyl acetate and washed with water. The organic phase is dried over anhydrous sodium sulfate and concentrated. The residue is chromatographed on a column of silica gel, eluting with cyclohexane, to give 1 g of the expected product.

$^1$H NMR δ in ppm (DMSO d6): 6.95 (d, 1H); 7.05-7.57 (unresolved complex, 8H)

EXAMPLE 8.2

(2-amino-5-fluorophenyl)-(2-chlorophenyl)methanol

To 0.5 g of (2-nitro-5-fluorophenyl)(2-chlorophenyl)methanone dissolved in 10 ml of ethanol are added 0.44 g of tin and 1.5 ml of 12M hydrochloric acid, and the mixture is left for 3 hours at room temperature. The reaction medium is concentrated and the residue is taken up in ethyl acetate and washed with 2M sodium hydroxide solution and then with saturated ammonium chloride solution. The organic phase is dried over anhydrous sodium sulfate and concentrated to give 0.453 g of the expected product.

$^1$H NMR δ in ppm (DMSO d6): 5.16 (s, 2H); 5.77 (d, 1H); 5.98 (d, 1H); 6.83-7.34 (unresolved complex, 7H).

EXAMPLE 8.3

N-{4-fluoro-2-[(2-chlorophenyl)(hydroxy)methyl]phenyl}-3,4-dimethoxybenzenesulfonamide Starting with 0.45 g of (2-amino-5-fluorophenyl)(2-chlorophenyl)methanol according to the process described in Example 1.1, 0.56 g of the expected product is obtained.

$^1$H NMR δ in ppm (DMSO d6): n.d.

EXAMPLE 8.4

$N^2$-{2-[(2-chlorophenyl)(hydroxy)methyl]-4-fluorophenyl}-$N^2$-[(3,4-dimethoxyphenyl)sulfonyl]glycinamide Starting with 0.56 g of N-{4-fluoro-2-[(2-chlorophenyl)(hydroxy)methyl]phenyl}-3,4-dimethoxybenzenesulfonamide, according to the process described in Example 4.3, 0.3 g of the expected product is obtained.

$^1$H NMR δ in ppm (DMSO d6): 3.76 (s, 3H); 3.86 (s, 3H); 4.05-4.46 (unresolved complex, 2H); 6.31 (d, 1H); 6.63 (m, 1H); 6.95-7.80 (unresolved complex, 12H). m.p.=232° C.

Table VII illustrates the chemical structures and the physical properties of a number of compounds of the invention obtained according to Example 8 (activation of the reaction by addition of trimethylsilane and chromium trichloride described in Example 8.1 was not used for compounds 69, 136 and 175).

TABLE VII

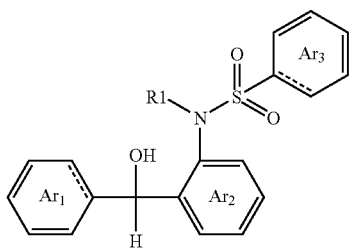

| Compound No. | Nature and position of the substituents | | | | m.p. (° C.) | MH+/retention time |
|---|---|---|---|---|---|---|
| | $Ar_1$ | $Ar_2$ | $R_1$ | $Ar_3$ | | |
| 69 | 2-Cl | 4-OMe | $CH_2CONH_2$ | 3,4-diOMe | 235.3 | 521/6.88 |

TABLE VII-continued

[Structure: Ar1-CH(OH)-[Ar2 with N(R1)-S(=O)2-Ar3 substituent]]

| Compound No. | Nature and position of the substituents | | | | m.p. (°C.) | MH+/ retention time |
|---|---|---|---|---|---|---|
| | Ar₁ | Ar₂ | R₁ | Ar₃ | | |
| 136 | 2-Cl | 4-Me | CH₂CONH₂ | 3,4-diOMe | 189.2 | 487/7.90 |
| 175 | 2-Cl | 5-Cl | CH₂CONH₂ | 3,4-diOMe | 197.1 | 507*/8.15 |

*the ion observed is the M-H₂O + H⁺

EXAMPLE 9

N²-{4-chloro-2-[(2,6-dichlorophenyl)(hydroxy)methyl]phenyl}-N²-[(3,4-dimethoxyphenyl)sulfonyl]glycinamide (compound 117)

EXAMPLE 9.1

(2-nitro-5-chlorophenyl)(2,6-dichlorophenyl)methanol

To 16.75 g of 1,3-dichlorobenzene dissolved in 250 ml of THF are added dropwise, at −70° C., 68 ml of a 1.6M solution in hexane of n-butyllithium. After one hour at −70° C., 10 g of 5-chloro-2-nitrobenzaldehyde dissolved in THF are introduced and the mixture is left for 3 hours at this temperature. The resulting mixture is hydrolysed by addition of 5 ml of acetic acid and is allowed to warm to room temperature. The resulting mixture is concentrated and the residue is chromatographed on a column of silica gel, eluting with a 90/10 (v/v) cyclohexane/ethyl acetate mixture to give 7.975 g of the expected product.

¹H NMR δ in ppm (DMSO d6): 6.82 (s, 2H); 7.32-7.46 (unresolved complex, 3H); 7.65 (d, 1H); 7.90 (m, 1H).

EXAMPLE 9.2

(2-amino-5-chlorophenyl)(2,6-dichlorophenyl)methanol

To 3.9 g of (2-nitro-5-chlorophenyl)(2,6-dichlorophenyl)methanol dissolved in 37 ml of methanol are added 5.25 g of ammonium formate and 0.374 g of platinum oxide. The mixture is left for 5 hours at room temperature and then heated at 50° C. for 18 hours. The resulting mixture is filtered through Celite and the filtrate is concentrated. The residue is taken up in ethyl acetate and washed with water. The organic phase is dried over anhydrous sodium sulfate and concentrated. The residue is chromatographed on a column of silica gel, eluting with a 90/10 (v/v) cyclohexane/ethyl acetate mixture to give 1.378 g of the expected product.

¹H NMR δ in ppm (DMSO d6): 5.16 (s, 2H); 6.17 (d, 1H); 6.35 (d, 1H); 6.64 (d, 1H); 6.72 (s, 1H); 7.01 (m, 1H); 7.38-7.55 (unresolved complex, 3H).

EXAMPLE 9.3

N-{4-chloro-2-[(2,6-dichlorophenyl)(hydroxy)methyl]phenyl}-3,4-dimethoxybenzenesulfonamide Starting with 1.9 g of (2-amino-5-chlorophenyl)(2,6-dichlorophenyl)methanol according to the process described in Example 4.2, 1.47 g of the expected product are obtained.

¹H NMR δ in ppm (DMSO d6): 3.76 (s, 3H); 3.84 (s, 3H); 6.53 (s, 1H); 6.83-7.48 (unresolved complex, 10H); 9.29 (s, 1H).

EXAMPLE 9.4

N²-{4-chloro-2-[(2,6-dichlorophenyl)(hydroxy)methyl]phenyl}-N²-[(3,4-dimethoxyphenyl)sulfonyl]glycinamide Starting with 0.7 g of N-{4-chloro-2-[(2,6-dichlorophenyl)(hydroxy)methyl]phenyl}-3,4-dimethoxybenzenesulfonamide according to the process described in Example 4.3, 0.23 g of the expected product is obtained.

¹H NMR δ in ppm (DMSO d6): 3.76 (s, 3H); 3.86 (s, 3H); 4.27 (q, 2H); 6.42 (s, 1H); 6.91-7.89 (unresolved complex, 9H); 8.02 (s, 1H). m.p.=128.3° C.

Table VIII illustrates the chemical structures and physical properties of a number of compounds of the invention obtained according to Example 9 (for all the compounds, the reduction described in Example 9.2 is performed using tin metal and 12M hydrochloric acid instead of ammonium formate and platinum oxide).

TABLE VIII

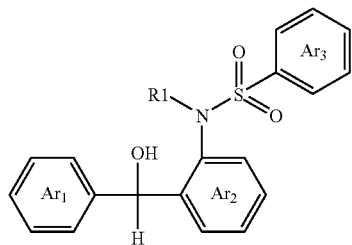

| Compound No. | Nature and position of the substituents | | | | m.p. (°C.) | MH+/retention time |
|---|---|---|---|---|---|---|
| | $Ar_1$ | $Ar_2$ | $R_1$ | $Ar_3$ | | |
| 147 | 2,6-diF | 4-Cl | $CH_2CONH_2$ | 3,5-diMe | 108.7 | 477/8.59 |
| 198 | 2,6-diF | 4-Me | $CH_2CONH_2$ | 3,4-diOMe | 175.7 | 439*/7.40 |
| 206 | 2,6-diF | 4-F | $CH_2CONH_2$ | 3,4-diOMe | 178.8 | 511/6.65 |
| 209 | 2,6-diF | 4-OMe | $CH_2CONH_2$ | 3,4-diOMe | 114.2 | 523/7.14 |
| 221 | 2,6-diF | 4,5-diCl | $CH_2CONH_2$ | 3,4-diOMe | 149.9 | 543/8.15 |
| 222 | 2-Cl, 6-F | 4-Cl | $CH_2CONH_2$ | 3,4-diOMe | 147 | 565**/8.20 |
| 225# | 2,6-diF | 6-OMe | $CH_2CONH_2$ | 3,4-diOMe | 228.7 | 523*/6.81 |
| 226# | 2,6-diF | 6-OMe | $CH_2CONH_2$ | 3,4-diOMe | 210.1 | 523*/7.25 |
| 101 | 2,6-diF | 4-Cl | $CH_2CONH_2$ | 3,4-diOMe | 134.1 | 527/7.02 |

*the ion observed is the M-$H_2O$ + $H^+$,
**the ion observed is the $MNa^+$,
rotamers

| | Enantiomers of compound 101 | |
|---|---|---|
| | Levorotatory enantiomer | Dextrorotatory enantiomer compound 251 |
| Optical rotation $[\alpha]_D$* | −64.4 | +62.4 |

C = 0.5 g/100 ml in methanol, at 25° C. and at 589 nm.

EXAMPLE 10

$N^2$-{4-chloro-2-[(2,5-dichlorophenyl)(hydroxy)methyl]phenyl}-$N^2$-[(3,4-dimethoxyphenyl)sulfonyl]glycinamide (compound 74)

EXAMPLE 10.1

(2-amino-5-chlorophenyl)(2,5-dichlorophenyl)methanone

To 28 ml of a 1M solution of trichloroborane at −5° C. are added 5.6 g of 4-chloroaniline dissolved in 30 ml of 1,2-dichloroethane. After 45 minutes at +15° C., 3.8 g of 2,5-dichlorobenzonitrile and 5 g of gallium trichloride are introduced and the mixture is refluxed for 3 hours. At room temperature, the resulting mixture is hydrolysed with 2M hydrochloric acid solution and maintained at 80° C. for 2 hours. The reaction medium is taken up in ethyl acetate and washed with water. The organic phase is dried over anhydrous sodium sulfate and concentrated. The residue is chromatographed on a column of silica gel, eluting with a cyclohexane/dichloromethane gradient to give 6.38 g of the expected product.

$^1$H NMR δ in ppm (DMSO d6): 6.90-6.96 (m, 2H); 7.37 (d, 1H); 7.60-7.72 (unresolved complex, 5H).

EXAMPLE 10.2

(2-amino-5-chlorophenyl)(2,5-dichlorophenyl)methanol

To 6.38 g of (2-amino-5-chlorophenyl)(2,5-dichlorophenyl)methanone dissolved in 50 ml of ethanol are added 2.4 g of sodium borohydride, and the mixture is left for 18 hours at room temperature. The resulting mixture is concentrated and the residue is taken up in ethyl acetate and washed with water. The organic phase is dried over anhydrous sodium sulfate and concentrated to give 2.016 g of the expected product.

$^1$H NMR δ in ppm (DMSO d6): 5.27 (s, 2H); 5.89 (d, 1H); 6.15 (d, 1H); 6.51 (d, 1H); 6.73 (d, 1H); 7.03 (d, 1H); 7.42-7.51 (m, 2H); 7.66 (s, 1H).

EXAMPLE 10.3

N-{4-chloro-2-[(2,5-dichlorophenyl)(hydroxy)methyl]phenyl}-3,4-dimethoxybenzenesulfonamide Starting with 2 g of (2-amino-5-chlorophenyl)(2,5-dichlorophenyl)methanol according to the process described in Example 4.2, 1.389 g of the expected product are obtained.

$^1$H NMR δ in ppm (DMSO d6): 3.77 (s, 3H); 3.84 (s, 3H); 6.29 (s, 2H); 6.91 (d, 1H); 7.06-7.50 (unresolved complex, 8H); 9.25 (s, 1H).

EXAMPLE 10.4

N²-{4-chloro-2-[(2,5-dichlorophenyl) (hydroxy) methyl]phenyl}-N²-[(3,4-dimethoxyphenyl)sulfonyl] glycinamide Starting with 2.42 g of N-{4-chloro-2-[(2,5-dichlorophenyl)(hydroxy)methyl]phenyl}-3,4-dimethoxybenzenesulfonamide, according to the process described in Example 4.3, 1.5 g of the expected product are obtained.

$^1$H NMR δ in ppm (DMSO d6): 3.77 (s, 3H); 3.88 (s, 3H); 4.30 (q, 2H); 6.57-6.63 (m, 2H); 6.94-7.78 (unresolved complex, 11H). m.p.=132° C.

Table IX illustrates the chemical structures and the physical properties of a number of compounds of the invention obtained according to Example 10 (for all these compounds in Example 10.1, the gallium trichloride is replaced with aluminium trichloride).

of 3-methoxy-4-methylaniline dissolved in 50 ml of dichloromethane, and 13.4 ml of triethylamine dissolved in 25 ml of dichloromethane. After 30 minutes at −20° C., 5.412 g of 2,6-difluorobenzaldehyde dissolved in 60 ml of dichloromethane are introduced. After 24 hours at room temperature, the mixture is hydrolysed with water. The organic phase is dried over anhydrous sodium sulfate and concentrated. To the oil obtained, dissolved in 80 ml of diethyl ether, are added 80 ml of 2M sodium hydroxide solution and the mixture is left stirring for 18 hours. The phases are separated by settling and the organic phase is dried over anhydrous sodium sulfate and concentrated. The residue is solidified with n-pentane to give 5.069 g of the expected product.

$^1$H NMR δ in ppm (DMSO d6): 1.98 (s, 3H); 3.69 (s, 3H); 4.74 (s, 2H); 5.79 (d, 1H); 5.98 (d, 1H); 6.30 (s, 1H); 6.75 (s, 1H); 7.06 (m, 2H); 7.41 (m, 1H).

TABLE IX

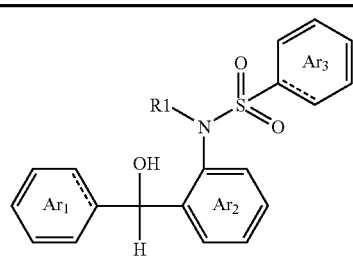

| Compound No. | Nature and position of the substituents | | | | m.p. (° C.) | MH⁺/ retention time |
|---|---|---|---|---|---|---|
| | Ar₁ | Ar₂ | R₁ | Ar₃ | | |
| 77 | 2-Cl | 4-OCF₃ | CH₂CONH₂ | 3,4-diOMe | 116 | n.d. |
| 120 | 2-thiazolyl | 4-Cl | CH₂CONH₂ | 3,4-diOMe | 93 | 497/6.42 |
| 121 | 2-thiazolyl | 4-Cl | CH₂CONHMe | 3,4-diOMe | 225 | 511/6.72 |
| 126 | 2,3-diF | 4-Cl | CH₂CONH₂ | 3,4-diOMe | 184.9 | 531**/8.16 |
| 127 | 2,3-diF | 4-Cl | CH₂CONHEt | 3,4-diOMe | 93.4 | 555/8.86 |
| 128 | 2,3-diF | 4-Cl | CH₂CON(Me)₂ | 3,4-diOMe | 100.5 | 537**/8.88 |
| 149 | 2-F, 6-OMe | 4-Cl | CH₂CONH₂ | 3,4-diOMe | 197.3 | 521*/7.66 |
| 146 | 2-thienyl | 4-Cl | CH₂CONHMe | 3,4-diOMe | 121.2 | 493**/8.20 |
| 155 | 2-thienyl | 4-Cl | CH₂CONH₂ | 3,4-diOMe | 119 | 479**/7.87 |
| 162 | 2,4,6-triF | 4-Cl | CH₂CONH₂ | 3,4-diOMe | 118.8 | 527*/7.96 |
| 163 | 2,4-diF | 4-Cl | CH₂CONH₂ | 3,4-diOMe | 161.9 | 509*/8.28 |
| 164 | 2-Cl | 4,5-diCl | CH₂CONH₂ | 3,4-diOMe | 146.7 | 541*/8.79 |
| 167 | 2-F, 4-Cl | 4-Cl | CH₂CONH₂ | 3,4-diOMe | 205.1 | 525*/8.79 |
| 176 | 2-F, 5-Cl | 4-Cl | CH₂CONH₂ | 3,4-diOMe | 195.2 | 525*/8.71 |
| 178 | 3,5-diF | 4-Cl | CH₂CONH₂ | 3,4-diOMe | 205.7 | 509*/8.93 |
| 184 | 4-pyridyl | 4-Cl | CH₂CONH₂ | 3,4-diOMe | 122 | 492/5.14 |
| 191 | 2-Cl, 6-Ome | 4-Cl | CH₂CONH₂ | 3,4-diOMe | 143.6 | 537*/8.10 |
| 194 | 2-F, 5-Me | 4-Cl | CH₂CONH₂ | 3,4-diOMe | 120.5 | 505*/8.40 |

*the ion observed is the M-H₂O + H⁺,
**the ion observed is the MNa⁺

EXAMPLE 11

N²-{2-[(2,6-difluorophenyl)(hydroxy)methyl]-5-methoxy-4-methylphenyl}-N²-[(3,4-dimethoxyphenyl)sulfonyl]glycinamide (compound 227)

EXAMPLE 11.1

(2-amino-4-methoxy-5-methylphenyl) (2,6-difluorophenyl)methanol

To 6.05 g of dichlorophenylborane dissolved in 40 ml of dichloromethane, at −20° C., are successively added 5.226 g

EXAMPLE 11.2

N-{2-[(2,6-difluorophenyl) (hydroxy)methyl]-5-methoxy-4-methylphenyl}-3,4-dimethoxybenzenesulfonamide Starting with 5.06 g of (2-amino-4-methoxy-5-methylphenyl) (2,6-difluorophenyl)methanol according to the process described in Example 4.2, 8.5 g of the expected product are obtained.

$^1$H NMR δ in ppm (DMSO d6): 2.03 (s, 3H); 3.38 (s, 3H); 3.78 (s, 3H); 3.84 (s, 3H); 5.99 (s, 1H); 6.17 (s, 1H); 6.42 (s, 1H); 6.98-7.40 (unresolved complex, 7H); 8.98 (s, 1H).

EXAMPLE 11.3

N²-{2-[(2,6-difluorophenyl)(hydroxy)methyl]-5-methoxy-4-methylphenyl}-N²-[(3,4-dimethoxyphenyl)sulfonyl]glycinamide Starting with 4.5 g of N-{2-[(2,6-difluorophenyl)(hydroxy)methyl]-5-methoxy-4-methylphenyl}-3,4-dimethoxybenzenesulfonamide, according to the process described in Example 4.3, 3.8 g of the expected product are obtained.

$^1$H NMR δ in ppm (DMSO d6): 2.18 (s, 3H); 3.43 (s, 3H); 3.79 (s, 3H); 3.87 (s, 3H); 4.09-4.37 (unresolved complex, 2H); 6.60 (d, 1H); 6.77-7.75 (unresolved complex, 11H). m.p.=203.8° C.

Table X illustrates the chemical structures and the physical properties of a number of compounds of the invention obtained according to Example 11.

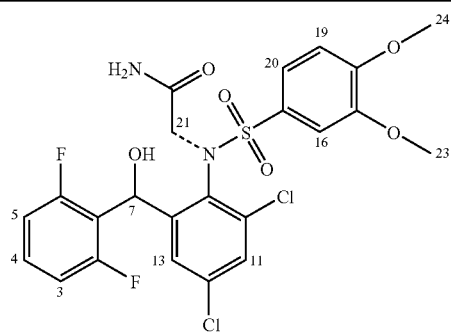

a.m.u.    □ = 7.11, s, 1H, NH₂; □ = 7.13, d, 1H,

TABLE X

| Compound No. | Ar₁ | Ar₂ | R₁ | Ar₃ | m.p. (° C.) | MH⁺/retention time |
|---|---|---|---|---|---|---|
| 213 | 2-Cl, 6-Me | 4-Cl | CH₂CONH₂ | 3,4-diOMe | 130 | 521/8.67 |
| 214# | 2,6-diF | 2,4-diCl | CH₂CONH₂ | 3,4-diOMe | 160.6 | 583**/7.80 |
| 216# | 2,6-diF | 2,4-diCl | CH₂CONH₂ | 3,4-diOMe | 235.1 | 583**/8.24 |

**the ion observed is the MNa⁺,
rotamers

Physical characteristics of the rotamers 214 and 216

| Compound 214 | $t_R$ = 7.80 min 543 a.m.u. (M-H₂O)H⁺ 583 | □ = 3.78, s, 3H, OCH₃23; □ = 3.85, s, 3H, OCH₃24; □ = 3.82, q, 2H, CH₂21; □ = 6.21, d, 1H, $J_{H7OH}$ = 5.2, OH; □ = 6.57, d, 1H, $J_{H7OH}$ = 5.2, H7; □ = 6.62, s, 1H, NH₂; □ = 6.90, t, 2H, $J_{H3H4} = J_{H5H4} = J_{H3F} = J_{H5F}$ = 8.4Hz, H3 and H5; (MNa+) $J_{H19H20}$ = 8.4, H19; □ = 7.29, m, 3H, H4, H16 and H20; □ = 7.51, s, 1H, $J_{H11H13}$ = 2.8, H11; □ = 7.88, s, 1H, H13 |
|---|---|---|
| Compound 216 | $t_R$ = 8.24 min 543 a.m.u. | □ = 3.76, s, 3H, OCH₃23; □ = 3.86, s, 3H, OCH₃24; □ = 4.04 and 4.53, d, 2H, CH₂21; □ = 7.04, d, 1H, $J_{H7OH}$ = 5.6, H7; □ = 7.07, s, 1H, H13; □ = 7.13, m, 4H, |

-continued

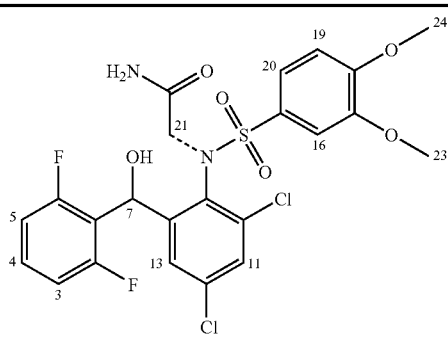

| (M-H₂O)H⁺ 583 a.m.u. (MNa+) | H3, H5, H16, H19; ☐ = 7.30, dd, 1H, J_{H20H19} = 8.8, J_{H20H16} = 1.6, H20; ☐ = 7.47, m, 1H, H4; ☐ = 7.58, s, 1H, NH₂; ☐ = 7.63, d, 1H, J_{H11H13} = 2.4, H11̄; ☐ = 7.70, d, 1H, J_{OHH7} = 5.6, OH; ☐ = 8.05, s, 1H, NH₂. |
|---|---|

¹H NMR spectra acquired in DMSO, at a frequency of 400 Mz, the chemical shifts ☐ are expressed in ppm, the coupling constants J in hertz.
Sample as a solution at 1 mg/ml of MeOH, 2 µL injected.
Mass spectrometry: positive electrospray, sweep from 120 to 1500 a.m.u.,

EXAMPLE 12

Ethyl N-[4-chloro-2-(2-chlorobenzyl)phenyl]-N-[(3-methoxyphenyl) sulfonyl]glycinate (compound 3)

EXAMPLE 12.1

[4-chloro-2-(2-chlorobenzyl)phenyl]amine

To 10 g of (2-amino-5-chlorophenyl) (2-chlorophenyl) methanone dissolved in 100 ml of dichloromethane are added at room temperature 18.7 ml of triethylsilane and 14.4 ml of trifluoroborane etherate, and the mixture is refluxed for 18 hours and then maintained at room temperature for 72 hours. The resulting mixture is hydrolysed with 2M sodium hydroxide solution, and the phases are separated by settling. The organic phase is dried over anhydrous sodium sulfate and concentrated. The residue is chromatographed on a column of silica gel, eluting with a cyclohexane/ethyl acetate solvent mixture to give 4.46 g of the expected product.
¹H NMR δ in ppm (DMSO d6): 3.86 (s, 2H); 5.17 (s, 2H); 6.50 (d, 1H); 6.70 (d, 1H); 7.00-7.53 (unresolved complex, 5H).

EXAMPLE 12.2

N-[4-chloro-2-(2-chlorobenzyl)phenyl]-3-methoxy-benzenesulfonamide

Starting with 0.71 g of [4-chloro-2-(2-chlorobenzyl)phenyl]amine dissolved in 5 ml of THF are added 0.4 ml of pyridine and 0.8 g of 3-methoxybenzenesulfonyl chloride, and the mixture is left at room temperature for 18 hours. The reaction medium is taken up in ethyl acetate and washed with water. The organic phase is dried over anhydrous sodium sulfate and concentrated. The residue is chromatographed on a column of silica gel, eluting with a 90/10 (v/v) cyclohexane/ ethyl acetate solvent mixture to give 0.666 g of expected product.
¹H NMR δ in ppm (DMSO d6): 3.78 (s, 3H); 3.97 (s, 2H); 6.71 (d, 1H); 6.96 (m, 2H); 7.23-7.34 (unresolved complex, 6H); 7.46-7.54 (unresolved complex, 2H); 9.89 (s, 1H).

EXAMPLE 12.3 ethyl-N-[4-chloro-2-(2-chlorobenzyl)phenyl]-N-[(3-methoxyphenyl)sulfonyl]glycinate To 0.525 g of N-[4-chloro-2-(2-chlorobenzyl)phenyl]-2-methoxybenzenesulfonamide dissolved in 6 ml of DMF is added, at 0° C., 0.065 g of sodium hydride, after 40 minutes at this temperature 0.14 ml of ethyl 2-bromoacetate is introduced, and the mixture is left at room temperature for 18 hours. The reaction medium is taken up in ethyl acetate and washed with water. The organic phase is dried over anhydrous sodium sulfate and concentrated. The residue is chromatographed on a column of silica gel, eluting with a 90/10 (v/v) cyclohexane/ethyl acetate solvent mixture to give 0.272 g of the expected product, in the form of an oil.
¹H NMR δ in ppm (DMSO d6): 1.18 (t, 3H); 3.82 (s, 3H); 3.98-4.12 (unresolved complex, 3H); 4.36 (s, 1H); 4.40 (q, 2H); 6.73 (d, 1H); 7.10-7.55 (unresolved complex, 10H).

Table XI illustrates the chemical structures and the physical properties of a number of compounds of the invention obtained according to Example 12.

TABLE XI

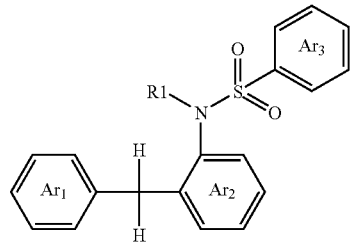

| Compound No. | Nature and position of the substituents | | | | m.p. (° C.) | MH⁺/ retention time |
|---|---|---|---|---|---|---|
| | Ar₁ | Ar₂ | R₁ | Ar₃ | | |
| 2 | H | 4-Cl | CH₂CO₂Et | 3,4-diOMe | 139 | 504/9.06 |
| 4 | 2-Cl | 4-Cl | CH₂CO₂Et | 2-OMe | oil | 508/10.03 |
| 5 | 2-Cl | 4-Cl | CH₂CO₂Et | 2,5-diOMe | 80 | 538/9.91 |
| 6 | 2-Cl | 4-Cl | CH₂CO₂Et | 2,4-diOMe | 80 | 538/9.98 |

EXAMPLE 13

N²-[4-chloro-2-(2-chlorobenzyl)phenyl]-N²-[(3-methoxyphenyl)sulfonyl]glycinamide (compound 27)

To 1 g of N-[4-chloro-2-(2-chlorobenzyl)phenyl]-3-methoxybenzenesulfonamide, obtained in Example 12.2, dissolved in 40 ml of acetonitrile are added at room temperature 1.34 ml of triethylamine, followed by 0.89 g of 2-bromoacetamide, and the mixture is refluxed for 18 hours. The reaction medium is taken up in ethyl acetate and washed with water. The organic phase is dried over anhydrous sodium sulfate and concentrated. The residue is chromatographed on a column of silica gel, eluting with a 90/10 (v/v) cyclohexane/ ethyl acetate solvent mixture to give 0.58 g of the expected product.
¹H NMR δ in ppm (DMSO d6): 3.82 (s, 3H); 4.08-4.58 (unresolved complex, 4H); 6.65 (s, 1H); 6.91 (d, 1H); 7.08-7.57 (unresolved complex, 11H). m.p.=65.7° C.

EXAMPLE 14

N-{4-chloro-2-[(2-chlorophenyl)(hydroxy)methyl]phenyl}-3,4-dimethoxy-N-[(2-methyl-2H-tetrazol-5-yl)methyl]benzenesulfonamide (compound 14) and N-{4-chloro-2-[(2-chlorophenyl)(hydroxy)methyl]phenyl}-3,4-dimethoxy-N-[(1-methyl-1H-tetrazol-5-yl)methyl]benzenesulfonamide (compound 15)

EXAMPLE 14.1

N-[4-chloro-2-(2-chlorobenzoyl)phenyl]-N-(cyanomethyl)3,4-dimethoxybenzenesulfonamide To 5.4 g of N-[4-chloro-2-(2-chlorobenzoyl)phenyl]-3,4-dimethoxybenzenesulfonamide, obtained in Example 1.1, dissolved in 60 ml of DMF is added, at 0° C., 0.57 g of sodium hydride; after 40 minutes at this temperature, 0.9 ml of 2-bromoacetonitrile is introduced and the mixture is left at room temperature for 18 hours. The reaction medium is taken up in ethyl acetate and washed with water. The organic phase is dried over anhydrous sodium sulfate and concentrated to give 5.3 g of the expected product.

$^1$H NMR δ in ppm (DMSO d6): 3.76 (s, 3H); 3.85 (s, 3H); 4.71 (m, 2H); 7.08-7.63 (unresolved complex, 9H); 7.81 (m, 1H). m.p.=164° C.

EXAMPLE 14.2

N-[4-chloro-2-(2-chlorobenzoyl)phenyl]-3,4-dimethoxy-N-(1H-tetrazol-5-ylmethyl)benzenesulfonamide To 1 g of N-[4-chloro-2-(2-chlorobenzoyl)phenyl]-N-(cyanomethyl)-3,4-dimethoxybenzenesulfonamide dissolved in 20 ml of THF are successively added 0.3 g of dibutyltin oxide and 2.6 ml of azidotrimethylsilane, and the mixture is refluxed for 18 hours. The reaction medium is taken up in ethyl acetate and washed with water. The organic phase is dried over anhydrous sodium sulfate and concentrated. The residue is purified by filtration on silica H, eluting with dichloromethane, to give 0.95 g of the expected product.

$^1$H NMR δ in ppm (DMSO d6): 3.87 (s, 3H); 5.00 (s, 2H); 6.88-7.76 (unresolved complex, 10H).

EXAMPLE 14.3

N-{4-chloro-2-[(2-chlorophenyl)(hydroxy)methyl]phenyl}-3,4-dimethoxy-N-(1H-tetrazol-5-ylmethyl)benzenesulfonamide To 0.95 g of N-[4-chloro-2-(2-chlorobenzoyl)phenyl]-3,4-dimethoxy-N-(1H-tetrazol-5-ylmethyl)benzenesulfonamide dissolved in 40 ml of ethanol is added 0.38 g of sodium borohydride, and the mixture is refluxed for 18 hours. The solvents are evaporated off and the residue is taken up in ethyl acetate and washed with water. The organic phase is dried over anhydrous sodium sulfate and concentrated to give 0.93 g of the expected product.

EXAMPLE 14.4

N-{4-chloro-2-[(2-chlorophenyl)(hydroxy)methyl]phenyl}-3,4-dimethoxy-N-[(2-methyl-2H-tetrazol-5-yl)methyl]benzenesulfonamide (compound 14) and N-{4-chloro-2-[(2-chlorophenyl)(hydroxy)methyl]phenyl}-3,4-dimethoxy-N-[(1-methyl-1H-tetrazol-5-yl)methyl]benzenesulfonamide (compound 15)

To 0.93 g of N-{4-chloro-2-[(2-chlorophenyl)(hydroxy)methyl]phenyl}-3,4-dimethoxy-N-(1H-tetrazol-5-ylmethyl)benzenesulfonamide dissolved in 25 ml of DMF are successively added 0.2 ml of iodomethane and 0.32 g of potassium carbonate, and the mixture is left for 18 hours at room temperature. The reaction medium is taken up in ethyl acetate and washed with water. The organic phase is dried over anhydrous sodium sulfate and concentrated. The residue is chromatographed on a column of silica gel, eluting with a 99/1 (v/v) dichloromethane/methanol solvent mixture to give 0.34 g of compound 14.

$^1$H NMR δ in ppm (DMSO d6): 3.77 (s, 3H); 3.87 (s, 3H); 4.15 (s, 3H); 4.70 (d, 1H); 5.15 (d, 1H); 6.01 (d, 1H); 6.60-7.83 (unresolved complex, 11H). m.p.=94.8° C.

0.19 g of compound 15 is obtained, the characteristics of which are as follows:

$^1$H NMR δ in ppm (DMSO d6): 3.60 (s, 3H); 3.79 (s, 3H); 3.88 (s, 3H); 4.25 (d, 1H); 4.77 (d, 1H); 5.96 (d, 1H); 6.36 (d, 1H); 6.65-7.79 (unresolved complex, 10H). m.p.=118.3° C.

The following compounds were synthesized according to this process:

Compound 11: N-{4-chloro-2-[(2-chlorophenyl)(hydroxy)methyl]phenyl}-N-[(2-ethyl-2H-tetrazol-5-yl)methyl]-3,4-dimethoxybenzenesulfonamide.
m.p.=113° C.

Compound 12: N-{4-chloro-2-[(2-chlorophenyl)(hydroxy)methyl]phenyl}-N-[(1-ethyl-1H-tetrazol-5-yl)methyl]-3,4-dimethoxybenzenesulfonamide.
m.p.=75° C.

EXAMPLE 15

$N^2$-[4-chloro-2-(2-chlorobenzyl)phenyl]-$N^2$-[(4-methoxyphenyl)sulfonyl]glycinamide (compound 39)

To 0.766 g of N-[4-chloro-2-(2-chlorobenzyl)phenyl]-4-methoxybenzenesulfonamide, obtained according to Example 12.2, dissolved in 5 ml of THF are successively added 0.214 g of potassium tert-butoxide and 0.263 g of 2-bromoacetamide, and the mixture is left for 18 hours at room temperature. The reaction medium is taken up in ethyl acetate and washed with water. The organic phase is dried over anhydrous sodium sulfate and concentrated. The residue is chromatographed on a column of silica gel, eluting with a dichloromethane/methanol gradient to give 0.50 g of the expected product.

$^1$H NMR δ in ppm (DMSO d6): 3.89 (s, 3H); 4.02-4.29 (m, 3H); 4.58 (d, 1H); 6.66 (d, 1H); 6.89 (d, 1H); 7.14-7.65 (unresolved complex, 11H). m.p.=150° C.

Table XII illustrates the chemical structures and the physical properties of a number of compounds of the invention obtained according to an adaptation of Example 15.

TABLE XII

| Compound No. | Ar₁ | Ar₂ | R₁ | Ar₃ | m.p. (°C.) | MH⁺/retention time |
|---|---|---|---|---|---|---|
| 40 | 2-Cl | 4-Cl | CH₂CONH₂ | 2,5-diOMe | 125 | 509/8.93 |
| 42 | 2-Cl | 4-Cl | CH₂CONH₂ | 3-CF₃ | 119 | 517/9.25 |
| 43 | 2-Cl | 4-Cl | CH₂CONH₂ | 3-OCF₃ | 129 | 533/9.38 |
| 45 | 2-Cl | 4-Cl | CH₂CONH₂ | 2-OMe | 114 | 479/8.18 |
| 46 | 2-Cl | 4-Cl | CH₂CONHMe | 3,4-diOMe | 146 | 523/8.42 |
| 47 | 2-Cl | 4-Cl | CH₂CONH₂ | 4-Cl | 205 | 483/9.06 |
| 48 | 2-Cl | 4-Cl | CH₂CONH₂ | 3,4-diCl | 166 | 517/9.64 |
| 49 | 2-Cl | 4-Cl | CH₂CONH₂ | 2,5-diMe, 4-Cl | 214.5 | 511/9.76 |
| 50 | 2-Cl | 4-Cl | CH₂CONH₂ | 2-Cl | 97 | 483/8.44 |
| 53 | 2-Cl | 4-Cl | CH₂CONH₂ | H | 150 | 449/8.40 |
| 55 | 2-F | 4-Cl | CH₂CONH₂ | 3,4-diOMe | 183.3 | 493/7.80 |
| 62 | 2-Cl | 4-Cl | CH₂CONH₂ | 3-Me | 95 | 463/8.66 |
| 63 | 2-Cl | 4-Cl | CH₂CONH₂ | 3,4-ethylenedioxy | 111.6 | 507/8.19 |
| 71 | 2-Cl | 4-Cl | CH₂CONH₂ | 3,4-methylenedioxy | 89 | 493/8.29 |
| 75 | 2-Cl | 4-Cl | CH₂CONHEt | 3,4-diOMe | 101 | 537/8.79 |
| 81 | 2-Cl | 4-Cl | CH₂CONH₂ | 2-Me | 160 | 463/9.32 |
| 82 | 2-Cl | 4-Cl | CH₂CONH₂ | 3,4-diMe | 166 | 477/9.64 |
| 89 | 2-Cl | 4-Cl | CH₂CONH₂ | 3,5-diMe | 84 | 477/9.24 |
| 105 | 2-Cl | 4-Cl | CH₂CONHMe | 2,5-diMe, 4-Cl | 172.6 | 525/10.24 |
| 109 | 2-Cl | 4-Cl | CH₂CONHMe | 2,4,5-triOMe | 160.4 | 553/8.17 |
| 104 | 2-Cl | 4-Cl | CH₂CONH₂ | 2,4,5-triOMe | 221.2 | 539/7.80 |
| 119 | 2-Cl | 4-Cl | CH₂CONH₂ | 3,5-diOMe | 110 | 509/8.71 |
| 118 | 2-Cl | 4-Cl | CH₂CON(Me)₂ | 2,5-diMe, 4-Cl | 166.4 | 539/10.71 |
| 134 | 2-Cl | 4-Cl | CH₂CONH₂ | 3-NO₂ | 91 | 494/8.72 |
| 173 | 2-Cl | 4-Cl | CH₂CONHMe | 2,4-diCl, 5-Me | 108 | 545/10.74 |
| 174 | 2-Cl | 4-Cl | CH₂CON(Me)₂ | 2,4-diCl, 5-Me | 204 | 559/11.27 |
| 54 | 2-Cl | 4-Cl | Me | 3,4-diOMe | 106.6 | 466/9.73 |
| 65 | H | 4-Cl | CH₂CONH₂ | 3,4-diOMe | 184 | 475/7.75 |
| 70 | 2-Cl | 4-Cl | CH₂CON(Me)₂ | 3,4-diOMe | 157.6 | 537/8.88 |
| 87 | 2-Cl | 4-Cl | CH₂CONH₂ | 2,6-diCl | 163 | 517/8.70 |
| 95 | H | 4-Cl | CH₂CON(Me)₂ | 3,4-diOMe | 144.2 | 503/8.67 |
| 96 | H | 4-Cl | CH₂CONHMe | 3,4-diOMe | 89.6 | 489/8.25 |
| 97 | 2-F | 4-Cl | CH₂CON(Me)₂ | 3,4-diOMe | oil | 521/8.63 |
| 98 | 2-F | 4-Cl | CH₂CONHMe | 3,4-diOMe | 107.5 | 507/8.23 |
| 99 | 2-Cl | 4-Cl | CH₂CONH₂ | 2,5-diOMe, 4-Me | 172.5 | 523/8.70 |
| 114 | 2-Cl | 4-Cl | CH₂CONH₂ | 2,4,5-triMe | 184.9 | 491/9.48 |
| 115 | 2-Cl | 4-Cl | CH₂CONHMe | 2,4,5-triMe | 188.5 | 505/9.82 |
| 84 | 2-Cl | 4-Cl | (3-methyl-1,2,4-oxadiazol-5-yl)methyl | 3,4-diOMe | 111.4 | 548/10.20 |
| 107 | 2-Cl | 4-Cl | (1-methyl-1H-imidazol-2-yl)methyl | 3,4-diOMe | 105 | 546/6.32 |
| 112 | 2-Cl | 4-Cl | (1-methyl-1H-imidazol-2-yl)methyl | 3,5-diMe | 112 | 514/6.98 |
| 135 | 2-Cl | 4-Cl | CH₂CONH₂ | 3-NH₂ | 103 | 464/8.44 |
| 188 | 2,6-diF | 4-Cl | CH₂CONH₂ | 3-NMe₂ | 190 | 494/9.17 |
| 189 | 2,6-diF | 4-Cl | CH₂CONH₂ | 3-NHMe | 195 | 480/8.65 |
| 249 | 2,6-diF | 4-Cl | CH₂CONH₂ | 2,5-diMe, 4-Cl | 196.8 | 513/9.50 |
| 263 | 2,6-diF | 4-Cl | CH₂CONH₂ | 4-tBut | 161.4 | 507/10.74 |
| 279 | 2,6-diF | 4-Cl | CH₂CONH₂ | 4-NH₂ | 111 | n.d. |
| 307 | 2,6-diF | 4-Cl | CH₂CONH₂ | 3,5-diOMe | 170.2 | 511/9.48 |
| 319 | 2,6-diF | 6-OMe | CH₂CONH₂ | 4-tBut | 173 | 503/10.1 |
| 320 | 2,6-diF | 6-OMe | CH₂CONH₂ | 3,4-diF | 259 | 483/9.13 |

Compound 84 is obtained by alkylation with the derivative 5-bromomethyl-3-methyl-[1,2,4]oxadiazole (synthesis described according to Example 4.3).

Compound 135 is obtained from 1.25 g of compound 134 by reduction of the nitro function as described in Example 8.2.

Compounds 188 and 189 are obtained by alkylation reaction with iodomethane in the presence of caesium carbonate in THF of $N^2$-[3-aminophenyl)sulfonyl]-$N^2$-[4-chloro-2-(2,6-difluorobenzyl)phenyl]glycinamide.

For compounds 54, 65, 95, 96, 97 and 98, the potassium tert-butoxide is replaced with sodium hydride.

Compound 312 is obtained according to this process, starting with 3-methoxybiphenyl-2-amine.

MH⁺=457; the retention time is 8.04 minutes m.p.=86.8° C.

EXAMPLE 16

$N^2$-[4-chloro-2-(2-methoxybenzyl)phenyl]-$N^2$-[(3,4-dimethoxyphenyl)sulfonyl]glycinamide (compound 56)

EXAMPLE 16.1

(2-amino-5-chlorophenyl)(2-methoxyphenyl)methane

To 1.438 g of (2-amino-5-chlorophenyl)(2-methoxyphenyl)methanone, obtained according to the process described in Example 10.1, dissolved in 16 ml of dichloromethane are successively added 2.61 ml of triethylsilane and 4 ml of boron trifluoride etherate, and the mixture is refluxed for 18 hours. The cooled reaction medium is poured onto ice containing 2M sodium hydroxide solution, and, after separation of the phases by settling, the organic phase is dried over anhydrous sodium sulfate and concentrated. The residue is chromatographed on a column of silica gel to give 0.571 g of the expected product.

$^1$H NMR δ in ppm (DMSO d6): 3.70 (s, 2H); 3.80 (s, 3H); 5.05 (s, 2H); 6.65 (m, 2H); 6.88-7.29 (unresolved complex, 5H).

EXAMPLE 16.2

N-[4-chloro-2-(2-methoxybenzyl)phenyl]-3,4-dimethoxybenzenesulfonamide

To 0.57 g of (2-amino-5-chlorophenyl)(2-methoxyphenyl) methane dissolved in 5 ml of THF are successively added 0.2 ml of pyridine and 0.547 g of 3,4-dimethoxybenzenesulfonyl chloride, and the mixture is left for 18 hours at room temperature. The reaction medium is taken up in ethyl acetate and washed with water. The organic phase is dried over anhydrous sodium sulfate and concentrated. The residue is chromatographed on a column of silica gel, eluting with dichloromethane, to give 0.832 g of the expected product.

$^1$H NMR δ in ppm (DMSO d6): 3.70 (s, 2H); 3.76 (s, 3H); 3.85 (s, 3H); 6.77-7.28 (unresolved complex, 10H) 9.52 (s, 1H).

EXAMPLE 16.3

$N^2$-[4-chloro-2-(2-methoxybenzyl)phenyl]-$N^2$-[(3,4-dimethoxyphenyl)sulfonyl]glycinamide To 0.83 g of N-[4-chloro-2-(2-methoxybenzyl)phenyl]-3,4-methoxybenzenesulfonamide dissolved in 10 ml of DMF is added, at 0° C., 0.081 g of sodium hydride. After 40 minutes at this temperature, 0.28 g of 2-bromoacetamide is introduced and the mixture is left for 18 hours at room temperature. The reaction medium is taken up in ethyl acetate and washed with water. The organic phase is dried over anhydrous sodium sulfate and concentrated. The residue is chromatographed on a column of silica gel, eluting with dichloromethane, to give 0.77 g of the expected product.

$^1$H NMR δ in ppm (DMSO d6): 3.80 (s, 6H); 3.88 (s, 3H); 3.91 (d, 1H); 4.18 (s, 2H); 4.30 (d, 1H); 6.75 (d, 1H); 6.91-7.28 (s, 11H).

Table XIII illustrates the chemical structures and the physical properties of a number of compounds of the invention obtained according to Example 16.

TABLE XIII

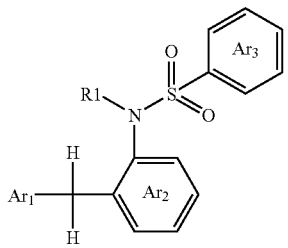

| Compound No. | Nature and position of the substituents | | | | m.p. (° C.) | MH+/ retention time |
|---|---|---|---|---|---|---|
| | Ar$_1$ | Ar$_2$ | R$_1$ | Ar$_3$ | | |
| 58 | 3-OMe phenyl | 4-Cl | CH$_2$CONH$_2$ | 3,4-diOMe | 109 | 505/7.79 |
| 60 | 4-OMe phenyl | 4-Cl | CH$_2$CONH$_2$ | 3,4-diOMe | 214 | 505/7.73 |
| 73 | 2-Me phenyl | 4-Cl | CH$_2$CONH$_2$ | 3,4-diOMe | 88 | 489/8.12 |
| 116 | 3-Cl phenyl | 4-Cl | CH$_2$CONH$_2$ | 3,4-diOMe | 181.8 | 509/8.39 |

TABLE XIII-continued

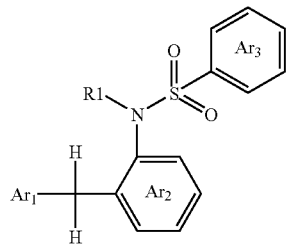

| Compound No. | Nature and position of the substituents | | | | m.p. (° C.) | MH+/ retention time |
|---|---|---|---|---|---|---|
| | Ar$_1$ | Ar$_2$ | R$_1$ | Ar$_3$ | | |
| 212 | 2-Me thienyl | 4-Cl | CH$_2$CONH$_2$ | 3,4-diOMe | 100.1 | 495/8.86 |

EXAMPLE 17

$N^2$-[4-chloro-2-(2,6-dichlorobenzyl)phenyl]-$N^2$-[(3,4-dimethoxyphenyl)sulfonyl]glycinamide (compound 78)

EXAMPLE 17.1

(2-amino-5-chlorophenyl)(2,6-dichlorophenyl)methane

To 4.85 g of (2-nitro-5-chlorophenyl)(2,6-dichlorophenyl) methanol, obtained in Example 9.1, dissolved in 58 ml of ethanol are added 5.042 g of tin and 19 ml of 12M hydrochloric acid, and the mixture is refluxed overnight. The reaction medium is concentrated and the residue is taken up in ethyl acetate and washed with water containing 2M sodium hydroxide solution. The organic phase is dried over anhydrous sodium sulfate and concentrated to give 3.71 g of the expected product.

$^1$H NMR δ in ppm (DMSO d6): 3.99 (s, 2H); 6.00 (d, 1H); 6.73 (d, 1H); 6.98 (d, 1H); 7.39-7.61 (unresolved complex, 3H).

EXAMPLE 17.2

N-[4-chloro-2-(2,6-dichlorobenzyl)phenyl]-3,4-methoxybenzenesulfonamide

Starting with 2 g of (2-amino-5-chlorophenyl)(2,6-dichlorophenyl)methane according to the process described in Example 12.2, 0.389 g of the expected product is obtained.

EXAMPLE 17.3

$N^2$-[4-chloro-2-(2,6-dichlorobenzyl)phenyl]-$N^2$-[(3,4-dimethoxyphenyl)sulfonyl]glycinamide To 0.38 g of N-[4-chloro-2-(2,6-dichlorobenzyl)phenyl]-3,4-methoxybenzenesulfonamide dissolved in 4 ml of DMF is added, at 0° C., 0.035 g of sodium hydride; after 40 minutes at this temperature, 0.121 g of 2-bromoacetamide is added and the mixture is left for 18 hours at room temperature. The reaction medium is taken up in ethyl acetate and washed with water. The organic phase is dried over anhydrous sodium sulfate and concentrated. The residue is chromatographed on a column of silica gel, eluting with a 98/2 (v/v) dichloromethane/methanol mixture to give 0.225 g of the expected product.

$^1$H NMR δ in ppm (DMSO d6): 3.80 (s, 3H); 3.88 (s, 3H); 4.10-4.70 (unresolved complex, 4H); 6.30 (d, 1H); 7.03-7.61 (unresolved complex, 10H). m.p.=195.3° C.

Table XIV illustrates the chemical structures and the physical properties of a number of compounds of the invention obtained according to Example 17.

TABLE XIV

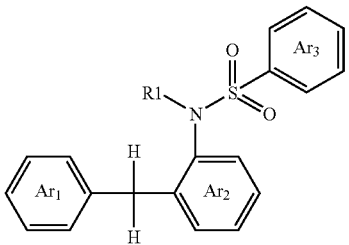

| Compound No. | Nature and position of the substituents | | | | m.p. (° C.) | MH$^+$/ retention time |
|---|---|---|---|---|---|---|
| | Ar$_1$ | Ar$_2$ | R$_1$ | Ar$_3$ | | |
| 130 | 2,6-diCl | 4-Cl | CH$_2$CONHMe | 3,4-diOMe | 149.3 | 557/9.13 |
| 166 | 2,6-diCl | 4-Cl | CH$_2$CON(Me)$_2$ | 3,4-diOMe | 102.7 | 571/9.63 |
| 67 | 2-Cl | H | CH$_2$CONH$_2$ | 3,4-diOMe | 240.2 | 475/7.45 |
| 91 | 2,6-diF | 4-Cl | CH$_2$CONH$_2$ | 3,4-diOMe | 231.6 | 511/8.48 |
| 242 | 2,6-diF | 4-Br | CH$_2$CONH$_2$ | 3,4-diOMe | 209.7 | 555/8.31 |
| 280 | 2,6-diF | 4-Me | CH$_2$CONH$_2$ | 3,4-diOMe | 180.4 | 490/8.80 |
| 286 | 2,6-diF | 4-Cl | CH$_2$CONH$_2$ | 3,4-diOMe | 165.3 | 511/8.89 |
| 297 | 2,6-diF | 6-OMe | CH$_3$ | 3,4-diOMe | 116 | 464/9.92 |
| 308 | 2,6-diF | 4-Cl | CH$_2$CONH$_2$ | 3,4-diOMe | 169 | 495/9.84 |
| 314 | 2,6-diF | 4-Cl | CH$_2$CONH$_2$ | 2-F; 4,5-diOMe | 212.3 | 525/8.96 |

EXAMPLE 18

N$^2$-[4-chloro-2-(2,6-difluorobenzyl)phenyl]-N$^2$-[(3,4-dimethoxyphenyl)sulfonyl]-N$^1$-methylglycinamide (compound 139)

EXAMPLE 18.1

(2-amino-5-chlorophenyl)(2,6-fluorophenyl)methane

To 1 g of (2-amino-5-chlorophenyl)(2,6-fluorophenyl)methanol, obtained according to Example 9.2, dissolved in 10 ml of dichloromethane are added 1.8 ml of triethylsilane and 0.86 ml of trifluoroacetic acid, and the mixture is maintained at 50° C. for 6 hours. The reaction medium is added to ice and taken up in dichloromethane and 100 ml of 2M sodium hydroxide solution. The organic phase is dried over anhydrous sodium sulfate and concentrated. The residue is chromatographed on a column of silica gel, eluting with a dichloromethane/cyclohexane mixture to give 0.997 g of the expected product.

$^1$H NMR δ in ppm (DMSO d6): 3.77 (s, 2H); 5.26 (s, 2H); 6.36 (s, 1H); 6.70 (d, 1H); 6.99 (m, 1H); 7.18 (t, 2H); 7.48 (m, 1H).

EXAMPLE 18.2

N-[4-chloro-2-(2,6-difluorobenzyl)phenyl]-3,4-dimethoxybenzenesulfonamide

Starting with 0.97 g of (2-amino-5-chlorophenyl)(2,6-fluorophenyl)methane according to an adaptation of the process described in Example 12.2, 1.58 g of the expected product are obtained.

$^1$H NMR δ in ppm (DMSO d6): 3.76 (s, 3H); 3.85 (s, 3H); 3.96 (s, 2H); 6.64 (s, 1H); 6.90 (d, 1H); 7.10-7.50 (unresolved complex, 7H); 9.69 (s, 1H). m.p.=144° C.

EXAMPLE 18.3

N$^2$-[4-chloro-2-(2,6-difluorobenzyl)phenyl]-N$^2$-[(3,4-dimethoxyphenyl)sulfonyl]-N$^1$-methylglycinamide Starting with 0.7 g of N-[4-chloro-2-(2,6-difluorobenzyl)phenyl]-3,4-dimethoxybenzenesulfonamide according to an adaptation of process 15 (presence of co-solvent such as DMF and of sodium iodide), 0.669 g of the expected product is obtained.

$^1$H NMR δ in ppm (DMSO d6): 2.53 (s, 3H); 3.81 (s, 3H); 3.89 (s, 3H); 4.02-4.61 (unresolved complex, 4H); 6.62 (s, 1H); 6.86 (d, 1H); 7.15-7.31 (unresolved complex, 6H); 7.47 (m, 1H); 7.90(m, 1H). m.p.=92.9° C.

Table XV illustrates the chemical structures and the physical properties of a number of compounds of the invention obtained according to Example 18.

TABLE XV

| Compound No. | Ar₁ | Ar₂ | R₁ | Ar₃ | m.p. (°C.) | MH⁺/retention time |
|---|---|---|---|---|---|---|
| 140 | 2,6-diF | 4-Cl | propyl | 3,4-diOMe | 135.1 | 496/10.82 |
| 150 | 2,6-diF | 4-Cl | CH₂CON(Me)₂ | 3,4-diOMe | 130.2 | 539/9.2 |
| 145 | 2,6-diF | 4-Cl | (CH₂)₂N(Me)₂ | 3,4-diOMe | 121.2 | 525/6.47 |
| 144 | 2,6-diF | 4-Cl | Me | 3,4-diOMe | 191.8 | 468/10.05 |
| 156 | 2,6-diF | 4-Cl | (6,7-dimethoxy-1,2,3,4-tetrahydroisoquinolin-2-yl)carbonylmethyl | 3,4-diOMe | 128.2 | 687/9.78 |
| 169 | 2,6-diF | 4-Cl | CH₂CONH₂ | 3,5-diMe | 146 | 479/9.49 |
| 171 | 2,6-diF | 4-Cl | CH₂CONHMe | 3,5-diMe | 196 | 493/9.80 |
| 185 | 2,6-diF | 4-Cl | prop-2-yn-1-yl | 3,4-diOMe | 172 | 492/10.13 |
| 193 | 2,6-diF | 4-OMe | CH₂CONH₂ | 3,4-diOMe | 189.7 | 507/7.93 |
| 195 | 2,6-diF | 3-Cl | CH₂CONH₂ | 3,4-diOMe | 193.5 | 511/8.33 |
| 285 | 2,5-diF | 6-OMe | CH₂CONH₂ | 3,4-diOMe | 193 | 507/8.58 |
| 200 | 2,6-diF | 4-Me | CH₂CONH₂ | 3,4-diOMe | 196 | 491/8.20 |
| 202 | 2,6-diF | 5-N(Me)₂ | CH₂CONH₂ | 3,4-diOMe | 141 | 520/7.84 |
| 205 | 2,6-diF | 4-Me | CH(Et)CONH₂ | 3,4-diOMe | 197.6 | 519/8.84 |
| 211 | 2,6-diF | 4-Cl | CH₂CN | 3,4-diOMe | 61.7 | 493/9.84 |
| 220 | 2,6-diF | 4-F | CH₂CONH₂ | 3,4-diOMe | 184.7 | 495/8.16 |
| 224 | 2-Cl, 6-F | 4-Cl | CH₂CONH₂ | 3,4-diOMe | 230 | 527/8.77 |
| 181 | 2,6-diF | 4-Cl | (1-methyl-1H-imidazol-2-yl)methyl | 3,4-diOMe | 87 | 547/6.65 |
| 210 | 2,6-diF | 3,6-diOMe | CH₂CONH₂ | 3,4-diOMe | 242.9 | 537/7.88 |
| 246 | 2,6-diF | 4-Cl | CH(CH₃)CN | 3,4-diOMe | 143.4 | 507/10.82 |
| 288 | 2,6-diF | 6-Me | CH₂CONH₂ | 3,4-diOMe | 225.6 | 491/8.61 |
| 293 | 2,6-diF | 6-Cl | CH₂CONH₂ | 3,4-diOMe | 227.4 | 511/8.63 |

For compounds 193, 195 and 220, the potassium tert-butoxide is replaced with sodium hydride.

EXAMPLE 19

N²-[4-chloro-2-(2,5-dichlorobenzyl)phenyl]-N²-[(3,4-dimethoxyphenyl)sulfonyl]glycinamide (compound 80)

EXAMPLE 19.1

(2-amino-5-chlorophenyl)(2,5-dichlorophenyl)methane

Starting with 1.72 g of (2-amino-5-chlorophenyl)(2,5-dichlorophenyl)methanol, obtained in Example 10.2 according to the process described in Example 18.1, 1.41 g of the expected product are obtained.

EXAMPLE 19.2

N-[4-chloro-2-(2,5-chlorobenzyl)phenyl]-3,4-methoxybenzenesulfonamide

Starting with 1.41 g of (2-amino-5-chlorophenyl)(2,5-dichlorophenyl)methane according to an adaptation of the process described in Example 12.2, 2.3 g of the expected product are obtained.

EXAMPLE 19.3

N²-[4-chloro-2-(2,5-dichlorobenzyl)phenyl]-N²-[(3,4-dimethoxyphenyl)sulfonyl]glycinamide Starting with 2.3 g of N-[4-chloro-2-(2,5-chlorobenzyl)phenyl]-3,4-methoxybenzenesulfonamide according to an adaptation of the process described in Example 15, 1 g of the expected product is obtained.

¹H NMR δ in ppm (DMSO d6): 3.80 (s, 3H); 3.89 (s, 3H); 4.01-4.69 (unresolved complex, 4H); 6.72 (s, 1H); 6.89 (d, 1H); 7.15-7.61 (unresolved complex, 9H). m.p.=200° C.

Table XVI illustrates the chemical structures and physical properties of a number of compounds of the invention obtained according to Example 19.

TABLE XVI

| Compound No. | Nature and position of the substituents | | | | m.p. (° C.) | MH+/ retention time |
|---|---|---|---|---|---|---|
| | Ar$_1$ | Ar$_2$ | R$_1$ | Ar$_3$ | | |
| 142 | 2,3-diFphenyl | 4-Cl | CH$_2$CONH$_2$ | 3,4-diOMe | 172.2 | 511/8.70 |
| 143 | 2,3-diFphenyl | 4-Cl | CH$_2$CON(Me)$_2$ | 3,4-diOMe | 88.2 | 539/9.43 |
| 141 | 2,3-diFphenyl | 4-Cl | CH$_2$CONHMe | 3,4-diOMe | 150.9 | 525/9.01 |
| 170 | 2-F, 6-OMe phenyl | 4-Cl | CH$_2$CONH$_2$ | 3,4-diOMe | 160 | 523/8.56 |
| 180 | 2-thienyl | 4-Cl | CH$_2$CONH$_2$ | 3,4-diOMe | 183.9 | 481/8.41 |
| 192 | 2-Cl, 6-OMe phenyl | 4-Cl | CH$_2$CONH$_2$ | 3,4-diOMe | 180.6 | 539/8.82 |

EXAMPLE 20

N$^2$-[4,5-dichloro-2-(2-chlorobenzyl)phenyl]-N$^2$-[(3,4-dimethoxyphenyl)sulfonyl]glycinamide (compound 161)

To 0.9 g of (N$^2$-{4,5-dichloro-2-[(2-chlorophenyl)(hydroxy)methyl]phenyl}-N$^2$[(phenyl)sulfonyl]glycinamide, obtained according to Example 10.4, dissolved in 10 ml of dichloromethane are added 0.77 ml of triethylsilane and 1.2 ml of trifluoroborane etherate, and the mixture is maintained at 40° C. for 3 hours. The reaction medium is taken up in dichloromethane and 100 ml of 2M sodium hydroxide solution. After separation of the phases by settling, the organic phase is dried over anhydrous sodium sulfate and concentrated. The residue is chromatographed on a column of silica gel, eluting with a dichloromethane/ethyl acetate mixture to give 0.622 g of the expected product.

$^1$H NMR δ in ppm (DMSO d6): 3.81 (s, 3H); 3.90 (s, 3H); 4.07-4.19 (unresolved complex, 3H); 4.51 (d, 1H); 6.87 (s, 1H); 7.14-7.57 (unresolved complex, 10H). m.p.=163° C.

Table XVII illustrates the chemical structures and physical properties of a number of compounds of the invention obtained according to Example 20.

TABLE XVII

| Compound No. | Nature and position of the substituents | | | | m.p. (° C.) | MH+/ retention time |
|---|---|---|---|---|---|---|
| | Ar$_1$ | Ar$_2$ | R$_1$ | Ar$_3$ | | |
| 177 | 2,5-diF | 4-Cl | CH$_2$CONH$_2$ | 3,4-diOMe | 216.5 | 511/8.75 |
| 182 | 2-F, 5-Cl | 4-Cl | CH$_2$CONH$_2$ | 3,4-diOMe | 210.3 | 527/9.09 |
| 183 | 3,5-diF | 4-Cl | CH$_2$CONH$_2$ | 3,4-diOMe | 184 | 511/8.96 |
| 196 | 2-F, 5-Me | 4-Cl | CH$_2$CONH$_2$ | 3,4-diOMe | 231.6 | 507/8.98 |
| 100 | 2-Cl | 4-Cl | CH$_2$CONH$_2$ | 2,4-diCl, 5-Me | 228.3 | 531/9.72 |
| 168 | 2-F, 4-Cl | 4-Cl | CH$_2$CONH$_2$ | 3,4-diOMe | 195.2 | 527/9.32 |
| 208 | 2,6-diF | 4,6-diOMe | CH$_2$CONH$_2$ | 3,4-diOMe | 191 | 537/7.98 |
| 228 | 2,6-diF | 4,5-diCl | CH$_2$CONH$_2$ | 3,4-diOMe | 181.1 | 545/8.98 |
| 103 | 2-Cl | 4-Et | CH$_2$CONMe$_2$ | 3,4-diOMe | 142.7 | 531/8.99 |
| 93 | 2-Cl | 4-Et | CH$_2$CONH$_2$ | 3,4-diOMe | 86 | 503/8.21 |

Compound 247 is prepared from (N$^2$-{2-[{2,6-difluorophenyl)(hydroxy)methyl]-6-methoxyphenyl}-N$^2$-[(3,4-dimethoxyphenyl}sulfonyl]glycinamide obtained according to Example 9.4.

m.p.=244.9; MH$^+$=507; the retention time is 8.37 minutes.

EXAMPLE 21

N-[4-chloro-2-(2,6-difluorobenzyl)phenyl]-3,4-dimethoxy-N-[(1-methyl-1H-tetrazol-5-yl)methyl]benzenesulfonamide (compound 152) and N-[4-chloro-2-(2,6-difluorobenzyl)phenyl]-3,4-dimethoxy-N-[(2-methyl-2H-tetrazol-5-yl)methyl]benzenesulfonamide (compound 151)

EXAMPLE 21.1

N-[4-chloro-2-(2,6-difluorobenzyl)phenyl]-3,4-dimethoxy-N-[(1H-tetrazol-5-yl)methyl]benzenesulfonamide To 8.7 g of N-[4-chloro-2-(2,6-difluorobenzyl)phenyl]-N-(cyanomethyl)-3,4-dimethoxybenzenesulfonamide (compound 211), obtained in Example 18, dissolved in 100 ml of THF are added, at room temperature, 10 g of azidotrimethylsilane and 2.29 g of dibutyltin oxide, and the mixture is refluxed for 8 hours. The reaction medium is concentrated and the residue is chromatographed on a column of silica gel, eluting with a 99/1 (v/v) dichloromethane/methanol mixture to give 7 g of the expected product.

¹H NMR δ in ppm (DMSO d6): 3.82 (s, 3H); 3.90 (s, 3H); 4.05 (q, 2H); 4.88 (d, 1H); 5.29 (d, 1H); 6.60 (s, 1H); 6.85 (d, 1H); 7.12-7.49 (unresolved complex, 7H).

EXAMPLE 21.2

N-[4-chloro-2-(2,6-difluorobenzyl)phenyl]-3,4-dimethoxy-N-[(1-methyl-1H-tetrazol-5-yl)methyl]benzenesulfonamide To 2.7 g of N-[4-chloro-2-(2,6-difluorobenzyl)phenyl]-3,4-dimethoxy-N-[(1H-tetrazol-5-yl)methyl]benzenesulfonamide dissolved in 50 ml of DMF are added, at room temperature, 1.07 g of iodomethane and 1.04 g of potassium carbonate. After 48 hours at room temperature, the medium is poured into water and then extracted with ethyl acetate. The organic phase is dried over anhydrous sodium sulfate and concentrated. The residue is chromatographed on a column of silica gel, eluting with a 90/10 (v/v) toluene/ethyl acetate mixture to give 1 g of N-[4-chloro-2-(2,6-difluorobenzyl)phenyl]-3,4-dimethoxy-N-[(1-methyl-1H-tetrazol-5-yl)methyl]benzenesulfonamide (compound 152) ¹H NMR δ in ppm (DMSO d6): 3.81 (s, 3H); 3.90 (s, 3H); 3.93 (q, 1H); 4.05 (m, 4H); 4.93 (d, 1H); 5.42 (d, 1H); 6.58 (s, 1H); 7.00 (d, 1H); 7.10-7.46 (unresolved complex, 7H). m.p.=180.8° C. and 0.71 g of N-[4-chloro-2-(2,6-difluorobenzyl)phenyl]-3,4-dimethoxy-N-[(2-methyl-2H-tetrazol-5-yl)methyl]benzenesulfonamide (compound 151) ¹H NMR δ in ppm (DMSO d6): 3.81 (s, 3H); 3.89 (s, 3H); 4.13 (s, 2H); 4.26 (s, 3H); 4.77 (d, 1H); 5.25 (d, 1H); 6.57 (s, 1H); 6.86 (d, 1H); 7.11-7.47 (unresolved complex, 7H). m.p.=136.3° C.

Table XVIII illustrates the chemical structures and the physical properties of a number of compounds of the invention obtained according to Example 21.

TABLE XVIII

| Compound No. | Nature and position of the substituents | | | | m.p. (° C.) | MH⁺/retention time |
|---|---|---|---|---|---|---|
| | Ar₁ | Ar₂ | R₁ | Ar₃ | | |
| 153 | 2,6-diF | 4-Cl | (2-ethyl-2H-tetrazol-5-yl)methyl | 3,4-diOMe | 139.7 | 564/9.81 |
| 154 | 2,6-diF | 4-Cl | (1-ethyl-1H-tetrazol-5-yl)methyl | 3,4-diOMe | 150.9 | 564/9.48 |
| 159 | 2,6-diF | 4-Cl | (2-ethyl-2H-tetrazol-5-yl)methyl | 3,5-diMe | 105.5 | 532/10.84 |
| 160 | 2,6-diF | 4-Cl | (1-ethyl-1H-tetrazol-5-yl)methyl | 3,5-diMe | 134 | 532/10.46 |
| 157 | 2,6-diF | 4-Cl | (2-methyl-2H-tetrazol-5-yl)methyl | 3,5-diMe | 159 | 518/10.53 |
| 158 | 2,6-diF | 4-Cl | (1-methyl-1H-tetrazol-5-yl)methyl | 3,5-diMe | 240 | 518/10.20 |
| 122 | 2-Cl | 4-Cl | (2-ethyl-2H-tetrazol-5-yl)methyl | 3,5-diMe | oil | 530/10.65 |
| 123 | 2-Cl | 4-Cl | (1-ethyl-1H-tetrazol-5-yl)methyl | 3,5-diMe | 158 | 530/10.27 |
| 108 | 2-Cl | 4-Cl | (1-isopropyl-1H-tetrazol-5-yl)methyl | 3,4-diOMe | 79 | 576/9.52 |
| 111 | 2-Cl | 4-Cl | (1-benzyl-1H-tetrazol-5-yl)methyl | 3,4-diOMe | 98 | 624/9.89 |
| 90 | 2-Cl | 4-Cl | (1-ethyl-1H-tetrazol-5-yl)methyl | 3,4-diOMe | 168.3 | 562/9.25 |
| 88 | 2-Cl | 4-Cl | (1-methyl-1H-tetrazol-5-yl)methyl | 3,4-diOMe | 200.6 | 548/8.96 |
| 243 | 2,6-diF | 4-Cl | 1-(2-methyl-2H-tetrazol-5-yl)ethyl | 3,4-diOMe | 259.3 | 564/9.85 |
| 244 | 2,6-diF | 4-Cl | 1-(1-methyl-1H-tetrazol-5-yl)ethyl | 3,4-diOMe | 178.1 | 564/10.44 |
| 310 | 2,6-diF | 6-OMe | (2-ethyl-2H-tetrazol-5-yl)methyl | 3,4-diOMe | 136.3 | 560/9.61 |
| 311 | 2,6-diF | 6-OMe | (1-ethyl-1H-tetrazol-5-yl)methyl | 3,4-diOMe | 161.4 | 560/9.30 |

EXAMPLE 22

N²-[2-(2-chlorobenzyl)-4-methylphenyl]-N²-[(3,4-dimethoxyphenyl)sulfonyl]glycinamide (compound 165)

EXAMPLE 22.1

N-[4-methyl-2-(2-chlorobenzyl)phenyl]-3,4-dimethoxybenzenesulfonamide

Starting with 1 g of N-{4-methyl-2-[(2-chlorophenyl)(hydroxy)methyl]phenyl}-3,4-dimethoxybenzenesulfonamide, obtained according to Example 8, according to an adaptation of the process described in Example 18.1, 0.47 g of the expected product is obtained.

¹H NMR δ in ppm (DMSO d6): 2.14 (s, 3H); 3.73 (s, 3H); 3.84 (s, 3H); 4.04 (s, 2H); 6.60 (s, 1H); 6.81-7.47 (unresolved complex, 9H); 9.43 (s, 1H).

EXAMPLE 22.2

$N^2$-[2-(2-chlorobenzyl)-4-methylphenyl]-$N^2$-[(3,4-dimethoxyphenyl)sulfonyl]glycinamide To 0.47 g of N-{4-methyl-2-[(2-chlorophenyl)(hydroxy)methyl]phenyl}-3,4-dimethoxybenzenesulfonamide dissolved in 5.7 ml of DMF is added, at 0° C., 0.048 g of sodium hydride. After 1 hour at this temperature, 0.166 g of 2-bromoacetamide is introduced and the mixture is left for 18 hours at room temperature. The medium is poured into water and then extracted with ethyl acetate. The organic phase is dried over anhydrous sodium sulfate and concentrated. The residue is chromatographed on a column of silica gel, eluting with a 90/10 (v/v) cyclohexane/ethyl acetate mixture to give 0.4 g of the expected product.

$^1$H NMR δ in ppm (DMSO d6): 2.16 (s, 3H); 3.79 (s, 3H); 3.88 (s, 3H); 4.05-4.25 (unresolved complex, 3H); 4.52 (d, 1H); 6.54 (s, 1H); 6.76 (d, 1H); 6.94-7.53 (unresolved complex, 10H). m.p.=140.6° C.

$N^2$-[5-Chloro-2-(2-chlorobenzyl)phenyl]-$N^2$-[(3,4-dimethoxyphenyl)sulfonyl]glycinamide (compound 179) is synthesized according to this process starting with N-{5-chloro-2-[(2-chlorophenyl)(hydroxy)methyl]phenyl}-3,4-dimethoxybenzenesulfonamide obtained according to Example 9.3, m.p.=86.4° C.

$N^2$-[2-(2-Chlorobenzyl)-4-methoxyphenyl]-$N^2$-[(3,4-dimethoxyphenyl)sulfonyl]glycinamide (compound 138) is synthesized according to this process.

m.p.=184.6° C.

EXAMPLE 23

N-[4-chloro-2-(2,6-difluorobenzyl)phenyl]-N-[3-(dimethylamino)propyl]-3,4-dimethoxybenzenesulfonamide (compound 197)

To 0.45 g of [4-chloro-2-(2,6-difluorobenzyl)phenyl]-3,4-dimethoxybenzenesulfonamide (prepared according to Example 18.2) are successively added 0.207 g of potassium carbonate, 0.1 g of tetrabutylammonium bromide, 20 ml of toluene and 0.237 g of 3-dimethylamino-1-bromopropane, and the mixture is refluxed for 24 hours. 0.168 g of potassium tert-butoxide and 0.237 g of 3-dimethylamino-1-bromopropane are added and the mixture is refluxed for 4 hours. The reaction medium is poured into water and extracted with ethyl acetate. The organic phase is dried over anhydrous sodium sulfate and concentrated. The residue is chromatographed on a column of silica gel, eluting with a 99/1 (v/v) dichloromethane/methanol mixture. The oil obtained is dissolved in methanol and poured into a 0.5M sodium hydroxide solution, and the precipitate formed is filtered off and dried under vacuum to give 0.504 g of the expected product.

$^1$H NMR δ in ppm (DMSO d6): 1.34-1.48 (unresolved complex, 2H); 2.01 (s, 6H); 2.14 (t, 2H); 3.13 (m, 1H); 3.75 (s, 3H); 3.78 (m, 1H); 3.85 (s, 3H); 4.13 (d, 1H); 4.31 (d, 1H); 6.72-7.51 (unresolved complex, 9H). m.p.=134° C.

Table XIX illustrates the chemical structures and the physical properties of a number of compounds of the invention obtained according to Example 23.

TABLE XIX

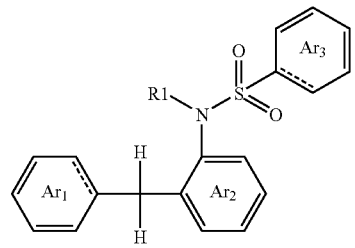

| Compound No. | Nature and position of the substituents | | | | m.p. (° C.) | MH+/retention time |
|---|---|---|---|---|---|---|
| | $Ar_1$ | $Ar_2$ | $R_1$ | $Ar_3$ | | |
| 199 | 2,6-diF | 4-Cl | 2-pyrrolidin-1-ylethyl | 3,4-diOMe | 131.4 | 551/6.61 |
| 201 | 2,6-diF | 4-Cl | 2-(dimethylamino)-1-methylethyl | 3,4-diOMe | 128.6 | 539/6.44 |
| 203 | 2,6-diF | 4-Cl | 2-[benzyl(methyl)-amino]ethyl | 3,4-diOMe | 104.8 | 601/7.18 |
| 231 | 2,6-diF | 4-Cl | $(CH_2)_2NHCONH_2$ | 3,4-diOMe | 124.5 | 539/8.27 |
| 229 | 2,6-diF | 4-Cl | $(CH_2)_3SO_2NEt_2$ | 3,4-diOMe | 71.2 | 630/10.27 |
| 230 | 2,6-diF | 4-Cl | $(CH_2)_3SO_2NMe_2$ | 3,4-diOMe | 76.8 | 602/9.71 |
| 234 | 2,6-diF | 4-Cl | 2-(2-oxopyrrolidin-1-yl)ethyl | 3,4-diOMe | 138.6 | 565/8.80 |
| 236 | 2,6-diF | 4-Cl | 2-methoxyethyl | 3,4-diOMe | 83.8 | 512/9.38 |
| 241 | 2,6-diF | 5-Br | $CH_3CONH_2$ | 3,4-diOMe | 93.5 | 555/8.99 |
| 248 | 2,6-diF | 4-Cl | cyclopropylmethyl | 3,4-diOMe | 163.4 | 508/11.42 |
| 259 | 2,6-diF | 4-Cl | $CH_3CONH_2$ | 3-Me, 4-OMe | 156.6 | 495/9.07 |
| 268 | 2,6-diF | 4-Cl | 2-(1,3-dioxolan-2-yl)ethyl | 3,4-diOMe | 288.8 | 554/10.50 |
| 283 | 2,6-diF | 4-Cl | $CH_3CONH_2$ | 6-OMe pyrid-3-yl | 164 | 482/9.27 |

EXAMPLE 24

N-{4-chloro-2-[(2-chlorophenyl)(hydroxy)methyl]phenyl}-N-(2-hydroxyethyl)-3,4-dimethoxybenzenesulfonamide (compound 24)

EXAMPLE 24.1

N-{4-chloro-2-[(2-chlorophenyl)(hydroxy)methyl]phenyl}-3,4-dimethoxy-N-[2-(tetrahydro-2H-pyran-2-yloxy)ethyl]benzenesulfonamide To 1 g of N-{4-chloro-2-[(2-chlorophenyl)(hydroxy)methyl]phenyl}-3,4-dimethoxybenzenesulfonamide, obtained in Example 1.2, dissolved in 40 ml of acetonitrile are successively added 1.2 ml of triethylamine and 1.29 ml of 2-(2-bromoethoxytetrahydro-2H-pyran, and the mixture is refluxed for 18 hours. The reaction medium is taken up in ethyl acetate and washed with water. The organic phase is dried over anhydrous sodium sulfate and concentrated. The residue is chromatographed on a column of silica gel, eluting with a cyclohexane/ethyl acetate solvent mixture to give 0.479 g of the expected product.

EXAMPLE 24.2

N-{4-chloro-2-[(2-chlorophenyl)(hydroxy)methyl]phenyl}-N-(2-hydroxyethyl)-3,4-dimethoxybenzenesulfonamide To 0.479 g of N-{4-chloro-2-[(2-chlorophenyl)(hydroxy)methyl]phenyl}-3,4-dimethoxy-N-[2-(tetrahydro-2H-pyran-2-yloxy)ethyl]benzenesulfonamide dissolved in 4.7 ml of THF are added 9.15 ml of acetic acid and 2.25 ml of water, and the mixture is maintained at 40° C. for 48 hours. The reaction medium is taken up in ethyl acetate and washed with water. The organic phase is dried over anhydrous sodium sulfate and concentrated. The residue is chromatographed on a column of silica gel, eluting with a cyclohexane/ethyl acetate solvent mixture to give 0.209 g of the expected product.

$^1$H NMR δ in ppm (DMSO d6): 3.02 (m, 2H); 3.40 (m, 2H); 3.75 (s, 3H); 3.88 (s, 3H); 4.40 (t, 1H); 6.01 (d, 1H); 6.70-7.51 (unresolved complex, 10H); 7.86 (s, 1H). m.p.=86.2° C.

In the same manner, compound 237 is prepared, the physical properties of which are as follows:

MH$^+$=498, the retention time is 8.99 minutes m.p.=165.3° C.

EXAMPLE 25

N$^2$-{4-chloro-2-[1-(2-chlorophenyl)-1-hydroxyethyl]phenyl}-N$^2$-[(3,4-dimethoxyphenyl)sulfonyl]glycinamide (compound 172)

EXAMPLE 25.1

1-(2-amino-5-chlorophenyl)-1-(2-chlorophenyl)ethanol

To 5 g of 2-amino-2',5-dichlorobenzophenone dissolved in 100 ml of diethyl ether, at −30° C., are added 12.5 ml of 3M methylmagnesium bromide solution, and the mixture is maintained at room temperature for 18 hours. 6 ml of 3M methylmagnesium bromide solution are added and the mixture is left at room temperature for 1 hour. The resulting mixture is hydrolysed with 2M hydrochloric acid solution and washed with water. The organic phase is dried over anhydrous sodium sulfate to give 4.3 g of the expected product.

$^1$H NMR δ in ppm (DMSO d6): 1.99 (s, 3H); 4.91 (s, 2H); 6.11 (s, 1H); 6.53 (d, 1H); 6.97-7.42 (unresolved complex, 5H); 7.97 (d, 1H).

EXAMPLE 25.2

N-{4-chloro-2-[1-(2-chlorophenyl)-1-hydroxyethyl]phenyl}-3,4-dimethoxybenzenesulfonamide To 1.5 g of 1-(2-amino-5-chlorophenyl)-1-(2-chlorophenyl)ethanol according to an adaptation of the process described in Example 1.1, 2.9 g of the expected product are obtained.

$^1$H NMR δ in ppm (DMSO d6): 1.78 (s, 3H); 3.75 (s, 3H); 3.83 (s, 3H); 4.05 (q, 1H); 6.87 (s, 1H); 7.04-7.54 (unresolved complex, 5H); 7.82 (m, 2H); 8.60 (d, 2H); 10.00 (s, 1H).

EXAMPLE 25.3

N-{4-chloro-2-[1-(2-chlorophenyl)-1-hydroxyethyl]phenyl}N-[(3,4-dimethoxyphenyl)sulfonyl]glycinamide To 1.3 g of N-{4-chloro-2-[1-(2-chlorophenyl)-1-hydroxyethyl]phenyl}-3,4-dimethoxybenzenesulfonamide dissolved in diethyl ether are successively added, at −5° C., 1.3 ml of a 2M solution of lithium diisopropylamine in hexane, and 0.45 g of 2-bromoacetamide. After 18 hours at room temperature, 0.5 g of 2-bromoacetamide and 1.4 g of sodium iodide are successively added and the mixture is refluxed for 4 hours. The reaction medium is taken up in ethyl acetate and washed with water. The organic phase is dried over anhydrous sodium sulfate and concentrated. The residue is chromatographed on a column of silica gel, eluting with a 95/5 (v/v) dichloromethane/methanol mixture to give 0.51 g of the expected product.

$^1$H NMR δ in ppm (DMSO d6): 2.11 (s, 3H); 3.74-3.98 (unresolved complex, 8H); 6.25 (s, 1H); 6.96-7.97 (unresolved complex, 12H).

EXAMPLE 26

N$^2$-{4-chloro-2-[1-(2-chlorophenyl)ethyl]phenyl}-N$^2$-[(3,4-dimethoxyphenyl)sulfonyl]glycinamide (compound 186)

EXAMPLE 26.1

4-chloro-2-[1-(2-chlorophenyl)ethyl]phenylamine

To 54 ml of a 1M solution of lithium aluminium hydride in THF are added portionwise 7.1 g of aluminium trichloride. To this solution are added 4 g of 1-(2-amino-5-chlorophenyl)-1-(2-chlorophenyl)ethanol, obtained in Example 25.1, dissolved in diethyl ether, and the mixture is stirred for 18 hours at room temperature and then refluxed for 4 hours. The reaction medium is taken up in ethyl acetate and washed with water. The organic phase is dried over anhydrous sodium sulfate and concentrated. The residue is chromatographed on a column of silica gel, eluting with a 40/60 (v/v) dichloromethane/cyclohexane mixture to give 0.9 g of the expected product.

$^1$H NMR δ in ppm (DMSO d6): 1.45 (d, 3H); 4.43 (q, 1H); 4.96 (s, 2H); 6.65 (m, 2H); 6.94 (d, 1H); 7.30-7.47 (unresolved complex, 4H).

EXAMPLE 26.2

N-{4-chloro-2-[1-(2-chlorophenyl)ethyl]phenyl}-3,4-dimethoxybenzenesulfonamide

Starting with 0.9 g of 4-chloro-2-[1-(2-chlorophenyl)ethyl]phenylamine according to the process described in Example 1.1, 1.7 g of the expected product are obtained.

EXAMPLE 26.3

N$^2$-{4-chloro-2-[1-(2-chlorophenyl)ethyl]phenyl}-N$^2$-[(3,4-dimethoxyphenyl)sulfonyl]glycinamide Starting with 0.9 g of N-(4-chloro-2-[1-(2-chlorophenyl)ethyl]phenyl}-3,4-dimethoxybenzenesulfonamide according to the process described in Example 12.3, 0.9 g of the expected product are obtained.

$^1$H NMR δ in ppm (DMSO d6): 1.35 (d, 3H); 2.75 (d, 1H); 3.79 (s, 3H); 3.86 (s, 3H); 4.25 (d, 1H); 4.74 (q, 1H); 6.92-7.64 (unresolved complex, 12H). m.p.=150° C.

Compound 187 is obtained according to this process. m.p.=151° C.

EXAMPLE 27

N-(2-aminoethyl)N-[2-(2,6-difluorobenzyl)-4-methylphenyl]-3,4-dimethoxybenzenesulfonamide (compound 215)

To 1 g of N-[4-methyl-2-(2,6-difluorobenzyl)phenyl]-N-[2-(phthalimido)ethyl]-3,4-dimethoxybenzenesulfonamide, obtained according to an adaptation of the process described in Example 18, dissolved in 15 ml of ethanol is added 0.4 g of hydrazine hydrate, and the mixture is refluxed for 3 hours. At room temperature, the insoluble material is filtered off and the filtrate is concentrated. The residue is chromatographed on a column of silica gel, eluting with a 99/1 (v/v) dichloromethane/methanol mixture to give 0.26 g of the expected product.

$^1$H NMR δ in ppm (DMSO d6): 1.62 (s, 2H); 2.17 (s, 3H); 2.40-2.67 (unresolved complex, 2H); 3.12 (m, 1H); 3.69 (m, 1H); 3.75 (s, 3H); 3.88 (s, 3H); 4.09 (d, 1H); 4.26 (d, 1H); 6.56 (m, 2H); 6.97-7.43 (unresolved complex, 7H). m.p.=251.8° C.

Table XX illustrates the chemical structures and the physical properties of a number of compounds of the invention obtained according to Example 28.

TABLE XX

| Compound No. | Ar$_1$ | Ar$_2$ | R$_1$ | Ar$_3$ | m.p. (° C.) | MH$^+$/ retention time |
|---|---|---|---|---|---|---|
| 256 | 2,6-diF | 4-Cl | 2-aminoethyl | 3,4-diOMe | 163.4 | 497/6.82 |
| 257 | 2,5-diF | 4-Me | 2-aminoethyl | 3,4-diOMe | 61.1 | 477/6.69 |
| 262 | 2,5-diF | 4-Cl | 2-aminoethyl | 3,4-diOMe | 141.1 | 497/6.88 |
| 281 | 2,6-diF | 6-OMe | 2-aminoethyl | 3,4-diOMe | 137.8 | 493/6.47 |
| 287 | 2,6-diF | 4-Cl | 3-aminopropyl | 3,4-diOMe | 149.1 | 511/6.91 |
| 294 | 2,5-diF | 6-OMe | 2-aminoethyl | 3,4-diOMe | 114.8 | 493/6.47 |
| 300 | 2,6-diF | 4-Cl, 6-OMe | 2-aminoethyl | 3,4-diOMe | 185.4 | 527/6.82 |

EXAMPLE 28

N-(2-{[(benzylamino)carbonyl]amino}ethyl)-N-[2-(2,6-difluorobenzyl)-4-methylphenyl]-3,4-dimethoxybenzenesulfonamide (compound 218)

To 1 g of N-(2-aminoethyl)-N-[2-(2,6-difluorobenzyl)-4-methylphenyl]-3,4-dimethoxybenzenesulfonamide (compound 215) dissolved in 20 ml of THF is added 0.266 g of benzyl isocyanate, and, after refluxing for 3 hours, the medium is evaporated to dryness. The residue is chromatographed on a column of silica gel, eluting with an 8/2 (v/v) toluene/ethyl acetate mixture to give 0.65 g of the expected product.

$^1$H NMR δ in ppm (DMSO d6): 2.17 (s, 3H); 3.05 (m, 2H); 3.24 (m, 1H); 3.74 (s, 3H); 3.78 (m, 1H); 3.87 (s, 3H); 4.07-4.25 (unresolved complex, 4H); 5.99 (t, 1H); 6.50 (t, 1H); 6.58 (d, 2H); 6.98-7.43 (unresolved complex, 12H). m.p.=100.4° C.

Table XXI illustrates the chemical structures and the physical properties of a number of compounds of the invention obtained according to Example 28.

TABLE XXI

| Compound No. | Ar$_1$ | Ar$_2$ | R$_1$ | Ar$_3$ | m.p. (° C.) | MH$^+$/ retention time |
|---|---|---|---|---|---|---|
| 217 | 2,6-diF | 4-Me | 2-[(anilino-carbonyl)amino]-ethyl | 3,4-diOMe | 163.4 | n.d |
| 238 | 2,6-diF | 4-Cl | 2-({[(3-chlorophenyl)-amino]-carbonyl}-amino)-ethyl | 3,4-diOMe | 149.3 | 650/10.87 |
| 240 | 2,6-diF | 4-Cl | 2-({[(2-chlorophenyl)-amino]-carbonyl}-amino)-ethyl | 3,4-diOMe | 136.3 | 650/10.77 |
| 252 | 2,6-diF | 4-Cl | 2-({[(3,4-dimethoxyphenyl)-amino] carbonyl}-amino) ethyl | 3,4-diOMe | 169.7 | 676/9.80 |

EXAMPLE 29

N-(2-{[2-(2,6-difluorobenzyl)-4-methylphenyl][(3,4-dimethoxyphenyl)sulfonyl]amino}ethyl)acetamide (compound 219)

To 1 g of N-(2-aminoethyl)N-[2-(2,6-difluorobenzyl)-4-methylphenyl]-3,4-dimethoxybenzenesulfonamide (compound 215) dissolved in 25 ml of THF are added 0.167 ml of pyridine and 0.22 g of acetic anhydride. After 48 hours at room temperature, the reaction medium is concentrated. The residue is chromatographed on a column of silica gel, eluting with a 99/1 (v/v) dichloromethane/methanol mixture to give 0.505 g of the expected product.

¹H NMR δ in ppm (DMSO d6): 1.74 (s, 3H); 2.17 (s, 3H); 3.05-3.28 (m, 3H); 3.72 (m, 1H); 3.76 (s, 3H); 3.87 (s, 3H); 4.05 (d, 1H); 4.22 (d, 1H); 6.60 (d, 2H); 6.99-7.46 (unresolved complex, 7H); 7.85 (t, 1H). m.p.=79.7° C.

EXAMPLE 30

$N^2$-{4-chloro-2-[methyl(phenyl)amino]phenyl}-$N^2$-[(3,4-dimethoxyphenyl)sulfonyl]-$N^1$-methylglycinamide (compound 124)

EXAMPLE 30.1

5-chloro-2-nitro-N-diphenyl-N-methylamine

To 10 g of 5-chloro-2-nitrodiphenylamine dissolved in 20 ml of DMF are successively added 2.8 ml of iodomethane and 14.71 g of caesium carbonate, and the mixture is stirred for 18 hours at room temperature. The reaction medium is taken up in ethyl acetate and washed with water. The organic phase is dried over anhydrous sodium sulfate and concentrated. The residue is chromatographed on a column of silica gel, eluting with 97/3 (v/v) cyclohexane/ethyl acetate mixture to give 10.51 g of the expected product.

¹H NMR δ in ppm (DMSO d6): 3.32 (s, 3H); 6.78-6.93 (unresolved complex, 3H); 7.19-7.26 (m, 2H); 7.40 (d, 1H); 7.65 (d, 1H); 7.93(d, 1H).

EXAMPLE 30.2

2-amino-5-chloro-N-diphenyl-N-methylamine

To 10.49 g of 5-chloro-2-nitro-N-diphenyl-N-methylamine dissolved in 100 ml of ethanol are successively added 14.22 g of tin metal and 50 ml of 12M hydrochloric acid solution, and the mixture is refluxed for 1 hour. After evaporating off the ethanol, the reaction medium is taken up in ethyl acetate, basified and washed with water. The organic phase is dried over anhydrous sodium sulfate and concentrated to give 9.37 g of the expected product.

¹H NMR δ in ppm (DMSO d6): 3.11 (s, 3H); 5.07 (s, 2H) 6.57-7.21 (unresolved complex, 8H).

EXAMPLE 30.3

N-{4-chloro-2-[methyl(phenyl)amino]phenyl}-3,4-dimethoxybenzenesulfonamide

Starting with 1.5 g of 2-amino-5-chloro-N-diphenyl-N-methylamine, the process is performed according to Example 1.1 to give 1.122 g of the expected product.

¹H NMR δ in ppm (DMSO d6): 2.93 (s, 3H); 3.67 (s, 3H); 3.84 (s, 3H); 6.37 (d, 2H); 6.74 (t, 1H); 7.05-7.37 (unresolved complex, 7H); 7.54 (d, 1H); 9.46 (s, 1H).

EXAMPLE 30.4

$N^2$-{4-chloro-2-[methyl(phenyl)amino]phenyl}-$N^2$-[(3,4-dimethoxyphenyl)sulfonyl]-$N^1$-methylglycinamide Starting with 0.8 g of N-{4-chloro-2-[methyl(phenyl)amino]phenyl}-3,4-dimethoxybenzenesulfonamide according to the process described in Example 4.3, 0.766 g of the expected product is obtained.

¹H NMR δ in ppm (DMSO d6): 2.41 (d, 3H); 3.16 (s, 3H); 3.77 (s, 3H); 3.88 (s, 3H); 4.12 (s, 2H); 6.66-6.84 (unresolved complex, 3H); 7.10-7.43 (unresolved complex, 8H); 7.72 (t, 1H). m.p.=148.6° C.

Compound 92 is obtained by this process:
m.p.=192.5° C.

EXAMPLE 31

4-{[4-chloro-2-(2,6-difluorobenzyl)phenyl][(3,4-dimethoxyphenyl)sulfonyl]-amino}butanamide (compound 204)

EXAMPLE 31.1

4-{[4-chloro-2-{[2-(2,6-difluorobenzyl)phenyl][((3,4-dimethoxyphenyl}sulfonyl]amino}butanoic acid To 2.6 g of ethyl 4-{[4-chloro-2-{[2-(2,6-difluorobenzyl)phenyl][((3,4-dimethoxyphenyl}sulfonyl]amino}butanoate, obtained according to Example 18, dissolved in 50 ml of ethanol are added 22.8 ml of sodium hydroxide, and the mixture is left for 18 hours at room temperature. The solvent is evaporated off and the residue is taken up in 40 ml of 1M hydrochloric acid solution and extracted with ethyl acetate. The organic phase is dried over anhydrous sodium sulfate and concentrated. The residue is solidified with diisopropyl ether to give 1.7 g of the expected product.

¹H NMR δ in ppm (DMSO d6): 1.54 (m, 2H); 2.27 (t, 2H); 3.27 (m, 1H); 3.76 (s, 3H); 3.85 (s, 3H); 4.23 (m, 2H); 6.75-7.51 (unresolved complex, 10H); 12.09 (s, 1H).

EXAMPLE 31.2

{[4-chloro-2-(2,6-difluorobenzyl)phenyl][(3,4-dimethoxyphenyl)sulfonyl]amino}butanamide To 1.7 g of 4-{[4-chloro-2-{[2-(2,6-difluorobenzyl)phenyl][((3,4-dimethoxyphenyl}sulfonyl]amino}butanoic acid dissolved in 30 ml of THF, at 0° C., are added 0.42 ml of N-ethylmorpholine and 0.42 ml of ethyl chloroformate; after 30 minutes at this temperature, a solution of ammonia in THF is introduced dropwise and the mixture is left for 1 hour at 20° C. The resulting mixture is poured into saturated sodium hydrogencarbonate solution and taken up in ethyl acetate. The organic phase is dried over anhydrous sodium sulfate and concentrated, and the residue is solidified with diethyl ether to give, after drying, 1.41 g of the expected product.

¹H NMR δ in ppm (DMSO d6): 1.51 (m, 2H); 2.07 (t, 2H); 3.21 (m, 1H); 3.74 (m, 1H); 3.78 (s, 3H); 3.89 (s, 3H); 4.23 (q, 2H); 6.75 (m, 3H); 7.04-7.51 (unresolved complex, 8H). m.p.=197° C.

Table XXII illustrates the chemical structures and the physical properties of a number of compounds of the invention obtained according to this example.

TABLE XXII

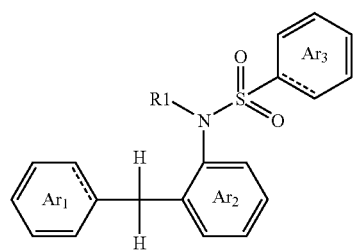

| Compound No. | Nature and position of the substituents | | | | m.p. (°C.) | MH+/retention time |
|---|---|---|---|---|---|---|
| | Ar₁ | Ar₂ | R₁ | Ar₃ | | |
| 235 | 2,6-diF | 4-Cl | CH₂CH₂CH₂CONH₂ | 2,5-diMe, 4-Cl | n.d | 541/10.03 |
| 266 | 2,5-diF | 4-Cl | CH₂CH₂CH₂CONH₂ | 3,4-diOMe | 150 | 539/9.15 |
| 272 | 2,6-diF | 6-OMe | CH₂CH₂CH₂CONH₂ | 3,4-diOMe | 207.8 | 535/8.42 |
| 299 | 2,5-diF | 6-OMe | CH₂CH₂CH₂CONH₂ | 3,4-diOMe | 189.3 | 535/8.54 |

EXAMPLE 32

N²-{4-chloro-2-[2-(trifluoromethyl)benzyl]phenyl}-N²-[(3,4-dimethoxyphenyl)sulfonyl]glycinamide (compound 207)

EXAMPLE 32.1

(2-amino-5-chlorophenyl)(2-trifluoromethylphenyl)methanol

To 1.9 g of (2-amino-5-chlorophenyl)(2-trifluoromethylphenyl)methanone, obtained in Example 7.2, dissolved in 87 ml of ethanol is added 0.775 g of sodium borohydride, and the mixture is left at 20° C. for 18 hours. The solvent is evaporated off and the residue is taken up in ethyl acetate and washed with water. The organic phase is dried over anhydrous sodium sulfate and concentrated to give 1.96 g of the expected product.

¹H NMR δ in ppm (DMSO d6): 5.15 (s, 2H); 5.97 (d, 1H); 6.11 (d, 1H); 6.35 (d, 1H); 6.72 (d, 1H); 6.99 (d, 1H); 7.53-7.81 (unresolved complex, 4H).

EXAMPLE 32.2

N-{4-chloro-2-[(2-trifluoromethylphenyl)(hydroxy)methyl]phenyl}-3,4-dimethoxybenzenesulfonamide Starting with 1.28 g of (2-amino-5-chlorophenyl)(2-trifluoromethylphenyl)methanol according to the process described in Example 1.1, 2.06 g of the expected product are obtained.

¹H NMR δ in ppm (DMSO d6): 3.76 (s, 3H); 3.85 (s, 3H); 6.34 (s, 2H); 6.89 (d, 1H); 6.98 (s, 1H); 7.08 (d, 1H); 7.23-7.33 (unresolved complex, 4H); 7.53-7.77 (unresolved complex, 3H); 9.25 (s, 1H).

EXAMPLE 32.3

N-[4-chloro-2-(2-trifluoromethylbenzyl)phenyl]-3-methoxybenzenesulfonamide

Starting with 2.06 g of N-{4-chloro-2-[(2-trifluoromethylphenyl)(hydroxy)methyl]phenyl}-3,4-dimethoxybenzenesulfonamide according to the method described in Example 22.1, 0.94 g of the expected product is obtained.

¹H NMR δ in ppm (DMSO d6): 3.73 (s, 3H); 3.85 (s, 3H); 4.06 (s, 2H); 6.64 (s, 1H); 6.89-7.28 (unresolved complex, 6H); 7.48-7.60 (m, 2H); 7.75 (d, 1H); 9.72 (s, 1H).

EXAMPLE 32.4

N²-{4-chloro-2-[2-(trifluoromethyl)benzyl]phenyl}-N²-[(3,4-dimethoxyphenyl)sulfonyl]glycinamide Starting with 0.94 g of N-[4-chloro-2-(2-trifluoromethylbenzyl)phenyl]-3-methoxybenzenesulfonamide according to Example 16.3, 0.723 g of the expected product is obtained.

¹H NMR δ in ppm (DMSO d6): 3.80 (s, 3H); 3.89 (s, 3H); 4.03 (d, 1H); 4.27 (q, 2H); 4.74 (d, 1H); 6.55 (s, 1H); 6.88 (d, 1H); 7.12-7.63 (unresolved complex, 9H); 7.82 (d, 1H). m.p.=133° C.

EXAMPLE 33

N-[4-chloro-2-(2,6-difluorobenzyl)phenyl]-N-[(3,4-dimethoxyphenyl)sulfonyl]-2,2,2-trifluoroacetamide (compound 223)

To 2.2 g of N-[4-chloro-2-(2,6-difluorobenzyl)phenyl]-3,4-dimethoxybenzenesulfonamide, obtained in Example 18.2, dissolved in 40 ml of dichloromethane are added 0.8 ml of triethylamine and 1.46 g of trifluoroacetyl triflate, and, after 10 minutes, the medium is hydrolysed and concentrated. The residue is chromatographed on a column of silica gel, eluting with a dichloromethane/cyclohexane mixture to give 1.1 g of the expected product.

¹H NMR δ in ppm (DMSO d6): 3.86 (s, 3H); 3.93 (s, 3H); 4.19 (s, 2H); 6.92 (s, 1H); 7.17-7.54 (unresolved complex, 7H); 7.71 (d, 1H). m.p.=79.7° C.

EXAMPLE 34

N-[4-chloro-2-(2,6-difluorobenzyl)phenyl]-3,4-dimethoxy-N-(2,2,2-trifluoroethyl)benzenesulfonamide (compound 190)

To 1.48 g of N-[4-chloro-2-(2,6-difluorobenzyl)phenyl]-3,4-dimethoxybenzenesulfonamide, obtained in Example 18.2, dissolved in 40 ml of xylene are added 2.3 g of 2,2,2-trifluoroethyl trichloromethanesulfonate, 0.44 g of potassium tert-butoxide and 20 ml of N-methylpyrrolidone, and the mixture is maintained at 150° C. for 8 hours. The reaction medium is taken up in ethyl acetate and washed with water. The organic phase is dried over anhydrous sodium sulfate and concentrated. The residue is chromatographed on a column of silica gel, eluting with dichloromethane, to give 0.455 g of the expected product.

¹H NMR δ in ppm (DMSO d6): 3.82 (s, 3H); 3.90 (s, 3H); 4.14-4.35 (unresolved complex, 3H); 4.82 (m, 1H); 6.63 (s, 1H); 6.80 (d, 1H); 7.17-7.54 (unresolved complex, 7H). m.p.=70° C.

EXAMPLE 35

N-[4-chloro-2-(2,6-difluorobenzyl)phenyl]-3,4-dimethoxy-N-(3-pyrid-3-ylpropyl)benzenesulfonamide (compound 232)

To 1.5 g of triphenylphosphine dissolved in 25 ml of THF is added 0.909 g of diisopropyl azodicarboxylate. After 15 minutes at room temperature, 0.61 g of 3-pyrid-3-ylpropan-1-ol is introduced and the mixture is left at 20° C. for 15 minutes. 1.36 g of N-[4-chloro-2-(2,6-difluorobenzyl)phenyl]-3,4-dimethoxybenzenesulfonamide are introduced and the mixture is left at room temperature for 18 hours. The medium is concentrated and the residue is chromatographed on a column of silica gel, eluting with a toluene/ethyl acetate mixture passing from a ratio of 9/1 to 5/5 (v/v). 5 ml of 2M hydrochloric acid are added to the product obtained, dissolved in diethyl ether, and the solvents are then evaporated off. The residue is taken up in diisopropyl ether to give, after filtration, 0.55 g of the expected product.

m.p.=102.8° C.

Table XXIII illustrates the chemical structures and the physical properties of a number of compounds of the invention obtained according to this example.

TABLE XXIII

| Compound No. | Ar₁ | Ar₂ | R₁ | Ar₃ | m.p. (° C.) | MH⁺/retention time |
|---|---|---|---|---|---|---|
| 245 | 2,6-diF | 4-Cl | 3-pyrid-3-ylpropyl | 3,4-diOMe | 102.8 | 573/8.10 |
| 250 | 2,6-diF | 4-Cl | 2-pyrid-2-ylethyl | 3,4-diOMe | 75.1 | 559/8.24 |
| 254 | 2,6-diF | 4-Cl | 2-pyrid-3-ylethyl | 3,4-diOMe | 90.3 | 559/7.14 |
| 255 | 2,6-diF | 4-Cl | 2-pyrid-4-ylethyl | 3,4-diOMe | 164.3 | 559/8.29 |
| 260 | 2,6-diF | 4-Cl | 2-phenoxyethyl | 3,4-diOMe | 64.3 | 574/10.88 |
| 274 | 2,6-diF | 4-Cl | (2R)-pyrrolidin-2-ylmethyl | 3,4-diOMe | 204.8 | 537/7.07 |
| 275 | 2,6-diF | 4-Cl | (2S)-pyrrolidin-2-ylmethyl | 3,4-diOMe | 214.1 | 537/7.07 |
| 278 | 2,6-diF | 4-Cl | {[2-(dimethylamino)-ethyl]-amino}ethyl | 3,4-diOMe | 103 | 568/6.29 |
| 290 | 2,6-diF | 4-Cl | 1,3-thiazol-2-ylmethyl | 3,4-diOMe | 184 | 551/10.26 |
| 291 | 2,6-diF | 4-Cl | pyrimid-2-ylmethyl | 3,4-diOMe | 104 | 546/9.89 |
| 292 | 2,6-diF | 4-Cl | 2-morpholino-4-ylethyl | 3,4-diOMe | 185.3 | 567/7.35 |
| 295 | 2,6-diF | 4-Cl | pyrid-2-ylmethyl | 3,4-diOMe | 200.8 | 545/16.9 |
| 315 | 2,6-diF | 6-OMe | CH(CH₃)COOEt | 3,4-diOMe | 94.3 | 536/9.98 |
| 316 | 2,6-diF | 6-OMe | CH(CH₃)COOEt | 3,4-diOMe | 130.2 | 536/9.89 |
| 317 | 2,6-diF | 6-OMe | CH(CH₃)COOEt | 3,4-diOMe | 73.3 | 536/9.98 |
| 318 | 2,6-diF | 6-OMe | CH(CH₃)COOEt | 3,4-diOMe | 130.8 | 536/9.89 |

Compound 315
$[\alpha_D]^{20}$ = +97.59 c = 0.66 (CH₂Cl₂)

Compound 316
$[\alpha_D]^{20}$ = −106.25 c = 0.66 (CH₂Cl₂)

Compound 317
$[\alpha_D]^{20}$ = −101.53 c = 0.45 (CH₂Cl₂)

Compound 318
$[\alpha_D]^{20}$ = +106.66 c = 0.66 (CH₂Cl₂)

Compounds 315/316 and 317/318 are pairs of atropoisomers. Each atropoisomer is characterized by its optical rotation ($\alpha_D$). The centre of atropoisomerism is generated by the steric hindrance around the N-aromatic bond.

EXAMPLE 36 ethyl N-[(2,6-difluorobenzyl)-4-methylphenyl]-3,4-dimethoxy-N-[2-(methylamino)ethyl]benzenesulfonamide (compound 258)

EXAMPLE 36.1 ethyl N-(2-bromoethyl)-N-[2-(2,6-difluorobenzyl)-4-methylphenyl]-3,4-dimethoxybenzenesulfonamide To 1 g of N-[2-(2,6-difluorobenzyl)-4-methylphenyl]-3,4-dimethoxybenzenesulfonamide dissolved in 1.1 ml of dimethylformamide are successively added 0.38 g of potassium carbonate and 0.48 ml of 1,2-dibromoethane, and the mixture is maintained at 100° C. for 4 hours. After cooling to room temperature, the reaction medium is hydrolysed and extracted with ethyl acetate. The organic phase is dried over anhydrous sodium sulfate and concentrated to give 1.24 g of expected product.

$^1$H NMR δ in ppm (DMSO d6): 2.17 (s, 3H); 3.42 (m, 2H); 3.73 (m, 1H); 3.76 (s, 3H); 3.88 (s, 3H); 4.03-4.15 (unresolved complex, 2H); 4.45 (d, 1H); 6.63 (d, 1H); 6.98-7.48 (unresolved complex, 8H).

EXAMPLE 36.2 ethyl N-[(2,6-difluorobenzyl)-4-methylphenyl]-3,4-dimethoxy-N-[2-(methylamino)ethyl]benzenesulfonamide hydrobromide To 1.24 g of N-(2-bromoethyl)-N-[2-(2,6-difluorobenzyl)-4-methylphenyl]-3,4-dimethoxybenzenesulfonamide are added 10.7 ml of 2M solution of methylamine in methanol and the mixture is maintained at 105° C. for 4 hours. The reaction is completed by addition of 10 ml of 2M solution of methylamine in methanol with refluxing for 8 hours. After cooling to room temperature, the medium is concentrated and the residue is chromatographed to give 0.849 g of the expected product.

m.p.=208.5° C. $^1$H NMR δ in ppm (DMSO d6): 2.20 (s, 3H); 2.58 (s, 3H); 2.85 (m, 1H); 3.06 (m, 1H); 3.52 (m, 1H); 3.77 (s, 3H); 3.90 (s, 3H); 3.99-4.07 (unresolved complex, 2H); 4.27 (d, 1H); 6.58-6.64 (unresolved complex, 2H); 7.01-7.49 (unresolved complex, 2H); 8.48 (s, 2H).

Table XXIV illustrates the chemical structures and the physical properties of a number of compounds of the invention obtained according to this example.

TABLE XXIV

| Compound No. | Nature and position of the substituents | | | | m.p. (° C.) | MH+/ retention time |
|---|---|---|---|---|---|---|
| | Ar$_1$ | Ar$_2$ | R$_1$ | Ar$_3$ | | |
| 277 | 2,6-diF | 4-Cl | 2-(1H-1,2,4-triazol-1-yl)ethyl | 3,4-diOMe | 129.1 | n.d. |
| 282 | 2,6-diF | 6-OMe | methylaminoethyl | 3,4-diOMe | 262.9 | 507/6.54 |
| 284 | 2,6-diF | 4-Cl | methylaminoethyl | 3,4-diOMe | 54 | 511/6.94 |
| 306 | 2,6-diF | 6-OMe | 2-(1H-1,2,4-triazol-1-yl)ethyl | 3,4-diOMe | 132.1 | 545/8.76 |

EXAMPLE 37

N-[4-chloro-2-(2,6-difluorobenzyl)phenyl]-N-(3-hydroxypropyl)-3,4-dimethoxybenzenesulfonamide (compound 270)

EXAMPLE 37.1

N-(3-{[tertbutyl(dimethyl)silyl]oxy}propyl)-N-[4-chloro-2-(2,6-difluorobenzyl)phenyl]-3,4-dimethoxybenzenesulfonamide To 4.3 g of triphenylphosphine in 20 ml of tetrahydrofuran are added, at room temperature, 3.25 ml of diisopropyl azodicarboxylate. After 30 minutes, 3.5 ml of 3-[tert-butyl(dimethyl)silyloxy]propanol dissolved in 30 ml of tetrahydrofuran are introduced. The mixture is left at room temperature for 30 minutes, and 5 g of N-[4-chloro-2-(2,6-difluorobenzyl)phenyl]-3,4-dimethoxybenzenesulfonamide are then introduced. After 48 hours at room temperature, the reaction medium is concentrated and then chromatographed on a column of silica gel to give 8.09 g of the expected product.

$^1$H NMR δ in ppm (DMSO d6): -0.04 (s, 3H); -0.02 (s, 3H); 0.82 (s, 9H); 1.40-1.56 (unresolved complex, 2H); 3.18 (m, 1H); 3.54 (m, 2H); 3.76 (s, 3H); 3.82 (m, 1H); 3.90 (s, 3H); 4.13 (d, 1H); 4.26 (d, 1H); 6.72-7.23 (unresolved complex, 9H).

EXAMPLE 37.2

N-[4-chloro-2-(2,6-difluorobenzyl)phenyl]-N-(3-hydroxypropyl)-3,4-dimethoxybenzenesulfonamide To 8 g of N-(3-{[tertbutyl(dimethyl)silyl]oxy}propyl)-N-[4-chloro-2-(2,6-difluorobenzyl)phenyl]-3,4-dimethoxybenzenesulfonamide in 80 ml of tetrahydrofuran at 0° C. are added 2.98 g of tetrabutylammonium fluoride trihydrate. After 40 minutes at 25° C., the reaction medium is concentrated and then chromatographed on a column of silica gel, eluting with dichloromethane, to give 3.28 g of the expected product.

m.p.=138.3° C. $^1$H NMR δ in ppm (DMSO d6): 1.35-1.55 (unresolved complex, 2H); 3.18 (m, 1H); 3.41 (m, 1H); 3.77

(s, 3H); 3.85 (m, 2H); 3.88 (s, 3H); 4.13 (d, 1H); 4.29 (d, 1H); 4.48 (t, 1H); 6.71-7.50 (unresolved complex, 9H)

EXAMPLE 38

N-[4-chloro-2-(2,6-difluorobenzyl)phenyl]-N-(2-hydroxy-1-methylethyl)-3,4-dimethoxybenzenesulfonamide (compound 264)

To 1.1 g of methyl N-[4-chloro-2-(2,6-difluorobenzyl)phenyl]-N-[(3,4-dimethoxyphenyl)sulfonyl]alaninate in 15 ml of tetrahydrofuran are added, at room temperature, 158 mg of lithium aluminium hydride. After refluxing for 5 hours, the mixture is cooled to room temperature and hydrolysed with 15% sodium hydroxide solution. The medium is taken up in ethyl acetate and washed with water, the phases are separated by settling and the organic phase is dried over anhydrous sodium sulfate. The organic phase is concentrated and the residue is chromatographed on a column of silica gel, eluting with a 90/10 (v/v) toluene/ethyl acetate mixture to give 0.215 g of the expected product.

m.p.=169.2° C. $^1$H NMR δ in ppm (DMSO d6): 1.18 (d, 3H); 3.47 (m, 2H); 3.77 (s, 3H); 3.88 (s, 3H); 4.07-4.52 (unresolved complex, 3H); 4.98 (t, 1H); 6.61-7.49 (unresolved complex, 9H)

EXAMPLE 39

2-{[4-chloro-2-(2,6-difluorobenzyl)phenyl][(3,4-dimethoxyphenyl)sulfonyl]amino}-2-ethoxyacetamide (compound 276)

EXAMPLE 39.1 ethyl {[4-chloro-2-{2,6-difluorobenzyl}phenyl][(3,4-dimethoxyphenyl}sulfonyl]amino(fluoro)acetate To 2 g of N-[4-chloro-2-(2,6-difluorobenzyl)phenyl]-3,4-dimethoxybenzenesulfonamide in 15 ml of tetrahydrofuran are successively added, at room temperature, 0.742 g of potassium tert-butoxide and 0.78 ml of ethyl bromo(fluoro)acetate, and the mixture is left at room temperature for 18 hours. To complete the reaction, 0.742 g of potassium tert-butoxide and 0.6 ml of ethyl bromo(fluoro) acetate are added. After 24 hours at room temperature, the reaction medium is concentrated and the residue is taken up in ethyl acetate and washed with water. The organic phase is dried over anhydrous sodium sulfate and concentrated. The residue is chromatographed on a column of silica gel, eluting with a toluene/ethyl acetate mixture (100% toluene to 80% toluene/20% ethyl acetate) to give 0.825 g of product (HPLC purity 77%).

$^1$H NMR δ in ppm (DMSO d6): 0.92 (t, 3H); 3.78 (s, 3H); 3.87 (s, 3H); 4.12-4.38 (unresolved complex, 5H); 6.73-7.33 (unresolved complex, 9H).

EXAMPLE 39.2

5-chloro-3-(2,6-difluorophenyl)-1-[(3,4-dimethoxyphenyl)sulfonyl]indoline-2-carboxylic acid To 0.825 g of ethyl {[4-chloro-2-(2,6-difluorobenzyl}phenyl][(3,4-dimethoxyphenyl)sulfonyl]amino(fluoro)acetate in 10 ml of ethanol and 10 ml of 1,4-dioxane is added, at room temperature, 0.062 g of lithium hydroxide hydrate, and the mixture is left at room temperature for 6 hours. The reaction medium is concentrated and the residue is taken up in ethyl acetate and washed with 1M hydrochloric acid solution. The organic phase is dried over anhydrous sodium sulfate and concentrated. The residue is chromatographed on a column of silica gel, eluting with a dichloromethane/methanol mixture (100% dichloromethane to 90% dichloromethane/10% methanol) to give 0.345 g of product (50% HPLC purity).

$^1$H NMR δ in ppm (DMSO d6): 3.74 (s, 3H); 3.84 (s, 3H); 4.17 (d, 1H); 4.40 (d, 1H); 5.57 (s, 1H); 6.49 (s, 1H); 6.78-7.47 (unresolved complex, 8H).

EXAMPLE 39.3

2-{[4-chloro-2-(2,6-difluorobenzyl)phenyl][(3,4-dimethoxy phenyl)sulfonyl]amino}-2-ethoxyacetamide To 0.34 g of 5-chloro-3-(2,6-difluorophenyl)-1-[(3,4-dimethoxyphenyl)sulfonyl]indoline-2-carboxylic acid in 10 ml of tetrahydrofuran are successively added, at 0° C., 90 µl of N-ethylmorpholine and 68 µl of ethyl chloroformate, the mixture is left at this temperature for 30 minutes, and 0.5 ml of 6M aqueous ammonia solution is introduced. The reaction medium is concentrated and the residue is taken up in ethyl acetate and washed with water. The organic phase is dried over anhydrous sodium sulfate and concentrated. The residue is chromatographed on a column of silica gel, eluting with a dichloromethane/methanol mixture (100% dichloromethane to 98% dichloromethane/2% methanol) to give 0.256 g of product (99.6% HPLC purity).

m.p.=153.6° C. $^1$H NMR δ in ppm (DMSO d6): 1.25 (t, 3H); 3.57 (m, 2H); 3.84 (s, 3H); 3.87 (s, 3H); 4.31 (q, 2H); 6.53 (s, 1H); 6.52-7.55 (unresolved complex, 11H)

EXAMPLE 40 phenyl (2-{[4-chloro-2-(2,6-difluorobenzyl)phenyl][(3,4-dimethoxyphenyl) sulfonyl]amino}ethylcarbamate (compound 269)

To 1.4 g of ethyl N-[2,6-difluorobenzyl)-4-chlorophenyl]-3,4-dimethoxy-N-[2-(methylamino)ethyl]benzenesulfonamide in 6 ml of tetrahydrofuran are successively added, at 0° C., 0.29 ml of pyridine and 0.37 ml of phenyl chloroformate, and the mixture is left at room temperature for 18 hours. The reaction medium is taken up in ethyl acetate and washed successively with 1M hydrochloric acid solution, sodium hydrogen carbonate solution, and water. The organic phase is dried over anhydrous sodium sulfate and concentrated. The residue is chromatographed on a column of silica gel to give 1.07 g of the expected product.

m.p.=137.5° C. $^1$H NMR δ in ppm (DMSO d6): 3.05-3.24 (unresolved complex, 4H); 3.76 (s, 3H); 3.87 (s, 3H); 4.09 (d, 1H); 4.30 (d, 1H); 6.78-7.46 (unresolved complex, 14H); 7.77 (t, 1H).

EXAMPLE 41

N-[4-chloro-2-(2,6-difluorobenzyl)phenyl]-3,4-dimethoxy-N-(2-{[(methylamino)carbonyl]amino}ethyl)benzenesulfonamide (compound 253)

To 0.42 g of phenyl(2-{[4-chloro-2-(2,6-difluorobenzyl) phenyl][(3,4-dimethoxyphenyl)sulfonyl] amino}ethylcarbamate in 1.2 ml of dimethyl sulfoxide is added, at room temperature, 0.053 ml of an aqueous solution of methylamine, and the mixture is left at room temperature for 18 hours. The reaction medium is taken up in ethyl acetate and washed with water. The organic phase is dried over anhydrous sodium sulfate and concentrated. The residue is chromatographed on a column of silica gel to give 0.326 g of the expected product.

m.p.=105.7° C. $^1$H NMR δ in ppm (DMSO d6): 2.48 (s, 3H); 3.18 (q, 2H); 3.24 (m, 1H); 3.68 (m, 1H); 3.76 (s, 3H); 3.88 (s, 3H); 4.20 (q, 2H); 5.75-5.94 (unresolved complex, 2H); 6.73-7.51 (unresolved complex, 9H).

In the same manner, compound 239 is prepared, the physical properties of which are as follows:

MH+=568; the retention time is 9.44 minutes m.p.=99.5° C.

EXAMPLE 42

N-[4-chloro-2-(2,6-difluorobenzyl)phenyl]-N-[2-(1H-imidazol-1-yl)ethyl]-3,4-dimethoxybenzenesulfonamide (compound 271)

To 2 ml of dimethylformamide are added, at room temperature, 51 mg of sodium hydride at 50% in oil, followed by 72 mg of imidazole. After 30 minutes at this temperature, 0.4 g of ethyl N-(2-bromoethyl)-N-[2-(2,6-difluorobenzyl)-4-chlorophenyl]-3,4-dimethoxybenzenesulfonamide dissolved in 5 ml of dimethylformamide is introduced. The reaction medium is left for 18 hours at room temperature and then taken up in ethyl acetate and washed with water. The organic phase is dried over anhydrous sodium sulfate and concentrated. The residue is chromatographed on a column of silica gel, eluting with a 97/3 (v/v) toluene/ethyl acetate mixture to give 0.082 g of the expected product.

m.p.=159.5° C. $^1$H NMR δ in ppm (DMSO d6): 3.66 (m, 1H); 3.76 (s, 3H); 3.89 (s, 3H); 3.99-4.15 (unresolved complex, 5H); 6.72-7.56 (unresolved complex, 12H).

In the same manner, compound 301 is prepared, the physical properties of which are as follows:

MH+=544; the retention time is 6.62 minutes m.p.=153.6° C.

EXAMPLE 43

N$^3$-[4-chloro-2-(2,6-difluorobenzyl)phenyl]-N$^3$-[(3,4-dimethoxyphenyl)sulfonyl]-β-alaninamide (compound 273)

EXAMPLE 43.1

N-[4-chloro-2-(2,6-difluorobenzyl)phenyl]-N-[(3,4-dimethoxyphenyl)sulfonyl]-β-alanine To 2.63 g of N-[4-chloro-2-(2,6-difluorobenzyl)phenyl]-N-(3-hydroxypropyl)-3,4-dimethoxybenzenesulfonamide (Example 37) dissolved in 35 ml of acetonitrile are added, at room temperature, 0.069 g of ruthenium trichloride, 1.65 g of sodium periodate and 2.7 ml of water. The mixture is left for 10 hours at room temperature. The reaction medium is filtered through talc and then concentrated. The residue is taken up in dichloromethane and washed with 1M hydrochloric acid solution. The organic phase is dried over anhydrous sodium sulfate and concentrated to give 3.13 g of the expected product.

$^1$H NMR δ in ppm (DMSO d6): 2.3 (m, 2H); 3.45 (m, 1H); 3.71 (s, 3H); 3.86 (m, 1H); 3.90 (s, 3H); 4.1-4.35 (unresolved complex, 2H); 6.74-7.47 (unresolved complex, 9H); 12.3 (s, 1H).

EXAMPLE 43.2

N$^3$-[4-chloro-2-(2,6-difluorobenzyl)phenyl]-N$^3$-[(3,4-dimethoxyphenyl)sulfonyl]-β-alaninamide To 0.8 g of N-[4-chloro-2-(2,6-difluorobenzyl)phenyl]-N-[(3,4-dimethoxyphenyl)sulfonyl]-β-alanine dissolved in 16 ml of tetrahydrofuran are added, at 0° C., 0.21 ml of N-ethylmorpholine and 0.16 ml of ethyl chloroformate. The mixture is left at room temperature for 1 hour, and 1.36 ml of ammonia (20%) in water are then introduced. After 48 hours at room temperature, the reaction medium is taken up in ethyl acetate and washed with water. The organic phase is dried over anhydrous sodium sulfate and concentrated, and the residue is chromatographed on a column of silica gel, eluting with a 98/2 (v/v) dichloromethane/methanol mixture to give 0.295 g of the expected product.

m.p.=189.4° C. $^1$H NMR δ in ppm (DMSO d6): 2.08-2.25 (unresolved complex, 2H); 3.42 (m, 1H); 3.76 (s, 3H); 3.88 (s, 3H) 3.92 (m, 1H); 4.13 (d, 1H); 4.27 (d, 1H); 6.75-7.51 (unresolved complex, 11H)

In the same manner, compound 298 is prepared, the physical properties of which are as follows:

MH+=539; the retention time is 9.15 minutes m.p.=189.3° C.

EXAMPLE 44

N$^2$-[4-chloro-2-(2,6-difluorobenzyl)phenyl]-N$^2$-[(3,4-dimethoxyphenyl)sulfonyl]-β-alaninamide (compound 261)

EXAMPLE 44.1 methyl N-[4-chloro-2-(2,6-difluorobenzyl)phenyl]-N-[(3,4-dimethoxyphenyl)sulfonyl]alaninate By reaction of 2 g of N-[4-chloro-2-(2,6-difluorobenzyl)phenyl]-3,4-dimethoxybenzenesulfonamide with methyl lactate according to process 35, 1.393 g of the expected product are obtained.

$^1$H NMR δ in ppm (DMSO d6): 1.12 (t, 3H); 1.25 (d, 3H); 3.75 (s, 3H); 3.86 (s, 3H); 3.98 (d, 1H); 4.19 (q, 2H); 4.65 (d, 1H); 4.87 (q, 1H); 6.55 (s, 1H) 7.04-7.48 (unresolved complex, 8H).

EXAMPLE 44.2

N-[4-chloro-2-(2,6-difluorobenzyl)phenyl]-N-[(3,4-dimethoxyphenyl)sulfonyl]alanine To 1.373 g of methyl N-[4-chloro-2-(2,6-difluorobenzyl)phenyl]-N-[(3,4-dimethoxyphenyl)sulfonyl]alaninate dissolved in 20 ml of ethanol is added 0.52 g of lithium hydroxide monohydrate, and the mixture is left at room temperature for 18 hours. The medium is concentrated and the residue is taken up in ethyl acetate and washed with 5% potassium hydrogen sulfate solution. The organic phase is dried over anhydrous sodium sulfate and concentrated. The residue is chromatographed on a column of silica gel, eluting with a 90/10 (v/v) dichloromethane/methanol mixture to give 0.494 g of the expected product.

$^1$H NMR δ in ppm (DMSO d6): 1.17 (d, 3H); 3.76 (s, 3H); 3.87 (s, 3H); 3.92 (d, 1H); 4.19 (d, 1H); 4.75 (q, 1H); 6.53-7.52 (unresolved complex, 9H); 12.9 (s, 1H).

EXAMPLE 44.3

N²-[4-chloro-2-(2,6-difluorobenzyl)phenyl]-N²-[(3,4-dimethoxyphenyl)sulfonyl]-β-alaninamide To 0.47 g of N-[4-chloro-2-(2,6-difluorobenzyl)phenyl]-N-[(3,4-dimethoxyphenyl)sulfonyl]alanine dissolved in 20 ml of tetrahydrofuran are added, at 0° C., 0.13 ml of N-ethylmorpholine and 0.094 ml of ethyl chloroformate. The mixture is left at room temperature for 1 hour, and 0.75 ml of ammonia (20%) in water is then introduced. After 24 hours at room temperature, the reaction medium is taken up in ethyl acetate and washed with water. The organic phase is dried over anhydrous sodium sulfate and concentrated, and the residue is chromatographed on a column of silica gel, eluting with a 95/5 (v/v) dichloromethane/methanol mixture to give 0.295 g of the expected product.

m.p.=108° C. ¹H NMR δ in ppm (DMSO d6): 1.04 (d, 3H); 3.77 (s, 3H); 3.84 (s, 3H); 3.93 (d, 1H); 4.19 (d, 1H); 4.85 (q, 1H); 4.89 (d, 1H); 6.53-7.52 (unresolved complex, 9H).

The enantiomers of compound 261 are separated by chiral chromatography.

Laevorotatory enantiomer, compound 305
[α]$_D$ (C=0.5 g/100 ml in methanol)=−28.2

Dextrorotatory enantiomer, compound 304
[α]$_D$ (C=0.5 g/100 ml in methanol)=+25.4

Table XXV illustrates the chemical structures and the physical properties of a number of compounds of the invention obtained according to this example.

TABLE XXV

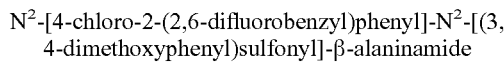

| Compound No. | Nature and position of the substituents | | | | m.p. (° C.) | MH⁺/ retention time |
| --- | --- | --- | --- | --- | --- | --- |
| | Ar₁ | Ar₂ | R₁ | Ar₃ | | |
| 304 | 2,6-diF | 4-Cl | CH(CH₃)CONH₂ | 3,4-diOMe | 105.3 | 525/9.29 |
| 305 | 2,6-diF | 4-Cl | CH(CH₃)CONH₂ | 3,4-diOMe | 94.1 | 525/9.29 |

EXAMPLE 45

N²-[2-(2-chlorobenzyl)-4-(dimethylamino)phenyl]-N²-[(3,4-dimethoxyphenyl)sulfonyl]glycinamide (compound 265)

EXAMPLE 45.1

N²-[4-amino-2-(2-chlorobenzyl)phenyl]-N²-[(3,4-dimethoxyphenyl)sulfonyl]glycinamide To 2 g of N²-[2-(2-chlorobenzyl)-4-nitrophenyl]-N²-[(3,4-dimethoxyphenyl)sulfonyl]glycinamide, obtained according to Example 15, dissolved in 150 ml of ethanol are successively added, at room temperature, 0.91 g of tin and 3.2 ml of 12M hydrochloric acid. After 18 hours, the medium is concentrated, taken up in ethyl acetate and washed with sodium hydroxide solution (pH 14). The organic phase is dried over anhydrous sodium sulfate and concentrated. The residue is chromatographed on a column of silica gel, eluting with a 95/5 (v/v) dichloromethane/methanol mixture to give 0.287 g of the expected product.

¹H NMR δ in ppm (DMSO d6): 3.79 (s, 3H); 3.88 (s, 3H); 3.94-4.40 (unresolved complex, 4H); 5.15 (s, 2H); 5.94 (d, 1H); 6.22 (d, 1H); 6.50 (d, 1H); 7.04-7.49 (unresolved complex, 9H).

EXAMPLE 45.2

N²-[2-(2-chlorobenzyl)-4-(dimethylamino)phenyl]-N²-[(3,4-dimethoxyphenyl)sulfonyl]glycinamide To 0.6 g of N²-[4-amino-2-(2-chlorobenzyl)phenyl]-N²-[(3,4-dimethoxyphenyl)sulfonyl]glycinamide dissolved in N-methylpyrrolidine are added 0.42 g of caesium carbonate and 0.9 ml of iodomethane, and the mixture is left at room temperature for 18 hours. The medium is taken up in ethyl acetate and washed with water. The organic phase is dried over anhydrous sodium sulfate and concentrated. The residue is chromatographed on a column of silica gel, eluting with a 100% to 90%/10% dichloromethane/acetone gradient to give the expected product.

m.p.=130.4° C. ¹H NMR δ in ppm (DMSO d6): 2.73 (s, 6H); 3.78 (s, 3H); 3.84 (s, 3H); 3.98-4.08 (unresolved complex, 3H); 4.40 (d, 1H); 6.04 (d, 1H); 6.43 (d, 1H); 6.70 (d, 1H); 7.02-7.51 (unresolved complex, 9H).

EXAMPLE 46 ethyl N-[4-chloro-2-(2-chlorophenyl)]-3,4-dimethoxy-N-vinylbenzenesulfonamide (compound 289)

To 0.18 g of 1-methyl-2-imidazolidone dissolved in N-methylpyrrolidone is added 0.086 g of sodium hydride at 50% in oil, the mixture is left at room temperature for 15 minutes, and 1 g of ethyl N-(2-bromoethyl)-N-[2-(2,6-difluorobenzyl)-4-chlorophenyl]-3,4-dimethoxybenzenesulfonamide is introduced. After 18 hours, the reaction medium is taken up in ethyl acetate and washed with water. The organic phase is dried over anhydrous sodium sulfate and concentrated, and the residue is chromatographed on a column of silica gel, eluting with dichloromethane, to give 0.67 g of the expected product.

m.p.=153° C. ¹H NMR δ in ppm (DMSO d6): 3.54 (d, 1H); 3.79 (s, 3H); 3.89 (s, 3H); 3.94-4.20 (unresolved complex, 2H); 4.22 (d, 1H); 6.50 (d, 1H); 7.06-7.45 (unresolved complex, 9H).

EXAMPLE 47

N²-[2-(2,6-difluorobenzyl)-5-methoxyphenyl]-N²-[(3,4-dimethoxyphenyl)sulfonyl]glycinamide (compound 296)

EXAMPLE 47.1

(2-amino-4-methoxyphenyl)(2,6-difluorophenyl) methane

To 6.22 g of (2-amino-4-methoxyphenyl)(2,6-difluorophenyl)methanol, obtained according to Example 11.1, dissolved in 95 ml of dichloromethane are successively added, at room temperature, 11.7 ml of triethylsilane and 10.7 ml of trifluoroacetic acid. After refluxing for 4 hours, the medium is hydrolysed with 6M sodium hydroxide solution. The organic phase is dried over anhydrous sodium sulfate and concentrated. The residue is chromatographed on a column of silica gel, eluting with dichloromethane to give 1.505 g of the expected product.

$^1$H NMR δ in ppm (DMSO d6): 3.69 (s, 3H); 4.93 (s, 2H); 6.04 (d, 1H); 6.21 (s, 1H); 6.48 (d, 1H); 7.01-7.35 (unresolved complex, 3H).

EXAMPLE 47.2

N-[2-(2,6-difluorobenzyl)-5-methoxyphenyl]-3,4-dimethoxybenzenesulfonamide

Starting with 1.5 g of (2-amino-4-methoxyphenyl)(2,6-difluorophenyl)methane according to Example 12.2, 0.32 g of the expected product is obtained.

$^1$H NMR δ in ppm (DMSO d6): 3.55 (s, 3H); 3.74 (s, 3H); 3.82 (s, 3H); 3.85 (d, 2H); 6.42 (d, 1H); 6.56-7.42 (unresolved complex, 8H); 9.54 (s, 1H).

EXAMPLE 47.3

N$^2$-[2-(2,6-difluorobenzyl)-5-methoxyphenyl]-N$^2$-[(3,4-dimethoxyphenyl)sulfonyl]glycinamide Starting with 0.312 g of N-[2-(2,6-difluorobenzyl)-5-methoxyphenyl]-3,4-dimethoxybenzenesulfonamide according to Example 12.3, 0.219 g of the expected product is obtained.

m.p.=188.2° C. $^1$H NMR δ in ppm (DMSO d6): 3.55 (s, 3H); 3.78 (s, 3H); 3.88 (s, 3H); 4.10-4.24 (unresolved complex, 3H); 4.43 (d, 1H); 6.41 (d, 1H); 6.57 (d, 1H); 6.83 (d, 1H); 7.05-7.48 (unresolved complex, 8H).

Table XXVI illustrates the chemical structures and the physical properties of a number of compounds of the invention obtained according to this example.

TABLE XXVI

| Compound No. | Nature and position of the substituents | | | | m.p. (° C.) | MH$^+$/ retention time |
|---|---|---|---|---|---|---|
| | Ar$_1$ | Ar$_2$ | R$_1$ | Ar$_3$ | | |
| 302 | 2,6-diF | 4-Cl, 6-OMe | CH$_2$CONH$_2$ | 3,4-diOMe | 238.5 | 541/8.89 |
| 303 | 2,6-diF | 4-Cl, 6-Me | CH$_2$CONH$_2$ | 3,4-diOMe | 217 | 521/8.61 |

EXAMPLE 48

N-[4-chloro-2-(2,6-difluorobenzyl)phenyl]-3,4-dimethoxy-N-{2-[(methylsulfonyl)amino]ethyl}-benzenesulfonamide (compound 313)

To 0.543 g of compound 256 dissolved in 10 ml of tetrahydrofuran are added 106 μl of pyridine and 102 μl of methanesulfonyl chloride, and the mixture is left at room temperature for 18 hours. The reaction medium is concentrated and the residue is chromatographed on a column of silica gel, eluting with a dichloromethane/methanol mixture to give 0.425 g of the expected product.

m.p.=133.2° C. $^1$H NMR δ in ppm (DMSO d6): 2.85 (s, 3H); 2.90 (m, 1H); 3.12 (m, 1H); 3.35 (m, 1H); 3.78 (s, 3H); 3.83 (m, 1H); 3.86 (s, 3H); 4.09 (d, 1H); 4.31 (d, 1H); 6.78-7.51 (unresolved complex, 10H).

EXAMPLE 49

N$^2$-[2-(2,6-difluorobenzyl)-6-methoxyphenyl]-N$^2$-[(3,4-dimethoxyphenyl)sulfonyl]-N-ethylglycinamide (compound 309)

EXAMPLE 49.1

N-[2-(2,6-difluorobenzyl)-6-methoxyphenyl]-N-[(3,4-dimethoxyphenyl)sulfonyl]glycine To 1.8 g of ethyl N-[2-(2,6-difluorobenzyl)-6-methoxyphenyl]-N-[(3,4-dimethoxyphenyl)sulfonyl]-glycinate dissolved in 50 ml of ethanol are added 10 ml of 2M sodium hydroxide solution. After 18 hours at room temperature, the medium is extracted with diethyl ether and the aqueous phase is acidified and extracted with dichloromethane. The organic phase is dried over anhydrous sodium sulfate and then concentrated to give 1.8 g of the expected product.

$^1$H NMR δ in ppm (DMSO d6): 3.18 (s, 3H); 3.72 (s, 3H); 3.82 (d, 1H); 3.90 (s, 3H); 4.29 (d, 1H); 4.53 (d, 1H); 5.01 (d, 1H); 6.26 (d, 1H); 6.78 (d, 1H); 7.01-7.47 (unresolved complex, 7H); 12.75 (s, 1H).

EXAMPLE 49.2

N$^2$-[2-(2,6-difluorobenzyl)-6-methoxyphenyl]-N$^2$-[(3,4-dimethoxyphenyl)sulfonyl]-N-ethylglycinamide To 1.8 g of N-[2-(2,6-difluorobenzyl)-6-methoxyphenyl]-N-[(3,4-dimethoxyphenyl)sulfonyl]glycine dissolved in 30 ml of tetrahydrofuran at 0° C. are introduced 0.5 ml of N-ethylmorpholine and 0.38 ml of ethyl chloroformate. After 15 minutes at 10° C., 0.8 g of ethylamine dissolved in tetrahydrofuran is added and the mixture is left at room temperature for 30 minutes. The medium is taken up in ethyl acetate and washed with water, and the organic phase is dried over anhydrous sodium sulfate and concentrated to give 1.4 g of the expected product.

m.p.=180° C. $^1$H NMR δ in ppm (DMSO d6): 0.98 (t, 3H); 3.07 (m, 2H); 3.26 (s, 3H); 3.76 (s, 3H); 3.79 (m, 1H); 3.87 (s, 3H); 4.26 (d, 1H); 4.43 (d, 1H); 4.94 (d, 1H); 6.20 (d, 1H); 6.81 (d, 1H); 7.09-7.45 (unresolved complex, 7H); 7.88 (t, 1H).

EXAMPLE 50

N$^2$-[4-chloro-2-(2,5-difluorobenzyl)phenyl]-N$^2$-[(4-chloro-2,5-dimethylphenyl)sulfonyl]glycinamide (compound 267)

EXAMPLE 50.1

(2-nitro-5-chlorophenyl)(2,5-difluorophenyl)methanol

To 15 g of 2,5-difluorobenzene dissolved in 150 ml of tetrahydrofuran are added, at −70° C., 50 ml of 1.6M butyllithium solution. After 2 hours at −70° C., 9.616 g of 2-nitro- 5-chlorobenzaldehyde are introduced and the mixture is left at this temperature for 3 hours and then at room temperature for 18 hours. The medium is hydrolysed with ammonium chloride solution and extracted with ethyl acetate. The organic phase is dried over anhydrous sodium sulfate and concentrated. The residue is filtered through silica, eluting with dichloromethane, to give 8.89 g of the expected product.

EXAMPLE 50.2

(2-amino-5-chlorophenyl)(2,5-difluorophenyl)methanol

Starting with 8.55 g of (2-nitro-5-chlorophenyl)(2,5-difluorophenyl)methanol according to process 8.2, 2.7 g of the expected product are obtained.

$^1$H NMR δ in ppm (DMSO d6): 5.18 (s, 2H); 5.89 (d, 1H); 6.15 (d, 1H); 6.68-7.36 (unresolved complex, 6H)

EXAMPLE 50.3

(2-amino-5-chlorophenyl)(2,5-difluorophenyl)methane

Starting with 2.7 g of (2-amino-5-chlorophenyl)(2,5-difluorophenyl)methanol according to process 18.1, 1.947 g of the expected product are obtained.

$^1$H NMR δ in ppm (DMSO d6): 3.80 (s, 2H); 5.18 (s, 2H); 6.60 (unresolved complex, 6H)

EXAMPLE 50.4

N-[4-chloro-2-(2,5-difluorobenzyl)phenyl]-2,5-dimethyl-4-chlorobenzenesulfonamide Starting with 0.484 g of (2-amino-5-chlorophenyl)(2,5-difluorophenyl)methane according to the process described in Example 12.2, 0.837 g of the expected product is obtained.

$^1$H NMR δ in ppm (DMSO d6): 2.28 (s, 3H); 2.45 (s, 3H); 3.98 (s, 2H); 6.60 (m, 1H); 6.94-7.61 (unresolved complex, 8H), 9.93 (s, 1H)

EXAMPLE 50.5

N$^2$-[4-chloro-2-(2,5-difluorobenzyl)phenyl]-N$^2$-[(4-chloro-2,5-dimethylphenyl)sulfonyl]glycinamide Starting with 0.83 g of N-[4-chloro-2-(2,5-difluorobenzyl)phenyl]-2,5-dimethyl-4-chlorobenzenesulfonamide according to Example 15, 0.424 g of the expected product is obtained.

$^1$H NMR δ in ppm (DMSO d6): 2.16 (s, 3H); 2.36 (s, 3H); 3.92 (d, 1H); 4.23 (d, 1H); 4.40 (d, 1H); 6.87 (s, 1H) 6.96-7.75 (unresolved complex, 8H) m.p.=169.7° C.

EXAMPLE 51

N$^2$-[4-chloro-2-(pyrid-2-ylmethyl)phenyl]-N$^2$-[(3,4-dimethoxyphenyl)sulfonyl]glycinamide

EXAMPLE 51.1

2-(5-chloro-2-nitrobenzyl)pyridine

To 22.44 g of potassium tert-butoxide in 500 ml of dimethyl sulfoxide are slowly added 8.66 g of 4-chloronitrobenzene and 8.2 g of 2-chloromethylpyridine dissolved in 100 ml of dimethyl sulfoxide. After 18 hours at room temperature, the mixture is hydrolysed with saturated ammonium chloride solution and extracted three times with dichloromethane. The organic phase is dried over anhydrous sodium sulfate and concentrated. The residue is filtered through silica H, eluting with dichloromethane, to give 10.695 g of the expected product.

$^1$H NMR δ in ppm (DMSO d6): 4.49 (s, 2H); 7.20-7.31 (unresolved complex, 2H); 7.60-7.78 (unresolved complex, 3H); 8.03 (d, 1H); 8.41 (d, 1H) m.p.=69° C.

EXAMPLE 51.2

4-chloro-2-(pyrid-2-ylmethyl)aniline

Starting with 5 g of 2-(5-chloro-2-nitrobenzyl)pyridine according to Example 8.2, 3.86 g of the expected product are obtained.

$^1$H NMR δ in ppm (DMSO d6): 3.93 (s, 2H); 5.33 (s, 2H); 6.66 (d, 1H); 6.93-7.06 (unresolved complex, 2H); 7.21-7.38 (unresolved complex, 2H); 7.76 (m, 1H); 8.47 (d, 1H)

EXAMPLE 51.3

N-[4-chloro-2-(pyrid-2-ylmethyl)phenyl]-3,4-dimethoxybenzenesulfonamide

Starting with 1.86 g of 4-chloro-2-(pyrid-2-ylmethyl)aniline according to Example 12.2, 2.12 g of the expected product are obtained.

$^1$H NMR δ in ppm (DMSO d6): 3.71 (s, 3H); 3.83 (s, 3H); 3.94 (s, 2H); 7.07-7.32 (unresolved complex, 8H); 7.74 (m, 1H); 8.54 (d, 1H)

EXAMPLE 51.4

N$^2$-[4-chloro-2-(pyrid-2-ylmethyl)phenyl]-N$^2$-[(3,4-dimethoxy]phenyl)sulfonyl]glycinamide Starting with 0.5 g of N-[4-chloro-2-(pyrid-2-ylmethyl)phenyl]-3,4-dimethoxybenzenesulfonamide according to Example 12.3, 0.257 g of the expected product is obtained.

$^1$H NMR δ in ppm (DMSO d6): 3.79 (s, 3H); 3.88 (s, 3H); 4.03-4.48 (unresolved complex, 4H)); 6.93-7.37 (unresolved complex, 10H); 7.74 (t, 1H); 8.54 (d, 1H) m.p.=88° C.

EXAMPLE 52

N$^2$-[2-(2,6-difluorobenzyl)-6-methoxyphenyl]-N$^2$[(3,4-dimethoxyphenyl)sulfonyl]-(R)-alaninamide (compound 321)

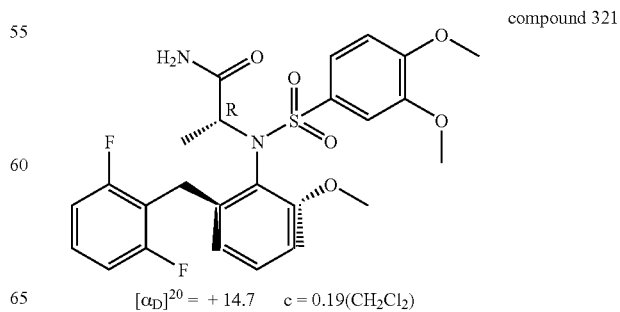

compound 321

$[α_D]^{20}$ = +14.7    c = 0.19(CH$_2$Cl$_2$)

EXAMPLE 52.1

N-[2-(2,6-difluorobenzyl)-6-methoxyphenyl]-N-[(3,4-dimethoxyphenyl)sulfonyl]-(R)-alanine To 0.164 g of methyl N-[2-(2,6-difluorobenzyl)-6-methoxyphenyl]-N-[(3,4-dimethoxyphenyl)sulfonyl]-(R)-alaninate dissolved in 8 ml of a 1,4-dioxane/water mixture (4/1) is added, at room temperature, 0.015 g of lithium hydroxide monohydrate. The mixture is left at room temperature for 48 hours. The reaction medium is washed with 1M hydrochloric acid solution and extracted with ethyl acetate. The organic phase is dried over anhydrous sodium sulfate and concentrated. The residue is chromatographed on a column of silica gel, eluting with a dichloromethane/ethanol mixture to give 0.08 g of the expected product.

$^1$H NMR δ in ppm (DMSO d6): 1.64 (d, 3H); 3.22 (s, 3H); 3.70 (s, 3H); 3.85 (s, 3H); 4.11 (d, 1H); 4.22 (q, 1H); 4.77 (d, 1H); 6.31 (d, 1H); 6.78 (d, 1H); 7.02-7.44 (unresolved complex, 7H), 12.5 (s, 1H).

EXAMPLE 52.2

$N^2$-[2-(2,6-difluorobenzyl)-6-methoxyphenyl]-$N^2$[(3,4-dimethoxyphenyl)sulfonyl]-(R)-alaninamide Starting with 0.098 g of N-[2-(2,6-difluorobenzyl)-6-methoxyphenyl]-N-[(3,4-dimethoxyphenyl)sulfonyl]-(R)-alanine according to Example 43.2, 0.08 g of the expected product is obtained.

$^1$H NMR δ in ppm (DMSO d6): 1.34 (d, 3H); 3.32 (s, 3H); 3.74 (s, 3H); 3.85 (s, 3H); 4.22 (d, 2H); 4.41 (q, 1H); 6.27 (d, 1H); 6.88 (d, 1H); 7.07-7.44 (unresolved complex, 9H).

According to this process, $N^2$-[2-(2,6-difluorobenzyl)-6-methoxyphenyl]-$N^2$-[(3,4-dimethoxyphenyl)sulfonyl]-(S)-alaninamide (compound 322) is synthesized.

$^1$H NMR δ in ppm (DMSO d6): 1.34 (d, 3H); 3.32 (s, 3H); 3.74 (s, 3H); 3.85 (s, 3H); 4.22 (d, 2H); 4.41 (q, 1H); 6.27 (d, 1H); 6.88 (d, 1H); 7.07-7.44 (unresolved complex, 9H).

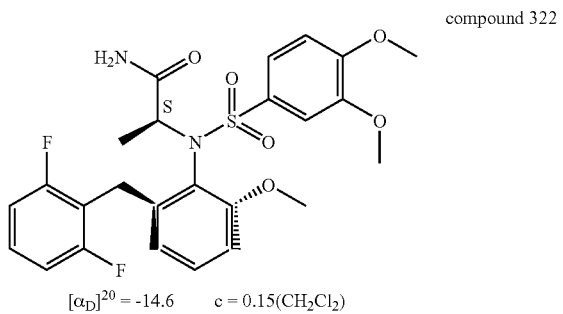

compound 322

[α$_D$]$^{20}$ = -14.6    c = 0.15(CH$_2$Cl$_2$)

EXAMPLE 53

$N^2$-[2-methoxy-6-(2-phenylethyl)phenyl]-$N^2$-[(3,4-dimethoxyphenyl)sulfonyl]glycinamide (compound 323)

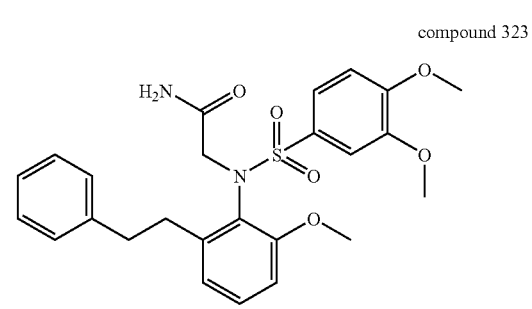

compound 323

EXAMPLE 53.1

1-methoxy-2-nitro-3-[(E)-2-phenylvinyl]benzene

To 10 ml of ethanol is added, at room temperature, 0.31 g of sodium. The mixture is left at room temperature for 15 minutes, and 4.05 g of benzyltriphenylphosphonium chloride and 2 g of 2-nitro-3-methoxybenzaldehyde are successively introduced. After 18 hours at room temperature, the reaction medium is taken up in dichloromethane and washed with water. The organic phase is dried over anhydrous sodium sulfate and concentrated. The residue is chromatographed on a column of silica gel to give 2.254 g of the expected product.

$^1$H NMR δ in ppm (DMSO d6): 3.92 (s, 3H); 6.55-7.56 (unresolved complex, 10H).

EXAMPLE 53.2

2-methoxy-6-(2-phenylethyl)aniline 2.25 g of 1-methoxy-2-nitro-3-[(E)-2-phenylvinyl]benzene are added to 0.18 g of palladium-on-charcoal (10%) suspended in 90 ml of methanol, and placed under 4 bar of hydrogen. After 18 hours, the reaction medium is filtered through talc and the filtrate is concentrated to give 2.115 g of the expected product.

$^1$H NMR δ in ppm (DMSO d6): 2.74-2.88 (unresolved complex, 4H); 3.78 (s, 3H); 4.55 (s, 2H); 6.55-7.31 (unresolved complex, 8H).

EXAMPLE 53.3

N-[2-methoxy-6-(2-phenylethyl)phenyl](3,4-dimethoxyphenyl)sulfonamide

Starting with 2.11 g of 2-methoxy-6-(2-phenylethyl)aniline according to Example 12.2, 0.5 g of the expected product is obtained.

$^1$H NMR δ in ppm (DMSO d6): 2.83 (m, 2H); 3.01 (m, 2H); 3.22 (s, 3H); 3.73 (s, 3H); 3.84 (s, 3H); 6.71-7.33 (unresolved complex, 11H); 8.99 (s, 1H).

EXAMPLE 53.4

N²-[2-methoxy-6-(2-phenylethyl)phenyl]-N²-[(3,4-dimethoxyphenyl)sulfonyl]glycinamide Starting with 0.5 g of N-[2-methoxy-6-(2-phenylethyl)phenyl](3,4-dimethoxyphenyl)sulfonamide according to Example 12.3, 0.187 g of the expected product is obtained.

$^1$H NMR δ in ppm (DMSO d6): 2.83 (m, 3H); 3.26 (s, 3H); 3.40 (m, 1H); 3.73 (s, 3H); 3.84 (s, 3H); 6.76 (d, 1H); 7.03-7.36 (unresolved complex, 12H). m.p.=243.9° C.

The compounds of the invention underwent pharmacological trials that demonstrated their advantage as therapeutically active substances.

They were in particular tested as regards their effects. More particularly, the affinity of the compounds of the invention for the orexin 2 receptors was determined in a test of in vitro binding according to the technique described below. This method consists in studying the displacement of radio-iodinated orexin A bound to human orexin 2 receptors expressed in CHO cells. The test is performed on membranes in a Hepes 50 mM, MgCl$_2$ 1 mM, CaCl$_2$ 25 mM, NaN$_3$ 0.025%, bovine serum albumin (BSA) 1% incubation buffer and 100 pM of ligand, for 30 minutes at 25° C. The reaction is quenched by filtration and washing on a Whatman GF/C filter. The non-specific binding is measured in the presence of 10$^{-6}$M of human orexin B. The IC$_{50}$ values (concentration that inhibits 50% of the binding of the radio-iodinated orexin A to its receptors) are low, less than 300 nM, in particular less than 100 nM and more particularly less than 30 nM.

The affinity of the compounds according to the invention for the orexin 1 receptors was also studied in a test of in vitro binding according to the same technique using radio-iodinated orexin A as ligand in a membrane preparation of CHO cells expressing the human orexin 1 receptors. The compounds according to the invention show little or no affinity for the orexin 1 receptors.

The agonist or antagonist nature of the compounds is determined in vitro in a test of measurement of intracellular calcium (FLIPR) on a cell preparation expressing the orexin 2 receptors, according to the general technique described in Sullivan et al., Methods Mol. Biol., 1999, vol. 114, 125-133, using 1 µM of Fluo-4 AM as fluorescent calcium indicator. For the antagonist test, the compounds are preincubated for 30 minutes before addition of 0.25 nM or orexin B. The IC$_{50}$ values for the orexin 2 receptors measured in these studies are low and more particularly less than 100 nM.

The table below illustrates the affinity of a number of compounds according to the invention for the orexin receptors in a test of in vitro binding according to the technique described above, and also their antagonist nature determined in vitro in a test of measurement of intracellular calcium (FLIPR) according to the general technique mentioned above.

| Compound No. | IC$_{50}$ OX 2 (nM) | IC$_{50}$ OX 1 (nM) | Measurement of [Ca$^{2+}$]i IC$_{50}$ OX 2 (nM) - FLIPR |
|---|---|---|---|
| 1 | 13 | 446 | 5 |
| 28 | 62 | 1500 | 19 |
| 30 | 82 | 966 | 26 |
| 44 | 85 | >10 µM | 54 |
| 107 | 20 | 899 | 11 |
| 124 | 50 | >10 µM | 65 |
| 137 | 19 | >10 µM | 10 |
| 138 | 8 | 4760 | 11 |
| 202 | 9 | 1870 | 7 |

The biological results show that the compounds according to the invention are quite clearly specific antagonists of the orexin 2 receptors.

Thus, the compounds according to the present invention, as orexin 2 receptor antagonists, may be used in the prophylaxis and treatment of all diseases involving dysfunction associated with these receptors.

The compounds of the invention may be used for the preparation of a medicament for the prophylaxis or treatment of all diseases involving dysfunction associated with the orexin 2 receptor, and more particularly in the prophylaxis or treatment of pathologies in which an orexin 2 receptor antagonist affords therapeutic benefit. Such pathologies are, for example, obesity, appetite or taste disorders including cachexia, anorexia and bulimia (Smart et al., Eur. J. Pharmacol., 2002, 440, 2-3, 199-212), diabetes (Ouedraogo et al., Diabetes, 2002, 52, 111-117), metabolic syndromes (Sakurai, Curr. Opin. Nutr. Metab. Care, 2003, 6, 353-360), vomiting and nausea (U.S. Pat. No. 6,506,774), depression and anxiety (Salomon et al., Biol. Psychiatry, 2003, 54, 96-104; Jaszberenyi et al., J. Neuroendocrinol., 2000, 12, 1174-1178), addictions (Georgescu et al., J. Neurosci., 2003, 23, 8, 3106-3111; Kane et al., Endocrinology, 2000, 141, 10, 3623-3629), mood and behaviour disorders, schizophrenia (Nishino et al., Psychiatry Res., 2002, 110, 1-7), sleep disorders (Sakurai, Neuroreport, 2002, 13, 8, 987-995), restless legs syndrome (Allen et al., Neurology, 2002, 59, 4, 639-641), memory learning disorders (van den Pol et al., 2002, J. Physiol., 541(1), 169-185; Jaeger et al., Peptides, 2003, 23, 1683-1688; Telegdy et Adamik, Regul. Pept., 2002, 104, 105-110), sexual and psychosexual dysfunctions (Gulia et al., Neuroscience, 2003, 116, 921-923), pain, visceral or neuropathic pain, hyperalgesia, allodynia (U.S. Pat. No. 6,506,774; Suyama et al., In vivo, 2004, 18, 2, 119-123), digestive disorders (Takakashi et al., Biochem. Biophy. Res. Comm., 1999, 254, 623-627; Matsuo et al., Eur. J. Pharmacol., 2002, 105-109), irritable bowel syndrome (U.S. Pat. No. 6,506,774), neuronal degenerescence (van den Pol, Neuron, 2000, 27, 415-418), ischaemic or haemorrhagic attacks (Irving et al., Neurosci. Lett., 2002, 324, 53-56), Cushing's disease, Guillain-Barré syndrome (Kanbayashi et al., Psychiatry Clin. Neurosci., 2002, 56, 3, 273-274), myotonic dystrophy (Martinez-Rodriguez et al., Sleep, 2003, 26, 3, 287-290), urinary incontinence (Blackstone et al., AGS Annual Meeting, poster P491, 2002), hyperthyroidism (Malendowicz et al., Biomed. Res., 2001, 22, 5, 229-233), pituitary function disorders (Voisin et al., Cell. Mol. Life. Sci., 2003, 60, 72-78) and hypertension or hypotension (Samson et al., Brain Res., 1999, 831, 1-2, 248-253).

The use of the compounds according to the invention for the preparation of a medicament for preventing or treating the pathologies mentioned above forms an integral part of the invention.

A subject of the invention is also medicaments comprising a compound of formula (I). These medicaments find their therapeutic use especially in the prophylaxis or treatment of the pathologies mentioned above.

According to another of its aspects, the present invention relates to pharmaceutical compositions containing, as active principle, at least one compound according to the invention. These pharmaceutical compositions contain an effective dose of a compound according to the invention and optionally one or more pharmaceutically acceptable excipients.

The said excipients are chosen, according to the pharmaceutical form and the desired mode of administration, from the usual excipients known to those skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or the possible salt, solvate or hydrate thereof, may be administered in a unit administration form, as a mixture with standard pharmaceutical excipients, to man and animals for the prophylaxis or treatment of the above disorders or diseases.

The appropriate unit forms of administration include oral forms such as tablets, soft or hard gel capsules, powders, granules, chewing gums and oral solutions or suspensions, sublingual, buccal, intratracheal, intraocular or intranasal administration forms, forms for administration by inhalation, subcutaneous, intramuscular or intravenous administration forms, and rectal or vaginal administration forms. For topical application, the compounds according to the invention may be used in creams, ointments or lotions.

For example, when a solid composition in the form of tablets is prepared, the main active ingredient is mixed with a pharmaceutical excipient, such as gelatin, starch, lactose, magnesium stearate, talc, gum arabic or the like. The tablets may be coated with sucrose, a cellulose derivative or other materials. The tablets may be made via various techniques, direct compression, dry granulation, wet granulation or hot-melting.

In order to obtain the desired prophylactic or therapeutic effect, the dose of active principle may range between 0.1 mg and 200 mg per kg of body weight and per day. Although these dosages are examples of an average situation, there may be particular cases in which higher or lower dosages are appropriate, and such dosages also form part of the invention. According to the usual practice, the dosage that is appropriate to each patient is determined by the doctor according to the mode of administration, the weight and the response of the said patient.

Each unit dose may contain from 0.1 to 1000 mg and preferably from 0.1 to 500 mg of active principle in combination with one or more pharmaceutical excipients. This unit dose may be administered 1 to 5 times a day so as to administer a daily dosage of from 0.5 to 5000 mg and preferably from 0.5 to 2500 mg.

According to another of its aspects, the present invention also relates to a method for preventing or treating the pathologies indicated above, which comprises the administration of a compound according to the invention, a pharmaceutically acceptable salt, a solvate or a hydrate of the said compound.

The invention claimed is:

1. A compound having the formula (I)

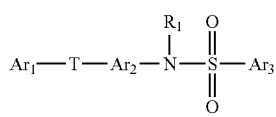

(I)

wherein
Ar$_1$ is
phenyl optionally substituted with one or more substituents independently selected from the group consisting of: halogen, a (C$_1$-C$_4$) alkyl group, a (C$_1$-C$_4$) alkoxy group, a fluoro(C$_1$-C$_4$)alkyl group, a cyano group, —CO—NR$_a$R$_b$, and —NR$_a$R$_b$, R$_a$ and R$_b$ being, independently of each other, hydrogen or a (C$_1$-C$_4$) alkyl group;

T is selected from
—(CH$_2$)$_n$— where n=0, 1 or 2,

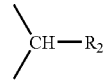

where R$_2$ is a hydroxyl group or a (C$_1$-C$_4$) alkyl group, or

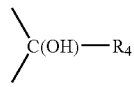

where R$_4$ is a (C$_1$-C$_4$) alkyl group;

Ar$_2$ is phenyl optionally substituted with one or more substituents independently selected from: halogen, C$_1$-C$_4$) alkyl, (C$_1$-C$_4$) alkoxy, fluoro(C$_1$-C$_4$)alkyl, fluoro(C$_1$-C$_4$)alkoxy, and —NR$_c$R$_d$ wherein R$_c$ and R$_d$ are, independently of each other, hydrogen or (C$_1$-C$_4$) alkyl, Ar$_3$ is phenyl optionally substituted with one or more substituents independently selected from: halogen, (C$_1$-C$_4$) alkyl, (C$_1$-C$_4$) alkoxy, fluoro(C$_1$-C$_4$)alkyl, fluoro(C$_1$-C$_4$)alkoxy, nitro, hydroxyl, —NR$_5$R$_6$ where R$_5$ and R$_6$ are, independently of each other, hydrogen or (C$_1$-C$_4$) alkyl, R$_1$ is a group of formula

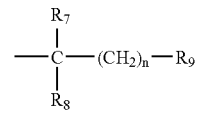

in which
n=0, 1, 2 or 3
R$_7$ is hydrogen, (C$_1$-C$_4$) alkyl, fluorine or (C$_1$-C$_4$) alkoxy, —(CH$_2$)$_m$-aryl, where m=1 or 2 and aryl is a phenyl group optionally substituted with halogen, (C$_1$-C$_4$) alkyl or (C$_1$-C$_4$) alkoxy,
R$_8$ is hydrogen, fluorine or (C$_1$-C$_4$) alkyl, and
R$_9$ is
—CO—NR$_{12}$R$_{13}$ where R$_{12}$ and R$_{13}$ are, independently of each other, hydrogen, (C$_1$-C$_4$) alkyl, optionally substituted with a —C≡N group,
or, alternatively, R$_{12}$ and R$_{13}$ form, together with the nitrogen atom that bears them, a group

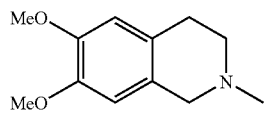

or a salt, an enantiomer, a diastereoisomer, a rotamer, an atropoisomer or mixtures thereof.

2. The compound of claim 1, in which
Ar₁ is
phenyl optionally substituted with one or more substituents selected, independently of each other, from: halogen, ($C_1$-$C_4$) alkyl, ($C_1$-$C_4$) alkoxy, fluoro($C_1$-$C_4$)alkyl,
T is
—($CH_2$)—,

where $R_2$ is hydroxyl or ($C_1$-$C_4$) alkyl,

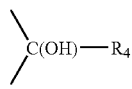

where $R_4$ is ($C_1$-$C_4$) alkyl;
Ar₂ is
phenyl optionally substituted with one or more substituents selected, independently of each other, from: halogen, ($C_1$-$C_4$) alkyl, ($C_1$-$C_4$) alkoxy, fluoro($C_1$-$C_4$)alkoxy, —$NR_cR_d$ where $R_c$ and $R_d$ are, independently of each other, hydrogen or ($C_1$-$C_4$) alkyl;
Ar₃ is
phenyl optionally substituted with one or more substituents selected, independently of each other, from: halogen, ($C_1$-$C_4$) alkyl, ($C_1$-$C_4$) alkoxy, fluoro($C_1$-$C_4$)alkyl, fluoro($C_1$-$C_4$)alkoxy, nitro, and —$NR_5R_6$ where $R_5$ and $R_6$ are, independently of each other, hydrogen or ($C_1$-$C_4$) alkyl,
R₁ is
a group of formula

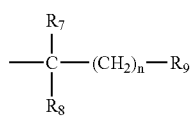

in which
n=0, 1 or 2,
R₇ is
hydrogen or ($C_1$-$C_4$) alkyl,
R₈ is
hydrogen, and
R₉ is
—CO—$NR_{12}R_{13}$ where $R_{12}$ and $R_{13}$ are, independently of each other, hydrogen or ($C_1$-$C_4$) alkyl,
or, alternatively, $R_{12}$ and $R_{13}$ form, together with the nitrogen atom that bears them, a group

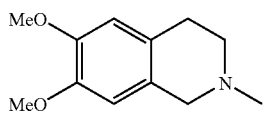

or a salt, an enantiomer, a diastereoisomer, a rotamer, an atropoisomer or mixtures thereof.

3. The compound of claim 1, in which
Ar₁ is
phenyl optionally substituted with one or more substituents selected, independently of each other, from the following: halogen, ($C_1$-$C_4$) alkyl, ($C_1$-$C_4$) alkoxy, and fluoro ($C_1$-$C_4$)alkyl,
T is
—($CH_2$)$_n$— where n=1, or

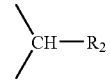

where $R_2$ is hydroxyl;
Ar₂ is
phenyl optionally substituted with one or more substituents selected, independently of each other, from: halogen, ($C_1$-$C_4$) alkyl, ($C_1$-$C_4$) alkoxy; —$NR_cR_d$ where $R_c$ and $R_d$ are, independently of each other, hydrogen or ($C_1$-$C_4$) alkyl;
Ar₃ is
phenyl, optionally substituted with one or more substituents selected, independently of each other, from: halogen, ($C_1$-$C_4$) alkyl, ($C_1$-$C_4$) alkoxy, or —$NR_5R_6$ where $R_5$ and $R_6$ are, independently of each other, hydrogen or ($C_1$-$C_4$) alkyl;
R₁ is
a group of formula

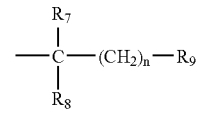

in which
n=0, 1 or 2,
R₇ is hydrogen or ($C_1$-$C_4$) alkyl,
R₈ is hydrogen, and
R₉ is
a group —CO—$NR_{12}R_{13}$ where $R_{12}$ and $R_{13}$ are, independently of each other, hydrogen or ($C_1$-$C_4$) alkyl,
or a salt, an enantiomer, a diastereoisomer, a rotamer, an atropoisomer or mixtures thereof.

4. The compound of claim 1, in which
Ar₁ is
phenyl optionally substituted with one or more substituents selected, independently of each other, from: halogen, ($C_1$-$C_4$) alkyl, and ($C_1$-$C_4$) alkoxy, or
T is
—($CH_2$)—,
Ar₂ is
a phenyl group optionally substituted with one or more substituents selected, independently of each other, from: halogen, ($C_1$-$C_4$) alkyl, ($C_1$-$C_4$) alkoxy, and —$NR_cR_d$ where $R_c$ and $R_d$ are, independently of each other, hydrogen or ($C_1$-$C_4$) alkyl;
Ar₃ is
a phenyl group optionally substituted with one or more substituents selected, independently of each other, from: halogen, ($C_1$-$C_4$) alkyl, ($C_1$-$C_4$) alkoxy, or —$NR_5R_6$ where $R_5$ and $R_6$ are, independently of each other, hydrogen or ($C_1$-$C_4$) alkyl;

$R_1$ is
a group of formula

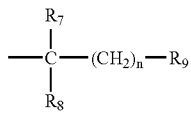

in which
n=0, 1 or 2,
$R_7$ is
  hydrogen or ($C_1$-$C_4$) alkyl;
$R_8$ is
  hydrogen; and
$R_9$ is
  —CO—$NR_{12}R_{13}$ where $R_{12}$ and $R_{13}$ are, independently of each other, hydrogen or ($C_1$-$C_4$) alkyl, or a salt, an enantiomer, a diastereoisomer, a rotamer, an atropoisomer or mixtures thereof.

5. A medicament which comprises a compound as claimed in claim 1.

6. A pharmaceutical composition comprising at least one compound as claimed in claim 1 and one or more pharmaceutically acceptable excipients.

7. A pharmaceutical composition comprising at least one compound as claimed in claim 2 and one or more pharmaceutically acceptable excipients.

8. A pharmaceutical composition comprising at least one compound as claimed in claim 3 and one or more pharmaceutically acceptable excipients.

9. A pharmaceutical composition comprising at least one compound as claimed in claim 4 and one or more pharmaceutically acceptable excipients.

* * * * *